US006656681B1

United States Patent
Harris et al.

(10) Patent No.: US 6,656,681 B1
(45) Date of Patent: Dec. 2, 2003

(54) POLYCYSTIC KIDNEY DISEASE 12 GENE AND USES THEREOF

(76) Inventors: Peter Charles Harris, 65 Freelands Road, Oxford (GB), OX4 4BS; Belen Peral, 77 Lock Crescent, Kidlington, Oxford (GB), OX5 1HF; Christopher J. Ward, 30 Benson Road, Oxford (GB), OX3 7EH; James Hughes, 25 Cowley Road, Oxford (GB), OX4 1XD; Martin Hendrik Breuning, Brigantijnstraat 57 503 BR, Zaandam (NL); Dorothea Johanna Maria Peters, Zuster Meijboomstraat 267, 2331 PH, Leiden (NL); Jeroen Hendrik Roelfsema, Vijf Meilaan 2006 2321 RR, Leiden (NL); Julian Sampson, 34 Bridge Street, Cardiff (GB), CF5 2EL; Dirkje Jorijntje Johanna Halley, van Aerssenlaan 35 d, 3039 KD, Rotterdam (NL); Mark David Nellist, Noordmolenstraat 57b, 3053 RG, Rotterdam (NL); Lambertus Antonius Jacobus Janssen, Schokker 37, 2991 DJ Barendrecht (NL); Ajenne Lique Wilhelma Hesseling, Haya van Someren Downerpad 7, 3207 DK Spijkenisse (NL)

( * ) Notice: Subject to any disclaimer, the term of this patent is extended or adjusted under 35 U.S.C. 154(b) by 0 days.

(21) Appl. No.: 09/052,262
(22) Filed: Mar. 31, 1998

Related U.S. Application Data

(62) Division of application No. 08/422,582, filed on Apr. 14, 1995, which is a continuation of application No. PCT/GB94/02822, filed on Dec. 23, 1994.

(30) Foreign Application Priority Data

Dec. 24, 1993 (GB) .............................................. 9326470
Jun. 14, 1994 (GB) .............................................. 9411900

(51) Int. Cl.[7] ........................... C12Q 1/68; C12P 19/34; C07H 21/04
(52) U.S. Cl. ........................ 435/6; 435/91.2; 536/23.1; 536/24.3; 536/24.31; 536/24.33
(58) Field of Search .................. 435/6, 91.2; 536/23.1, 536/24.3, 24.31, 24.33

(56) References Cited

U.S. PATENT DOCUMENTS 5,654,170 A * 8/1997 Klinger et al. ............. 435/69.1
5,891,628 A * 4/1999 Reeders et al. ................ 435/6

OTHER PUBLICATIONS

An Introduction to Genetic Analysis, Griffiths et al. eds. W.H. Freeman and Company, Fifth ed., pp. 427, 453–461, Dec. 1993.*

Turco et al. Prenatal Diagnosis of Autosomal Dominant Polycystic Kidney Disease using Flanking DNA Markers and the Polymerase Chain Reaction. Prenatal Diagnosis, 12: 513–524, 1992.*

Engelman, et al., "Identifying nonpolar transbilayer helices in amino acid sequences of membrane proteins," Ann. Rev. Biophys. Chem., 15:321–53 (1986).

Aksentijevich, et al., Refined Mapping of the Gene Causing Familial Mediterranean Fever, by Linkage and Homozygosity Studies, Am. J. Hum. Genet., 53:451–461 (1993).

Altschul, et al., "Basic Local Alignment Search Tool", J. Mol. Biol., 215, 403–410 (1990).

Bevilacqua, et al., "Endothelial Leukocyte Adhesion Molecule 1: An Inducible Receptor for Neutrophils Related to Complement Regulatory Proteins and Lectins", Science, vol. 243, 1160–1187 (1989).

Breuning, et al., "Improved early diagnosis of adult polycystic kidney disease with flanking DNA markers", The Lancet, 1359–1361, Dec. 12, 1987.

Breuning, et al., "Genetic Heterogeneity of Polycystic Kidney Disease in Europe", Contrib. Nephrol., vol. 97, pp. 128–139 (1992).

Breuning, et al., Map of 16 polymorphic loci on the short arm of chromosome 16 close to the polycystic kidney disease gene (PKD1), F. Med Genet, vol. 27:603–613 (1990).

Brook–Carter, et al., "Deletion of the TSC2 and PKD1 genes associated with severe infantile polycystic kidney disease—a contiguous gene syndrome", Nature Genetics, vol. 8: 328–332, (1994).

Brown, et al., "X chromosome inactivation of the human TIMP gene," Nucleic Acids Research, vol. 18, No. 14 (1990).

Brümmendorf, et al., "Protein Profile", vol. 1, 1994, pp. 951–962.

Buckle, et al., "Fluorescent in situ hybridization", Human Genetic Disease, pp. 59–82.

Carone, et al., "Biology of Polycystic Kidney Disease", Laboratory Investigation, vol. 70, No. 4, p. 437 (1994).

Carone, et al., "Impaired tubulogenesis of cyst–derived cells from autosomal dominant polycystic kidneys," Kidney International, vol. 47 (1995) pp. 861–868.

Calvet, et al., "Polycystic kidney disease: Primary extracellular matrix abnormality or defective cellular differentiation?", Kidney International, vol. 43 (1993) pp. 101–108.

Chapman, et al., "Intracranial aneurysms in autosomal dominant polycystic kidney disease", The New England Journal of Medicine, vol. 504, (1992).

(List continued on next page.)

Primary Examiner—Christopher S. F. Low
Assistant Examiner—Holly Schnizer

(57) ABSTRACT

The present invention relates to the polycystic kidney disease 1 (PKD1) gene and its nucleic acid sequence, mutations thereof in patients having PKD1-associated disorders, the protein encoded by the PKD1 gene or its mutants, and their uses in disease diagnosis and therapy.

16 Claims, 88 Drawing Sheets

OTHER PUBLICATIONS

Chao, "Neurotrophin Receptors: A Window into Neural Differentiation", Neuron, vol. 9, 583–593, Oct. (1992).

Chomczynski, et al., "Single–Step Method of RNA Isolation by Acid Guanidinium Thiocyanate–Phenol–Chloroform Extraction", Analytical Biochemistry, 162, 156–159 (1987).

Curtis, et al., "Sequence and expression of a membrane–associated C–type lectin that exhibits CD4–independent binding of human immunodeficiency virus envelope glycoprotein gp120", Proc. Natl. Acad. Sci. USA, vol. 89, pp. 8356–8360 (1992).

Dalgaard, "Bilateral Polycystic Disease of the Kidneys", Copenhagen (1957).

Daoust, et al., "Evidence for a Third Genetic Locus for Autosomal Dominant Polycystic Kidney Disease", Genomics 25, 733–736 (1995).

Davies, et al., Polycystic Kidney Disease Re–evaluated: A Population–based Study, Quarterly Journal of Medicine, New Series 79, No. 290, pp. 477–485 (1991).

Deisseroth, et al., "Activation of phenotypic expression of human globin genes from nonerythroid cells by chromosome–dependent transfer to tetraploid mouse erythroleukemia cells", Proc. Natl. Acad. Sci. USA vol. 76, No. 5, pp. 2185–2189 (1979).

Dodé, et al., "Locus assignment of human α globin mutations by selective amplification and direct sequencing", British Journal of Haematology, vol. 76, 275–281 (1990).

Drickamer, et al., "Membrane receptors that mediate glycoprotein endocytosis: Structure and biosynthesis", Kidney International, vol. 32, Suppl. 23, pp. S–167–S–180, (1987).

Drickamer, "Two Distinct Classes of Carbohydrate–recognition Domains in Animal Lectins", The Journal of Biological Chemistry, vol. 263, No. 20, pp. 9557–9560 (1988).

Ekblom, "Developmentally regulated conversion of mesenchyme to epithelium", The FASEB Journal, vol. 3, (1989).

European Polycystic Kidney Disease Consortium, "The Polycystic Kidney Disease 1 Gene Encodes a 14 kb Transcript and Lies within a Duplicated Region on Chromosome 16", Cell. vol. 77, 881–894, (1994).

The European Chromosome 16 Tuberous Sclerosis Consortium, "Identification and Characterization of the Tuberous Sclerosis Gene on Chromosome 16", Cell. vol. 75, 1305–1315 (1993).

Fick, et al., "Characteristics of Very Early Onset Autosomal Dominant Polycystic Kidney Disease", Journal of the American Society of Nephrology, vol. 3 (1989).

Fick, et al., "Is there evidence for anticipation in autosomal–dominant polycystic kidney disease?", Kidney International, vol. 45, pp. 1153–1162 (1994).

Gabow, "Polycystic kidney disease: Clues to pathogenesis", Kidney International, vol. 40, pp. 989–996 (1991).

Gabow, "Autosomal Dominant Polycystic Kidney Disease", The New England Journal of Medicine, vol. 5 (1993).

Gabow, "Autosomal Dominant Polycystic Kidney Disease—More Than a Renal Disease", American Journal Kidney Diseases, vol. XVI, No. 5 (1990).

Germino, et al., "Identification of a Locus Which Shows No Genetic Recombination with the Autosomal Dominant Polycystic Kidney Disease Gene on Chromosome 16", Am. J. Hum. Genet. 46:925–933 (1990).

Germino, et al., "The Gene for Autosomal Dominant Polycystic Kidney Disease Lies in a 750–kb CpG–Rich Region", Genomics 13, 144–151 (1992).

Gower, et al., "Alternative Splicing Generates a Secreted Form of N–CAM in Muscle and Brain", Cell. vol. 55, 955–964 (1988).

Green, et al., "Loss of heterozygosity on chromosome 16p13.3 in hamartomas from tuberous sclerosis patients", Nature Genetics, vol. 6 (1994).

Harpaz, et al., "Many of the Immunoglobulin Superfamily Domains in Cell Adhesion Moleculces and Surface Receptors Belong to a New Structural Set Which is Close to That Containing Variable Domains", J. Mol. Biol., vol. 238, 529–539 (1994).

Harris, et al., "A Long–Range Restriction Map between the α–Globin Complex and a Marker Closely Linked to the Polycystic Kidney Disease 1 (PKD1) Locus", Genomics, vol. 7, 195–206 (1990).

Harris, et al., "Rapid genetic analysis of families with polycystic kidney disease 1 by means of a microsatellite marker", vol. 338 (1991).

Hartmann, et al., "Predicting the orientation of eukaryotic membrane–spanning proteins", Proc. Natl. Acad. Sci. USA, vol. 86, pp. 5786–5790 (1989).

Henikoff, "Unidirectional digestion with exonuclease III creates targeted breakpoints for DNA sequencing", Gene 28 351–359 (1984).

Heijne, "A new method for predicting signal sequence cleavage sites", Nucleic Acids Research, vol. 14 (1986).

Himmelbauer, et al., "Saturating the Region of the Polycystic Kidney Disease Gene with NotI Linking Clones", Am. J. Hum. Genet. 48:325–334 (1991).

Hossack, et al., "Echocardiographic Findings In Autosomal Dominant Polycystic Kidney Disease", The New England Journal of Medicine, vol. 319, No. 14 (1988).

Huston, III, et al., "Value of Magnetic Resonance Angiography for the Detection of Intracranial Aneurysms in Autosomal Dominant Polycystic Kidney Disease", Journal of the American Society of Nephrology, vol. 3, No. 12 (1993).

Hyland, et al., "Probe, VK5B, is located in the same interval as the autosomal dominant adult polycystic kidney disease locus, PKD1", Hum. Genet 84:286–288 (1990).

Jia, et al., "The Proto–oncogene of v–eyk (v–ryk) Is a Novel Receptor–type Protein Tyrosine Kinase with Extracellular Ig/FN–III Domains", The Journal of Biological Chemistry, vol. 269, No. 3, pp. 1839–1844 (1994).

Jones, et al., "Crystal structure of an integrin–binding fragment of vascular cell adhesion molecule–1 at 1.8 A resolution", Nature, vol. 373 (1995).

Keen, et al., "Rapid detection of single base mismatches as heteroduplexes on Hydrolink gels", TIG, vol. 7, No. 1, (1991).

Kimberling, et al., Autosomal Dominant Polycystic Kidney Disease: Localization of the Second Gene to Chromosome 4q13–q23, Genomics, vol. 18, 467–472 (1993).

Kimberling, et al., "Linkage Heterogeneity of Autosomal Dominant Polycystic Kidney Disease", The New England Journal of Medicine, vol. 319, No. 14 (1988).

Kobe, et al., "The leucine–rich repeat: a versatile binding motif," TIBS, vol. 19, (1994).

Kornblihtt, et al., "Primary structure of human fibronectin: differential splicing may generate at least 10 polypeptides from a single gene", The EMBO Journal, vol. 4, No. 7, pp. 1755–1759 (1985).

Kozak, An analysis of 5'–noncoding sequences from 699 vertebrate messenger RNAs, Nuclear Acids Research, vol. 15, No. 20 (1987).

Kuma, et al., Motifs of Cadherin– and Fibronectin Type III–related Sequences and Evolution of the Receptor–Type–Protein Tyrosine Kinases: Sequence Similarity between Proto–Oncogene ret and Cadherin Family, Mol. Biol. Evol., 10(3):539–551 (1993).

Kwon, et al., "A melanocyte–specific gene, Pmel 17, maps near the silver coat color locus on mouse chromosome 10 and is in a syntenic region on human chromosome 12", Proc. Natl. Acad. Sci. USA vol. 88, pp. 9288–9232 (1991).

Lamballe, et al., trkC, a New Member of the trk Family of Tyrosine Protein Kinases, Is a Receptor for Neurotropin–3, Cell, vol. 66, 967–979 (1991).

Legius, et al., "Somatic deletion of the neurofibromatosis type 1 gene in a neurofibrosarcoma supports a tumour suppressor gene hypothesis", Nature Genetics, vol. 3 (1993).

Love, et al., "An autosomal transcript in skeletal muscle with homology to dystrophin", Nature, vol. 339, No. 6219, pp. 55–58 (1989).

Mandel, "Questions of expansion", Nature Genetics, vol. 4 (1989).

Matsushita, et al., "Purification and Characterization of a Clostridium perfringens 120–Kilodalton Collagenase and Nucleotide Sequence of the Corresponding Gene", Journal of Bacteriology, pp. 149–156 (Jan. 1994).

McFarland, et al., "Lutropin–Choriogonadotropin Receptor: An Unusual Member of the G Protein–Coupled Receptor Family", Science, vol. 245.

Melton, et al., "Efficient in vitro synthesis of biologically active RNA and RNA hybridization probes from plasmids containing a bacteriophage SP6 promoter", vol. 12, No. 18 (1984).

Milutinovic, et al., "Liver Cysts in Patients with Autosomal Dominant Polycystic Kidney Disease", The American Journal of Medicine, vol. 68 (1980).

Milutinovic, et al., "Autosomal Dominant Polycystic Kidney Disease—Early Diagnosis and Consideration of Pathogenesis", vol. 73, No. 6 (1980).

Nakashima, et al., "The amino acid composition is different between the cytoplasmic and extracellular sides in membrane proteins", vol. 303, No. 2, 3, 141–146 (1992).

Oldberg, et al., "A collagen–binding 59–kd protien (fibromodulin) is structurally related to the small interstitial proteoglycans PG–S1 and PG–S2 (decorin)", The EMBO Journal, vol. 8, No. 9, pp. 2601–2604 (1989).

Oldberg, et al., "The partial amino acid sequence of bovine cartilage proteoglycan, deduced from a cDNA clone, contains numerous Ser–Gly sequences arranged in homologous repeats", Biochem. J., vol. 243, 255–259 (1987).

Parfrey, et al., "The Diagnosis And Prognosis of Autosomal Dominant Polycystic Kidney Disease", The New England Journal of Medicine, vol. 323, No. 16 (1990).

Pearson, et al., "Improved tools for biological sequence comparison", Proc. Natl. Acad. Sci. USA, vol. 85, pp. 2444–2448 (1988).

Peral, et al., "Evidence of Linkage Disequilibrium in the Spanish Polycystic Kidney Disease I Population", Am. J. Hum. Genet. 54:899–908 (1944).

Peral, et al., "Splicing mutations of the polycystic kidney disease 1 (PKD1) gene induced by intronic deletion", Human Molecular Genetics, vol. 4, No. 4 569–574 (1995).

Peters, et al., "Chromosome 4 localization of a second gene for autosomal dominant polycystic kidney disease", Nature Genetics, vol. 5, (1993).

Pound, et al., "Evidence of linkage disequilibrium between D16S94 and the adult onset polycystic kidney disease (PKD1) gene", Med. Genet, 29:247–248 (1992).

Ravine, et al., "Treatable complications in undiagnosed cases of autosomal dominant polycystic kidney disease", The Lancet, vol. 337, No. 8734 (1991).

Ravine, et al., "Phenotype and genotype heterogeneity in autosomal dominant polycystic kidney disease", The Lancet, vol. 340 (1992).

Reeders, "Multilocus polycystic disease", Nature Genetics, vol. 1 (1992).

Royle et al., "A hypervariable locus D16S309 located at the distal end of 16p", Nucleic Acids Research, vol. 20, No. 5.

Reeders, et al., "A highly polymorphic DNA marker linked to adult polycystic kidney disease on chromosome 16", Nature, vol. 317 (1985).

Reeders, et al., "Regional Localization of the Autosomal Dominant Polycystic Kidney Disease Locus", Genomics 3, 150–155 (1988).

Romeo, et al., "A Second Genetic Locus For Autosomal Dominant Polycystic Kidney Disease", The Lancet (Jul. 2, 1988).

Roth, "Developing Relationships: Arterial Platelet Adhesion, Glycoprotein Ib, and Leucine–Rich Glycoproteins", Blood, vol. 77, No. 1 (1991).

Rothberg, et al., "slit: an extracellular protien necessary for development of midline glia and commissural axon pathways contains both EGF and LRR domains", Genes & Development, 4:2169–2187 (1990).

Ryynanen, et al., "Localisation of a mutation producing autosomal dominant polycystic kidney disease without renal failure", Journal of Medical Genetics 24, 462–465 (1987).

Schafer, et al., "Characterization of the Han: SPRD rat model for hereditary polycystic kidney disease", Kidney International, vol. 46, pp. 134–152 (1994).

Scheff, et al., "Diverticular Disease in Patients with Chronic Renal Failure Due to Polycystic Kidney Disease", Annals of Internal Medicine, 92(Part 1):202–204 (1980).

Sipos, et al., "Predicting the topology of eukaryotic membrane proteins", Eur. J. Biochem. 213 1333–1340 (1993).

Snarey, et al., "Linkage Disequilibrium in the Regional of the Autosomal Dominant Polycystic Kidney Disease Gene (PKDI)", Am. J. Hum. Genet. 55:365–371 (1994).

Somlo, et al., "Fine Genetic Localization of the Gene for Autosomal Dominant Polycystic Kidney Disease (PKD1) with Respect to Physically Mapped Markers", Genomics 13, 152–158 (1992).

Somlo, et al., "A Kindred Exhibiting Cosegregation of an Overlap Connective Tissue Disorder and the Chromosome 16 Linked Form of Autosomal Dominant Polycystic Kidney Disease", Journal of the American Society of Nephrology, vol. 4 (1993).

Streuli, et al., "A New Member Of The Immunoglobulin Superfamily That Has A Cytoplasmic Region Homologous To The Leukocyte Common Antigen", J. Exp. Med. vol. 168 (1988).

Takagi, et al., Primary Structure of the Target of Calcium Vector Protein of Amphioxus, Journal of Biological Chemistry, vol. 265, pp. 19721–19727 (1990).

Taylor, et al., Primary Structure of the Mannose Receptor Contains Multiple Motif Resembling Carbohydrate–recognition Domains, The Journal of Biological Chemistry, vol. 265, pp. 12156–12162 (1990).

Thompson, et al., "Isolation and Characterization of (AC)$_n$ Microsatellite Genetic Markers from Human Chromosome 16", Genomics 13, 402–406 (1992).

Volkmer, et al., "Structure of the Axonal Surface Recognition Molecule Neurofascin and Its Relationship to a Neural Subgroup of the Immunoglobulin Superfamily", The Journal of Cell Biology, vol. 118, 149–161 (1992).

Weis, et al., "Structure of a C–type mannose–binding protein complexed with an oligosaccharide", Nature, vol. 360 (1992).

Wieringa, et al., "A Minimal Intron Length but No Specific Internal Sequence is Required for Splicing the Large Rabbit B–Globin Intron", Cell, vol. 37, 915–925 (1984).

Williams, et al., "The Immunoglobulin Superfamily—Domains for Cell Surface Recognition", Ann. Rev. Immunol. 6:381–405 (1988).

Wilson, et al., "Tubulocystic epithelium", International Society of Nephrology, vol. 39, pp. 450–563 (1991).

Wright, et al., "Sample Preparation From Paraffin–Embedded Tissues", PCR Protocols: A Guide to Methods and Applications (1990).

Zerres, et al., "Childhood onset autosomal dominant polycystic kidney disease in sibs: clinical picture and recurrence risk", J Med Genet, 30:583–588 (1993).

Bork, et al., "Fibronectin type III modules in the receptor phosphatase CD45 and tapeworm antigens", Protein Science, 2: 1185–1187, (1993).

Frohman et al., "Rapid production of full–length cDNAs from rare transcripts: Amplification using a single gene–specific oligonucleotide primer", Proc. Natl. Acad. Sci. USA, vol. 85: 8998–9002, (Dec. 1988).

Adams et al., File Medicine Abstract No. 93364420, *Nature Genetics* 4:256–267 (1993).

Adams et al., File Medicine Abstract No. 94004965, *Nature Genetics* 4:373–380 (1993).

Burn et al., *Human Molecular Genetics* 4(4):575–582 (1995).

Germino et al., *Kidney International,* vol. 43, Supp. 39, S–20–S–25 (1993).

*An Introduction to Geneic Analysis;* W.H. Freeman and Company, Fifth Ed., pp 427, 453–461 (1993).

Mulley et al., *Current Opinion in Genetics and Development* 3:425–431 (1993).

* cited by examiner

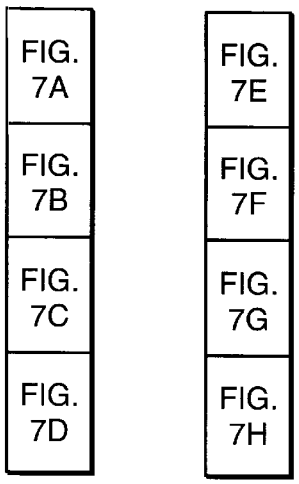

FIG. 7

```
  1 CTCAACGAGGAGCCCCTGACGCTGGCGGGCGAGGAGATCGTGGCCCAGGGCAAGCGCTCG  60
  1 L  N  E  E  P  L  T  L  A  G  E  E  I  V  A  Q  G  K  R  S   20

61 GACCCGCGGAGCCTGCTGTGCTATGGCGGCGCCCCAGGGCCTGGCTGCCACTTCTCCATC 120
 21 D  P  R  S  L  L  C  Y  G  G  A  P  G  P  G  C  H  F  S  I   40

121 CCCGAGGCTTTCAGCGGGGCCCTGGCCAACCTCAGTGACGTGGTGCAGCTCATCTTTCTG 180
 41 P  E  A  F  S  G  A  L  A  N  L  S  D  V  V  Q  L  I  F  L   60

181 GTGGACTCCAATCCCTTTCCCTTTGGCTATATCAGCAACTACACCGTCTCCACCAAGGTG 240
 61 V  D  S  N  P  F  P  F  G  Y  I  S  N  Y  T  V  S  T  K  V   80

241 GCCTCGATGGCATTCCAGACACAGGCCGCGCCCAGATCCCCATCGAGCGGCTGGCCTCA 300
 81 A  S  M  A  F  Q  T  Q  A  G  A  Q  I  P  I  E  R  L  A  S  100

301 GAGCGCGCCATCACCGTGAAGGTGCCCAACAACTCGGACTGGGCTGCCCGGGGCCACCGC 360
101 E  R  A  I  T  V  K  V  P  N  N  S  D  W  A  A  R  G  H  R  120

361 AGCTCCGCCAACTCCGCCAACTCCGTTGTGGTCCAGCCCCAGGCCTCCGTCGGTGCTGTG 420
121 S  S  A  N  S  A  N  S  V  V  V  Q  P  Q  A  S  V  G  A  V  140

421 GTCACCCTGGACAGCAGCAACCCTGCGGCCGGGCTGCATCTGCAGCTCAACTATACGCTG 480
141 V  T  L  D  S  S  N  P  A  A  G  L  H  L  Q  L  N  Y  T  L  160

481 CTGGACGGCCACTACCTGTCTGAGGAACCTGAGCCCTACCTGGCAGTCTACCTACACTCG 540
161 L  D  G  H  Y  L  S  E  E  P  E  P  Y  L  A  V  Y  L  H  S  180

541 GAGCCCCGGCCCAATGAGCACAACTGCTCGGCTAGCAGGAGGATCCGCCCAGAGTCACTC 600
181 E  P  R  P  N  E  H  N  C  S  A  S  R  R  I  R  P  E  S  L  200
```

FIG. 7A

```
601  CAGGGTGCTGACCACCGGCCCTACACCTTCTTCATTTCCCCGGGGAGCAGAGACCCAGCG  660
201   Q  G  A  D  H  R  P  Y  T  F  F  I  S  P  G  S  R  D  P  A   220

661  GGGAGTTACCATCTGAACCTCTCCAGCCACTTCCGCTGGTCGGCGCTGCAGGTGTCCGTG  720
221   G  S  Y  H  L  N  L  S  S  H  F  R  W  S  A  L  Q  V  S  W   240

721  GGCCTGTACACGTCCCTGTGCCAGTACTTCAGCGAGGAGGACATGGTGTGGCGGACAGAG  780
241   G  L  Y  T  S  L  C  Q  Y  F  S  E  E  D  M  V  W  R  T  E   260

781  GGGCTGCTGCCCCTGGAGGAGACCTCGCCCCGCCAGGCCGTCTGCCTCACCCGCCACCTC  840
261   G  L  L  P  L  E  E  T  S  P  R  Q  A  V  C  L  T  R  H  L   280

841  ACCGCCTTCGGCGCCAGCCTCTTCGTGCCCCCAAGCCATGTCCGCTTTGTGTTTCCTGAG  900
281   T  A  F  G  A  S  L  F  V  P  P  S  H  V  R  F  V  F  P  E   300

901  CCGACAGCGGATGTAAACTACATCGTCATGCTGACATGTGCTGTGTGCCTGGTGACCTAC  960
301   P  T  A  D  V  N  Y  I  V  M  L  T  C  A  V  C  L  V  T  Y   320

961  ATGGTCATGGCCGCCATCCTGCACAAGCTGGACCAGTTGGATGCCAGCCGGGGCCGCGCC  1020
321   M  V  M  A  A  I  L  H  K  L  D  Q  L  D  A  S  R  G  R  A   340

1021 ATCCCTTTCTGTGGGCAGCGGGGCCGCTTCAAGTACGAGATCCTCGTCAAGACAGGCTGG  1080
341   I  P  F  C  G  Q  R  G  R  F  K  Y  E  I  L  V  K  T  G  W   360

1081 GGCCGGGGCTCAGGTACCACGGCCCACGTGGGCATCATGCTGTATGGGGTGGACAGCCGG  1140
361   G  R  G  S  G  T  T  A  H  V  G  I  M  L  Y  G  V  D  S  R   380

1141 AGCGGCCACCGGCACCTGGACGGCGACAGAGCCTTCCACCGCAACAGCCTGGACATCTTC  1200
381   S  G  H  R  H  L  D  G  D  R  A  F  H  R  N  S  L  D  I  F   400

1201 CGGATCGCCACCCCGCACAGCCTGGGTAGCGTGTGGAAGATCCGAGTGTGGCACGACAAC  1260
401   R  I  A  T  P  H  S  L  G  S  V  W  K  I  R  V  W  H  D  N   420
```

FIG. 7B

```
1261  AAAGGGCTCAGCCCTGCCTGGTTCCTGCAGCACGTCATCGTCAGGGACCTGCAGACGGCA  1320
421    K  G  L  S  P  A  W  F  L  Q  H  V  I  V  R  D  L  Q  T  A   440

1321  CGCAGCGCCTTCTTCCTGGTCAATGACTGGCTTTCGGTGGAGACGGAGGCCAACGGGGGC  1380
441    R  S  A  F  F  L  V  N  D  W  L  S  V  E  T  E  A  N  G  G   460

1381  CTGGTGGAGAAGGAGGTGCTGGCCGCGAGCGACGCAGCCCTTTTGCGCTTCCGGCGCCTG  140
461    L  V  E  K  E  V  L  A  A  S  D  A  A  L  L  R  F  R  R  L   480

1441  CTGGTGGCTGAGCTGCAGCGTGGCTTCTTTGACAAGCACATCTGGCTCTCCATATGGGAC  1500
481    L  V  A  E  L  Q  R  G  F  F  D  K  H  I  W  L  S  I  W  D   500

1501  CGGCCGCCTCGTAGCCGTTTCACTCGCATCCAGAGGGCCACCTGCTGCGTTCTCCTCATC  1560
501    R  P  P  R  S  R  F  T  R  I  Q  R  A  T  C  C  V  L  L  I   520

1561  TGCCTCTTCCTGGGCGCCAACGCCGTGTGGTACGGGGCTGTTGGCGACTCTGCCTACAGC  1620
521    C  L  F  L  G  A  N  A  V  W  Y  G  A  V  G  D  S  A  Y  S   540

1621  ACGGGGCATGTGTCCAGGCTGAGCCCGCTGAGCGTCGACACAGTCGCTGTTGGCCTCGTG  1680
541    T  G  H  V  S  R  L  S  P  L  S  V  D  T  V  A  V  G  L  V   560

1681  TCCAGCGTGGTTGTCTATCCCGTCTACCTGGCCATCCTTTTTCTCTTCCGGATGTCCCGG  1740
561    S  S  V  V  V  Y  P  V  Y  L  A  I  L  F  L  F  R  M  S  R   580

1741  AGCAAGGTGGCTGGGAGCCCGAGCCCCCACACTGCCGGGCAGCAGGTGCTGGACATCGAC  1800
581    S  K  V  A  G  S  P  S  P  T  P  A  G  Q  Q  V  L  D  I  D   600

1801  AGCTGCCTGGACTCGTCCGTGCTGGACAGCTCCTTCCTCACGTTCTCAGGCCTCCACGCT  1860
601    S  C  L  D  S  S  V  L  D  S  S  F  L  T  F  S  G  L  H  A   620

1861  GAGGCCTTTGTTGGACAGATGAAGAGTGACTTGTTTCTGGATGATTCTAAGAGTCTGGTG  1920
621    E  A  F  V  G  Q  M  K  S  D  L  F  L  D  D  S  K  S  L  V   640
```

FIG. 7C

| | | |
|---|---|---|
| 1921 | TGCTGGCCCTCCGGCGAGGGAACGCTCAGTTGGCCGCACCTGCTCAGTGACCCGTCCATT | 1980 |
| 641 | C W P S G E G T L S W P D L L S D P S I | 660 |
| 1981 | GTGGGTAGCAATCTGCGGCAGCTGGCACGGGGCCAGGCGGGCCATGGGCTGGGCCCAGAG | 2040 |
| 661 | V G S N L R Q L A R G Q A G H G L G P E | 680 |
| 2041 | GAGGACGGCTTCTCCCTGGCCAGCCCCTCCTCGCCTGCCAAATCCTTCTCAGCATCAGAT | 2100 |
| 681 | E D G F S L A S P Y S P A K S F S A S D | 700 |
| 2101 | GAAGACCTGATCCAGGAGGTCCTTGCCGAGGGGGTCAGCAGCCCAGCCCCTACCCAAGAC | 2160 |
| 701 | E D L I Q Q V L A E G V S S P A P T Q D | 720 |
| 2161 | ACCCACATGGAAACGGACCTGCTCAGCAGCCTGTCCAGCACTCCTGGGGAGAAGACAGAG | 2220 |
| 721 | T H M E T D L L S S L S S T P G E K T E | 740 |
| 2221 | ACGCTGGCGCTGCAGAGGCTGGGGGAGCTGGGGCCACCCAGCCCAGGCCTGAACTGGGAA | 2280 |
| 741 | T L A L Q R L G E L G P P S P G L N W E | 760 |
| 2281 | CAGCCCCAGGCAGCGAGGCTGTCCAGGACAGGACTGGTGGAGGGTCTGCGGAAGCGCCTG | 2340 |
| 761 | Q P Q A A R L S R T G L V E G L R K R L | 780 |
| 2341 | CTGCCGGCCTGGTGTGCCTCCCTGGCCCACGGGCTCAGCCTGCTCCTGGTGGCTGTGGCT | 2400 |
| 781 | L P A W C A S L A H G L S L L L V A V A | 800 |
| 2401 | GTGGCTGTCTCAGGGTGGGTGGGTGCGAGCTTCCCCCCGGGCCTGAGTGTTGCGTGGCTC | 2460 |
| 801 | V A V S G W V G A S F P P G L S V A W L | 820 |
| 2461 | CTGTCCAGCAGCGCCAGCTTCCTGGCCTCATTCCTCGGCTGGGAGCCACTGAAGGTCTTG | 2520 |
| 821 | L S S S A S F L A S F L G W E P L K V L | 840 |

FIG. 7D

| | | |
|---|---|---|
| 2521 | CTGGAAGCCCTGTACTTCTCACTGGTGGCCAAGCGGCTGCACCCGGATGAAGATGACACC | 2580 |
| 841 | L E A L Y F S L V A K R L H P D E D D T | 860 |
| 2581 | CTGGTAGAGAGCCCGGCTGTGACGCCTGTGAGCGCACGTGTGCCCCGCGTACGGCCACCC | 2640 |
| 861 | L V E S P A V T P V S A R V P R V R P P | 880 |
| 2641 | CACGGCTTTGCACTCTTCCTGGCCAAGGAAGAAGCCCGCAAGGTCAAGAGGCTACATGGC | 2700 |
| 881 | H G F A L F L A K E E A R K V K R L H G | 900 |
| 2701 | ATGCTGCGGAGCCTCCTGGTGTACATGCTTTTTCTGCTGGTGACCCTGCTGGCCAGCTAT | 2760 |
| 901 | M L R S L L V Y M L F L L V T L L A S Y | 920 |
| 2761 | GGGGATGCCTCATGCCATGGGCACGCCTACCGTCTGCAAAGCGCCATCAAGCAGGAGCTG | 2820 |
| 921 | G D A S C H G H A Y R L Q S A I K Q E L | 940 |
| 2821 | CACAGCCGGGCCTTCCTGGCCATCACGCGGGTCTGAGGAGCTCTGGCCATGGATGGCCCAC | 2880 |
| 941 | H S R A F L A I T R S E E L W P W M A H | 960 |
| 2881 | GTGCTGCTGCCCTACGTCCACGGGAACCAGTCCAGCCCAGAGCTGGGGCCCCACGGCTG | 2940 |
| 961 | V L L P Y V H G N Q S S P E L G P P R L | 980 |
| 2941 | CGGCAGGTGCGGCTGCAGGAAGCACTCTACCCAGACCCTCCCGGCCCC'AGGGTCCACACG | 3000 |
| 981 | R Q V R L Q E A L Y P D P P G P R V H T | 1000 |
| 3001 | TGCTCGGCCGCAGGAGGCTTCAGCACCAGCGATTACGACGTTGGCTGGGAGAGTCCTCAC | 3060 |
| 1001 | C S A A G G F S T S D Y D V G W E S P H | 1020 |
| 3061 | AATGGCTCGGGGACGTGGGCCTATTCAGCGCCGGATCTGCTGGGGGCATGGTCCTGGGGC | 3120 |
| 1021 | N G S G T W A Y S A P D L L G A W S W G | 1040 |

FIG. 7E

```
3121  TCCTGTGCCGTGTATGACAGCGGGGGCTACGTGCAGGAGCTGGGCCTGAGCCTGGAGGAG  3180
1041   S  C  A  V  Y  D  S  G  G  Y  V  Q  E  L  G  L  S  L  E  E    1060

3181  AGCCGCGACCGGCTGCGCTTCCTGCAGCTGCACAACTGGCTGGACAACAGGAGCCGCGCT  3240
1061   S  R  D  R  L  R  F  L  Q  L  H  N  W  L  D  N  R  S  R  A    1080

3241  GTGTTCCTGGAGCTCACGCGCTACAGCCCGGCCGTGGGGCTGCACGCCGCCGTCACGCTG  3300
1081   V  F  L  E  L  T  R  Y  S  P  A  V  G  L  H  A  A  V  T  L    1100

3301  CGCCTCGAGTTCCCGGCGGCCGGCCGCGCCCTGGCCGCCCTCAGCGTCCGCCCCTTTGCG  3360
1101   R  L  E  F  P  A  A  G  R  A  L  A  A  L  S  V  R  P  F  A    1120

3361  CTGCGCCGCCTCAGCGCGGGCCTCTCGCTGCCTCTGCTCACCTCGGTGTGCCTGCTGCTG  3420
1121   L  R  R  L  S  A  G  L  S  L  P  L  L  T  S  V  C  L  L  L    1140

3421  TTCGCCGTGCACTTCGCCGTGGCCGAGGCCCGTACTTGGCACAGGGAAGGGCGCTGGCGC  3480
1141   F  A  V  H  F  A  V  A  E  A  R  T  W  H  R  E  G  R  W  R    1160

3481  GTGCTGCGGCTCGGAGCCTGGGCGCGGTGGCTGCTGGTGGCGCTGACGGCGGCCACGGCA  3540
1161   V  L  R  L  G  A  W  A  R  W  L  L  V  A  L  T  A  A  T  A    1180

3541  CTGGTACGCCTCGCCCAGCTGGGTGCCGCTGACCGCCAGTGGACCCGTTTCGTGCGCGGC  3600
1181   L  V  R  L  A  Q  L  G  A  A  D  R  Q  W  T  R  F  V  R  G    1200

3601  CGCCCGCGCCGCTTCACTAGCTTCGACCAGGTGGCGCACGTGAGCTCCGCAGCCCGTGGC  3660
1201   R  P  R  R  F  T  S  F  D  Q  V  A  H  V  S  S  A  A  R  G    1220

3661  CTGGCGGCCTCGCTGCTCTTCCTGCTTTTGGTCAAGGCTGCCCAGCACGTACGCTTCGTG  3720
1221   L  A  A  S  L  L  F  L  L  L  V  K  A  A  Q  H  V  R  F  V    1240

3721  CGCCAGTGGTCCGTCTTTGGCAAGACATTATGCCGAGCTCTGCCAGAGCTCCTGGGGGTC  3780
1241   R  Q  W  S  V  F  G  K  T  L  C  R  A  L  P  E  L  L  G  V    1260
```

FIG. 7F

| | | |
|---|---|---|
| 3781 | ACCTTGGGCCTGGTGGTGCTCGGGGTAGCCTACGCCCAGCTGGCCATCCTGCTCGTGTCT | 3840 |
| 1261 | T L G L V V L G V A Y A Q L A I L L V S | 1280 |
| 3841 | TCCTGTGTGGACTCCCTCTGGAGCGTGGCCCAGGCCCTGTTGGTGCTGTGCCCTGGGACT | 3900 |
| 1281 | S C V D S L W S V A Q A L L V L C P G T | 1300 |
| 3901 | GGGCTCTCTACCCTGTGTCCTGCCGAGTCCTGGCACCTGTCACCCCTGCTGTGTGTGGGG | 3960 |
| 1301 | G L S T L C P A E S W H L S P L L C V G | 1320 |
| 3961 | CTCTGGGCACTGCGGCTGTGGGGCGCCCTACGGCTGGGGGCTGTTATTCTCCGCTGGCGC | 4020 |
| 1321 | L W A L R L W G A L R L G A V I L R W R | 1340 |
| 4021 | TACCACGCCTTGCGTGGAGAGCTGTACCGGCCGGCCTGGGAGCCCCAGGACTACGAGATG | 4080 |
| 1341 | Y H A L R G E L Y R P A W E P Q D Y E M | 1360 |
| 4081 | GTGGAGTTGTTCCTGCGCAGGCTGCGCCTCTGGATGGGCCTCAGCAAGGTCAAGGAGTTC | 4140 |
| 1361 | V E L F L R R L R L W M G L S K V K E F | 1380 |
| 4141 | CGCCACAAAGTCCGCTTTGAAGGGATGGAGCCGCTGCCCTCTCGCTCCTCCAGGGGCTCC | 4200 |
| 1381 | R H K V R F E G M E P L P S R S S R G S | 1400 |
| 4201 | AAGGTATCCCCGGATGTGCCCCCACCCAGCGCTGGCTCCGATGCCTCGCACCCCTCCACC | 4260 |
| 1401 | K V S P D V P P P S A G S D A S H P S T | 1420 |
| 4261 | TCCTCCAGCCAGCTGGATGGGCTGAGCGTGAGCCTGGGCCGGCTGGGGACAAGGTGTGAG | 4320 |
| 1421 | S S S Q L D G L S V S L G R L G T R C E | 1440 |
| 4321 | CCTGAGCCCTCCCGCCTCCAAGCCGTGTTCGAGGCCCTGCTCACCCAGTTTGACCGACTC | 4380 |
| 1441 | P E P S R L Q A V F E A L L T Q F D R L | 1460 |

FIG. 7G

| | | |
|---|---|---|
| 4381 | AACCAGGCCACAGAGGACGTCTACCAGCTGGAGCAGCAGCTGCACAGCCTGCAAGGCCGC | 4440 |
| 1461 | N Q A T E D V Y Q L E Q Q L H S L Q G R | 1480 |
| 4441 | AGGAGCAGCCGGGCGCCCGCCGGATCTTCCCGTGGCCCATCCCCGGGCCTGCGGCCAGCA | 4500 |
| 1481 | R S S R A P A G S S R G P S P G L R P A | 1500 |
| 4501 | CTGCCCAGCCGCCTTGCCCGGGCCAGTGGGGTGTGGACCTGGCCACTGGCCCCAGCAGG | 4560 |
| 1501 | L P S R L A R A S R G V D L A T G P S R | 1520 |
| 4561 | ACACCTTCGGGCCAAGAACAAGGTCCACCCCAGCAGCACTTAGTCCTCCTTCCTGGCGGG | 4620 |
| 1521 | T P S G Q E Q G P P Q Q H L V L L P G G | 1540 |
| 4621 | GGTGGGCCGTGGAGTCGGAGTGGACACCGCTCAGTATTACTTTCTGCCGCTGTCAAGGCC | 4689 0 |
| 1541 | G G P W S R S G H R S V L L S A A V K A | 1560 |
| 4681 | GAGGGCCAGGCAGAATGGCTGCACGTAGGTTCCCCAGAGAGCAGGCAGGGGCATCTGTCT | 4740 |
| 1561 | E G Q A E W L H V G S P E S R Q G H L S | 1580 |
| 4741 | GTCTGTGGGCTTCAGCACTTTAAAGAGGCTGTGTGGCCAACCAGGACCCAGGGTCCCCTC | 4800 |
| 1581 | V C G L Q H F K E A V W P T R T Q G P L | 1600 |
| 4801 | CCCAGCTCCCTTGGGAAGGACACAGCAGTATTGGACGGTTTCTAGCCTCTGAGATGCTAA | 4860 |
| 1601 | P S S L G K D T A V L D G F | 1620 |
| 4861 | TTTATTTCCCCGAGTCCTCAGGTACAGCGGGCTGTGCCCGGCCCCACCCCCTGGGCAGAT | 4920 |
| 4921 | GTCCCCCACTGCTAAGGCTGCTGGCTTCAGGGAGGGTTAGCCTGCACCGCCGCCACCCTG | 4980 |
| 4981 | CCCCTAAGTTATTACCTCTCCAGTTCCTACCGTACTCCCTGCACCGTCTCACTGTGTGTC | 5040 |
| 5041 | TCGTCTCAGTAATTTATATGGTGTTAAAATGTGTATATTTTTGTATGTCACTATTTTCAC | 5100 |
| 5101 | TAGGGCTGAGGGGCCTGCGCCCAGAGCTGGCCTCCCCCAACACCTGCTGCGCTTGGTAGG | 5160 |
| 5161 | TGTGGTGGCGTTATGGCAGCCCGGCTGCTGCTTGGATGCGAGCTTGGCCTTGGGCCGGTG | 5220 |
| 5221 | CTGGGGGCACAGCTGTCTGCCAGGCACTCTCATCACCCCAGAGGCCTTGTCATCCTCCCT | 5280 |
| 5281 | TGCCCCAGGCCAGGTAGCAAGAGAGCAGCGCCCAGGCCTGCTGGCATCAGGTCTGGGCAA | 5340 |
| 5341 | CTAGCAGGACTAGGCATGTCAGAGGACCCCAGGGTGGTTAGAGGAAAAGACTCCTCCTGG | 5400 |
| 5401 | GGGCTGGCTCCCAGGGTGGAGGAAGGTGACTGTGTGTGTGTGTGTGTGCGCGCGCGACGC | 5460 |
| 5461 | GCGACTGTGCTGTATGGCCCAGGCACGCTCAAGGCCCTCGGAGCTGGCTGTGCCTGCTTC | 5520 |
| 5521 | TGTGTACCACTTCTGTGGGCATGGCCGCTTCTAGAGCCTCGACACCCCCCCAACCCCCGC | 5580 |
| 5581 | ACCAAGCAGACAAAGTCAATAAAAGAGCTGTCTGACTGCAAAAAAAAAAAA 5631 | |

FIG. 7H

| | |
|---|---|
| AGCTTGGCAC CATCAAGGGC CAGTTCAACT TTGTCCACGT GATCGTCACC CCGCTGGACT | 60 |
| ACGAGTGCAA CCTGGTGTCC CTGCAGTGCA GGAAAGACAT GGAGGGCCTT GTGGACACCA | 120 |
| GCGTGGCCAA GATCGTGTCT GACCGCAACC TGCCCTTCGT GGCCCGCCAG ATGGCCCTGC | 180 |
| ACGCAAATAT GGCCTCACAG GTGCATCATA GCCGCTCCAA CCCACCGAT ATCTACCCCT | 240 |
| CCAAGTGGAT TGCCCGGCTC CGCCACATCA AGCGGCTCCG CCAGCGGATC TGCGAGGAAG | 300 |
| CCGCCTACTC CAACCCCAGC CTACCTCTGG TGCACCCTCC GTCCCATAGC AAAGCCCCTG | 360 |
| CACAGACTCC AGCCGAGCCC ACACCTGGCT ATGAGGTGGG CCAGCGGAAG CGCCTCATCT | 420 |
| CCTGGGTGGA GGACTTCACC GAGTTTGTGT GAGGCCGGGG CCCTCCCTCC TGCACTGGCC | 480 |
| TTGGACGGTA TTGCCTGTCA GTGAAATAAA TAAAGTCCTG ACCCCAGTGC ACAGACATAG | 540 |
| AGGCACAGAT TGC | 553 |

| | |
|---|---|
| CTGGTGTGTG TGAGACGTGC GGGGCTGGGA AGTGTTGGCA GAGCCGCGAG TACCGTCCTC | 60 |
| ACTCCTTTTG TTCTTTTGAC GTAAGCTGGC GAGTGGCACT GCCTGAGTTC CGCTCAGTGC | 120 |
| CCGCCCTGAT GTGCGGACCC CGCTGCATTC TTGCTGTTAG GTGGTGGCGG TGTGCGCTGT | 180 |
| CGCTGGTGGG CACCGAGAGT CTTTGGGAGC TTTGGGGAGG TTGTGCCAAG CCTGAGCCTC | 240 |
| GACGTCCCCC TTCCGGCTT TCTGTTGGCT CTTCTGAGGC CAGGGCATCT CTATGAGGGC | 300 |
| CTCCTGCTGG AGCCGTCTCT GTGGATCTCC TCTGCCATCC TGGCCCATGA GTGGGTGATG | 360 |
| CGCTGGCCAC CATCTGGTGA CAGTGGCCGG GCACCGCTGC CAAATGTGGG TCCCGCATCT | 420 |
| GCAAGCCCCT CCCTGGGTCC CCTAGGGTAT GGGGTGGTTC TGCCACTGCC CTCGCTCCCC | 480 |
| CACCTTGGGG TGCCTCTCCC CCTGCTCGTG GGGAGA | 517 |

| | |
|---|---|
| 1   AGGCAGGTCT CCCCCACGAG CAGGGAGAG GCACCCAAGG T | |

```
  C GGC GCC GCC TGC CGC GTC AAC TGC TCG GGC CGC GGG CTG CGG ACG         46
    Gly Ala Ala Cys Arg Val Asn Cys Ser Gly Arg Gly Leu Arg Thr
     1               5                   10                  15

CTC GGT CCC GCG CTG CGC ATC CCC GCG GAC GCC ACA GCG CTA GAC GTC       94
  Leu Gly Pro Ala Leu Arg Ile Pro Ala Asp Ala Thr Ala Leu Asp Val
                  20                  25                  30

TCC CAC AAC CTG CTC CGG GCG CTG GAC GTT GGG CTC CTG GCG AAC CTC      142
  Ser His Asn Leu Leu Arg Ala Leu Asp Val Gly Leu Leu Ala Asn Leu
                  35                  40                  45

TCG GCG CTG GCA GAG CTG GAT ATA AGC AAC AAC AAG ATT TCT ACG TTA      190
  Ser Ala Leu Ala Glu Leu Asp Ile Ser Asn Asn Lys Ile Ser Thr Leu
                  50                  55                  60

GAA GAA GGA ATA TTT GCT AAT TTA TTT AAT TTA AGT GAA ATA AAC CTG      238
  Glu Glu Gly Ile Phe Ala Asn Leu Phe Asn Leu Ser Glu Ile Asn Leu
           65                  70                  75

AGT GGG AAC CCG TTT GAG TGT GAC TGT GGC CTG GCG TGG CTG CCG CGA      286
  Ser Gly Asn Pro Phe Glu Cys Asp Cys Gly Leu Ala Trp Leu Pro Arg
   80                  85                  90                  95

TGG GCG GAG GAG CAG CAG GTG CGG GTG GTG CAG CCC GAG GCA GCC ACG      334
  Trp Ala Glu Glu Gln Gln Val Arg Val Val Gln Pro Glu Ala Ala Thr
                  100                 105                 110

TGT GCT GGG CCT GGC TCC CTG GCT GGC CAG CCT CTG CTT GGC ATC CCC      382
  Cys Ala Gly Pro Gly Ser Leu Ala Gly Gln Pro Leu Leu Gly Ile Pro
                  115                 120                 125
```

FIG. 10A

```
TTG CTG GAC AGT GGC TGT GGT GAG GAG TAT GTC GCC TGC CTC CCT GAC      430
Leu Leu Asp Ser Gly Cys Gly Glu Glu Tyr Val Ala Cys Leu Pro Asp
        130             135                 140

AAC AGC TCA GGC ACC GTG GCA GCA GTG TCC TTT TCA GCT GCC CAC GAA      478
Asn Ser Ser Gly Thr Val Ala Ala Val Ser Phe Ser Ala Ala His Glu
        145             150                 155

GGC CTG CTT CAG CCA GAG GCC TGC AGC GCC TTC TGC TTC TCC ACC GGC      526
Gly Leu Leu Gln Pro Glu Ala Cys Ser Ala Phe Cys Phe Ser Thr Gly
160             165                 170                 175

CAG GGC CTC GCA GCC CTC TCG GAG CAG GGC TGG TGC CTG TGT GGG GCG      574
Gln Gly Leu Ala Ala Leu Ser Glu Gln Gly Trp Cys Leu Cys Gly Ala
                180                 185                 190

GCC CAG CCC TCC AGT GCC TCC TTT GCC TGC CTG TCC CTC TGC TCC GGC      622
Ala Gln Pro Ser Ser Ala Ser Phe Ala Cys Leu Ser Leu Cys Ser Gly
                195                 200                 205

CCC CCG CCA CCT CCT GCC CCC ACC TGT AGG GGC CCC ACC CTC CTC CAG      670
Pro Pro Pro Pro Pro Ala Pro Thr Cys Arg Gly Pro Thr Leu Leu Gln
        210                 215                 220

CAC GTC TTC CCT GCC TCC CCA GGG GCC ACC CTG GTG GGG CCC CAC GGA      718
His Val Phe Pro Ala Ser Pro Gly Ala Thr Leu Val Gly Pro His Gly
        225                 230                 235
```

FIG. 10B

```
CCT CTG GCC TCT GGC CAG CTA GCA GCC TTC CAC ATC GCT GCC CCG CTC        766
Pro Leu Ala Ser Gly Gln Leu Ala Ala Phe His Ile Ala Ala Pro Leu
240             245                 250                 255

CCT GTC ACT GCC ACA CGC TGG GAC TTC GGA GAC GGC TCC GCC GAG GTG        814
Pro Val Thr Ala Thr Arg Trp Asp Phe Gly Asp Gly Ser Ala Glu Val
                260                 265                 270

GAT GCC GCT GGG CCG GCT GCC TCG CAT CGC TAT GTG CTG CCT GGG CGC        862
Asp Ala Ala Gly Pro Ala Ala Ser His Arg Tyr Val Leu Pro Gly Arg
                275                 280                 285

TAT CAC GTG ACG GCC GTG CTG GCC CTG GGG GCC GGC TCA GCC CTG CTG        910
Tyr His Val Thr Ala Val Leu Ala Leu Gly Ala Gly Ser Ala Leu Leu
                290                 295                 300

GGG ACA GAC GTG CAG GTG GAA GCG GCA CCT GCC GCC CTG GAG CTC GTG        958
Gly Thr Asp Val Gln Val Glu Ala Ala Pro Ala Ala Leu Glu Leu Val
305                 310                 315

TGC CCG TCC TCG GTG CAG AGT GAC GAG AGC CTT GAC CTC AGC ATC CAG        1006
Cys Pro Ser Ser Val Gln Ser Asp Glu Ser Leu Asp Leu Ser Ile Gln
320                 325                 330                 335

AAC CGC GGT GGT TCA GGC CTG GAG GCC GCC TAC AGC ATC GTG GCC CTG        1054
Asn Arg Gly Gly Ser Gly Leu Glu Ala Ala Tyr Ser Ile Val Ala Leu
                340                 345                 350

GGC GAG GAG CCG GCC CGA GCG GTG CAC CCG CTC TGC CCC TCG GAC ACG        1102
Gly Glu Glu Pro Ala Arg Ala Val His Pro Leu Cys Pro Ser Asp Thr
                355                 360                 365
```

FIG. 10C

```
GAG ATC TTC CCT GGC AAC GGG CAC TGC TAC CGC CTG GTG GTG GAG AAG        1150
Glu Ile Phe Pro Gly Asn Gly His Cys Tyr Arg Leu Val Val Glu Lys
        370                 375                 380

GCG GCC TGG CTG CAG GCG CAG GAG CAG TGT CAG GCC TGG GCC GGG GCC        1198
Ala Ala Trp Leu Gln Ala Gln Glu Gln Cys Gln Ala Trp Ala Gly Ala
        385                 390                 395

GCC CTG GCA ATG GTG GAC AGT CCC GCC GTG CAG CGC TTC CTG GTC TCC        1246
Ala Leu Ala Met Val Asp Ser Pro Ala Val Gln Arg Phe Leu Val Ser
400                 405                 410                 415

CGG GTC ACC AGG AGC CTA GAC GTG TGG ATC GGC TTC TCG ACT GTG CAG        1294
Arg Val Thr Arg Ser Leu Asp Val Trp Ile Gly Phe Ser Thr Val Gln
                420                 425                 430

GGG GTG GAG GTG GGC CCA GCG CCG CAG GGC GAG GCC TTC AGC CTG GAG        1342
Gly Val Glu Val Gly Pro Ala Pro Gln Gly Glu Ala Phe Ser Leu Glu
                435                 440                 445

AGC TGC CAG AAC TGG CTG CCC GGG GAG CCA CAC CCA GCC ACA GCC GAG        1390
Ser Cys Gln Asn Trp Leu Pro Gly Glu Pro His Pro Ala Thr Ala Glu
                450                 455                 460

CAC TGC GTC CGG CTC GGG CCC ACC GGG TGG TGT AAC ACC GAC CTG TGC        1438
His Cys Val Arg Leu Gly Pro Thr Gly Trp Cys Asn Thr Asp Leu Cys
        465                 470                 475
```

FIG. 10D

```
TCA GCG CCG CAC AGC TAC GTC TGC GAG CTG CAG CCC GGA GGC CCA GTG      1486
Ser Ala Pro His Ser Tyr Val Cys Glu Leu Gln Pro Gly Gly Pro Val
480             485             490             495

CAG GAT GCC GAG AAC CTC CTC GTG GGA GCG CCC AGT GGG GAC CTG CAG      1534
Gln Asp Ala Glu Asn Leu Leu Val Gly Ala Pro Ser Gly Asp Leu Gln
            500             505             510

GGA CCC CTG ACG CCT CTG GCA CAG CAG GAC GGC CTC TCA GCC CCG CAC      1582
Gly Pro Leu Thr Pro Leu Ala Gln Gln Asp Gly Leu Ser Ala Pro His
            515             520             525

GAG CCC GTG GAG GTC ATG GTA TTC CCG GGC CTG CGT CTG AGC CGT GAA      1630
Glu Pro Val Glu Val Met Val Phe Pro Gly Leu Arg Leu Ser Arg Glu
            530             535             540

GCC TTC CTC ACC ACG GCC GAA TTT GGG ACC CAG GAG CTC CGG CGG CCC      1678
Ala Phe Leu Thr Thr Ala Glu Phe Gly Thr Gln Glu Leu Arg Arg Pro
545             550             555

GCC CAG CTG CGG CTG CAG GTG TAC CGG CTC CTC AGC ACA GCA GGG ACC      1726
Ala Gln Leu Arg Leu Gln Val Tyr Arg Leu Leu Ser Thr Ala Gly Thr
560             565             570             575

CCG GAG AAC GGC AGC GAG CCT GAG AGC AGG TCC CCG GAC AAC AGG ACC      1774
Pro Glu Asn Gly Ser Glu Pro Glu Ser Arg Ser Pro Asp Asn Arg Thr
            580             585             590

CAG CTG GCC CCC GCG TGC ATG CCA GGG GGA CGC TGG TGC CCT GGA GCC      1822
Gln Leu Ala Pro Ala Cys Met Pro Gly Gly Arg Trp Cys Pro Gly Ala
            595             600             605
```

FIG. 10E

```
AAC ATC TGC TTG CCG CTG GAC GCC TCT TGC CAC CCC CAG GCC TGC GCC         1870
Asn Ile Cys Leu Pro Leu Asp Ala Ser Cys His Pro Gln Ala Cys Ala
        610             615                 620

AAT GGC TGC ACG TCA GGG CCA GGG CTA CCC GGG GCC CCC TAT GCG CTA         1918
Asn Gly Cys Thr Ser Gly Pro Gly Leu Pro Gly Ala Pro Tyr Ala Leu
        625             630                 635

TGG AGA GAG TTC CTC TTC TCC GTT GCC GCG GGG CCC CCC GCG CAG TAC         1966
Trp Arg Glu Phe Leu Phe Ser Val Ala Ala Gly Pro Pro Ala Gln Tyr
640             645                 650                 655

TCG GTC ACC CTC CAC GGC CAG GAT GTC CTC ATG CTC CCT GGT GAC CTC         2014
Ser Val Thr Leu His Gly Gln Asp Val Leu Met Leu Pro Gly Asp Leu
                    660             665                 670

GTT GGC TTG CAG CAC GAC GCT GGC CCT GGC GCC CTC CTG CAC TGC TCG         2062
Val Gly Leu Gln His Asp Ala Gly Pro Gly Ala Leu Leu His Cys Ser
                675             680                 685

CCG GCT CCC GGC CAC CCT GGT CCC CAG GCC CCG TAC CTC TCC GCC AAC         2110
Pro Ala Pro Gly His Pro Gly Pro Gln Ala Pro Tyr Leu Ser Ala Asn
        690             695                 700

GCC TCG TCA TGG CTG CCC CAC TTG CCA GCC CAG CTG GAG GGC ACT TGG         2158
Ala Ser Ser Trp Leu Pro His Leu Pro Ala Gln Leu Glu Gly Thr Trp
        705             710                 715
```

FIG. 10F

```
GCC TGC CCT GCC TGT GCC CTG CGG CTG CTT GCA GCC ACG GAA CAG CTC    2206
Ala Cys Pro Ala Cys Ala Leu Arg Leu Leu Ala Ala Thr Glu Gln Leu
720             725                 730                 735

ACC GTG CTG CTG GGC TTG AGG CCC AAC CCT GGA CTG CGG ATG CCT GGG    2254
Thr Val Leu Leu Gly Leu Arg Pro Asn Pro Gly Leu Arg Met Pro Gly
                740                 745                 750

CGC TAT GAG GTC CGG GCA GAG GTG GGC AAT GGC GTG TCC AGG CAC AAC    2302
Arg Tyr Glu Val Arg Ala Glu Val Gly Asn Gly Val Ser Arg His Asn
            755                 760                 765

CTC TCC TGC AGC TTT GAC GTG GTC TCC CCA GTG GCT GGG CTG CGG GTC    2350
Leu Ser Cys Ser Phe Asp Val Val Ser Pro Val Ala Gly Leu Arg Val
            770                 775                 780

ATC TAC CCT GCC CCC CGC GAC GGC CGC CTC TAC GTG CCC ACC AAC GGC    2398
Ile Tyr Pro Ala Pro Arg Asp Gly Arg Leu Tyr Val Pro Thr Asn Gly
        785                 790                 795

TCA GCC TTG GTG CTC CAG GTG GAC TCT GGT GCC AAC GCC ACG GCC ACG    2446
Ser Ala Leu Val Leu Gln Val Asp Ser Gly Ala Asn Ala Thr Ala Thr
800             805                 810                 815

GCT CGC TGG CCT GGG GGC AGT GTC AGC GCC CGC TTT GAG AAT GTC TGC    2494
Ala Arg Trp Pro Gly Gly Ser Val Ser Ala Arg Phe Glu Asn Val Cys
                820                 825                 830

CCT GCC CTG GTG GCC ACC TTC GTG CCC GGC TGC CCC TGG GAG ACC AAC    2542
Pro Ala Leu Val Ala Thr Phe Val Pro Gly Cys Pro Trp Glu Thr Asn
                835                 840                 845
```

FIG. 10G

```
GAT ACC CTG TTC TCA GTG GTA GCA CTG CCG TGG CTC AGT GAG GGG GAG        2590
Asp Thr Leu Phe Ser Val Val Ala Leu Pro Trp Leu Ser Glu Gly Glu
        850             855             860

CAC GTG GTG GAC GTG GTG GTG GAA AAC AGC GCC AGC CGG GCC AAC CTC        2638
His Val Val Asp Val Val Val Glu Asn Ser Ala Ser Arg Ala Asn Leu
        865             870             875

AGC CTG CGG GTG ACG GCG GAG GAG CCC ATC TGT GGC CTC CGC GCC ACG        2686
Ser Leu Arg Val Thr Ala Glu Glu Pro Ile Cys Gly Leu Arg Ala Thr
    880             885             890             895

CCC AGC CCC GAG GCC CGT GTA CTG CAG GGA GTC CTA GTG AGG TAC AGC        2734
Pro Ser Pro Glu Ala Arg Val Leu Gln Gly Val Leu Val Arg Tyr Ser
            900             905             910

CCC GTG GTG GAG GCC GGC TCG GAC ATG GTC TTC CGG TGG ACC ATC AAC        2782
Pro Val Val Glu Ala Gly Ser Asp Met Val Phe Arg Trp Thr Ile Asn
                915             920             925

GAC AAG CAG TCC CTG ACC TTC CAG AAC GTG GTC TTC AAT GTC ATT TAT        2830
Asp Lys Gln Ser Leu Thr Phe Gln Asn Val Val Phe Asn Val Ile Tyr
        930             935             940

CAG AGC GCG GCG GTC TTC AAG CTC TCA CTG ACG GCC TCC AAC CAC GTG        2878
Gln Ser Ala Ala Val Phe Lys Leu Ser Leu Thr Ala Ser Asn His Val
    945             950             955
```

FIG. 10H

```
AGC AAC GTC ACC GTG AAC TAC AAC GTA ACC GTG GAG CGG ATG AAC AGG        2926
Ser Asn Val Thr Val Asn Tyr Asn Val Thr Val Glu Arg Met Asn Arg
960             965             970             975

ATG CAG GGT CTG CAG GTC TCC ACA GTG CCG GCC GTG CTG TCC CCC AAT        2974
Met Gln Gly Leu Gln Val Ser Thr Val Pro Ala Val Leu Ser Pro Asn
        980             985             990

GCC ACA CTG GTA CTG ACG GGT GGT GTG CTG GTG GAC TCA GCT GTG GAG        3022
Ala Thr Leu Val Leu Thr Gly Gly Val Leu Val Asp Ser Ala Val Glu
        995             1000            1005

GTG GCC TTC CTG TGG AAC TTT GGG GAT GGG GAG CAG GCC CTC CAC CAG        3070
Val Ala Phe Leu Trp Asn Phe Gly Asp Gly Glu Gln Ala Leu His Gln
        1010            1015            1020

TTC CAG CCT CCG TAC AAC GAG TCC TTC CCG GTT CCA GAC CCC TCG GTG        3118
Phe Gln Pro Pro Tyr Asn Glu Ser Phe Pro Val Pro Asp Pro Ser Val
        1025            1030            1035

GCC CAG GTG CTG GTG GAG CAC AAT GTC ATG CAC ACC TAC GCT GCC CCA        3166
Ala Gln Val Leu Val Glu His Asn Val Met His Thr Tyr Ala Ala Pro
1040            1045            1050            1055

GGT GAG TAC CTC CTG ACC GTG CTG GCA TCT AAT GCC TTC GAG AAC CTG        3214
Gly Glu Tyr Leu Leu Thr Val Leu Ala Ser Asn Ala Phe Glu Asn Leu
        1060            1065            1070

ACG CAG CAG GTG CCT GTG AGC GTG CGC GCC TCC CTG CCC TCC GTG GCT        3262
Thr Gln Gln Val Pro Val Ser Val Arg Ala Ser Leu Pro Ser Val Ala
        1075            1080            1085
```

FIG. 10I

```
GTG GGT GTG AGT GAC GGC GTC CTG GTG GCC GGC CGG CCC GTC ACC TTC      3310
Val Gly Val Ser Asp Gly Val Leu Val Ala Gly Arg Pro Val Thr Phe
        1090            1095                1100

TAC CCG CAC CCG CTG CCC TCG CCT GGG GGT GTT CTT TAC ACG TGG GAC      3358
Tyr Pro His Pro Leu Pro Ser Pro Gly Gly Val Leu Tyr Thr Trp Asp
    1105                1110                1115

TTC GGG GAC GGC TCC CCT GTC CTG ACC CAG AGC CAG CCG GCT GCC AAC      3406
Phe Gly Asp Gly Ser Pro Val Leu Thr Gln Ser Gln Pro Ala Ala Asn
1120            1125                1130                1135

CAC ACC TAT GCC TCG AGG GGC ACC TAC CAC GTG CGC CTG GAG GTC AAC      3454
His Thr Tyr Ala Ser Arg Gly Thr Tyr His Val Arg Leu Glu Val Asn
                1140                1145                1150

AAC ACG GTG AGC GGT GCG GCG GCC CAG GCG GAT GTG CGC GTC TTT GAG      3502
Asn Thr Val Ser Gly Ala Ala Ala Gln Ala Asp Val Arg Val Phe Glu
            1155                1160                1165

GAG CTC CGC GGA CTC AGC GTG GAC ATG AGC CTG GCC GTG GAG CAG GGC      3550
Glu Leu Arg Gly Leu Ser Val Asp Met Ser Leu Ala Val Glu Gln Gly
        1170                1175                1180

GCC CCC GTG GTG GTC AGC GCC GCG GTG CAG ACG GGC GAC AAC ATC ACG      3598
Ala Pro Val Val Val Ser Ala Ala Val Gln Thr Gly Asp Asn Ile Thr
        1185                1190                1195
```

FIG. 10J

```
TGG ACC TTC GAC ATG GGG GAC GGC ACC GTG CTG TCG GGC CCG GAG GCA        3646
Trp Thr Phe Asp Met Gly Asp Gly Thr Val Leu Ser Gly Pro Glu Ala
1200            1205            1210            1215

ACA GTG GAG CAT GTG TAC CTG CGG GCA CAG AAC TGC ACA GTG ACC GTG        3694
Thr Val Glu His Val Tyr Leu Arg Ala Gln Asn Cys Thr Val Thr Val
        1220            1225            1230

GGT GCG GCC AGC CCC GCC GGC CAC CTG GCC CGG AGC CTG CAC GTG CTG        3742
Gly Ala Ala Ser Pro Ala Gly His Leu Ala Arg Ser Leu His Val Leu
            1235            1240            1245

GTC TTC GTC CTG GAG GTG CTG CGC GTT GAA CCC GCC GCC TGC ATC CCC        3790
Val Phe Val Leu Glu Val Leu Arg Val Glu Pro Ala Ala Cys Ile Pro
        1250            1255            1260

ACG CAG CCT GAC GCG CGG CTC ACG GCC TAC GTC ACC GGG AAC CCG GCC        3838
Thr Gln Pro Asp Ala Arg Leu Thr Ala Tyr Val Thr Gly Asn Pro Ala
    1265            1270            1275

CAC TAC CTC TTC GAC TGG ACC TTC GGG GAT GGC TCC TCC AAC ACG ACC        3886
His Tyr Leu Phe Asp Trp Thr Phe Gly Asp Gly Ser Ser Asn Thr Thr
1280            1285            1290            1295

GTG CGG GGG TGC CCG ACG GTG ACA CAC AAC TTC ACG CGG AGC GGC ACG        3934
Val Arg Gly Cys Pro Thr Val Thr His Asn Phe Thr Arg Ser Gly Thr
            1300            1305            1310

TTC CCC CTG GCG CTG GTG CTG TCC AGC CGC GTG AAC AGG GCG CAT TAC        3982
Phe Pro Leu Ala Leu Val Leu Ser Ser Arg Val Asn Arg Ala His Tyr
        1315            1320            1325

TTC ACC AGC ATC TGC GTG GAG CCA GAG GTG GGC AAC GTC ACC CTG CAG        4030
Phe Thr Ser Ile Cys Val Glu Pro Glu Val Gly Asn Val Thr Leu Gln
    1330            1335            1340
```

FIG. 10K

```
TTC ACC AGC ATC TGC GTG GAG CCA GAG GTG GGC AAC GTC ACC CTG CAG      4030
Phe Thr Ser Ile Cys Val Glu Pro Glu Val Gly Asn Val Thr Leu Gln
        1330            1335            1340

CCA GAG AGG CAG TTT GTG CAG CTC GGG GAC GAG GCC TGG CTG GTG GCA      4078
Pro Glu Arg Gln Phe Val Gln Leu Gly Asp Glu Ala Trp Leu Val Ala
        1345            1350            1355

TGT GCC TGG CCC CCG TTC CCC TAC CGC TAC ACC TGG GAC TTT GGC ACC      4126
Cys Ala Trp Pro Pro Phe Pro Tyr Arg Tyr Thr Trp Asp Phe Gly Thr
1360            1365            1370            1375

GAG GAA GCC GCC CCC ACC CGT GCC AGG GGC CCT GAG GTG ACG TTC ATC      4174
Glu Glu Ala Ala Pro Thr Arg Ala Arg Gly Pro Glu Val Thr Phe Ile
                1380            1385            1390

TAC CGA GAC CCA GGC TCC TAT CTT GTG ACA GTC ACC GCG TCC AAC AAC      4222
Tyr Arg Asp Pro Gly Ser Tyr Leu Val Thr Val Thr Ala Ser Asn Asn
            1395            1400            1405

ATC TCT GCT GCC AAT GAC TCA GCC CTG GTG GAG GTG CAG GAG CCC GTG      4270
Ile Ser Ala Ala Asn Asp Ser Ala Leu Val Glu Val Gln Glu Pro Val
        1410            1415            1420

CTG GTC ACC AGC ATC AAG GTC AAT GGC TCC CTT GGG CTG GAG CTG CAG      4318
Leu Val Thr Ser Ile Lys Val Asn Gly Ser Leu Gly Leu Glu Leu Gln
        1425            1430            1435
```

FIG. 10L

```
CAG CCG TAC CTG TTC TCT GCT GTG GGC CGT GGG CGC CCC GCC AGC TAC        4366
Gln Pro Tyr Leu Phe Ser Ala Val Gly Arg Gly Arg Pro Ala Ser Tyr
1440            1445            1450            1455

CTG TGG GAT CTG GGG GAC GGT GGG TGG CTC GAG GGT CCG GAG GTC ACC        4414
Leu Trp Asp Leu Gly Asp Gly Gly Trp Leu Glu Gly Pro Glu Val Thr
            1460            1465            1470

CAC GCT TAC AAC AGC ACA GGT GAC TTC ACC GTT AGG GTG GCC GGC TGG        4462
His Ala Tyr Asn Ser Thr Gly Asp Phe Thr Val Arg Val Ala Gly Trp
        1475            1480            1485

AAT GAG GTG AGC CGC AGC GAG GCC TGG CTC AAT GTG ACG GTG AAG CGG        4510
Asn Glu Val Ser Arg Ser Glu Ala Trp Leu Asn Val Thr Val Lys Arg
        1490            1495            1500

CGC GTG CGG GGG CTC GTC GTC AAT GCA AGC CGC ACG GTG GTG CCC CTG        4558
Arg Val Arg Gly Leu Val Val Asn Ala Ser Arg Thr Val Val Pro Leu
        1505            1510            1515

AAT GGG AGC GTG AGC TTC AGC ACG TCG CTG GAG GCC GGC AGT GAT GTG        4606
Asn Gly Ser Val Ser Phe Ser Thr Ser Leu Glu Ala Gly Ser Asp Val
1520            1525            1530            1535

CGC TAT TCC TGG GTG CTC TGT GAC CGC TGC ACG CCC ATC CCT GGG GGT        4654
Arg Tyr Ser Trp Val Leu Cys Asp Arg Cys Thr Pro Ile Pro Gly Gly
            1540            1545            1550

CCT ACC ATC TCT TAC ACC TTC CGC TCC GTG GGC ACC TTC AAT ATC ATC        4702
Pro Thr Ile Ser Tyr Thr Phe Arg Ser Val Gly Thr Phe Asn Ile Ile
        1555            1560            1565
```

FIG. 10M

```
GTC ACG GCT GAG AAC GAG GTG GGC TCC GCC CAG GAC AGC ATC TTC GTC        4750
Val Thr Ala Glu Asn Glu Val Gly Ser Ala Gln Asp Ser Ile Phe Val
    1570            1575                1580

TAT GTC CTG CAG CTC ATA GAG GGG CTG CAG GTG GTG GGC GGT GGC CGC        4798
Tyr Val Leu Gln Leu Ile Glu Gly Leu Gln Val Val Gly Gly Gly Arg
    1585            1590                1595

TAC TTC CCC ACC AAC CAC ACG GTA CAG CTG CAG GCC GTG GTT AGG GAT        4846
Tyr Phe Pro Thr Asn His Thr Val Gln Leu Gln Ala Val Val Arg Asp
1600            1605                1610                1615

GGC ACC AAC GTC TCC TAC AGC TGG ACT GCC TGG AGG GAC AGG GGC CCG        4894
Gly Thr Asn Val Ser Tyr Ser Trp Thr Ala Trp Arg Asp Arg Gly Pro
        1620            1625                1630

GCC CTG GCC GGC AGC GGC AAA GGC TTC TCG CTC ACC GTG CTC GAG GCC        4942
Ala Leu Ala Gly Ser Gly Lys Gly Phe Ser Leu Thr Val Leu Glu Ala
            1635            1640                1645

GGC ACC TAC CAT GTG CAG CTG CGG GCC ACC AAC ATG CTG GGC AGC GCC        4990
Gly Thr Tyr His Val Gln Leu Arg Ala Thr Asn Met Leu Gly Ser Ala
        1650            1655                1660

TGG GCC GAC TGC ACC ATG GAC TTC GTG GAG CCT GTG GGG TGG CTG ATG        5038
Trp Ala Asp Cys Thr Met Asp Phe Val Glu Pro Val Gly Trp Leu Met
        1665            1670                1675
```

FIG. 10N

```
GTG ACC GCC TCC CCG AAC CCA GCT GCC GTC AAC ACA AGC GTC ACC CTC         5086
Val Thr Ala Ser Pro Asn Pro Ala Ala Val Asn Thr Ser Val Thr Leu
1680            1685                1690                1695

AGT GCC GAG CTG GCT GGT GGC AGT GGT GTC GTA TAC ACT TGG TCC TTG         5134
Ser Ala Glu Leu Ala Gly Gly Ser Gly Val Val Tyr Thr Trp Ser Leu
                1700            1705                1710

GAG GAG GGG CTG AGC TGG GAG ACC TCC GAG CCA TTT ACC ACC CAT AGC         5182
Glu Glu Gly Leu Ser Trp Glu Thr Ser Glu Pro Phe Thr Thr His Ser
            1715                1720                1725

TTC CCC ACA CCC GGC CTG CAC TTG GTC ACC ATG ACG GCA GGG AAC CCG         5230
Phe Pro Thr Pro Gly Leu His Leu Val Thr Met Thr Ala Gly Asn Pro
                1730            1735                1740

CTG GGC TCA GCC AAC GCC ACC GTG GAA GTG GAT GTG CAG GTG CCT GTG         5278
Leu Gly Ser Ala Asn Ala Thr Val Glu Val Asp Val Gln Val Pro Val
            1745                1750                1755

AGT GGC CTC AGC ATC AGG GCC AGC GAG CCC GGA GGC AGC TTC GTG GCG         5326
Ser Gly Leu Ser Ile Arg Ala Ser Glu Pro Gly Gly Ser Phe Val Ala
1760            1765                1770                1775

GCC GGG TCC TCT GTG CCC TTT TGG GGG CAG CTG GCC ACG GGC ACC AAT         5374
Ala Gly Ser Ser Val Pro Phe Trp Gly Gln Leu Ala Thr Gly Thr Asn
                1780            1785                1790

GTG AGC TGG TGC TGG GCT GTG CCC GGC GGC AGC AGC AAG CGT GGC CCT         5422
Val Ser Trp Cys Trp Ala Val Pro Gly Gly Ser Ser Lys Arg Gly Pro
            1795                1800                1805
```

FIG. 10O

```
CAT GTC ACC ATG GTC TTC CCG GAT GCT GGC ACC TTC TCC ATC CGG CTC       5470
His Val Thr Met Val Phe Pro Asp Ala Gly Thr Phe Ser Ile Arg Leu
    1810            1815                1820

AAT GCC TCC AAC GCA GTC AGC TGG GTC TCA GCC ACG TAC AAC CTC ACG       5518
Asn Ala Ser Asn Ala Val Ser Trp Val Ser Ala Thr Tyr Asn Leu Thr
    1825            1830                1835

GCG GAG GAG CCC ATC GTG GGC CTG GTG CTG TGG GCC AGC AGC AAG GTG       5566
Ala Glu Glu Pro Ile Val Gly Leu Val Leu Trp Ala Ser Ser Lys Val
    1840            1845                1850            1855

GTG GCG CCC GGG CAG CTG GTC CAT TTT CAG ATC CTG CTG GCT GCC GGC       5614
Val Ala Pro Gly Gln Leu Val His Phe Gln Ile Leu Leu Ala Ala Gly
                1860                1865                1870

TCA GCT GTC ACC TTC CGC CTG CAG GTC GGC GGG GCC AAC CCC GAG GTG       5662
Ser Ala Val Thr Phe Arg Leu Gln Val Gly Gly Ala Asn Pro Glu Val
        1875                1880                1885

CTC CCC GGG CCC CGT TTC TCC CAC AGC TTC CCC CGC GTC GGA GAC CAC       5710
Leu Pro Gly Pro Arg Phe Ser His Ser Phe Pro Arg Val Gly Asp His
        1890                1895                1900

GTG GTG AGC GTG CGG GGC AAA AAC CAC GTG AGC TGG GCC CAG GCG CAG       5758
Val Val Ser Val Arg Gly Lys Asn His Val Ser Trp Ala Gln Ala Gln
        1905                1910                1915
```

FIG. 10P

```
GTG CGC ATC GTG GTG CTG GAG GCC GTG AGT GGG CTG CAG ATG CCC AAC          5806
Val Arg Ile Val Val Leu Glu Ala Val Ser Gly Leu Gln Met Pro Asn
1920            1925                1930                1935

TGC TGC GAG CCT GGC ATC GCC ACG GGC ACT GAG AGG AAC TTC ACA GCC          5854
Cys Cys Glu Pro Gly Ile Ala Thr Gly Thr Glu Arg Asn Phe Thr Ala
                1940                1945                1950

CGC GTG CAG CGC GGC TCT CGG GTC GCC TAC GCC TGG TAC TTC TCG CTG          5902
Arg Val Gln Arg Gly Ser Arg Val Ala Tyr Ala Trp Tyr Phe Ser Leu
                1955                1960                1965

CAG AAG GTC CAG GGC GAC TCG CTG GTC ATC CTG TCG GGC CGC GAC GTC          5950
Gln Lys Val Gln Gly Asp Ser Leu Val Ile Leu Ser Gly Arg Asp Val
                1970                1975                1980

ACC TAC ACG CCC GTG GCC GCG GGG CTG TTG GAG ATC CAG GTG CGC GCC          5998
Thr Tyr Thr Pro Val Ala Ala Gly Leu Leu Glu Ile Gln Val Arg Ala
1985            1990                1995

TTC AAC GCC CTG GGC AGT GAG AAC CGC ACG CTG GTG CTG GAG GTT CAG          6046
Phe Asn Ala Leu Gly Ser Glu Asn Arg Thr Leu Val Leu Glu Val Gln
2000            2005                2010                2015

GAC GCC GTC CAG TAT GTG GCC CTG CAG AGC GGC CCC TGC TTC ACC AAC          6094
Asp Ala Val Gln Tyr Val Ala Leu Gln Ser Gly Pro Cys Phe Thr Asn
                2020                2025                2030

CGC TCG GCG CAG TTT GAG GCC GCC ACC AGC CCC AGC CCC CGG CGT GTG          6142
Arg Ser Ala Gln Phe Glu Ala Ala Thr Ser Pro Ser Pro Arg Arg Val
                2035                2040                2045
```

FIG. 10Q

```
GCC TAC CAC TGG GAC TTT GGG GAT GGG TCG CCA GGG CAG GAC ACA GAT      6190
Ala Tyr His Trp Asp Phe Gly Asp Gly Ser Pro Gly Gln Asp Thr Asp
    2050            2055            2060

GAG CCC AGG GCC GAG CAC TCC TAC CTG AGG CCT GGG GAC TAC CGC GTG      6238
Glu Pro Arg Ala Glu His Ser Tyr Leu Arg Pro Gly Asp Tyr Arg Val
    2065            2070            2075

CAG GTG AAC GCC TCC AAC CTG GTG AGC TTC TTC GTG GCG CAG GCC ACG      6286
Gln Val Asn Ala Ser Asn Leu Val Ser Phe Phe Val Ala Gln Ala Thr
2080            2085            2090            2095

GTG ACC GTC CAG GTG CTG GCC TGC CGG GAG CCG GAG GTG GAC GTG GTC      6334
Val Thr Val Gln Val Leu Ala Cys Arg Glu Pro Glu Val Asp Val Val
            2100            2105            2110

CTG CCC CTG CAG GTG CTG ATG CGG CGA TCA CAG CGC AAC TAC TTG GAG      6382
Leu Pro Leu Gln Val Leu Met Arg Arg Ser Gln Arg Asn Tyr Leu Glu
            2115            2120            2125

GCC CAC GTT GAC CTG CGC GAC TGC GTC ACC TAC CAG ACT GAG TAC CGC      6430
Ala His Val Asp Leu Arg Asp Cys Val Thr Tyr Gln Thr Glu Tyr Arg
        2130            2135            2140

TGG GAG GTG TAT CGC ACC GCC AGC TGC CAG CGG CCG GGG CGC CCA GCG      6478
Trp Glu Val Tyr Arg Thr Ala Ser Cys Gln Arg Pro Gly Arg Pro Ala
    2145            2150            2155
```

FIG. 10R

```
CGT GTG GCC CTG CCC GGC GTG GAC GTG AGC CGG CCT CGG CTG GTG CTG    6526
Arg Val Ala Leu Pro Gly Val Asp Val Ser Arg Pro Arg Leu Val Leu
2160          2165            2170            2175

CCG CGG CTG GCG CTG CCT GTG GGG CAC TAC TGC TTT GTG TTT GTC GTG    6574
Pro Arg Leu Ala Leu Pro Val Gly His Tyr Cys Phe Val Phe Val Val
         2180            2185            2190

TCA TTT GGG GAC ACG CCA CTG ACA CAG AGC ATC CAG GCC AAT GTG ACG    6622
Ser Phe Gly Asp Thr Pro Leu Thr Gln Ser Ile Gln Ala Asn Val Thr
         2195            2200            2205

GTG GCC CCC GAG CGC CTG GTG CCC ATC ATT GAG GGT GGC TCA TAC CGC    6670
Val Ala Pro Glu Arg Leu Val Pro Ile Ile Glu Gly Gly Ser Tyr Arg
         2210            2215            2220

GTG TGG TCA GAC ACA CGG GAC CTG GTG CTG GAT GGG AGC GAG TCC TAC    6718
Val Trp Ser Asp Thr Arg Asp Leu Val Leu Asp Gly Ser Glu Ser Tyr
         2225            2230            2235

GAC CCC AAC CTG GAG GAC GGC GAC CAG ACG CCG CTC AGT TTC CAC TGG    6766
Asp Pro Asn Leu Glu Asp Gly Asp Gln Thr Pro Leu Ser Phe His Trp
2240            2245            2250            2255

GCC TGT GTG GCT TCG ACA CAG AGG GAG GCT GGC GGG TGT GCG CTG AAC    6814
Ala Cys Val Ala Ser Thr Gln Arg Glu Ala Gly Gly Cys Ala Leu Asn
         2260            2265            2270

TTT GGG CCC CGC GGG AGC AGC ACG GTC ACC ATT CCA CGG GAG CGG CTG    6862
Phe Gly Pro Arg Gly Ser Ser Thr Val Thr Ile Pro Arg Glu Arg Leu
         2275            2280            2285
```

FIG. 10S

```
GCG GCT GGC GTG GAG TAC ACC TTC AGC CTG ACC GTG TGG AAG GCC GGC        6910
Ala Ala Gly Val Glu Tyr Thr Phe Ser Leu Thr Val Trp Lys Ala Gly
        2290            2295            2300

CGC AAG GAG GAG GCC ACC AAC CAG ACG GTG CTG ATC CGG AGT GGC CGG        6958
Arg Lys Glu Glu Ala Thr Asn Gln Thr Val Leu Ile Arg Ser Gly Arg
        2305            2310            2315

GTG CCC ATT GTG TCC TTG GAG TGT GTG TCC TGC AAG GCA CAG GCC GTG        7006
Val Pro Ile Val Ser Leu Glu Cys Val Ser Cys Lys Ala Gln Ala Val
2320            2325            2330            2335

TAC GAA GTG AGC CGC AGC TCC TAC GTG TAC TTG GAG GGC CGC TGC CTC        7054
Tyr Glu Val Ser Arg Ser Ser Tyr Val Tyr Leu Glu Gly Arg Cys Leu
        2340            2345            2350

AAT TGC AGC AGC GGC TCC AAG CGA GGG CGG TGG GCT GCA CGT ACG TTC        7102
Asn Cys Ser Ser Gly Ser Lys Arg Gly Arg Trp Ala Ala Arg Thr Phe
        2355            2360            2365

AGC AAC AAG ACG CTG GTG CTG GAT GAG ACC ACC ACA TCC ACG GGC AGT        7150
Ser Asn Lys Thr Leu Val Leu Asp Glu Thr Thr Thr Ser Thr Gly Ser
        2370            2375            2380

GCA GGC ATG CGA CTG GTG CTG CGG CGG GGC GTG CTG CGG GAC GGC GAG        7198
Ala Gly Met Arg Leu Val Leu Arg Arg Gly Val Leu Arg Asp Gly Glu
        2385            2390            2395
```

FIG. 10T

```
GGA TAC ACC TTC ACG CTC ACG GTG CTG GGC CGC TCT GGC GAG GAG GAG        7246
Gly Tyr Thr Phe Thr Leu Thr Val Leu Gly Arg Ser Gly Glu Glu Glu
2400            2405            2410            2415

GGC TGC GCC TCC ATC CGC CTG TCC CCC AAC CGC CCG CCG CTG GGG GGC        7294
Gly Cys Ala Ser Ile Arg Leu Ser Pro Asn Arg Pro Pro Leu Gly Gly
            2420            2425            2430

TCT TGC CGC CTC TTC CCA CTG GGC GCT GTG CAC GCC CTC ACC ACC AAG        7342
Ser Cys Arg Leu Phe Pro Leu Gly Ala Val His Ala Leu Thr Thr Lys
            2435            2440            2445

GTG CAC TTC GAA TGC ACG GGC TGG CAT GAC GCG GAG GAT GCT GGC GCC        7390
Val His Phe Glu Cys Thr Gly Trp His Asp Ala Glu Asp Ala Gly Ala
            2450            2455            2460

CCG CTG GTG TAC GCC CTG CTG CTG CGG CGC TGT CGC CAG GGC CAC TGC        7438
Pro Leu Val Tyr Ala Leu Leu Leu Arg Arg Cys Arg Gln Gly His Cys
            2465            2470            2475

GAG GAG TTC TGT GTC TAC AAG GGC AGC CTC TCC AGC TAC GGA GCC GTG        7486
Glu Glu Phe Cys Val Tyr Lys Gly Ser Leu Ser Ser Tyr Gly Ala Val
2480            2485            2490            2495

CTG CCC CCG GGT TTC AGG CCA CAC TTC GAG GTG GGC CTG GCC GTG GTG        7534
Leu Pro Pro Gly Phe Arg Pro His Phe Glu Val Gly Leu Ala Val Val
            2500            2505            2510

GTG CAG GAC CAG CTG GGA GCC GCT GTG GTC GCC CTC AAC AGG TCT TTG        7582
Val Gln Asp Gln Leu Gly Ala Ala Val Val Ala Leu Asn Arg Ser Leu
            2515            2520            2525
```

FIG. 10U

```
GCC ATC ACC CTC CCA GAG CCC AAC GGC AGC GCA ACG GGG CTC ACA GTC         7630
Ala Ile Thr Leu Pro Glu Pro Asn Gly Ser Ala Thr Gly Leu Thr Val
        2530            2535            2540

TGG CTG CAC GGG CTC ACC GCT AGT GTG CTC CCA GGG CTG CTG CGG CAG         7678
Trp Leu His Gly Leu Thr Ala Ser Val Leu Pro Gly Leu Leu Arg Gln
        2545            2550            2555

GCC GAT CCC CAG CAC GTC ATC GAG TAC TCG TTG GCC CTG GTC ACC GTG         7726
Ala Asp Pro Gln His Val Ile Glu Tyr Ser Leu Ala Leu Val Thr Val
        2560            2565            2570            2575

CTG AAC GAG TAC GAG CGG GCC CTG GAC GTG GCG GCA GAG CCC AAG CAC         7774
Leu Asn Glu Tyr Glu Arg Ala Leu Asp Val Ala Ala Glu Pro Lys His
                2580            2585            2590

GAG CGG CAG CAC CGA GCC CAG ATA CGC AAG AAC ATC ACG GAG ACT CTG         7822
Glu Arg Gln His Arg Ala Gln Ile Arg Lys Asn Ile Thr Glu Thr Leu
                2595            2600            2605

GTG TCC CTG AGG GTC CAC ACT GTG GAT GAC ATC CAG CAG ATC GCT GCT         7870
Val Ser Leu Arg Val His Thr Val Asp Asp Ile Gln Gln Ile Ala Ala
        2610            2615            2620

GCG CTG GCC CAG TGC ATG GGG CCC AGC AGG GAG CTC GTA TGC CGC TCG         7918
Ala Leu Ala Gln Cys Met Gly Pro Ser Arg Glu Leu Val Cys Arg Ser
        2625            2630            2635
```

FIG. 10V

```
TGC CTG AAG CAG ACG CTG CAC AAG CTG GAG GCC ATG ATG CTC ATC CTG      7966
Cys Leu Lys Gln Thr Leu His Lys Leu Glu Ala Met Met Leu Ile Leu
2640            2645            2650            2655

CAG GCA GAG ACC ACC GCG GGC ACC GTG ACG CCC ACC GCC ATC GGA GAC      8014
Gln Ala Glu Thr Thr Ala Gly Thr Val Thr Pro Thr Ala Ile Gly Asp
        2660            2665            2670

AGC ATC CTC AAC ATC ACA GGA GAC CTC ATC CAC CTG GCC AGC TCG GAC      8062
Ser Ile Leu Asn Ile Thr Gly Asp Leu Ile His Leu Ala Ser Ser Asp
            2675            2680            2685

GTG CGG GCA CCA CAG CCC TCA GAG CTG GGA GCC GAG TCA CCA TCT CGG      8110
Val Arg Ala Pro Gln Pro Ser Glu Leu Gly Ala Glu Ser Pro Ser Arg
                2690            2695            2700

ATG GTG GCG TCC CAG GCC TAC AAC CTG ACC TCT GCC CTC ATG CGC ATC      8158
Met Val Ala Ser Gln Ala Tyr Asn Leu Thr Ser Ala Leu Met Arg Ile
    2705            2710            2715

CTC ATG CGC TCC CGC GTG CTC AAC GAG GAG CCC CTG ACG CTG GCG GGC      8206
Leu Met Arg Ser Arg Val Leu Asn Glu Glu Pro Leu Thr Leu Ala Gly
2720            2725            2730            2735

GAG GAG ATC GTG GCC CAG GGC AAG CGC TCG GAC CCG CGG AGC CTG CTG      8254
Glu Glu Ile Val Ala Gln Gly Lys Arg Ser Asp Pro Arg Ser Leu Leu
            2740            2745            2750

TGC TAT GGC GGC GCC CCA GGG CCT GGC TGC CAC TTC TCC ATC CCC GAG      8302
Cys Tyr Gly Gly Ala Pro Gly Pro Gly Cys His Phe Ser Ile Pro Glu
        2755            2760            2765
```

FIG. 10W

```
GCT TTC AGC GGG GCC CTG GCC AAC CTC AGT GAC GTG GTG CAG CTC ATC           8350
Ala Phe Ser Gly Ala Leu Ala Asn Leu Ser Asp Val Val Gln Leu Ile
        2770            2775            2780

TTT CTG GTG GAC TCC AAT CCC TTT CCC TTT GGC TAT ATC AGC AAC TAC           8398
Phe Leu Val Asp Ser Asn Pro Phe Pro Phe Gly Tyr Ile Ser Asn Tyr
        2785            2790            2795

ACC GTC TCC ACC AAG GTG GCC TCG ATG GCA TTC CAG ACA CAG GCC GGC           8446
Thr Val Ser Thr Lys Val Ala Ser Met Ala Phe Gln Thr Gln Ala Gly
2800            2805            2810            2815

GCC CAG ATC CCC ATC GAG CGG CTG GCC TCA GAG CGC GCC ATC ACC GTG           8494
Ala Gln Ile Pro Ile Glu Arg Leu Ala Ser Glu Arg Ala Ile Thr Val
        2820            2825            2830

AAG GTG CCC AAC AAC TCG GAC TGG GCT GCC CGG GGC CAC CGC AGC TCC           8542
Lys Val Pro Asn Asn Ser Asp Trp Ala Ala Arg Gly His Arg Ser Ser
        2835            2840            2845

GCC AAC TCC GCC AAC TCC GTT GTG GTC CAG CCC CAG GCC TCC GTC GGT           8590
Ala Asn Ser Ala Asn Ser Val Val Val Gln Pro Gln Ala Ser Val Gly
        2850            2855            2860

GCT GTG GTC ACC CTG GAC AGC AGC AAC CCT GCG GCC GGG CTG CAT CTG           8638
Ala Val Val Thr Leu Asp Ser Ser Asn Pro Ala Ala Gly Leu His Leu
        2865            2870            2875
```

FIG. 10X

```
CAG CTC AAC TAT ACG CTG CTG GAC GGC CAC TAC CTG TCT GAG GAA CCT    8686
Gln Leu Asn Tyr Thr Leu Leu Asp Gly His Tyr Leu Ser Glu Glu Pro
2880            2885            2890            2895

GAG CCC TAC CTG GCA GTC TAC CTA CAC TCG GAG CCC CGG CCC AAT GAG    8734
Glu Pro Tyr Leu Ala Val Tyr Leu His Ser Glu Pro Arg Pro Asn Glu
                2900            2905            2910

CAC AAC TGC TCG GCT AGC AGG AGG ATC CGC CCA GAG TCA CTC CAG GGT    8782
His Asn Cys Ser Ala Ser Arg Arg Ile Arg Pro Glu Ser Leu Gln Gly
                2915            2920            2925

GCT GAC CAC CGG CCC TAC ACC TTC TTC ATT TCC CCG GGG AGC AGA GAC    8830
Ala Asp His Arg Pro Tyr Thr Phe Phe Ile Ser Pro Gly Ser Arg Asp
                2930            2935            2940

CCA GCG GGG AGT TAC CAT CTG AAC CTC TCC AGC CAC TTC CGC TGG TCG    8878
Pro Ala Gly Ser Tyr His Leu Asn Leu Ser Ser His Phe Arg Trp Ser
                2945            2950            2955

GCG CTG CAG GTG TCC GTG GGC CTG TAC ACG TCC CTG TGC CAG TAC TTC    8926
Ala Leu Gln Val Ser Val Gly Leu Tyr Thr Ser Leu Cys Gln Tyr Phe
2960            2965            2970            2975

AGC GAG GAG GAC ATG GTG TGG CGG ACA GAG GGG CTG CTG CCC CTG GAG    8974
Ser Glu Glu Asp Met Val Trp Arg Thr Glu Gly Leu Leu Pro Leu Glu
                2980            2985            2990

GAG ACC TCG CCC CGC CAG GCC GTC TGC CTC ACC CGC CAC CTC ACC GCC    9022
Glu Thr Ser Pro Arg Gln Ala Val Cys Leu Thr Arg His Leu Thr Ala
                2995            3000            3005
```

FIG. 10Y

```
TTC GGC GCC AGC CTC TTC GTG CCC CCA AGC CAT GTC CGC TTT GTG TTT      9070
Phe Gly Ala Ser Leu Phe Val Pro Pro Ser His Val Arg Phe Val Phe
        3010            3015            3020

CCT GAG CCG ACA GCG GAT GTA AAC TAC ATC GTC ATG CTG ACA TGT GCT      9118
Pro Glu Pro Thr Ala Asp Val Asn Tyr Ile Val Met Leu Thr Cys Ala
    3025            3030            3035

GTG TGC CTG GTG ACC TAC ATG GTC ATG GCC GCC ATC CTG CAC AAG CTG      9166
Val Cys Leu Val Thr Tyr Met Val Met Ala Ala Ile Leu His Lys Leu
3040            3045            3050            3055

GAC CAG TTG GAT GCC AGC CGG GGC CGC GCC ATC CCT TTC TGT GGG CAG      9214
Asp Gln Leu Asp Ala Ser Arg Gly Arg Ala Ile Pro Phe Cys Gly Gln
                3060            3065            3070

CGG GGC CGC TTC AAG TAC GAG ATC CTC GTC AAG ACA GGC TGG GGC CGG      9262
Arg Gly Arg Phe Lys Tyr Glu Ile Leu Val Lys Thr Gly Trp Gly Arg
            3075            3080            3085

GGC TCA GGT ACC ACG GCC CAC GTG GGC ATC ATG CTG TAT GGG GTG GAC      9310
Gly Ser Gly Thr Thr Ala His Val Gly Ile Met Leu Tyr Gly Val Asp
        3090            3095            3100

AGC CGG AGC GGC CAC CGG CAC CTG GAC GGC GAC AGA GCC TTC CAC CGC      9358
Ser Arg Ser Gly His Arg His Leu Asp Gly Asp Arg Ala Phe His Arg
    3105            3110            3115
```

FIG. 10Z

```
AAC AGC CTG GAC ATC TTC CGG ATC GCC ACC CCG CAC AGC CTG GGT AGC      9406
Asn Ser Leu Asp Ile Phe Arg Ile Ala Thr Pro His Ser Leu Gly Ser
3120            3125             3130            3135

GTG TGG AAG ATC CGA GTG TGG CAC GAC AAC AAA GGG CTC AGC CCT GCC      9454
Val Trp Lys Ile Arg Val Trp His Asp Asn Lys Gly Leu Ser Pro Ala
             3140            3145             3150

TGG TTC CTG CAG CAC GTC ATC GTC AGG GAC CTG CAG ACG GCA CGC AGC      9502
Trp Phe Leu Gln His Val Ile Val Arg Asp Leu Gln Thr Ala Arg Ser
            3155             3160            3165

GCC TTC TTC CTG GTC AAT GAC TGG CTT TCG GTG GAG ACG GAG GCC AAC      9550
Ala Phe Phe Leu Val Asn Asp Trp Leu Ser Val Glu Thr Glu Ala Asn
        3170            3175            3180

GGG GGC CTG GTG GAG AAG GAG GTG CTG GCC GCG AGC GAC GCA GCC CTT      9598
Gly Gly Leu Val Glu Lys Glu Val Leu Ala Ala Ser Asp Ala Ala Leu
3185            3190            3195

TTG CGC TTC CGG CGC CTG CTG GTG GCT GAG CTG CAG CGT GGC TTC TTT      9646
Leu Arg Phe Arg Arg Leu Leu Val Ala Glu Leu Gln Arg Gly Phe Phe
3200            3205             3210            3215

GAC AAG CAC ATC TGG CTC TCC ATA TGG GAC CGG CCG CCT CGT AGC CGT      9694
Asp Lys His Ile Trp Leu Ser Ile Trp Asp Arg Pro Pro Arg Ser Arg
            3220            3225            3230

TTC ACT CGC ATC CAG AGG GCC ACC TGC TGC GTT CTC CTC ATC TGC CTC      9742
Phe Thr Arg Ile Gln Arg Ala Thr Cys Cys Val Leu Leu Ile Cys Leu
            3235            3240            3245
```

FIG. 10AA

```
TTC CTG GGC GCC AAC GCC GTG TGG TAC GGG GCT GTT GGC GAC TCT GCC      9790
Phe Leu Gly Ala Asn Ala Val Trp Tyr Gly Ala Val Gly Asp Ser Ala
    3250            3255            3260

TAC AGC ACG GGG CAT GTG TCC AGG CTG AGC CCG CTG AGC GTC GAC ACA      9838
Tyr Ser Thr Gly His Val Ser Arg Leu Ser Pro Leu Ser Val Asp Thr
    3265            3270            3275

GTC GCT GTT GGC CTG GTG TCC AGC GTG GTT GTC TAT CCC GTC TAC CTG      9886
Val Ala Val Gly Leu Val Ser Ser Val Val Val Tyr Pro Val Tyr Leu
    3280            3285            3290            3295

GCC ATC CTT TTT CTC TTC CGG ATG TCC CGG AGC AAG GTG GCT GGG AGC      9934
Ala Ile Leu Phe Leu Phe Arg Met Ser Arg Ser Lys Val Ala Gly Ser
        3300            3305            3310

CCG AGC CCC ACA CCT GCC GGG CAG CAG GTG CTG GAC ATC GAC AGC TGC      9982
Pro Ser Pro Thr Pro Ala Gly Gln Gln Val Leu Asp Ile Asp Ser Cys
        3315            3320            3325

CTG GAC TCG TCC GTG CTG GAC AGC TCC TTC CTC ACG TTC TCA GGC CTC      10030
Leu Asp Ser Ser Val Leu Asp Ser Ser Phe Leu Thr Phe Ser Gly Leu
        3330            3335            3340

CAC GCT GAG GCC TTT GTT GGA CAG ATG AAG AGT GAC TTG TTT CTG GAT      10078
His Ala Glu Ala Phe Val Gly Gln Met Lys Ser Asp Leu Phe Leu Asp
        3345            3350            3355
```

FIG. 10BB

```
GAT TCT AAG AGT CTG GTG TGC TGG CCC TCC GGC GAG GGA ACG CTC AGT      10126
Asp Ser Lys Ser Leu Val Cys Trp Pro Ser Gly Glu Gly Thr Leu Ser
3360            3365            3370            3375

TGG CCG GAC CTG CTC AGT GAC CCG TCC ATT GTG GGT AGC AAT CTG CGG      10174
Trp Pro Asp Leu Leu Ser Asp Pro Ser Ile Val Gly Ser Asn Leu Arg
            3380            3385            3390

CAG CTG GCA CGG GGC CAG GCG GGC CAT GGG CTG GGC CCA GAG GAG GAC      10222
Gln Leu Ala Arg Gly Gln Ala Gly His Gly Leu Gly Pro Glu Glu Asp
            3395            3400            3405

GGC TTC TCC CTG GCC AGC CCC TAC TCG CCT GCC AAA TCC TTC TCA GCA      10270
Gly Phe Ser Leu Ala Ser Pro Tyr Ser Pro Ala Lys Ser Phe Ser Ala
            3410            3415            3420

TCA GAT GAA GAC CTG ATC CAG CAG GTC CTT GCC GAG GGG GTC AGC AGC      10318
Ser Asp Glu Asp Leu Ile Gln Gln Val Leu Ala Glu Gly Val Ser Ser
            3425            3430            3435

CCA GCC CCT ACC CAA GAC ACC CAC ATG GAA ACG GAC CTG CTC AGC AGC      10366
Pro Ala Pro Thr Gln Asp Thr His Met Glu Thr Asp Leu Leu Ser Ser
3440            3445            3450            3455

CTG TCC AGC ACT CCT GGG GAG AAG ACA GAG ACG CTG GCG CTG CAG AGG      10414
Leu Ser Ser Thr Pro Gly Glu Lys Thr Glu Thr Leu Ala Leu Gln Arg
            3460            3465            3470

CTG GGG GAG CTG GGG CCA CCC AGC CCA GGC CTG AAC TGG GAA CAG CCC      10462
Leu Gly Glu Leu Gly Pro Pro Ser Pro Gly Leu Asn Trp Glu Gln Pro
            3475            3480            3485
```

FIG. 10CC

| | |
|---|---|
| CAG GCA GCG AGG CTG TCC AGG ACA GGA CTG GTG GAG GGT CTG CGG AAG<br>Gln Ala Ala Arg Leu Ser Arg Thr Gly Leu Val Glu Gly Leu Arg Lys<br>        3490                   3495                  3500 | 10510 |
| CGC CTG CTG CCG GCC TGG TGT GCC TCC CTG GCC CAC GGG CTC AGC CTG<br>Arg Leu Leu Pro Ala Trp Cys Ala Ser Leu Ala His Gly Leu Ser Leu<br>        3505                   3510                  3515 | 10558 |
| CTC CTG GTG GCT GTG GCT GTG GCT GTC TCA GGG TGG GTG GGT GCG AGC<br>Leu Leu Val Ala Val Ala Val Ala Val Ser Gly Trp Val Gly Ala Ser<br>3520                3525                3530               3535 | 10606 |
| TTC CCC CCG GGC GTG AGT GTT GCG TGG CTC CTG TCC AGC AGC GCC AGC<br>Phe Pro Pro Gly Val Ser Val Ala Trp Leu Leu Ser Ser Ser Ala Ser<br>           3540                 3545                3550 | 10654 |
| TTC CTG GCC TCA TTC CTC GGC TGG GAG CCA CTG AAG GTC TTG CTG GAA<br>Phe Leu Ala Ser Phe Leu Gly Trp Glu Pro Leu Lys Val Leu Leu Glu<br>        3555                 3560                3565 | 10702 |
| GCC CTG TAC TTC TCA CTG GTG GCC AAG CGG CTG CAC CCG GAT GAA GAT<br>Ala Leu Tyr Phe Ser Leu Val Ala Lys Arg Leu His Pro Asp Glu Asp<br>        3570                 3575                3580 | 10750 |
| GAC ACC CTG GTA GAG AGC CCG GCT GTG ACG CCT GTG AGC GCA CGT GTG<br>Asp Thr Leu Val Glu Ser Pro Ala Val Thr Pro Val Ser Ala Arg Val<br>        3585                 3590                3595 | 10798 |

FIG. 10DD

```
CCC CGC GTA CGG CCA CCC CAC GGC TTT GCA CTC TTC CTG GCC AAG GAA    10846
Pro Arg Val Arg Pro Pro His Gly Phe Ala Leu Phe Leu Ala Lys Glu
3600            3605            3610            3615

GAA GCC CGC AAG GTC AAG AGG CTA CAT GGC ATG CTG CGG AGC CTC CTG    10894
Glu Ala Arg Lys Val Lys Arg Leu His Gly Met Leu Arg Ser Leu Leu
        3620            3625            3630

GTG TAC ATG CTT TTT CTG CTG GTG ACC CTG CTG GCC AGC TAT GGG GAT    10942
Val Tyr Met Leu Phe Leu Leu Val Thr Leu Leu Ala Ser Tyr Gly Asp
            3635            3640            3645

GCC TCA TGC CAT GGG CAC GCC TAC CGT CTG CAA AGC GCC ATC AAG CAG    10990
Ala Ser Cys His Gly His Ala Tyr Arg Leu Gln Ser Ala Ile Lys Gln
        3650            3655            3660

GAG CTG CAC AGC CGG GCC TTC CTG GCC ATC ACG CGG TCT GAG GAG CTC    11038
Glu Leu His Ser Arg Ala Phe Leu Ala Ile Thr Arg Ser Glu Glu Leu
    3665            3670            3675

TGG CCA TGG ATG GCC CAC GTG CTG CTG CCC TAC GTC CAC GGG AAC CAG    11086
Trp Pro Trp Met Ala His Val Leu Leu Pro Tyr Val His Gly Asn Gln
3680            3685            3690            3695

TCC AGC CCA GAG CTG GGG CCC CCA CGG CTG CGG CAG GTG CGG CTG CAG    11134
Ser Ser Pro Glu Leu Gly Pro Pro Arg Leu Arg Gln Val Arg Leu Gln
        3700            3705            3710

GAA GCA CTC TAC CCA GAC CCT CCC GGC CCC AGG GTC CAC ACG TGC TCG    11182
Glu Ala Leu Tyr Pro Asp Pro Pro Gly Pro Arg Val His Thr Cys Ser
            3715            3720            3725
```

FIG. 10EE

```
GCC GCA GGA GGC TTC AGC ACC AGC GAT TAC GAC GTT GGC TGG GAG AGT    11230
Ala Ala Gly Gly Phe Ser Thr Ser Asp Tyr Asp Val Gly Trp Glu Ser
        3730            3735            3740

CCT CAC AAT GGC TCG GGG ACG TGG GCC TAT TCA GCG CCG GAT CTG CTG    11278
Pro His Asn Gly Ser Gly Thr Trp Ala Tyr Ser Ala Pro Asp Leu Leu
        3745            3750            3755

GGG GCA TGG TCC TGG GGC TCC TGT GCC GTG TAT GAC AGC GGG GGC TAC    11326
Gly Ala Trp Ser Trp Gly Ser Cys Ala Val Tyr Asp Ser Gly Gly Tyr
3760            3765            3770            3775

GTG CAG GAG CTG GGC CTG AGC CTG GAG GAG AGC CGC GAC CGG CTG CGC    11374
Val Gln Glu Leu Gly Leu Ser Leu Glu Glu Ser Arg Asp Arg Leu Arg
        3780            3785            3790

TTC CTG CAG CTG CAC AAC TGG CTG GAC AAC AGG AGC CGC GCT GTG TTC    11422
Phe Leu Gln Leu His Asn Trp Leu Asp Asn Arg Ser Arg Ala Val Phe
        3795            3800            3805

CTG GAG CTC ACG CGC TAC AGC CCG GCC GTG GGG CTG CAC GCC GCC GTC    11470
Leu Glu Leu Thr Arg Tyr Ser Pro Ala Val Gly Leu His Ala Ala Val
        3810            3815            3820

ACG CTG CGC CTC GAG TTC CCG GCG GCC GGC CGC GCC CTG GCC GCC CTC    11518
Thr Leu Arg Leu Glu Phe Pro Ala Ala Gly Arg Ala Leu Ala Ala Leu
        3825            3830            3835
```

FIG. 10FF

```
AGC GTC CGC CCC TTT GCG CTG CGC CGC CTC AGC GCG GGC CTC TCG CTG              11566
Ser Val Arg Pro Phe Ala Leu Arg Arg Leu Ser Ala Gly Leu Ser Leu
3840             3845             3850             3855

CCT CTG CTC ACC TCG GTG TGC CTG CTG CTG TTC GCC GTG CAC TTC GCC              11614
Pro Leu Leu Thr Ser Val Cys Leu Leu Leu Phe Ala Val His Phe Ala
                 3860             3865             3870

GTG GCC GAG GCC CGT ACT TGG CAC AGG GAA GGG CGC TGG CGC GTG CTG              11662
Val Ala Glu Ala Arg Thr Trp His Arg Glu Gly Arg Trp Arg Val Leu
             3875             3880             3885

CGG CTC GGA GCC TGG GCG CGG TGG CTG CTG GTG GCG CTG ACG GCG GCC              11710
Arg Leu Gly Ala Trp Ala Arg Trp Leu Leu Val Ala Leu Thr Ala Ala
         3890             3895             3900

ACG GCA CTG GTA CGC CTC GCC CAG CTG GGT GCC GCT GAC CGC CAG TGG              11758
Thr Ala Leu Val Arg Leu Ala Gln Leu Gly Ala Ala Asp Arg Gln Trp
     3905             3910             3915

ACC CGT TTC GTG CGC GGC CGC CCG CGC CGC TTC ACT AGC TTC GAC CAG              11806
Thr Arg Phe Val Arg Gly Arg Pro Arg Arg Phe Thr Ser Phe Asp Gln
3920             3925             3930             3935

GTG GCG CAC GTG AGC TCC GCA GCC CGT GGC CTG GCG GCC TCG CTG CTC              11854
Val Ala His Val Ser Ser Ala Ala Arg Gly Leu Ala Ala Ser Leu Leu
                 3940             3945             3950

TTC CTG CTT TTG GTC AAG GCT GCC CAG CAC GTA CGC TTC GTG CGC CAG              11902
Phe Leu Leu Leu Val Lys Ala Ala Gln His Val Arg Phe Val Arg Gln
             3955             3960             3965
```

FIG. 10GG

```
TGG TCC GTC TTT GGC AAG ACA TTA TGC CGA GCT CTG CCA GAG CTC CTG     11950
Trp Ser Val Phe Gly Lys Thr Leu Cys Arg Ala Leu Pro Glu Leu Leu
        3970            3975            3980

GGG GTC ACC TTG GGC CTG GTG GTG CTC GGG GTA GCC TAC GCC CAG CTG     11998
Gly Val Thr Leu Gly Leu Val Val Leu Gly Val Ala Tyr Ala Gln Leu
        3985            3990            3995

GCC ATC CTG CTC GTG TCT TCC TGT GTG GAC TCC CTC TGG AGC GTG GCC     12046
Ala Ile Leu Leu Val Ser Ser Cys Val Asp Ser Leu Trp Ser Val Ala
4000            4005            4010            4015

CAG GCC CTG TTG GTG CTG TGC CCT GGG ACT GGG CTC TCT ACC CTG TGT     12094
Gln Ala Leu Leu Val Leu Cys Pro Gly Thr Gly Leu Ser Thr Leu Cys
        4020            4025            4030

CCT GCC GAG TCC TGG CAC CTG TCA CCC CTG CTG TGT GTG GGG CTC TGG     12142
Pro Ala Glu Ser Trp His Leu Ser Pro Leu Leu Cys Val Gly Leu Trp
        4035            4040            4045

GCA CTG CGG CTG TGG GGC GCC CTA CGG CTG GGG GCT GTT ATT CTC CGC     12190
Ala Leu Arg Leu Trp Gly Ala Leu Arg Leu Gly Ala Val Ile Leu Arg
        4050            4055            4060

TGG CGC TAC CAC GCC TTG CGT GGA GAG CTG TAC CGG CCG GCC TGG GAG     12238
Trp Arg Tyr His Ala Leu Arg Gly Glu Leu Tyr Arg Pro Ala Trp Glu
        4065            4070            4075
```

FIG. 10HH

```
CCC CAG GAC TAC GAG ATG GTG GAG TTG TTC CTG CGC AGG CTG CGC CTC      12286
Pro Gln Asp Tyr Glu Met Val Glu Leu Phe Leu Arg Arg Leu Arg Leu
4080            4085            4090            4095

TGG ATG GGC CTC AGC AAG GTC AAG GAG TTC CGC CAC AAA GTC CGC TTT      12334
Trp Met Gly Leu Ser Lys Val Lys Glu Phe Arg His Lys Val Arg Phe
            4100            4105            4110

GAA GGG ATG GAG CCG CTG CCC TCT CGC TCC TCC AGG GGC TCC AAG GTA      12382
Glu Gly Met Glu Pro Leu Pro Ser Arg Ser Ser Arg Gly Ser Lys Val
        4115            4120            4125

TCC CCG GAT GTG CCC CCA CCC AGC GCT GGC TCC GAT GCC TCG CAC CCC      12430
Ser Pro Asp Val Pro Pro Pro Ser Ala Gly Ser Asp Ala Ser His Pro
        4130            4135            4140

TCC ACC TCC TCC AGC CAG CTG GAT GGG CTG AGC GTG AGC CTG GGC CGG      12478
Ser Thr Ser Ser Ser Gln Leu Asp Gly Leu Ser Val Ser Leu Gly Arg
        4145            4150            4155

CTG GGG ACA AGG TGT GAG CCT GAG CCC TCC CGC CTC CAA GCC GTG TTC      12526
Leu Gly Thr Arg Cys Glu Pro Glu Pro Ser Arg Leu Gln Ala Val Phe
4160            4165            4170            4175

GAG GCC CTG CTC ACC CAG TTT GAC CGA CTC AAC CAG GCC ACA GAG GAC      12574
Glu Ala Leu Leu Thr Gln Phe Asp Arg Leu Asn Gln Ala Thr Glu Asp
            4180            4185            4190

GTC TAC CAG CTG GAG CAG CAG CTG CAC AGC CTG CAA GGC CGC AGG AGC      12622
Val Tyr Gln Leu Glu Gln Gln Leu His Ser Leu Gln Gly Arg Arg Ser
            4195            4200            4205
```

FIG. 10II

```
AGC CGG GCG CCC GCC GGA TCT TCC CGT GGC CCA TCC CCG GGC CTG CGG        12670
Ser Arg Ala Pro Ala Gly Ser Ser Arg Gly Pro Ser Pro Gly Leu Arg
        4210            4215            4220

CCA GCA CTG CCC AGC CGC CTT GCC CGG GCC AGT CGG GGT GTG GAC CTG        12718
Pro Ala Leu Pro Ser Arg Leu Ala Arg Ala Ser Arg Gly Val Asp Leu
        4225            4230            4235

GCC ACT GGC CCC AGC AGG ACA CCT TCG GGC CAA GAA CAA GGT CCA CCC        12766
Ala Thr Gly Pro Ser Arg Thr Pro Ser Gly Gln Glu Gln Gly Pro Pro
4240            4245            4250            4255

CAG CAG CAC TTA GTC CTC CTT CCT GGC GGG GGT GGG CCG TGG AGT CGG        12814
Gln Gln His Leu Val Leu Leu Pro Gly Gly Gly Gly Pro Trp Ser Arg
        4260            4265            4270

AGT GGA CAC CGC TCA GTA TTA CTT TCT GCC GCT GTC AAG GCC GAG GGC        12862
Ser Gly His Arg Ser Val Leu Leu Ser Ala Ala Val Lys Ala Glu Gly
        4275            4280            4285

CAG GCA GAA TGG CTG CAC GTA GGT TCC CCA GAG AGC AGG CAG GGG CAT        12910
Gln Ala Glu Trp Leu His Val Gly Ser Pro Glu Ser Arg Gln Gly His
        4290            4295            4300

CTG TCT GTC TGT GGG CTT CAG CAC TTT AAA GAG GCT GTG TGG CCA ACC        12958
Leu Ser Val Cys Gly Leu Gln His Phe Lys Glu Ala Val Trp Pro Thr
        4305            4310            4315
```

FIG. 10JJ

```
AGG ACC CAG GGT CCC CTC CCC AGC TCC CTT GGG AAG GAC ACA GCA GTA    13006
Arg Thr Gln Gly Pro Leu Pro Ser Ser Leu Gly Lys Asp Thr Ala Val
4320            4325            4330            4335

TTG GAC GGT TTC TAGCCTCTGA GATGCTAATT TATTTCCCCG AGTCCTCAGG        13058
Leu Asp Gly Phe

TACAGCGGGC TGTGCCCGGC CCACCCCCT GGGCAGATGT CCCCCACTGC TAAGGCTGCT   13118

GGCTTCAGGG AGGGTTAGCC TGCACCGCCG CCACCCTGCC CCTAAGTTAT TACCTCTCCA  13178

GTTCCTACCG TACTCCCTGC ACCGTCTCAC TGTGTGTCTC GTGTCAGTAA TTTATATGGT  13238

GTTAAAATGT GTATATTTTT GTATGTCACT ATTTTCACTA GGGCTGAGGG GCCTGCGCCC  13298

AGAGCTGGCC TCCCCCAACA CCTGCTGCGC TTGGTAGGTG TGGTGGCGTT ATGGCAGCCC  13358

GGCTGCTGCT TGGATGCGAG CTTGGCCTTG GCCCGGTGCT GGGGCACAG CTGTCTGCCA   13418

GGCACTCTCA TCACCCCAGA GGCCTTGTCA TCCTCCCTTG CCCCAGGCCA GGTAGCAAGA  13478

GAGCAGCGCC CAGGCCTGCT GGCATCAGGT CTGGGCAAGT AGCAGGACTA GGCATGTCAG  13538

AGGACCCCAG GGTGGTTAGA GGAAAAGACT CCTCCTGGGG GCTGGCTCCC AGGGTGGAGG  13598

AAGGTGACTG TGTGTGTGTG TGTGTGCGCG CGCGACGCGC GAGTGTGCTG TATGGCCCAG  13658

GCAGCCTCAA GGCCCTCGGA GCTGGCTGTG CCTGCTTCTG TGTACCACTT CTGTGGGCAT  13718

GGCCGCTTCT AGAGCCTCGA CACCCCCCA ACCCCCGCAC CAAGCAGACA AAGTCAATAA   13778

AAGAGCTGTC TGACTGCAAA AAAAAAAA                                    13807
```

FIG. 10KK

```
  1  GCACTGCAGCGCCAGCGTCCGAGCGGGCGGCCGAGCTCCCGGAGCGGCCTGGCCCCGAGC   60

61  CCCGAGCGGGCGTCGCTCAGCAGCAGGTCGCGGCCGCGCAGCCCCATCCAGCCCCGCGCC  120

121  CGCCATGCCGTCCGCGGGCCCCGCCTGAGCTGCGGTCTCCGCGCGCGGGCGGGCCTGGGG  180

181  ACGGCGGGGCCATGCGCGCGCTGCCCTAACGATGCCGCCCGCCGCGCCCGCCCGCCTGGC  240
  1                                     M  P  P  A  A  P  A  R  L  A   10

241  GCTGGCCCTGGGCCTGGGCCTGTGGCTCGGGGCGCTGGCGGGGGGCCCCGGGCGCGGCTG  300
 11   L  A  L  G  L  G  L  W  L  G  A  L  A  G  G  P  G  R  G  C   30
                                          ▲

301  CGGGCCCTGCGAGCCCCCCTGCCTCTGCGGCCCAGCGCCCCGGCGCCGCCTGCCGCGTCAA  360
 31   G  P  C  E  P  P  C  L  C  G  P  A  P  G  A  A  C  R  V  N   50
                                                                  *

361  CTGCTCGGGCCGCGGGCTGCGGACGCTCGGTCCCGCGCTGCGCATCCCCGCGGACGCCAC  420
 51   C  S  G  R  G  L  R  T  L  G  P  A  L  R  I  P  A  D  A  T   70

421  AGCGCTAGACGTCTCCCACAACCTGCTCCGGGCGCTGGACGTTGGGCTCCTGGCGAACCT  480
 71   A  L  D  V  S  H  N  L  L  R  A  L  D  V  G  L  L  A  N  L   90
                                                               *

481  CTCGGCGCTGGCAGAGCTGGATATAAGCAACAACAAGATTTCTACGTTAGAAGAAGGAAT  540
 91   S  A  L  A  E  L  D  I  S  N  N  K  I  S  T  L  E  E  G  I  110

541  ATTTGCTAATTTATTTAATTTAAGTGAAATAAACCTGAGTGGGAACCCGTTTGAGTGTGA  600
111   F  A  N  L  F  N  L  S  E  I  N  L  S  G  N  P  F  E  C  D  130
                     *                 *
```

FIG. 15A

```
601  CTGTGGCCTGGCGTGGCTGCCGCGATGGGCGGAGGAGCAGCAGGTGCGGGTGGTGCAGCC  660
131   C  G  L  A  W  L  P  R  W  A  E  E  Q  Q  V  R  V  V  Q  P  150

661  CGAGGCAGCCACGTGTGCTGGGCCTGGCTCCCTGGCTGGCCAGCCTCTGCTTGGCATCCC  720
151   E  A  A  T  C  A  G  P  G  S  L  A  G  Q  P  L  L  G  I  P  170

721  CTTGCTGGACAGTGGCTGTGGTGAGGAGTATGTCGCCTGCCTCCCTGACAACAGCTCAGG  780
171   L  L  D  S  G  C  G  E  E  Y  V  A  C  L  P  D  N  S  S  G  190
                                                      *
781  CACCGTGGCAGCAGTGTCCTTTTCAGCTGCCCACGAAGGCCTGCTTCAGCCAGAGGCCTG  840
191   T  V  A  A  V  S  F  S  A  A  H  E  G  L  L  Q  P  E  A  C  210

841  CAGCGCCTTCTGCTTCTCCACCGGCCAGGGCCTCGCAGCCCTCTCGGAGCAGGGCTGGTG  900
211   S  A  F  C  F  S  T  G  Q  G  L  A  A  L  S  E  Q  G  W  C  230

901  CCTGTGTGGGGCGGCCCAGCCCTCCAGTGCCTCCTTTGCCTGCCTGTCCCTCTGCTCCGG  960
231   L  C  G  A  A  Q  P  S  S  A  S  F  A  C  L  S  L  C  S  G  250

961  CCCCCCGCCACCTCCTGCCCCCACCTGTAGGGGCCCCACCCTCCTCCAGCACGTCTTCCC  1020
251   P  P  P  P  A  P  T  C  R  G  P  T  L  L  Q  H  V  F  P  270

1021 TGCCTCCCCAGGGGCCACCCTGGTGGGGCCCCACGGACCTCTGGCCTCTGGCCAGCTAGC  1080
271   A  S  P  G  A  T  L  V  G  P  H  G  P  L  A  S  G  Q  L  A  290

1081 AGCCTTCCACATCGCTGCCCCGCTCCCTGTCACTGCCACACGCTGGGACTTCGGAGACGG  1140
291   A  F  H  I  A  A  P  L  P  V  T  A  T  R  W  D  F  G  D  G  310

1141 CTCCGCCGAGGTGGATGCCGCTGGGCCGGCTGCCTCGCATCGCTATGTGCTGCCTGGGCG  1200
311   S  A  E  V  D  A  A  G  P  A  A  S  H  R  Y  V  L  P  G  R  330
```

FIG. 15B

```
1201  CTATCACGTGACGGCCGTGCTGGCCCTGGGGGCCGGCTCAGCCCTGCTGGGGACAGACGT  1260
 331   Y   H   V   T   A   V   L   A   L   G   A   G   S   A   L   L   G   T   D   V   350

1261  GCAGGTGGAAGCGGCACCTGCCGCCCTGGAGCTCGTGTGCCCGTCCTCGGTGCAGAGTGA  1320
 351   Q   V   E   A   A   P   A   A   L   E   L   V   C   P   S   S   V   Q   S   D   370

1321  CGAGAGCCTTGACCTCAGCATCCAGAACCGCGGTGGTTCAGGCCTGGAGGCCGCCTACAG  1380
 371   E   S   L   D   L   S   I   Q   N   R   G   G   S   G   L   E   A   A   Y   S   390

1381  CATCGTGGCCCTGGGCGAGGAGCCGGCCCGAGCGGTGCACCCGCTCTGCCCCTCGGACAC  1440
 391   I   V   A   L   G   E   E   P   A   R   A   V   H   P   L   C   P   S   D   T   410

1441  GGAGATCTTCCCTGGCAACGGGCACTGCTACCGCCTGGTGGTGGAGAAGGCGGCCTGGCT  1500
 411   E   I   F   P   G   N   G   H   C   Y   R   L   V   V   E   K   A   A   W   L   430

1501  GCAGGCGCAGGAGCAGTGTCAGGCCTGGGCCGGGGCCGCCCTGGCAATGGTGGACAGTCC  1560
 431   Q   A   Q   E   Q   C   Q   A   W   A   G   A   A   L   A   M   V   D   S   P   450

1561  CGCCGTGCAGCGCTTCCTGGTCTCCCGGGTCACCAGGAGCCTAGACGTGTGGATCGGCTT  1620
 451   A   V   Q   R   F   L   V   S   R   V   T   R   S   L   D   V   W   I   G   F   470

1621  CTCGACTGTGCAGGGGGTGGAGGTGGGCCCAGCGCCGCAGGGCGAGGCCTTCAGCCTGGA  1680
 471   S   T   V   Q   G   V   E   V   G   P   A   P   Q   G   E   A   F   S   L   E   490

1681  GAGCTGCCAGAACTGGCTGCCCGGGGAGCCACACCCAGCCACAGCCGAGCACTGCGTCCG  1740
 491   S   C   Q   N   W   L   P   G   E   P   H   P   A   T   A   E   H   C   V   R   510

1741  GCTCGGGCCCACCGGGTGGTGTAACACCGACCTGTGCTCAGCGCCGCACAGCTACGTCTG  1800
 511   L   G   P   T   G   W   C   N   T   D   L   C   S   A   P   H   S   Y   V   C   530
```

FIG. 15C

```
1801  CGAGCTGCAGCCCGGAGGCCCAGTGCAGGATGCCGAGAACCTCCTCGTGGGAGCGCCCAG  1860
 531    E  L  Q  P  G  G  P  V  Q  D  A  E  N  L  L  V  G  A  P  S   550

1861  TGGGGACCTGCAGGGACCCCTGACGCCTCTGGCACAGCAGGACGGCCTCTCAGCCCCGCA  1920
 551    G  D  L  Q  G  P  L  T  P  L  A  Q  Q  D  G  L  S  A  P  H   570

1921  CGAGCCCGTGGAGGTCATGGTATTCCCGGGCCTGCGTCTGAGCCGTGAAGCCTTCCTCAC  1980
 571    E  P  V  E  V  M  V  F  P  G  L  R  L  S  R  E  A  F  L  T   590

1981  CACGGCCGAATTTGGGACCCAGGAGCTCCGGCGGCCCGCCCAGCTGCGGCTGCAGGTGTA  2040
 591    T  A  E  F  G  T  Q  E  L  R  R  P  A  Q  L  R  L  Q  V  Y   610

2041  CCCGGCTCCTCAGCACAGCAGGGACCCCGGAGAACGGCAGCGAGCCTGAGAGCAGGTCCCC  2100
 611    R  L  L  S  T  A  G  T  P  E  N  G  S  E  P  E  S  R  S  P   630
                                    *
2101  GGACAACAGGACCCAGCTGGCCCCCGCGTGCATGCCAGGGGGACGCTGGTGCCCTGGAGC  2160
 631    D  N  R  T  Q  L  A  P  A  C  M  P  G  G  R  W  C  P  G  A   650
         *
2161  CAACATCTGCTTGCCGCTGGACGCCTCTTGCCACCCCCAGGCCTGCGCCAATGGCTGCAC  2220
 651    N  I  C  L  P  L  D  A  S  C  H  P  Q  A  C  A  N  G  C  T   670

2221  GTCAGGGCCAGGGCTACCCGGGGCCCCCTATGCGCTATGGAGAGAGTTCCTCTTCTCCGT  2280
 671    S  G  P  G  L  P  G  A  P  Y  A  L  W  R  E  F  L  F  S  V   690

2281  TGCCGCGGGGCCCCCCGCGCAGTACTCGGTCACCCTCCACGGCCAGGATGTCCTCATGCT  2340
 691    A  A  G  P  P  A  Q  Y  S  V  T  L  H  G  Q  D  V  L  M  L   710

2341  CCCTGGTGACCTCGTTGGCTTGCAGCACGACGCTGGCCCTGGCGCCCTCCTGCACTGCTC  2400
 711    P  G  D  L  V  G  L  Q  H  D  A  G  P  G  A  L  L  H  C  S   730
```

FIG. 15D

```
2401  GCCGGCTCCCGGCCACCCTGGTCCCCAGGCCCCGTACCTCTCCGCCAACGCCTCGTCATG  2460
 731   P  A  P  G  H  P  G  P  Q  A  P  Y  L  S  A  N  A  S  S  W   750
                                                         *

2461  GCTGCCCCACTTGCCAGCCCAGCTGGAGGGCACTTGGGCCTGCCCTGCCTGTGCCCTGCG  2520
 751   L  P  H  L  P  A  Q  L  E  G  T  W  A  C  P  A  C  A  L  R   770

2521  GCTGCTTGCAGCCACGGAACAGCTCACCGTGCTGCTGGGCTTGAGGCCCAACCCTGGACT  2580
 771   L  L  A  A  T  E  Q  L  T  V  L  L  G  L  R  P  N  P  G  L   790

2581  GCGGATGCCTGGGCGCTATGAGGTCCGGGCAGAGGTGGGCAATGGCGTGTCCAGGCACAA  2640
 791   R  M  P  G  R  Y  E  V  R  A  E  V  G  N  G  V  S  R  H  N   810
                                                               *

2641  CCTCTCCTGCAGCTTTGACGTGGTCTCCCCAGTGGCTGGGCTGCGGGTCATCTACCCTGC  2700
 811   L  S  C  S  F  D  V  V  S  P  V  A  G  L  R  V  I  Y  P  A   830

2701  CCCCCGCGACGGCCGCCTCTACGTGCCCACCAACGGCTCAGCCTTGGTGCTCCAGGTGGA  2760
 831   P  R  D  G  R  L  Y  V  P  T  N  G  S  A  L  V  L  Q  V  D   850
                                             *

2761  CTCTGGTGCCAACGCCACGGCCACGGCTCGCTGGCCTGGGGGCAGTGTCAGCGCCCGCTT  2820
 851   S  G  A  N  A  T  A  T  A  R  W  P  G  G  S  V  S  A  R  F   870
             *

2821  TGAGAATGTCTGCCCTGCCCTGGTGGCCACCTTCGTGCCCGGCTGCCCCTGGGAGACCAA  2880
 871   E  N  V  C  P  A  L  V  A  T  F  V  P  G  C  P  W  E  T  N   890
                                                               *

2881  CGATACCCTGTTCTCAGTGGTAGCACTGCCGTGGCTCAGTGAGGGGGAGCACGTGGTGGA  2940
 891   D  T  L  F  S  V  V  A  L  P  W  L  S  E  G  E  H  V  V  D   910

2941  CGTGGTGGTGGAAAACAGCGCCAGCCGGGCCAACCTCAGCCTGCGGGTGACGGCGGAGGA  3000
 911   V  V  V  E  N  S  A  S  R  A  N  L  S  L  R  V  T  A  E  E   930
                            *

3001  GCCCATCTGTGGCCTCCGCGCCACGCCCAGCCCCGAGGCCCGTGTACTGCAGGGAGTCCT  3060
 931   P  I  C  G  L  R  A  T  P  S  P  E  A  R  V  L  Q  G  V  L   950
```

FIG. 15E

```
3061  AGTGAGGTACAGCCCCGTGGTGGAGGCCGGCTCGGACATGGTCTTCCGGTGGACCATCAA  3120
 951   V  R  Y  S  P  V  V  E  A  G  S  D  M  V  F  R  W  T  I  N   970

3121  CGACAAGCAGTCCCTGACCTTCCAGAACGTGGTCTTCAATGTCATTTATCAGAGCGCGGC  3180
 971   D  K  Q  S  L  T  F  Q  N  V  V  F  N  V  I  Y  Q  S  A  A   990

3181  GGTCTTCAAGCTCTCACTGACGGCCTCCAACCACGTGAGCAACGTCACCGTGAACTACAA  3240
 991   V  F  K  L  S  L  T  A  S  N  H  V  S  N  V  T  V  N  Y  N  1010
                                          *

3241  CGTAACCGTGGAGCGGATGAACAGGATGCAGGGTCTGCAGGTCTCCACAGTGCCGGCCGT  3300
1011   V  T  V  E  R  M  N  R  M  Q  G  L  Q  V  S  T  V  P  A  V  1030

3301  GCTGTCCCCCAATGCCACACTGGTACTGACGGGTGGTGTGCTGGTGGACTCAGCTGTGGA  3360
1031   L  S  P  N  A  T  L  V  L  T  G  G  V  L  V  D  S  A  V  E  1050
             *

3361  GGTGGCCTTCCTGTGGAACTTTGGGGATGGGGAGCAGGCCCTCCACCAGTTCCAGCCTCC  3420
1051   V  A  F  L  W  N  F  G  D  G  E  Q  A  L  H  Q  F  Q  P  P  1070

3421  GTACAACGAGTCCTTCCCGGTTCCAGACCCCTCGGTGGCCCAGGTGCTGGTGGAGCACAA  3480
1071   Y  N  E  S  F  P  V  P  D  P  S  V  A  Q  V  L  V  E  H  N  1090
          *

3481  TGTCATGCACACCTACGCTGCCCCAGGTGAGTACCTCCTGACCGTGCTGGCATCTAATGC  3540
1091   V  M  H  T  Y  A  A  P  G  E  Y  L  L  T  V  L  A  S  N  A  1110

3541  CTTCGAGAACCTGACGCAGCAGGTGCCTGTGAGCGTGCGCGCCTCCCTGCCCTCCGTGGC  3600
1111   F  E  N  L  T  Q  Q  V  P  V  S  V  R  A  S  L  P  S  V  A  1130
                *
```

FIG. 15F

```
3601  TGTGGGTGTGAGTGACGGCGTCCTGGTGGCCGGCCGGCCCGTCACCTTCTACCCGCACCC  3660
1131   V   G   V   S   D   G   V   L   V   A   G   R   P   V   T   F   Y   P   H   P   1150

3661  GCTGCCCTCGCCTGGGGGTGTTCTTTACACGTGGGACTTCGGGGACGGCTCCCCTGTCCT  3720
1151   L   P   S   P   G   G   V   L   Y   T   W   D   F   G   D   G   S   P   V   L   1170

3721  GACCCAGAGCCAGCCGGCTGCCAACCACACCTATGCCTCGAGGGGCACCTACCACGTGCG  3780
1171   T   Q   S   Q   P   A   A   N   H   T   Y   A   S   R   G   T   Y   H   V   R   1190
                               *

3781  CCTGGAGGTCAACAACACGGTGAGCGGTGCGGCGGCCCAGGCGGATGTGCGCGTCTTTGA  3840
1191   L   E   V   N   N   T   V   S   G   A   A   A   Q   A   D   V   R   V   F   E   1210
               *

3841  GGAGCTCCGCGGACTCAGCGTGGACATGAGCCTGGCCGTGGAGCAGGGCGCCCCCGTGGT  3900
1211   E   L   R   G   L   S   V   D   M   S   L   A   V   E   Q   G   A   P   V   V   1230

3901  GGTCAGCGCCGCGGTGCAGACGGGCGACAACATCACGTGGACCTTCGACATGGGGGACGG  3960
1231   V   S   A   A   V   Q   T   G   D   N   I   T   W   T   F   D   M   G   D   G   1250
                                       *

3961  CACCGTGCTGTCGGGCCCGGAGGCAACAGTGGAGCATGTGTACCTGCGGGCACAGAACTG  4020
1251   T   V   L   S   G   P   E   A   T   V   E   H   V   Y   L   R   A   Q   N   C   1270
                                                                           *

4021  CACAGTGACCGTGGGTGCGGCCAGCCCCGCCGGCCACCTGGCCCGGAGCCTGCACGTGCT  4080
1271   T   V   T   V   G   A   A   S   P   A   G   H   L   A   R   S   L   H   V   L   1290

4081  GGTCTTCGTCCTGGAGGTGCTGCGCGTTGAACCCGCCGCCTGCATCCCCACGCAGCCTGA  4140
1291   V   F   V   L   E   V   L   R   V   E   P   A   A   C   I   P   T   Q   P   D   1310

4141  CGCGCGGCTCACGGCCTACGTCACCGGGAACCCGGCCCACTACCTCTTCGACTGGACCTT  4200
1311   A   R   L   T   A   Y   V   T   G   N   P   A   H   Y   L   F   D   W   T   F   1330
```

FIG. 15G

```
4201  CGGGGATGGCTCCTCCAACACGACCGTGCGGGGGTGCCCGACGGTGACACACAACTTCAC  4260
1331   G   D   G   S   S   N   T   T   V   R   G   C   P   T   V   T   H   N   F   T   1350
                       *                                               *
4261  GCGGAGCGGCACGTTCCCCCTGGCGCTGGTGCTGTCCAGCCGCGTGAACAGGGCGCATTA  4320
1351   R   S   G   T   F   P   L   A   L   V   L   S   S   R   V   N   R   A   H   Y   1370

4321  CTTCACCAGCATCTGCGTGGAGCCAGAGGTGGGCAACGTCACCCTGCAGCCAGAGAGGCA  4380
1371   F   T   S   I   C   V   E   P   E   V   G   N   V   T   L   Q   P   E   R   Q   1390
                                                       *
4381  GTTTGTGCAGCTCGGGGACGAGGCCTGGCTGGTGGCATGTGCCTGGCCCCCGTTCCCCTA  4440
1391   F   V   Q   L   G   D   E   A   W   L   V   A   C   A   W   P   P   F   P   Y   1410

4441  CCGCTACACCTGGGACTTTGGCACCGAGGAAGCCGCCCCCACCCGTGCCAGGGGCCCTGA  4500
1411   R   Y   T   W   D   F   G   T   E   E   A   A   P   T   R   A   R   G   P   E   1430

4501  GGTGACGTTCATCTACCGAGACCCAGGCTCCTATCTTGTGACAGTCACCGCGTCCAACAA  4560
1431   V   T   F   I   Y   R   D   P   G   S   Y   L   V   T   V   T   A   S   N   N   1450
                                                                               *
4561  CATCTCTGCTGCCAATGACTCAGCCCTGGTGGAGGTGCAGGAGCCCGTGCTGGTCACCAG  4620
1451   I   S   A   A   N   D   S   A   L   V   E   V   Q   E   P   V   L   V   T   S   1470
                   *
4621  CATCAAGGTCAATGGCTCCCTTGGGCTGGAGCTGCAGCAGCCGTACCTGTTCTCTGCTGT  4680
1471   I   K   V   N   G   S   L   G   L   E   L   Q   Q   P   Y   L   F   S   A   V   1490
                   *
4681  GGGCCGTGGGCGCCCCGCCAGCTACCTGTGGGATCTGGGGGACGGTGGGTGGCTCGAGGG  4740
1491   G   R   G   R   P   A   S   Y   L   W   D   L   G   D   G   G   W   L   E   G   1510

4741  TCCGGAGGTCACCCACGCTTACAACAGCACAGGTGACTTCACCGTTAGGGTGGCCGGCTG  4800
1511   P   E   V   T   H   A   Y   N   S   T   G   D   F   T   V   R   V   A   G   W   1530
                               *
```

FIG. 15H

```
4801  GAATGAGGTGAGCCGCAGCGAGGCCTGGCTCAATGTGACGGTGAAGCGGCGCGTGCGGGG  4860
1531   N  E  V  S  R  S  E  A  W  L  N  V  T  V  K  R  R  V  R  G   1550
                                      *
4861  GCTCGTCGTCAATGCAAGCCGCACGGTGGTGCCCCTGAATGGGAGCGTGAGCTTCAGCAC  4920
1551   L  V  V  N  A  S  R  T  V  V  P  L  N  G  S  V  S  F  S  T   1570
             *                                *
4921  GTCGCTGGAGGCCGGCAGTGATGTGCGCTATTCCTGGGTGCTCTGTGACCGCTGCACGCC  4980
1571   S  L  E  A  G  S  D  V  R  Y  S  W  V  L  C  D  R  C  T  P   1590

4981  CATCCCTGGGGGTCCTACCATCTCTTACACCTTCCGCTCCGTGGGCACCTTCAATATCAT  5040
1591   I  P  G  G  P  T  I  S  Y  T  F  R  S  V  G  T  F  N  I  I   1610

5041  CGTCACGGCTGAGAACGAGGTGGGCTCCGCCCAGGACAGCATCTTCGTCTATGTCCTGCA  5100
1611   V  T  A  E  N  E  V  G  S  A  Q  D  S  I  F  V  Y  V  L  Q   1630

5101  GCTCATAGAGGGGCTGCAGGTGGTGGGCGGTGGCCGCTACTTCCCCACCAACCACACGGT  5160
1631   L  I  E  G  L  Q  V  V  G  G  G  R  Y  F  P  T  N  H  T  V   1650
                                                     *
5161  ACAGCTGCAGGCCGTGGTTAGGGATGGCACCAACGTCTCCTACAGCTGGACTGCCTGGAG  5220
1651   Q  L  Q  A  V  V  R  D  G  T  N  V  S  Y  S  W  T  A  W  R   1670
                            *
5221  GGACAGGGGCCCGGCCCTGGCCGGCAGCGGCAAAGGCTTCTCGCTCACCGTGCTCGAGGC  5280
1671   D  R  G  P  A  L  A  G  S  G  K  G  F  S  L  T  V  L  E  A   1690

5281  CGGCACCTACCATGTGCAGCTGCGGGCCACCAACATGCTGGGCAGCGCCTGGGCCGACTG  5340
1691   G  T  Y  H  V  Q  L  R  A  T  N  M  L  G  S  A  W  A  D  C   1710

5341  CACCATGGACTTCGTGGAGCCTGTGGGGTGGCTGATGGTGACCGCCTCCCCGAACCCAGC  5400
1711   T  M  D  F  V  E  P  V  G  W  L  M  V  T  A  S  P  N  P  A   1730
```

FIG. 15I

```
5341  CACCATGGACTTCGTGGAGCCTGTGGGGTGGCTGATGGTGACCGCCTCCCCGAACCCAGC  5400
1711   T   M   D   F   V   E   P   V   G   W   L   M   V   T   A   S   P   N   P   A   1730

5401  TGCCGTCAACACAAGCGTCACCCTCAGTGCCGAGCTGGCTGGTGGCAGTGGTGTCGTATA  5460
1731   A   V   N   T   S   V   T   L   S   A   E   L   A   G   G   S   G   V   V   Y   1750
               *

5461  CACTTGGTCCTTGGAGGAGGGGCTGAGCTGGGAGACCTCCGAGCCATTTACCACCCATAG  5520
1751   T   W   S   L   E   E   G   L   S   W   E   T   S   E   P   F   T   T   H   S   1770

5521  CTTCCCCACACCCGGCCTGCACTTGGTCACCATGACGGCAGGGAACCCGCTGGGCTCAGC  5580
1771   F   P   T   P   G   L   H   L   V   T   M   T   A   G   N   P   L   G   S   A   1790

5581  CAACGCCACCGTGGAAGTGGATGTGCAGGTGCCTGTGAGTGGCCTCAGCATCAGGGCCAG  5640
1791   N   A   T   V   E   V   D   V   Q   V   P   V   S   G   L   S   I   R   A   S   1810
           *

5641  CGAGCCCGGAGGCAGCTTCGTGGCGGCCGGGTCCTCTGTGCCCTTTTGGGGGCAGCTGGC  5700
1811   E   P   G   G   S   F   V   A   A   G   S   S   V   P   F   W   G   Q   L   A   1830

5701  CACGGGCACCAATGTGAGCTGGTGCTGGGCTGTGCCCGGCGGCAGCAGCAAGCGTGGCCC  5760
1831   T   G   T   N   V   S   W   C   W   A   V   P   G   G   S   S   K   R   G   P   1850
                           *

5761  TCATGTCACCATGGTCTTCCCGGATGCTGGCACCTTCTCCATCCGGCTCAATGCCTCCAA  5820
1851   H   V   T   M   V   F   P   D   A   G   T   F   S   I   R   L   N   A   S   N   1870
                                                                           *

5821  CGCAGTCAGCTGGGTCTCAGCCACGTACAACCTCACGGCGGAGGAGCCCATCGTGGGCCT  5880
1871   A   V   S   W   V   S   A   T   Y   N   L   T   A   E   E   P   I   V   G   L   1890
                                   *

5881  GGTGCTGTGGGCCAGCAGCAAGGTGGTGGCGCCCGGGCAGCTGGTCCATTTTCAGATCCT  5940
1891   V   L   W   A   S   S   K   V   V   A   P   G   Q   L   V   H   F   Q   I   L   1910

5941  GCTGGCTGCCGGCTCAGCTGTCACCTTCCGCCTGCAGGTCGGCGGGGCCAACCCCGAGGT  6000
1911   L   A   A   G   S   A   V   T   F   R   L   Q   V   G   G   A   N   P   E   V   1930
```

FIG. 15J

```
6001  GCTCCCCGGGCCCCGTTTCTCCCACAGCTTCCCCCGCGTCGGAGACCACGTGGTGAGCGT  6060
1931   L  P  G  P  R  F  S  H  S  F  P  R  V  G  D  H  V  V  S  V   1950

6061  GCGGGGCAAAAACCACGTGAGCTGGGCCCAGGCGCAGGTGCGCATCGTGGTGCTGGAGGC  6120
1951   R  G  K  N  H  V  S  W  A  Q  A  Q  V  R  I  V  V  L  E  A   1970

6121  CGTGAGTGGGCTGCAGATGCCCAACTGCTGCGAGCCTGGCATCGCCACGGGCACTGAGAG  6180
1971   V  S  G  L  Q  M  P  N  C  C  E  P  G  I  A  T  G  T  E  R   1990

6181  GAACTTCACAGCCCGCGTGCAGCGCGGCTCTCGGGTCGCCTACGCCTGGTACTTCTCGCT  6240
1991   N  F  T  A  R  V  Q  R  G  S  R  V  A  Y  A  W  Y  F  S  L   2010
       *
6241  GCAGAAGGTCCAGGGCGACTCGCTGGTCATCCTGTCGGGCCGCGACGTCACCTACACGCC  6300
2011   Q  K  V  Q  G  D  S  L  V  I  L  S  G  R  D  V  T  Y  T  P   2030

6301  CGTGGCCGCGGGGCTGTTGGAGATCCAGGTGCGCGCCTTCAACGCCCTGGGCAGTGAGAA  6360
2031   V  A  A  G  L  L  E  I  Q  V  R  A  F  N  A  L  G  S  E  N   2050
                                                              *
6361  CCGCACGCTGGTGCTGGAGGTTCAGGACGCCGTCCAGTATGTGGCCCTGCAGAGCGGCCC  6420
2051   R  T  L  V  L  E  V  Q  D  A  V  Q  Y  V  A  L  Q  S  G  P   2070

6421  CTGCTTCACCAACCGCTCGGCGCAGTTTGAGGCCGCCACCAGCCCCAGCCCCCGGCGTGT  6480
2071   C  F  T  N  R  S  A  Q  F  E  A  A  T  S  P  S  P  R  R  V   2090
             *
6481  GGCCTACCACTGGGACTTTGGGGATGGGTCGCCAGGGCAGGACACAGATGAGCCCAGGGC  6540
2091   A  Y  H  W  D  F  G  D  G  S  P  G  Q  D  T  D  E  P  R  A   2110

6541  CGAGCACTCCTACCTGAGGCCTGGGGACTACCGCGTGCAGGTGAACGCCTCCAACCTGGT  6600
2111   E  H  S  Y  L  R  P  G  D  Y  R  V  Q  V  N  A  S  N  L  V   2130
                                                  *
```

FIG. 15K

```
6601 GAGCTTCTTCGTGGCGCAGGCCACGGTGACCGTCCAGGTGCTGGCCTGCCGGGAGCCGGA 6660
2131  S  F  F  V  A  Q  A  T  V  T  V  Q  V  L  A  C  R  E  P  E  2150

6661 GGTGGACGTGGTCCTGCCCCTGCAGGTGCTGATGCGGCGATCACAGCGCAACTACTTGGA 6720
2151  V  D  V  V  L  P  L  Q  V  L  M  R  R  S  Q  R  N  Y  L  E  2170

6721 GGCCCACGTTGACCTGCGCGACTGCGTCACCTACCAGACTGAGTACCGCTGGGAGGTGTA 6780
2171  A  H  V  D  L  R  D  C  V  T  Y  Q  T  E  Y  R  W  E  V  Y  2190

6781 TCGCACCGCCAGCTGCCAGCGGCCGGGGCGCCCAGCGCGTGTGGCCCTGCCCGGCGTGGA 6840
2191  R  T  A  S  C  Q  R  P  G  R  P  A  R  V  A  L  P  G  V  D  2210

6841 CGTGAGCCGGCCTCGGCTGGTGCTGCCGCGGCTGGCGCTGCCTGTGGGGCACTACTGCTT 6900
2211  V  S  R  P  R  L  V  L  P  R  L  A  L  P  V  G  H  Y  C  F  2230

6901 TGTGTTTGTCGTGTCATTTGGGGACACGCCACTGACACAGAGCATCCAGGCCAATGTGAC 6960
2231  V  F  V  V  S  F  G  D  T  P  L  T  Q  S  I  Q  A  N  V  T  2250
                                                          *
6961 GGTGGCCCCCGAGCGCCTGGTGCCCATCATTGAGGGTGGCTCATACCGCGTGTGGTCAGA 7020
2251  V  A  P  E  R  L  V  P  I  I  E  G  G  S  Y  R  V  W  S  D  2270

7021 CACACGGGACCTGGTGCTGGATGGGAGCGAGTCCTACGACCCCAACCTGGAGGACGGCGA 7080
2271  T  R  D  L  V  L  D  G  S  E  S  Y  D  P  N  L  E  D  G  D  2290

7081 CCAGACGCCGCTCAGTTTCCACTGGGCCTGTGTGGCTTCGACACAGAGGGAGGCTGGCGG 7140
2291  Q  T  P  L  S  F  H  W  A  C  V  A  S  T  Q  R  E  A  G  G  2310

7141 GTGTGCGCTGAACTTTGGGCCCCGCGGGAGCAGCACGGTCACCATTCCACGGGAGCGGCT 7200
2311  C  A  L  N  F  G  P  R  G  S  S  T  V  T  I  P  R  E  R  L  2330
```

FIG. 15L

```
7201  GGCGGCTGGCGTGGAGTACACCTTCAGCCTGACCGTGTGGAAGGCCGGCCGCAAGGAGGA  7260
2331   A  A  G  V  E  Y  T  F  S  L  T  V  W  K  A  G  R  K  E  E   2350

7261  GGCCACCAACCAGACGGTGCTGATCCGGAGTGGCCGGGTGCCCATTGTGTCCTTGGAGTG  7320
2351   A  T  N  Q  T  V  L  I  R  S  G  R  V  P  I  V  S  L  E  C   2370
          *

7321  TGTGTCCTGCAAGGCACAGGCCGTGTACGAAGTGAGCCGCAGCTCCTACGTGTACTTGGA  7380
2371   V  S  C  K  A  Q  A  V  Y  E  V  S  R  S  S  Y  V  Y  L  E   2390

7381  GGGCCGCTGCCTCAATTGCAGCAGCGGCTCCAAGCGAGGGCGGTGGGCTGCACGTACGTT  7440
2391   G  R  C  L  N  C  S  S  G  S  K  R  G  R  W  A  A  R  T  F   2410
                *

7441  CAGCAACAAGACGCTGGTGCTGGATGAGACCACCACATCCACGGGCAGTGCAGGCATGCG  7500
2411   S  N  K  T  L  V  L  D  E  T  T  T  S  T  G  S  A  G  M  R   2430
       *

7501  ACTGGTGCTGCGGCGGGGCGTGCTGCGGGACGGCGAGGGATACACCTTCACGCTCACGGT  7560
2431   L  V  L  R  R  G  V  L  R  D  G  E  G  Y  T  F  T  L  T  V   2450

7561  GCTGGGCCGCTCTGGCGAGGAGGAGGGCTGCGCCTCCATCCGCCTGTCCCCCAACCGCCC  7620
2451   L  G  R  S  G  E  E  E  G  C  A  S  I  R  L  S  P  N  R  P   2470

7621  GCCGCTGGGGGGCTCTTGCCGCCTCTTCCCACTGGGCGCTGTGCACGCCCTCACCACCAA  7680
2471   P  L  G  G  S  C  R  L  F  P  L  G  A  V  H  A  L  T  T  K   2490

7681  GGTGCACTTCGAATGCACGGGCTGGCATGACGCGGAGGATGCTGGCGCCCCGCTGGTGTA  7740
2491   V  H  F  E  C  T  G  W  H  D  A  E  D  A  G  A  P  L  V  Y   2510

7741  CGCCCTGCTGCTGCGGCGCTGTCGCCAGGGCCACTGCGAGGAGTTCTGTGTCTACAAGGG  7800
2511   A  L  L  L  R  R  C  R  Q  G  H  C  E  E  F  C  V  Y  K  G   2530
```

FIG. 15M

```
7801 CAGCCTCTCCAGCTACGGAGCCGTGCTGCCCCCGGGTTTCAGGCCACACTTCGAGGTGGG  7860
2531  S  L  S  S  Y  G  A  V  L  P  P  G  F  R  P  H  F  E  V  G   2550

7861 CCTGGCCGTGGTGGTGCAGGACCAGCTGGGAGCCGCTGTGGTCGCCCTCAACAGGTCTTT  7920
2551  L  A  V  V  V  Q  D  Q  L  G  A  A  V  V  A  L  N  R  S  L   2570
                                                             *

7921 GGCCATCACCCTCCCAGAGCCCAACGGCAGCGCAACGGGGCTCACAGTCTGGCTGCACGG  7980
2571  A  I  T  L  P  E  P  N  G  S  A  T  G  L  T  V  W  L  H  G   2590
                        *        ‾‾‾‾‾‾‾‾‾‾‾‾‾‾‾‾‾‾‾‾‾‾‾‾‾‾‾‾‾‾
                                                         TM1

7981 GCTCACCGCTAGTGTGCTCCCAGGGCTGCTGCGGCAGGCCGATCCCCAGCACGTCATCGA  8040
2591  L  T  A  S  V  L  P  G  L  L  R  Q  A  D  P  Q  H  V  I  E   2610
     ‾‾‾‾‾‾‾‾‾‾‾‾‾‾‾‾‾‾‾‾‾‾‾‾‾‾‾‾‾

8041 GTACTCGTTGGCCCTGGTCACCGTGCTGAACGAGTACGAGCGGGCCCTGGACGTGGCGGC  8100
2611  Y  S  L  A  L  V  T  V  L  N  E  Y  E  R  A  L  D  V  A  A   2630

8101 AGAGCCCAAGCACGAGCGGCAGCACCGAGCCCAGATACGCAAGAACATCACGGAGACTCT  8160
2631  E  P  K  H  E  R  Q  H  R  A  Q  I  R  K  N  I  T  E  T  L   2650
                                                 *

8161 GGTGTCCCTGAGGGTCCACACTGTGGATGACATCCAGCAGATCGCTGCTGCGCTGGCCCA  8220
2651  V  S  L  R  V  H  T  V  D  D  I  Q  Q  I  A  A  A  L  A  Q   2670

8221 GTGCATGGGGCCCAGCAGGGAGCTCGTATGCCGCTCGTGCCTGAAGCAGACGCTGCACAA  8280
2671  C  M  G  P  S  R  E  L  V  C  R  S  C  L  K  Q  T  L  H  K   2690

8281 GCTGGAGGCCATGATGCTCATCCTGCAGGCAGAGACCACCGCGGGCACCGTGACGCCCAC  8340
2691  L  E  A  M  M  L  I  L  Q  A  E  T  T  A  G  T  V  T  P  T   2710
           ‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾
                                 TM2
```

FIG. 15N

```
8341  CGCCATCGGAGACAGCATCCTCAACATCACAGGAGACCTCATCCACCTGGCCAGCTCGGA  8400
2711   A   I   G   D   S   I   L   N   I   T   G   D   L   I   H   L   A   S   S   D   2730
       ___ ___ ___                       *

8401  CGTGCGGGCACCACAGCCCTCAGAGCTGGGAGCCGAGTCACCATCTCGGATGGTGGCGTC  8460
2731   V   R   A   P   Q   P   S   E   L   G   A   E   S   P   S   R   M   V   A   S   2750

8461  CCAGGCCTACAACCTGACCTCTGCCCTCATGCGCATCCTCATGCGCTCCCGCGTGCTCAA  8520
2751   Q   A   Y   N   L   T   S   A   L   M   R   I   L   M   R   S   R   V   L   N   2770
                   *

8521  CGAGGAGCCCCTGACGCTGGCGGGCGAGGAGATCGTGGCCCAGGGCAAGCGCTCGGACCC  8580
2771   E   E   P   L   T   L   A   G   E   E   I   V   A   Q   G   K   R   S   D   P   2790

8581  GCGGAGCCTGCTGTGCTATGGCGGCGCCCCAGGGCCTGGCTGCCACTTCTCCATCCCCGA  8640
2791   R   S   L   L   C   Y   G   G   A   P   G   P   G   C   H   F   S   I   P   E   2810

8641  GGCTTTCAGCGGGGCCCTGGCCAACCTCAGTGACGTGGTGCAGCTCATCTTTCTGGTGGA  8700
2811   A   F   S   G   A   L   A   N   L   S   D   V   V   Q   L   I   F   L   V   D   2830
                       *

8701  CTCCAATCCCTTTCCCTTTGGCTATATCAGCAACTACACCGTCTCCACCAAGGTGGCCTC  8760
2831   S   N   P   F   P   F   G   Y   I   S   N   Y   T   V   S   T   K   V   A   S   2850
                                       *

8761  GATGGCATTCCAGACACAGGCCGGCGCCCAGATCCCCATCGAGCGGCTGGCCTCAGAGCG  8820
2851   M   A   F   Q   T   Q   A   G   A   Q   I   P   I   E   R   L   A   S   E   R   2870

8821  CGCCATCACCGTGAAGGTGCCCAACAACTCGGACTGGGCTGCCCGGGGCCACCGCAGCTC  8880
2871   A   I   T   V   K   V   P   N   N   S   D   W   A   A   R   G   H   R   S   S   2890
                               *

8881  CGCCAACTCCGCCAACTCCGTTGTGGTCCAGCCCCAGGCCTCCGTCGGTGCTGTGGTCAC  8940
2891   A   N   S   A   N   S   V   V   V   Q   P   Q   A   S   V   G   A   V   V   T   2910
```

FIG. 15O

```
8941  CCTGGACAGCAGCAACCCTGCGGCCGGGCTGCATCTGCAGCTCAACTATACGCTGCTGGA  9000
2911   L   D   S   S   N   P   A   A   G   L   H   L   Q   L   N   Y   T   L   L   D   2930
                                                                       *

9001  CGGCCACTACCTGTCTGAGGAACCTGAGCCCTACCTGGCAGTCTACCTACACTCGGAGCC  9060
2931   G   H   Y   L   S   E   E   P   E   P   Y   L   A   V   Y   L   H   S   E   P   2950

9061  CCGGCCCAATGAGCACAACTGCTCGGCTAGCAGGAGGATCCGCCCAGAGTCACTCCAGGG  9120
2951   R   P   N   E   H   N   C   S   A   S   R   R   I   R   P   E   S   L   Q   G   2970
                       *

9121  TGCTGACCACCGGCCCTACACCTTCTTCATTTCCCCGGGGAGCAGAGACCCAGCGGGGAG  9180
2971   A   D   H   R   P   Y   T   F   F   I   S   P   G   S   R   D   P   A   G   S   2990

9181  TTACCATCTGAACCTCTCCAGCCACTTCCGCTGGTCGGCGCTGCAGGTGTCCGTGGGCCT  9240
2991   Y   H   L   N   L   S   S   H   F   R   W   S   A   L   Q   V   S   V   G   L   3010
               *

9241  GTACACGTCCCTGTGCCAGTACTTCAGCGAGGAGGACATGGTGTGGCGGACAGAGGGGCT  9300
3011   Y   T   S   L   C   Q   Y   F   S   E   E   D   M   V   W   R   T   E   G   L   3030

9301  GCTGCCCCTGGAGGAGACCTCGCCCCGCCAGGCCGTCTGCCTCACCCGCCACCTCACCGC  9360
3031   L   P   L   E   E   T   S   P   R   Q   A   V   C   L   T   R   H   L   T   A   3050

9361  CTTCGGCGCCAGCCTCTTCGTGCCCCCAAGCCATGTCCGCTTTGTGTTTCCTGAGCCGAC  9420
3051   F   G   A   S   L   F   V   P   P   S   H   V   R   F   V   F   P   E   P   T   3070

9421  AGCGGATGTAAACTACATCGTCATGCTGACATGTGCTGTGTGCCTGGTGACCTACATGGT  9480
3071   A   D   V   N   Y   I   V   M   L   T   C  A   V   C   L   V   T   Y   M   V   3090
                        ─────────────────────────────────────────────────
                                              TM3
9481  CATGGCCGCCATCCTGCACAAGCTGGACCAGTTGGATGCCAGCCGGGGCCGCGCCATCCC  9540
3091   M   A   A   I   L   H   K   L   D   Q   L   D   A   S   R   G   R   A   I   P   3110
       ─────────────────
```

FIG. 15P

```
9541  TTTCTGTGGGCAGCGGGGCCGCTTCAAGTACGAGATCCTCGTCAAGACAGGCTGGGGCCG  9600
3111   F  C  G  Q  R  G  R  F  K  Y  E  I  L  V  K  T  G  W  G  R   3130

9601  GGGCTCAGGTACCACGGCCCACGTGGGCATCATGCTGTATGGGGTGGACAGCCGGAGCGG  9660
3131   G  S  G  T  T  A  H  V  G  I  M  L  Y  G  V  D  S  R  S  G   3150

9661  CCACCGGCACCTGGACGGCGACAGAGCCTTCCACCGCAACAGCCTGGACATCTTCCGGAT  9720
3151   H  R  H  L  D  G  D  R  A  F  H  R  N  S  L  D  I  F  R  I   3170

9721  CGCCACCCCGCACAGCCTGGGTAGCGTGTGGAAGATCCGAGTGTGGCACGACAACAAAGG  9780
3171   A  T  P  H  S  L  G  S  V  W  K  I  R  V  W  H  D  N  K  G   3190

9781  GCTCAGCCCTGCCTGGTTCCTGCAGCACGTCATCGTCAGGGACCTGCAGACGGCACGCAG  9840
3191   L  S  P  A  W  F  L  Q  H  V  I  V  R  D  L  Q  T  A  R  S   3210

9841  CGCCTTCTTCCTGGTCAATGACTGGCTTTCGGTGGAGACGGAGGCCAACGGGGGCCTGGT  9900
3211   A  F  F  L  V  N  D  W  L  S  V  E  T  E  A  N  G  G  L  V   3230

9901  GGAGAAGGAGGTGCTGGCCGCGAGCGACGCAGCCCTTTTGCGCTTCCGGCGCCTGCTGGT  9960
3231   E  K  E  V  L  A  A  S  D  A  A  L  L  R  F  R  R  L  L  V   3250

9961  GGCTGAGCTGCAGCGTGGCTTCTTTGACAAGCACATCTGGCTCTCCATATGGGACCGGCC  10020
3251   A  E  L  Q  R  G  F  F  D  K  H  I  W  L  S  I  W  D  R  P   3270

10021 GCCTCGTAGCCGTTTCACTCGCATCCAGAGGGCCACCTGCTGCGTTCTCCTCATCTGCCT  10080
3271   P  R  S  R  F  T  R  I  Q  R  A  T  C  C  V  L  L  I  C  L   3290

10081 CTTCCTGGGCGCCAACGCCGTGTGGTACGGGGCTGTTGGCGACTCTGCCTACAGCACGGG  10140
3291   F  L  G  A  N  A  V  W  Y  G  A  V  G  D  S  A  Y  S  T  G   3310
       TM4
```

FIG. 15Q

```
10141  GCATGTGTCCAGGCTGAGCCCGCTGAGCGTCGACACAGTCGCTGTTGGCCTGGTGTCCAG   10200
 3311   H   V   S   R   L   S   P   L   S   V   D   T   V   A   V   G   L   V   S   S    3330
                                                        ─────────────────────

10201  CGTGGTTGTCTATCCCGTCTACCTGGCCATCCTTTTTCTCTTCCGGATGTCCCGGAGCAA   10260
 3331   V   V   V   Y   P   V   Y   L   A   I   L   F   L   F   R   M   S   R   S   K    3350
        ═══════════════════════════════════════════════
                         TM5

10261  GGTGGCTGGGAGCCCCGAGCCCCACACCTGCCGGGCAGCAGGTGCTGGACATCGACAGCTG   10320
 3351   V   A   G   S   P   S   P   T   P   A   G   Q   Q   V   L   D   I   D   S   C    3370

10321  CCTGGACTCGTCCGTGCTGGACAGCTCCTTCCTCACGTTCTCAGGCCTCCACGCTGAGGC   10380
 3371   L   D   S   S   V   L   D   S   S   F   L   T   F   S   G   L   H   A   E   A    3390

10381  CTTTGTTGGACAGATGAAGAGTGACTTGTTTCTGGATGATTCTAAGAGTCTGGTGTGCTG   10440
 3391   F   V   G   Q   M   K   S   D   L   F   L   D   D   S   K   S   L   V   C   W    3410

10441  GCCCTCCGGCGAGGGAACGCTCAGTTGGCCGGACCTGCTCAGTGACCCGTCCATTGTGGG   10500
 3411   P   S   G   E   G   T   L   S   W   P   D   L   L   S   D   P   S   I   V   G    3430

10501  TAGCAATCTGCGGCAGCTGGCACGGGGCCAGGCGGGCCATGGGCTGGGCCCAGAGGAGGA   10560
 3431   S   N   L   R   Q   L   A   R   G   Q   A   G   H   G   L   G   P   E   E   D    3450

10561  CGGCTTCTCCCTGGCCAGCCCCTACTCGCCTGCCAAATCCTTCTCAGCATCAGATGAAGA   10620
 3451   G   F   S   L   A   S   P   Y   S   P   A   K   S   F   S   A   S   D   E   D    3470

10621  CCTGATCCAGCAGGTCCTTGCCGAGGGGGTCAGCAGCCCAGCCCCTACCCAAGACACCCA   10680
 3471   L   I   Q   Q   V   L   A   E   G   V   S   S   P   A   P   T   Q   D   T   H    3490

10681  CATGGAAACGGACCTGCTCAGCAGCCTGTCCAGCACTCCTGGGGAGAAGACAGAGACGCT   10740
 3491   M   E   T   D   L   L   S   S   L   S   S   T   P   G   E   K   T   E   T   L    3510
```

FIG. 15R

```
10741  GGCGCTGCAGAGGCTGGGGGAGCTGGGGCCACCCAGCCCAGGCCTGAACTGGGAACAGCC  10800
 3511   A  L  Q  R  L  G  E  L  G  P  P  S  P  G  L  N  W  E  Q  P   3530

10801  CCAGGCAGCGAGGCTGTCCAGGACAGGACTGGTGGAGGGTCTGCGGAAGCGCCTGCTGCC  10860
 3531   Q  A  A  R  L  S  R  T  G  L  V  E  G  L  R  K  R  L  L  P   3550

10861  GGCCTGGTGTGCCTCCCTGGCCCACGGGCTCAGCCTGCTCCTGGTGGCTGTGGCTGTGGC  10920
 3551   A  W  C  A  S  L  A  H  G  L  S  L  L  L  V  A  V  A  V  A   3570
                                        TM6

10921  TGTCTCAGGGTGGGTGGGTGCGAGCTTCCCCCCGGGCGTGAGTGTTGCGTGGCTCCTGTC  10980
 3571   V  S  G  W  V  G  A  S  F  P  P  G  V  S  V  A  W  L  L  S   3590

10981  CAGCAGCGCCAGCTTCCTGGCCTCATTCCTCGGCTGGGAGCCACTGAAGGTCTTGCTGGA  11040
 3591   S  S  A  S  F  L  A  S  F  L  G  W  E  P  L  K  V  L  L  E   3610
              TM7

11041  AGCCCTGTACTTCTCACTGGTGGCCAAGCGGCTGCACCCGGATGAAGATGACACCCTGGT  11100
 3611   A  L  Y  F  S  L  V  A  K  R  L  H  P  D  E  D  D  T  L  V   3630

11101  AGAGAGCCCGGCTGTGACGCCTGTGAGCGCACGTGTGCCCCGCGTACGGCCACCCCACGG  11160
 3631   E  S  P  A  V  T  P  V  S  A  R  V  P  R  V  R  P  P  H  G   3650

11161  CTTTGCACTCTTCCTGGCCAAGGAAGAAGCCCGCAAGGTCAAGAGGCTACATGGCATGCT  11220
 3651   F  A  L  F  L  A  K  E  E  A  R  K  V  K  R  L  H  G  M  L   3670

11221  GCGGAGCCTCCTGGTGTACATGCTTTTTCTGCTGGTGACCCTGCTGGCCAGCTATGGGGA  11280
 3671   R  S  L  L  V  Y  M  L  F  L  L  V  T  L  L  A  S  Y  G  D   3690
                                   TM8
```

FIG. 15S

```
11281  TGCCTCATGCCATGGGCACGCCTACCGTCTGCAAAGCGCCATCAAGCAGGAGCTGCACAG  11340
 3691   A  S  C  H  G  H  A  Y  R  L  Q  S  A  I  K  Q  E  L  H  S    3710

11341  CCGGGCCTTCCTGGCCATCACGCGGTCTGAGGAGCTCTGGCCATGGATGGCCCACGTGCT  11400
 3711   R  A  F  L  A  I  T  R  S  E  E  L  W  P  W  M  A  H  V  L    3730

11401  GCTGCCCTACGTCCACGGGAACCAGTCCAGCCCAGAGCTGGGGCCCCCACGGCTGCGGCA  11460
 3731   L  P  Y  V  H  G  N  Q  S  S  P  E  L  G  P  P  R  L  R  Q    3750
                         *

11461  GGTGCGGCTGCAGGAAGCACTCTACCCAGACCCTCCCGGCCCCAGGGTCCACACGTGCTC  11520
 3751   V  R  L  Q  E  A  L  Y  P  D  P  P  G  P  R  V  H  T  C  S    3770

11521  GGCCGCAGGAGGCTTCAGCACCAGCGATTACGACGTTGGCTGGGAGAGTCCTCACAATGG  11580
 3771   A  A  G  G  F  S  T  S  D  Y  D  V  G  W  E  S  P  H  N  G    3790
                                                              *

11581  CTCGGGGACGTGGGCCTATTCAGCGCCGGATCTGCTGGGGGCATGGTCCTGGGGCTCCTG  11640
 3791   S  G  T  W  A  Y  S  A  P  D  L  L  G  A  W  S  W  G  S  C    3810

11641  TGCCGTGTATGACAGCGGGGGCTACGTGCAGGAGCTGGGCCTGAGCCTGGAGGAGAGCCG  11700
 3811   A  V  Y  D  S  G  G  Y  V  Q  E  L  G  L  S  L  E  E  S  R    3830

11701  CGACCGGCTGCGCTTCCTGCAGCTGCACAACTGGCTGGACAACAGGAGCCGCGCTGTGTT  11760
 3831   D  R  L  R  F  L  Q  L  H  N  W  L  D  N  R  S  R  A  V  F    3850
                                             *

11761  CCTGGAGCTCACGCGCTACAGCCCGGCCGTGGGGCTGCACGCCGCCGTCACGCTGCGCCT  11820
 3851   L  E  L  T  R  Y  S  P  A  V  G  L  H  A  A  V  T  L  R  L    3870

11821  CGAGTTCCCGGCGGCCGGCCGCGCCCTGGCCGCCCTCAGCGTCCGCCCCTTTGCGCTGCG  11880
 3871   E  F  P  A  A  G  R  A  L  A  A  L  S  V  R  P  F  A  L  R    3890
```

FIG. 15T

```
11881  CCGCCTCAGCGCGGGCCTCTCGCTGCCTCTGCTCACCTCGGTGTGCCTGCTGCTGTTCGC  11940
3891     R   L   S   A   G   L   S   L   P   L   L   T   S   V   C   L   L   L   F   A   3910
                         —————————————————————————————————————————————————
                                                TM9
11941  CGTGCACTTCGCCGTGGCCGAGGCCCGTACTTGGCACAGGGAAGGGCGCTGGCGCGTGCT  12000
3911     V   H   F   A   V   E   A   R   T   W   H   R   E   G   R   W   R   V   L   3930
         ═══════════════

12001  GCGGCTCGGAGCCTGGGCGCGGTGGCTGCTGGTGGCGCTGACGGCGGCCACGGCACTGGT  12060
3931     R   L   G   A   W   A   R   W   L   L   V   A   L   T   A   A   T   A   L   V   3950

12061  ACGCCTCGCCCAGCTGGGTGCCGCTGACCGCCAGTGGACCCGTTTCGTGCGCGGCCGCCC  12120
3951     R   L   A   Q   L   G   A   A   D   R   Q   W   T   R   F   V   R   G   R   P   3970

12121  GCGCCGCTTCACTAGCTTCGACCAGGTGGCGCACGTGAGCTCCGCAGCCCGTGGCCTGGC  12180
3971     R   R   F   T   S   F   D   Q   V   A   H   V   S   S   A   A   R   G   L   A   3990

12181  GGCCTCGCTGCTCTTCCTGCTTTTGGTCAAGGCTGCCCAGCACGTACGCTTCGTGCGCCA  12240
3991     A   S   L   L   F   L   L   L   V   K   A   A   Q   H   V   R   F   V   R   Q   4010

12241  GTGGTCCGTCTTTGGCAAGACATTATGCCGAGCTCTGCCAGAGCTCCTGGGGGTCACCTT  12300
4011     W   S   V   F   G   K   T   L   C   R   A   L   P   E   L   L   G   V   T   L   4030
                                                                         ═══════

12301  GGGCCTGGTGGTGCTCGGGGTAGCCTACGCCCAGCTGGCCATCCTGCTCGTGTCTTCCTG  12360
4031     G   L   V   V   L   G   V   A   Y   A   Q   L   A   I   L   L   V   S   C   4050
         ═══════════════════════════════════════════════════════════
                                    TM10
12361  TGTGGACTCCCTCTGGAGCGTGGCCCAGGCCCTGTTGGTGCTGTGCCCTGGGACTGGGCT  12420
4051     V   D   S   L   W   S   V   A   Q   A   L   L   V   L   C   P   G   T   G   L   4070
                         ═══════════════════════════════════════════
                                          TM11
12421  CTCTACCCTGTGTCCTGCCGAGTCCTGGCACCTGTCACCCCTGCTGTGTGTGGGGCTCTG  12480
4071     S   T   L   C   P   A   E   S   W   H   L   S   P   L   L   C   V   G   L   W   4090
         ═══════════════════
```

FIG. 15U

```
12481  GGCACTGCGGCTGTGGGGCGCCCTACGGCTGGGGGCTGTTATTCTCCGCTGGCGCTACCA  12540
 4091    A  L  R  L  W  G  A  L  R  L  G  A  V  I  L  R  W  R  Y  H    4110

12541  CGCCTTGCGTGGAGAGCTGTACCGGCCGGCCTGGGAGCCCCAGGACTACGAGATGGTGGA  12600
 4111    A  L  R  G  E  L  Y  R  P  A  W  E  P  Q  D  Y  E  M  V  E    4130

12601  GTTGTTCCTGCGCAGGCTGCGCCTCTGGATGGGCCTCAGCAAGGTCAAGGAGTTCCGCCA  12660
 4131    L  F  L  R  R  L  R  L  W  M  G  L  S  K  V  K  E  F  R  H    4150

12661  CAAAGTCCGCTTTGAAGGGATGGAGCCGCTGCCCTCTCGCTCCTCCAGGGGCTCCAAGGT  12720
 4151    K  V  R  F  E  G  M  E  P  L  P  S  R  S  S  R  G  S  K  V    4170

12721  ATCCCCGGATGTGCCCCCACCCAGCGCTGGCTCCGATGCCTCGCACCCCTCCACCTCCTC  12780
 4171    S  P  D  V  P  P  P  S  A  G  S  D  A  S  H  P  S  T  S  S    4190

12781  CAGCCAGCTGGATGGGCTGAGCGTGAGCCTGGGCCGGCTGGGGACAAGGTGTGAGCCTGA  12840
 4191    S  Q  L  D  G  L  S  V  S  L  G  R  L  G  T  R  C  E  P  E    4210

12841  GCCCTCCCGCCTCCAAGCCGTGTTCGAGGCCCTGCTCACCCAGTTTGACCGACTCAACCA  12900
 4211    P  S  R  L  Q  A  V  F  E  A  L  L  T  Q  F  D  R  L  N  Q    4230

12901  GGCCACAGAGGACGTCTACCAGCTGGAGCAGCAGCTGCACAGCCTGCAAGGCCGCAGGAG  12960
 4231    A  T  E  D  V  Y  Q  L  E  Q  Q  L  H  S  L  Q  G  R  R  S    4250

12961  CAGCCGGGCGCCCGCCGGATCTTCCCGTGGCCCATCCCCGGGCCTGCGGCCAGCACTGCC  13020
 4251    S  R  A  P  A  G  S  S  R  G  P  S  P  G  L  R  P  A  L  P    4270

13021  CAGCCGCCTTGCCCGGGCCAGTCGGGGTGTGGACCTGGCCACTGGCCCCAGCAGGACACC  13080
 4271    S  R  L  A  R  A  S  R  G  V  D  L  A  T  G  P  S  R  T  P    4290
```

FIG. 15V

| | | |
|---|---|---|
| 13081 | CCTTCGGGCCAAGAACAAGGTCCACCCCAGCAGCACTTAGTCCTCCTTCCTGGCGGGGGT | 13140 |
| 4291 | L R A K N K V H P S S T | 4310 |

13141 GGGCCGTGGAGTCGGAGTGGACACCGCTCAGTATTACTTTCTGCCGCTGTCAAGGCCGAG 13200

13201 GGCCAGGCAGAATGGCTGCACGTAGGTTCCCCAGAGAGCAGGCAGGGGCATCTGTCTGTC 13260

13261 TGTGGGCTTCAGCACTTTAAAGAGGCTGTGTGGCCAACCAGGACCCAGGGTCCCCTCCCC 13320

13321 AGCTCCCTTGGGAAGGACACAGCAGTATTGGACGGTTTCTAGCCTCTGAGATGCTAATTT 13380

13381 ATTTCCCCGAGTCCTCAGGTACAGCGGGCTGTGCCCGGCCCCACCCCCTGGGCAGATGTC 13440

13441 CCCCACTGCTAAGGCTGCTGGCTTCAGGGAGGGTTAGCCTGCACCGCCGCCACCCTGCCC 13500

13501 CTAAGTTATTACCTCTCCAGTTCCTACCGTACTCCCTGCACCGTCTCACTGTGTGTCTCG 13560

13561 TGTCAGTAATTTATATGGTGTTAAAATGTGTATATTTTTGTATGTCACTATTTTCACTAG 13620

13621 GGCTGAGGGGCCTGCGCCCAGAGCTGGCCTCCCCCAACACCTGCTGCGCTTGGTAGGTGT 13680

13681 GGTGGCGTTATGGCAGCCCGGCTGCTGCTTGGATGCGAGCTTGGCCTTGGGCCGGTGCTG 13740

13741 GGGGCACAGCTGTCTGCCAGGCACTCTCATCACCCCAGAGGCCTTGTCATCCTCCCTTGC 13800

13801 CCCAGGCCAGGTAGCAAGAGAGCAGCGCCCAGGCCTGCTGGCATCAGGTCTGGGCAAGTA 13860

13861 GCAGGACTAGGCATGTCAGAGGACCCCAGGGTGGTTAGAGGAAAAGACTCCTCCTGGGGG 13920

13921 CTGGCTCCCAGGGTGGAGGAAGGTGACTGTGTGTGTGTGTGTGCGCGCGCGACGCGCG 13980

13981 AGTGTGCTGTATGGCCCAGGCAGCCTCAAGGCCCTCGGAGCTGGCTGTGCCTGCTTCTGT 14040

14041 GTACCACTTCTGTGGGCATGGCCGCTTCTAGAGCCTCGACACCCCCCCAACCCCCGCACC 14100

14101 AAGCAGACAAAGTCAATAAAAGAGCTGTCTGACTGCAAAAAAAAAAAA 14148

| | | | | | |
|---|---|---|---|---|---|
| PKDLRR1 | | | | LDVSHNLIRAL | |
| PKDLRR2 | DVGLIANLSALAELDISNNKISTL | | | | |
| PKDLRR3 | EEGIFANLFNLSEINLSGN | | | | |
| CONCENSUS | L | L | LL NL L | | |
| | F | | a a | | |

| | | | | | |
|---|---|---|---|---|---|
| PKD1 | CP | CLCGPAPGAAC | RVNCSGR | GLR | TLGPA LRIPADATA |
| OMgp | CP | CHCTEHR | HVDCSGR | NLS | TL PSGLQE NIIH |
| SLIT1 | CP | CSCTGL | NVDCSHR | GLT | SV PRKTSA DVER |
| CHAOPTIN | CT | VMCTCSKSSTDLGIVHCKNV | | PPP | AL PRMVNQ SKVP |
| GPIB BETA | CP | CSCAGT | LVDCGRR | GLTWA | SL PTAHPV DTTE |
| BIGLYCAN | CP | CHCHLR | VVQCSDL | GLK | SV PKEISP DTTL |
| DECORIN | CP | CQCHLR | VVQCSDL | GLD | KV PKDLPP DTTL |
| FIBROMODULIN | CP | CDCPPNFPT | AMYCDNR | NLK | YL P FVVPS RMKY |
| Trk | CP | C CPHGSSG | LIRCTRD | GALDSLH HL | PGAENLT ELYI |
| LH-CG | CP | CDCAPDG | ALRCFGPRAGLARLSLTYL | | PVKVIPS QAFR |

| CONCENSUS | CP | C C | V CS | GL | L P DTT |
|---|---|---|---|---|---|
| | P | | a p | h | a h phh |

| | | | | |
|---|---|---|---|---|
| PKD1 | P | DCGLA | WLPPWAEEQQVRVVQPEAA | TCAGPGSLAGQPL LGIPLLDSGCGEEY |
| Slit 1 | P | DCHLS | WLSPFLRSATRLAPYT | RCQSPSQLKGQNV ADLHDQEFKCSGLT |
| Slit 2 | P | NCNLR | WLADYLHKIPIETSGA | RCESPKRMHRRI ESLREEKFKCSWGE |
| Toll-1 | P | DCTIL | WEIQLVRGVHKPQYSRQFKLRTDRLVCSQPNVLEGTPV | RQIEPQTLICPLDF |
| GPIX | P | DCSITYLRLMLEDRTPEALLQV | | RCASPSLAAHGPL RLTGYQLGSCGWQL |
| GP 1b BETA | P | DCRLVPLRAWLAGRPEFAPYRDL | | RCVAPPAL RGRLPYLAEDELRAACAP |
| Trk | | SCALR | WLQRWEEEGLGGVPEQKL | QCHGQGPL AHM PNASCGVPTLKVQV |

| CONCENSUS | P | DC L | WL | RC P L C C |
|---|---|---|---|---|
| | P | p a | h p pp | p p h h h |

```
PKD1             HPLCPSDTEIFPGNGHCYRLVVEKAAWLQAEQCQA WAGAAATAMVDSPAVQRFLVSRVTRSLD VWIGLSTV
BRA3             ECTCPGNLDMQEYDGHCYWASTYQVRWNDALACQTVHPGAYLATQSQLENAFLSETVSNNR IWIGLNDI
Kupffer          LQLIM    QDWKYFNGKEYYFSRDKKKSWHEAENFCVS QGAHLASVTSQEEQAFIVQITNAVDH  WIGLTDQ
C.S.P            QKLCE    EGWTKFQGHCYRHFPDRATWVDAESQCRK  QQSHISSIVTPEEQEFVNNAQDYQ    WIGINDK
ASIAL.           RTCCP    VNMVEHQGSCYWFSHSGKAMAEAEKYCQL  ENAHIWINSWEEQKFIVQHTNPFNT   WIGLTDS
E_Selectin       ALVFV    LLAGESTAWYMNASSELMTYDEASAYCQR  DYTHLVAIQNKEEINYLNSNLKHSPSYYWIGIRKV
GP120 binding    CHPCP    WEMTFFQGNCYFMSNSQRNMHDSITACKE  GAQLWIKSAEEQNFLQLQSSRSNRFTWMGLSDL

CONCENSUS        CP       W

| | E | | F | | G |
|---|---|---|---|---|---|
| PKDI | | | LPGRYHVTIAVLAIGAGSALIGTDVQVEAAP | | |
| PKDII | | | SEGEHVVDVVENSASRANLSRVTAEEPI | | |
| PKDIII | FSVVALPWL | | SAAVFKLSLTASNHVSNVTVNYNVTVERMN | | |
| PKDIV | SLTFQNMVENVLYQ | | VP | | |
| PKDIVcon | | | APGEMLILTVLASNAFENLITQQVPVSVRASL | | |
| PKDV | | | SRGTYHVRLEVNNTVSGAAAQADVRVFEEL | | |
| PKDVI | | | RAQNCTVTVGAASPAGHLARSIHVLIVFVLE | | |
| PKDVII | | | RSGIFPLAIVLSSRVNRAHYFTSICVEPEV | | |
| PKDVIII | | | DPGSYLVTTASNNISAANDSALVEVQEPV | | |
| PKDIX | | | STGDFTMRVAGWNEVSRSEAWLNVTVKRRV | | |
| PKDX | | | SVGTFNIIVTAENEVGSAQDSIFVYLQLI | | |
| PKDXI | | | EAGTYHVQLRAINMLGSAMADCTMDFVEPV | | |
| PKDXII | | | TPGLHLMIMTAGNPLGSANATVEVDMQVPV | | |
| PKDXIII | | | DAGIFSIRLNASNAVSWMSATYNITAEEPI | | |
| PKDXIV | | | RVGDHVVSSVRGKNHYSMAQAQVRIVVLEAV | | |
| PKDXV | | | AAGLIELQVRAFNALGSENRTLVLEVQDAV | | |
| PKDXVI | | | RPGDYRVQVNASNLVSFFEVAQATVTVQVLA | | |
| V.a colAi | | | SEGEYSVSLSVTDSEGLIATATHIVVISAL | | |
| C.p colA | | | KTIGEYEVKLIVTDNNGGINIESKKIKVVED | | |
| Pmel-17 | | | EPGPVTAQVLQAAIPLTSCGSSPVPGTTD | | |
| FLT4 | | | STGTYTLA | | |
| CaVPT | LKEVTEA | | LWNSAAGLRRNISLELVVNV | | |
| lg consensus | DKDGTFLIIRNADGDDVGTYTCQ | | ATNSFGEAFDSARLALEVDA | | |
| | h h | D G Y a | a N G | | h h h |

```
PKD1A      LEAHVDLRDCVTY         QIEIRMEVYRTASCQRGRPARVAIPGVDVSRP
     B     ESYDENLEDGDQT         PLSIHWACV
     C     RSSYVYLECRQLNCSSGSKRCRWAAR         ASTQREAGGCALNFGPRGSS
     D     CRLFPLGAVHALTTKVHFECTGWHDA         TFSNKTLVLDTTTSTGSAGM
NEUROGLIAN DNRSPILHYTLQE   NTSFIPASMDAA       EDAGAPLVYALLLRRCRQGHCEEFCVYKGSLSS
L1         DHNAPIEKYDIEYEDKEMAPEKMYSL         YEKYPNTD
F11        DNHSPISKYTLQSK  TFLSEEWKDA         GKVPGNQ
TAG1       DNHSPIAKYTLQAR  TPPAGKMKQV         KTEPSDYEGNME
F3         PSEAPTEVGVKVLS  SSELSVHMKHV        RTNPANLEGNAE
NCAM       TGGVPILKYKAEM   KSLGEEAWHSK        WYDAKEANMEGHDKEAAAHRVQVTSQEY
DOC        LSWRPPAEAKGNI   QTFIVFFSR          WTDAKEANMEG
LAR        PSAPPQKVMCVSM   GSTTVRVSMVPP       EGDNRERALNTTOPGSL
HPTP       TVPSPWKDLGISTI  KANSLLISWSHG       PADSRNGVITQYSVAHEAVDGEDRGRHVVDGISREHS
RN         VSDVP           RDLEVVAATPTSLLISMDAP  SGNVERYRLMLMDKGILVHGGVVDKHAT
                                              AVTVRYVBTTYGETGGNSPVQEFTVPGSKS

B strands           A              B              C                D

CONCENSUS     P       h h h    h  h    W   h  r                hph

                           SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
          (A) LENGTH: 5631 base pairs
          (B) TYPE: nucleic acid
          (C) STRANDEDNESS: unknown
          (D) TOPOLOGY: unknown (ii) MOLECULE TYPE: cDNA (vi) ORIGINAL SOURCE:
          (A) ORGANISM: Homo sapiens (ix) FEATURE:
```

(A) NAME/KEY: CDS
      (B) LOCATION:1..4842

(ix) FEATURE:
      (A) NAME/KEY: misc_feature
      (B) LOCATION:1..5631
      (D) OTHER INFORMATION:/function= "Original 3' end of the PKD1 gene"

(xi) SEQUENCE DESCRIPTION: SEQ ID NO: 1:

```
CTC AAC GAG GAG CCC CTG ACG CTG GCG GGC GAG GAG ATC GTG GCC CAG      48
Leu Asn Glu Glu Pro Leu Thr Leu Ala Gly Glu Glu Ile Val Ala Gln
 1               5                  10                  15

GGC AAG CGC TCG GAC CCG CGG AGC CTG CTG TGC TAT GGC GGC GCC CCA      96
Gly Lys Arg Ser Asp Pro Arg Ser Leu Leu Cys Tyr Gly Gly Ala Pro
             20                  25                  30

GGG CCT GGC TGC CAC TTC TCC ATC CCC GAG GCT TTC AGC GGG GCC CTG     144
Gly Pro Gly Cys His Phe Ser Ile Pro Glu Ala Phe Ser Gly Ala Leu
         35                  40                  45

GCC AAC CTC AGT GAC GTG GTG CAG CTC ATC TTT CTG GTG GAC TCC AAT     192
Ala Asn Leu Ser Asp Val Val Gln Leu Ile Phe Leu Val Asp Ser Asn
 50                  55                  60

CCC TTT CCC TTT GGC TAT ATC AGC AAC TAC ACC GTC TCC ACC AAG GTG     240
Pro Phe Pro Phe Gly Tyr Ile Ser Asn Tyr Thr Val Ser Thr Lys Val
 65                  70                  75                  80

GCC TCG ATG GCA TTC CAG ACA CAG GCC GGC GCC CAG ATC CCC ATC GAG     288
Ala Ser Met Ala Phe Gln Thr Gln Ala Gly Ala Gln Ile Pro Ile Glu
             85                  90                  95

CGG CTG GCC TCA GAG CGC GCC ATC ACC GTG AAG GTG CCC AAC AAC TCG     336
Arg Leu Ala Ser Glu Arg Ala Ile Thr Val Lys Val Pro Asn Asn Ser
            100                 105                 110

GAC TGG GCT GCC CGG GGC CAC CGC AGC TCC GCC AAC TCC GCC AAC TCC     384
Asp Trp Ala Ala Arg Gly His Arg Ser Ser Ala Asn Ser Ala Asn Ser
        115                 120                 125

GTT GTG GTC CAG CCC CAG GCC TCC GTC GGT GCT GTG GTC ACC CTG GAC     432
Val Val Val Gln Pro Gln Ala Ser Val Gly Ala Val Val Thr Leu Asp
    130                 135                 140

AGC AGC AAC CCT GCG GCC GGG CTG CAT CTG CAG CTC AAC TAT ACG CTG     480
Ser Ser Asn Pro Ala Ala Gly Leu His Leu Gln Leu Asn Tyr Thr Leu
145                 150                 155                 160

CTG GAC GGC CAC TAC CTG TCT GAG GAA CCT GAG CCC TAC CTG GCA GTC     528
Leu Asp Gly His Tyr Leu Ser Glu Glu Pro Glu Pro Tyr Leu Ala Val
                165                 170                 175

TAC CTA CAC TCG GAG CCC CGG CCC AAT GAG CAC AAC TGC TCG GCT AGC     576
Tyr Leu His Ser Glu Pro Arg Pro Asn Glu His Asn Cys Ser Ala Ser
            180                 185                 190

AGG AGG ATC CGC CCA GAG TCA CTC CAG GGT GCT GAC CAC CGG CCC TAC     624
Arg Arg Ile Arg Pro Glu Ser Leu Gln Gly Ala Asp His Arg Pro Tyr
        195                 200                 205

ACC TTC TTC ATT TCC CCG GGG AGC AGA GAC CCA GCG GGG AGT TAC CAT     672
Thr Phe Phe Ile Ser Pro Gly Ser Arg Asp Pro Ala Gly Ser Tyr His
    210                 215                 220

CTG AAC CTC TCC AGC CAC TTC CGC TGG TCG GCG CTG CAG GTG TCC GTG     720
Leu Asn Leu Ser Ser His Phe Arg Trp Ser Ala Leu Gln Val Ser Val
225                 230                 235                 240

GGC CTG TAC ACG TCC CTG TGC CAG TAC TTC AGC GAG GAG GAC ATG GTG     768
Gly Leu Tyr Thr Ser Leu Cys Gln Tyr Phe Ser Glu Glu Asp Met Val
                245                 250                 255

TGG CGG ACA GAG GGG CTG CTG CCC CTG GAG GAG ACC TCG CCC CGC CAG     816
Trp Arg Thr Glu Gly Leu Leu Pro Leu Glu Glu Thr Ser Pro Arg Gln
            260                 265                 270
```

```
GCC GTC TGC CTC ACC CGC CAC CTC ACC GCC TTC GGC GCC AGC CTC TTC        864
Ala Val Cys Leu Thr Arg His Leu Thr Ala Phe Gly Ala Ser Leu Phe
        275                 280                 285

GTG CCC CCA AGC CAT GTC CGC TTT GTG TTT CCT GAG CCG ACA GCG GAT        912
Val Pro Pro Ser His Val Arg Phe Val Phe Pro Glu Pro Thr Ala Asp
        290                 295                 300

GTA AAC TAC ATC GTC ATG CTG ACA TGT GCT GTG TGC CTG GTG ACC TAC        960
Val Asn Tyr Ile Val Met Leu Thr Cys Ala Val Cys Leu Val Thr Tyr
305                 310                 315                 320

ATG GTC ATG GCC GCC ATC CTG CAC AAG CTG GAC CAG TTG GAT GCC AGC       1008
Met Val Met Ala Ala Ile Leu His Lys Leu Asp Gln Leu Asp Ala Ser
                325                 330                 335

CGG GGC CGC GCC ATC CCT TTC TGT GGG CAG CGG GGC CGC TTC AAG TAC       1056
Arg Gly Arg Ala Ile Pro Phe Cys Gly Gln Arg Gly Arg Phe Lys Tyr
        340                 345                 350

GAG ATC CTC GTC AAG ACA GGC TGG GGC CGG GGC TCA GGT ACC ACG GCC       1104
Glu Ile Leu Val Lys Thr Gly Trp Gly Arg Gly Ser Gly Thr Thr Ala
        355                 360                 365

CAC GTG GGC ATC ATG CTG TAT GGG GTG GAC AGC CGG AGC GGC CAC CGG       1152
His Val Gly Ile Met Leu Tyr Gly Val Asp Ser Arg Ser Gly His Arg
        370                 375                 380

CAC CTG GAC GGC GAC AGA GCC TTC CAC CGC AAC AGC CTG GAC ATC TTC       1200
His Leu Asp Gly Asp Arg Ala Phe His Arg Asn Ser Leu Asp Ile Phe
385                 390                 395                 400

CGG ATC GCC ACC CCG CAC AGC CTG GGT AGC GTG TGG AAG ATC CGA GTG       1248
Arg Ile Ala Thr Pro His Ser Leu Gly Ser Val Trp Lys Ile Arg Val
                405                 410                 415

TGG CAC GAC AAC AAA GGG CTC AGC CCT GCC TGG TTC CTG CAG CAC GTC       1296
Trp His Asp Asn Lys Gly Leu Ser Pro Ala Trp Phe Leu Gln His Val
        420                 425                 430

ATC GTC AGG GAC CTG CAG ACG GCA CGC AGC GCC TTC TTC CTG GTC AAT       1344
Ile Val Arg Asp Leu Gln Thr Ala Arg Ser Ala Phe Phe Leu Val Asn
        435                 440                 445

GAC TGG CTT TCG GTG GAG ACG GAG GCC AAC GGG GGC CTG GTG GAG AAG       1392
Asp Trp Leu Ser Val Glu Thr Glu Ala Asn Gly Gly Leu Val Glu Lys
        450                 455                 460

GAG GTG CTG GCC GCG AGC GAC GCA GCC CTT TTG CGC TTC CGG CGC CTG       1440
Glu Val Leu Ala Ala Ser Asp Ala Ala Leu Leu Arg Phe Arg Arg Leu
465                 470                 475                 480

CTG GTG GCT GAG CTG CAG CGT GGC TTC TTT GAC AAG CAC ATC TGG CTC       1488
Leu Val Ala Glu Leu Gln Arg Gly Phe Phe Asp Lys His Ile Trp Leu
                485                 490                 495

TCC ATA TGG GAC CGG CCG CCT CGT AGC CGT TTC ACT CGC ATC CAG AGG       1536
Ser Ile Trp Asp Arg Pro Pro Arg Ser Arg Phe Thr Arg Ile Gln Arg
        500                 505                 510

GCC ACC TGC TGC GTT CTC CTC ATC TGC CTC TTC CTG GGC GCC AAC GCC       1584
Ala Thr Cys Cys Val Leu Leu Ile Cys Leu Phe Leu Gly Ala Asn Ala
        515                 520                 525

GTG TGG TAC GGG GCT GTT GGC GAC TCT GCC TAC AGC ACG GGG CAT GTG       1632
Val Trp Tyr Gly Ala Val Gly Asp Ser Ala Tyr Ser Thr Gly His Val
        530                 535                 540

TCC AGG CTG AGC CCG CTG AGC GTC GAC ACA GTC GCT GTT GGC CTG GTG       1680
Ser Arg Leu Ser Pro Leu Ser Val Asp Thr Val Ala Val Gly Leu Val
545                 550                 555                 560

TCC AGC GTG GTT GTC TAT CCC GTC TAC CTG GCC ATC CTT TTT CTC TTC       1728
Ser Ser Val Val Val Tyr Pro Val Tyr Leu Ala Ile Leu Phe Leu Phe
                565                 570                 575

CGG ATG TCC CGG AGC AAG GTG GCT GGG AGC CCG AGC CCC ACA CCT GCC       1776
Arg Met Ser Arg Ser Lys Val Ala Gly Ser Pro Ser Pro Thr Pro Ala
        580                 585                 590
```

```
GGG CAG CAG GTG CTG GAC ATC GAC AGC TGC CTG GAC TCG TCC GTG CTG      1824
Gly Gln Gln Val Leu Asp Ile Asp Ser Cys Leu Asp Ser Ser Val Leu
        595                 600                 605

GAC AGC TCC TTC CTC ACG TTC TCA GGC CTC CAC GCT GAG GCC TTT GTT      1872
Asp Ser Ser Phe Leu Thr Phe Ser Gly Leu His Ala Glu Ala Phe Val
    610                 615                 620

GGA CAG ATG AAG AGT GAC TTG TTT CTG GAT GAT TCT AAG AGT CTG GTG      1920
Gly Gln Met Lys Ser Asp Leu Phe Leu Asp Asp Ser Lys Ser Leu Val
625                 630                 635                 640

TGC TGG CCC TCC GGC GAG GGA ACG CTC AGT TGG CCG GAC CTG CTC AGT      1968
Cys Trp Pro Ser Gly Glu Gly Thr Leu Ser Trp Pro Asp Leu Leu Ser
            645                 650                 655

GAC CCG TCC ATT GTG GGT AGC AAT CTG CGG CAG CTG GCA CGG GGC CAG      2016
Asp Pro Ser Ile Val Gly Ser Asn Leu Arg Gln Leu Ala Arg Gly Gln
                660                 665                 670

GCG GGC CAT GGG CTG GGC CCA GAG GAG GAC GGC TTC TCC CTG GCC AGC      2064
Ala Gly His Gly Leu Gly Pro Glu Glu Asp Gly Phe Ser Leu Ala Ser
            675                 680                 685

CCC TAC TCG CCT GCC AAA TCC TTC TCA GCA TCA GAT GAA GAC CTG ATC      2112
Pro Tyr Ser Pro Ala Lys Ser Phe Ser Ala Ser Asp Glu Asp Leu Ile
    690                 695                 700

CAG CAG GTC CTT GCC GAG GGG GTC AGC AGC CCA GCC CCT ACC CAA GAC      2160
Gln Gln Val Leu Ala Glu Gly Val Ser Ser Pro Ala Pro Thr Gln Asp
705                 710                 715                 720

ACC CAC ATG GAA ACG GAC CTG CTC AGC AGC CTG TCC AGC ACT CCT GGG      2208
Thr His Met Glu Thr Asp Leu Leu Ser Ser Leu Ser Ser Thr Pro Gly
            725                 730                 735

GAG AAG ACA GAG ACG CTG GCG CTG CAG AGG CTG GGG GAG CTG GGG CCA      2256
Glu Lys Thr Glu Thr Leu Ala Leu Gln Arg Leu Gly Glu Leu Gly Pro
                740                 745                 750

CCC AGC CCA GGC CTG AAC TGG GAA CAG CCC CAG GCA GCG AGG CTG TCC      2304
Pro Ser Pro Gly Leu Asn Trp Glu Gln Pro Gln Ala Ala Arg Leu Ser
            755                 760                 765

AGG ACA GGA CTG GTG GAG GGT CTG CGG AAG CGC CTG CTG CCG GCC TGG      2352
Arg Thr Gly Leu Val Glu Gly Leu Arg Lys Arg Leu Leu Pro Ala Trp
770                 775                 780

TGT GCC TCC CTG GCC CAC GGG CTC AGC CTG CTC CTG GTG GCT GTG GCT      2400
Cys Ala Ser Leu Ala His Gly Leu Ser Leu Leu Leu Val Ala Val Ala
            785                 790                 795             800

GTG GCT GTC TCA GGG TGG GTG GGT GCG AGC TTC CCC CCG GGC GTG AGT      2448
Val Ala Val Ser Gly Trp Val Gly Ala Ser Phe Pro Pro Gly Val Ser
                805                 810                 815

GTT GCG TGG CTC CTG TCC AGC AGC GCC AGC TTC CTG GCC TCA TTC CTC      2496
Val Ala Trp Leu Leu Ser Ser Ser Ala Ser Phe Leu Ala Ser Phe Leu
            820                 825                 830

GGC TGG GAG CCA CTG AAG GTC TTG CTG GAA GCC CTG TAC TTC TCA CTG      2544
Gly Trp Glu Pro Leu Lys Val Leu Leu Glu Ala Leu Tyr Phe Ser Leu
835                 840                 845

GTG GCC AAG CGG CTG CAC CCG GAT GAA GAT GAC ACC CTG GTA GAG AGC      2592
Val Ala Lys Arg Leu His Pro Asp Glu Asp Asp Thr Leu Val Glu Ser
        850                 855                 860

CCG GCT GTG ACG CCT GTG AGC GCA CGT GTG CCC CGC GTA CGG CCA CCC      2640
Pro Ala Val Thr Pro Val Ser Ala Arg Val Pro Arg Val Arg Pro Pro
865                 870                 875                 880

CAC GGC TTT GCA CTC TTC CTG GCC AAG GAA GAA GCC CGC AAG GTC AAG      2688
His Gly Phe Ala Leu Phe Leu Ala Lys Glu Glu Ala Arg Lys Val Lys
            885                 890                 895

AGG CTA CAT GGC ATG CTG CGG AGC CTC CTG GTG TAC ATG CTT TTT CTG      2736
Arg Leu His Gly Met Leu Arg Ser Leu Leu Val Tyr Met Leu Phe Leu
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 900 |     |     |     |     | 905 |     |     |     |     | 910 |     |     |      |
| CTG | GTG | ACC | CTG | CTG | GCC | AGC | TAT | GGG | GAT | GCC | TCA | TGC | CAT | GGG | CAC | 2784 |
| Leu | Val | Thr | Leu | Leu | Ala | Ser | Tyr | Gly | Asp | Ala | Ser | Cys | His | Gly | His |      |
|     |     |     | 915 |     |     |     |     | 920 |     |     |     |     | 925 |     |     |      |
| GCC | TAC | CGT | CTG | CAA | AGC | GCC | ATC | AAG | CAG | GAG | CTG | CAC | AGC | CGG | GCC | 2832 |
| Ala | Tyr | Arg | Leu | Gln | Ser | Ala | Ile | Lys | Gln | Glu | Leu | His | Ser | Arg | Ala |      |
|     |     |     | 930 |     |     |     |     | 935 |     |     |     |     | 940 |     |     |      |
| TTC | CTG | GCC | ATC | ACG | CGG | TCT | GAG | GAG | CTC | TGG | CCA | TGG | ATG | GCC | CAC | 2880 |
| Phe | Leu | Ala | Ile | Thr | Arg | Ser | Glu | Glu | Leu | Trp | Pro | Trp | Met | Ala | His |      |
| 945 |     |     |     |     | 950 |     |     |     |     | 955 |     |     |     |     | 960 |      |
| GTG | CTG | CTG | CCC | TAC | GTC | CAC | GGG | AAC | CAG | TCC | AGC | CCA | GAG | CTG | GGG | 2928 |
| Val | Leu | Leu | Pro | Tyr | Val | His | Gly | Asn | Gln | Ser | Ser | Pro | Glu | Leu | Gly |      |
|     |     |     |     | 965 |     |     |     |     | 970 |     |     |     |     | 975 |     |      |
| CCC | CCA | CGG | CTG | CGG | CAG | GTG | CGG | CTG | CAG | GAA | GCA | CTC | TAC | CCA | GAC | 2976 |
| Pro | Pro | Arg | Leu | Arg | Gln | Val | Arg | Leu | Gln | Glu | Ala | Leu | Tyr | Pro | Asp |      |
|     |     |     | 980 |     |     |     |     | 985 |     |     |     |     | 990 |     |     |      |
| CCT | CCC | GGC | CCC | AGG | GTC | CAC | ACG | TGC | TCG | GCC | GCA | GGA | GGC | TTC | AGC | 3024 |
| Pro | Pro | Gly | Pro | Arg | Val | His | Thr | Cys | Ser | Ala | Ala | Gly | Gly | Phe | Ser |      |
|     |     |     | 995 |     |     |     |     | 1000|     |     |     |     | 1005|     |     |      |
| ACC | AGC | GAT | TAC | GAC | GTT | GGC | TGG | GAG | AGT | CCT | CAC | AAT | GGC | TCG | GGG | 3072 |
| Thr | Ser | Asp | Tyr | Asp | Val | Gly | Trp | Glu | Ser | Pro | His | Asn | Gly | Ser | Gly |      |
|     |     |     | 1010|     |     |     |     | 1015|     |     |     |     | 1020|     |     |      |
| ACG | TGG | GCC | TAT | TCA | GCG | CCG | GAT | CTG | CTG | GGG | GCA | TGG | TCC | TGG | GGC | 3120 |
| Thr | Trp | Ala | Tyr | Ser | Ala | Pro | Asp | Leu | Leu | Gly | Ala | Trp | Ser | Trp | Gly |      |
| 1025|     |     |     |     | 1030|     |     |     |     | 1035|     |     |     |     | 1040|      |
| TCC | TGT | GCC | GTG | TAT | GAC | AGC | GGG | GGC | TAC | GTG | CAG | GAG | CTG | GGC | CTG | 3168 |
| Ser | Cys | Ala | Val | Tyr | Asp | Ser | Gly | Gly | Tyr | Val | Gln | Glu | Leu | Gly | Leu |      |
|     |     |     |     | 1045|     |     |     |     | 1050|     |     |     |     | 1055|     |      |
| AGC | CTG | GAG | GAG | AGC | CGC | GAC | CGG | CTG | CGC | TTC | CTG | CAG | CTG | CAC | AAC | 3216 |
| Ser | Leu | Glu | Glu | Ser | Arg | Asp | Arg | Leu | Arg | Phe | Leu | Gln | Leu | His | Asn |      |
|     |     |     |     | 1060|     |     |     |     | 1065|     |     |     |     | 1070|     |      |
| TGG | CTG | GAC | AAC | AGG | AGC | CGC | GCT | GTG | TTC | CTG | GAG | CTC | ACG | CGC | TAC | 3264 |
| Trp | Leu | Asp | Asn | Arg | Ser | Arg | Ala | Val | Phe | Leu | Glu | Leu | Thr | Arg | Tyr |      |
|     |     |     | 1075|     |     |     |     | 1080|     |     |     |     | 1085|     |     |      |
| AGC | CCG | GCC | GTG | GGG | CTG | CAC | GCC | GCC | GTC | ACG | CTG | CGC | CTC | GAG | TTC | 3312 |
| Ser | Pro | Ala | Val | Gly | Leu | His | Ala | Ala | Val | Thr | Leu | Arg | Leu | Glu | Phe |      |
|     |     |     | 1090|     |     |     |     | 1095|     |     |     |     | 1100|     |     |      |
| CCG | GCG | GCC | GGC | CGC | GCC | CTG | GCC | GCC | CTC | AGC | GTC | CGC | CCC | TTT | GCG | 3360 |
| Pro | Ala | Ala | Gly | Arg | Ala | Leu | Ala | Ala | Leu | Ser | Val | Arg | Pro | Phe | Ala |      |
| 1105|     |     |     |     | 1110|     |     |     |     | 1115|     |     |     |     | 1120|      |
| CTG | CGC | CGC | CTC | AGC | GCG | GGC | CTC | TCG | CTG | CCT | CTG | CTC | ACC | TCG | GTG | 3408 |
| Leu | Arg | Arg | Leu | Ser | Ala | Gly | Leu | Ser | Leu | Pro | Leu | Leu | Thr | Ser | Val |      |
|     |     |     |     | 1125|     |     |     |     | 1130|     |     |     |     | 1135|     |      |
| TGC | CTG | CTG | CTG | TTC | GCC | GTG | CAC | TTC | GCC | GTG | GCC | GAG | GCC | CGT | ACT | 3456 |
| Cys | Leu | Leu | Leu | Phe | Ala | Val | His | Phe | Ala | Val | Ala | Glu | Ala | Arg | Thr |      |
|     |     |     |     | 1140|     |     |     |     | 1145|     |     |     |     | 1150|     |      |
| TGG | CAC | AGG | GAA | GGG | CGC | TGG | CGC | GTG | CTG | CGG | CTC | GGA | GCC | TGG | GCG | 3504 |
| Trp | His | Arg | Glu | Gly | Arg | Trp | Arg | Val | Leu | Arg | Leu | Gly | Ala | Trp | Ala |      |
|     |     |     | 1155|     |     |     |     | 1160|     |     |     |     | 1165|     |     |      |
| CGG | TGG | CTG | CTG | GTG | GCG | CTG | ACG | GCG | GCC | ACG | GCA | CTG | GTA | CGC | CTC | 3552 |
| Arg | Trp | Leu | Leu | Val | Ala | Leu | Thr | Ala | Ala | Thr | Ala | Leu | Val | Arg | Leu |      |
|     |     |     | 1170|     |     |     |     | 1175|     |     |     |     | 1180|     |     |      |
| GCC | CAG | CTG | GGT | GCC | GCT | GAC | CGC | CAG | TGG | ACC | CGT | TTC | GTG | CGC | GGC | 3600 |
| Ala | Gln | Leu | Gly | Ala | Ala | Asp | Arg | Gln | Trp | Thr | Arg | Phe | Val | Arg | Gly |      |
| 1185|     |     |     |     | 1190|     |     |     |     | 1195|     |     |     |     | 1200|      |
| CGC | CCG | CGC | CGC | TTC | ACT | AGC | TTC | GAC | CAG | GTG | GCG | CAC | GTG | AGC | TCC | 3648 |
| Arg | Pro | Arg | Arg | Phe | Thr | Ser | Phe | Asp | Gln | Val | Ala | His | Val | Ser | Ser |      |
|     |     |     |     | 1205|     |     |     |     | 1210|     |     |     |     | 1215|     |      |
| GCA | GCC | CGT | GGC | CTG | GCG | GCC | TCG | CTG | CTC | TTC | CTG | CTT | TTG | GTC | AAG | 3696 |

```
Ala Ala Arg Gly Leu Ala Ala Ser Leu Leu Phe Leu Leu Leu Val Lys
        1220                1225                1230

GCT GCC CAG CAC GTA CGC TTC GTG CGC CAG TGG TCC GTC TTT GGC AAG      3744
Ala Ala Gln His Val Arg Phe Val Arg Gln Trp Ser Val Phe Gly Lys
        1235                1240                1245

ACA TTA TGC CGA GCT CTG CCA GAG CTC CTG GGG GTC ACC TTG GGC CTG      3792
Thr Leu Cys Arg Ala Leu Pro Glu Leu Leu Gly Val Thr Leu Gly Leu
        1250                1255                1260

GTG GTG CTC GGG GTA GCC TAC GCC CAG CTG GCC ATC CTG CTC GTG TCT      3840
Val Val Leu Gly Val Ala Tyr Ala Gln Leu Ala Ile Leu Leu Val Ser
1265                1270                1275                1280

TCC TGT GTG GAC TCC CTC TGG AGC GTG GCC CAG GCC CTG TTG GTG CTG      3888
Ser Cys Val Asp Ser Leu Trp Ser Val Ala Gln Ala Leu Leu Val Leu
                1285                1290                1295

TGC CCT GGG ACT GGG CTC TCT ACC CTG TGT CCT GCC GAG TCC TGG CAC      3936
Cys Pro Gly Thr Gly Leu Ser Thr Leu Cys Pro Ala Glu Ser Trp His
                1300                1305                1310

CTG TCA CCC CTG CTG TGT GTG GGG CTC TGG GCA CTG CGG CTG TGG GGC      3984
Leu Ser Pro Leu Leu Cys Val Gly Leu Trp Ala Leu Arg Leu Trp Gly
                1315                1320                1325

GCC CTA CGG CTG GGG GCT GTT ATT CTC CGC TGG CGC TAC CAC GCC TTG      4032
Ala Leu Arg Leu Gly Ala Val Ile Leu Arg Trp Arg Tyr His Ala Leu
        1330                1335                1340

CGT GGA GAG CTG TAC CGG CCG GCC TGG GAG CCC CAG GAC TAC GAG ATG      4080
Arg Gly Glu Leu Tyr Arg Pro Ala Trp Glu Pro Gln Asp Tyr Glu Met
1345                1350                1355                1360

GTG GAG TTG TTC CTG CGC AGG CTG CGC CTC TGG ATG GGC CTC AGC AAG      4128
Val Glu Leu Phe Leu Arg Arg Leu Arg Leu Trp Met Gly Leu Ser Lys
                1365                1370                1375

GTC AAG GAG TTC CGC CAC AAA GTC CGC TTT GAA GGG ATG GAG CCG CTG      4176
Val Lys Glu Phe Arg His Lys Val Arg Phe Glu Gly Met Glu Pro Leu
                1380                1385                1390

CCC TCT CGC TCC TCC AGG GGC TCC AAG GTA TCC CCG GAT GTG CCC CCA      4224
Pro Ser Arg Ser Ser Arg Gly Ser Lys Val Ser Pro Asp Val Pro Pro
                1395                1400                1405

CCC AGC GCT GGC TCC GAT GCC TCG CAC CCC TCC ACC TCC TCC AGC CAG      4272
Pro Ser Ala Gly Ser Asp Ala Ser His Pro Ser Thr Ser Ser Ser Gln
        1410                1415                1420

CTG GAT GGG CTG AGC GTG AGC CTG GGC CGG CTG GGG ACA AGG TGT GAG      4320
Leu Asp Gly Leu Ser Val Ser Leu Gly Arg Leu Gly Thr Arg Cys Glu
1425                1430                1435                1440

CCT GAG CCC TCC CGC CTC CAA GCC GTG TTC GAG GCC CTG CTC ACC CAG      4368
Pro Glu Pro Ser Arg Leu Gln Ala Val Phe Glu Ala Leu Leu Thr Gln
                1445                1450                1455

TTT GAC CGA CTC AAC CAG GCC ACA GAG GAC GTC TAC CAG CTG GAG CAG      4416
Phe Asp Arg Leu Asn Gln Ala Thr Glu Asp Val Tyr Gln Leu Glu Gln
                1460                1465                1470

CAG CTG CAC AGC CTG CAA GGC CGC AGG AGC AGC CGG GCG CCC GCC GGA      4464
Gln Leu His Ser Leu Gln Gly Arg Arg Ser Ser Arg Ala Pro Ala Gly
        1475                1480                1485

TCT TCC CGT GGC CCA TCC CCG GGC CTG CGG CCA GCA CTG CCC AGC CGC      4512
Ser Ser Arg Gly Pro Ser Pro Gly Leu Arg Pro Ala Leu Pro Ser Arg
        1490                1495                1500

CTT GCC CGG GCC AGT CGG GGT GTG GAC CTG GCC ACT GGC CCC AGC AGG      4560
Leu Ala Arg Ala Ser Arg Gly Val Asp Leu Ala Thr Gly Pro Ser Arg
1505                1510                1515                1520

ACA CCT TCG GGC CAA GAA CAA GGT CCA CCC CAG CAG CAC TTA GTC CTC      4608
Thr Pro Ser Gly Gln Glu Gln Gly Pro Pro Gln Gln His Leu Val Leu
                1525                1530                1535
```

-continued

```
CTT CCT GGC GGG GGT GGG CCG TGG AGT CGG AGT GGA CAC CGC TCA GTA    4656
Leu Pro Gly Gly Gly Gly Pro Trp Ser Arg Ser Gly His Arg Ser Val
            1540                1545                1550

TTA CTT TCT GCC GCT GTC AAG GCC GAG GGC CAG GCA GAA TGG CTG CAC    4704
Leu Leu Ser Ala Ala Val Lys Ala Glu Gly Gln Ala Glu Trp Leu His
        1555                1560                1565

GTA GGT TCC CCA GAG AGC AGG CAG GGG CAT CTG TCT GTC TGT GGG CTT    4752
Val Gly Ser Pro Glu Ser Arg Gln Gly His Leu Ser Val Cys Gly Leu
    1570                1575                1580

CAG CAC TTT AAA GAG GCT GTG TGG CCA ACC AGG ACC CAG GGT CCC CTC    4800
Gln His Phe Lys Glu Ala Val Trp Pro Thr Arg Thr Gln Gly Pro Leu
1585                1590                1595                1600

CCC AGC TCC CTT GGG AAG GAC ACA GCA GTA TTG GAC GGT TTC            4842
Pro Ser Ser Leu Gly Lys Asp Thr Ala Val Leu Asp Gly Phe
                1605                1610

TAGCCTCTGA GATGCTAATT TATTTCCCCG AGTCCTCAGG TACAGCGGGC TGTGCCCGGC  4902

CCCACCCCCT GGGCAGATGT CCCCCACTGC TAAGGCTGCT GGCTTCAGGG AGGGTTAGCC  4962

TGCACCGCCG CCACCCTGCC CCTAAGTTAT TACCTCTCCA GTTCCTACCG TACTCCCTGC  5022

ACCGTCTCAC TGTGTGTCTC GTGTCAGTAA TTTATATGGT GTTAAAATGT GTATATTTTT  5082

GTATGTCACT ATTTTCACTA GGGCTGAGGG GCCTGCGCCC AGAGCTGGCC TCCCCCAACA  5142

CCTGCTGCGC TTGGTAGGTG TGGTGGCGTT ATGGCAGCCC GGCTGCTGCT GGATGCGAG   5202

CTTGGCCTTG GGCCGGTGCT GGGGGCACAG CTGTCTGCCA GGCACTCTCA TCACCCCAGA  5262

GGCCTTGTCA TCCTCCCTTG CCCCAGGCCA GGTAGCAAGA GAGCAGCGCC CAGGCCTGCT  5322

GGCATCAGGT CTGGGCAAGT AGCAGGACTA GGCATGTCAG AGGACCCCAG GGTGGTTAGA  5382

GGAAAAGACT CCTCCTGGGG GCTGGCTCCC AGGGTGGAGG AAGGTGACTG TGTGTGTGTG  5442

TGTGTGCGCG CGCGACGCGC GAGTGTGCTG TATGGCCCAG GCAGCCTCAA GGCCCTCGGA  5502

GCTGGCTGTG CCTGCTTCTG TGTACCACTT CTGTGGGCAT GGCCGCTTCT AGAGCCTCGA  5562

CACCCCCCCA ACCCCCGCAC CAAGCAGACA AAGTCAATAA AAGAGCTGTC TGACTGCAAA  5622

AAAAAAAAA                                                          5631
```

(2) INFORMATION FOR SEQ ID NO: 2:

(i) SEQUENCE CHARACTERISTICS:
        (A) LENGTH: 1614 amino acids
        (B) TYPE: amino acid
        (D) TOPOLOGY: linear (ii) MOLECULE TYPE: protein (xi) SEQUENCE DESCRIPTION: SEQ ID NO: 2:

```
Leu Asn Glu Glu Pro Leu Thr Leu Ala Gly Glu Glu Ile Val Ala Gln
 1               5                  10                  15

Gly Lys Arg Ser Asp Pro Arg Ser Leu Leu Cys Tyr Gly Gly Ala Pro
            20                  25                  30

Gly Pro Gly Cys His Phe Ser Ile Pro Glu Ala Phe Ser Gly Ala Leu
        35                  40                  45

Ala Asn Leu Ser Asp Val Val Gln Leu Ile Phe Leu Val Asp Ser Asn
    50                  55                  60

Pro Phe Pro Phe Gly Tyr Ile Ser Asn Tyr Thr Val Ser Thr Lys Val
65                  70                  75                  80

Ala Ser Met Ala Phe Gln Thr Gln Ala Gly Ala Gln Ile Pro Ile Glu
                85                  90                  95

Arg Leu Ala Ser Glu Arg Ala Ile Thr Val Lys Val Pro Asn Asn Ser
```

-continued

|   |   |   | 100 |   |   |   | 105 |   |   |   | 110 |   |
|---|---|---|---|---|---|---|---|---|---|---|---|---|

Asp Trp Ala Ala Arg Gly His Arg Ser Ser Ala Asn Ser Ala Asn Ser
              115                    120                  125

Val Val Val Gln Pro Gln Ala Ser Val Gly Ala Val Val Thr Leu Asp
 130                       135                  140

Ser Ser Asn Pro Ala Ala Gly Leu His Leu Gln Leu Asn Tyr Thr Leu
145                  150                  155                  160

Leu Asp Gly His Tyr Leu Ser Glu Glu Pro Glu Pro Tyr Leu Ala Val
              165                  170                175

Tyr Leu His Ser Glu Pro Arg Pro Asn Glu His Asn Cys Ser Ala Ser
          180                  185                190

Arg Arg Ile Arg Pro Glu Ser Leu Gln Gly Ala Asp His Arg Pro Tyr
            195                200                205

Thr Phe Phe Ile Ser Pro Gly Ser Arg Asp Pro Ala Gly Ser Tyr His
     210                  215                220

Leu Asn Leu Ser Ser His Phe Arg Trp Ser Ala Leu Gln Val Ser Val
225                  230                  235                  240

Gly Leu Tyr Thr Ser Leu Cys Gln Tyr Phe Ser Glu Glu Asp Met Val
            245                250                255

Trp Arg Thr Glu Gly Leu Leu Pro Leu Glu Glu Thr Ser Pro Arg Gln
         260                  265                270

Ala Val Cys Leu Thr Arg His Leu Thr Ala Phe Gly Ala Ser Leu Phe
            275                280                285

Val Pro Pro Ser His Val Arg Phe Val Phe Pro Glu Pro Thr Ala Asp
     290                  295                300

Val Asn Tyr Ile Val Met Leu Thr Cys Ala Val Cys Leu Val Thr Tyr
305                  310                  315                  320

Met Val Met Ala Ala Ile Leu His Lys Leu Asp Gln Leu Asp Ala Ser
              325                  330                335

Arg Gly Arg Ala Ile Pro Phe Cys Gly Gln Arg Gly Arg Phe Lys Tyr
            340                345                350

Glu Ile Leu Val Lys Thr Gly Trp Gly Arg Gly Ser Gly Thr Thr Ala
         355                  360                365

His Val Gly Ile Met Leu Tyr Gly Val Asp Ser Arg Ser Gly His Arg
 370                      375                  380

His Leu Asp Gly Asp Arg Ala Phe His Arg Asn Ser Leu Asp Ile Phe
385                  390                  395                  400

Arg Ile Ala Thr Pro His Ser Leu Gly Ser Val Trp Lys Ile Arg Val
              405                410                415

Trp His Asp Asn Lys Gly Leu Ser Pro Ala Trp Phe Leu Gln His Val
         420                  425                430

Ile Val Arg Asp Leu Gln Thr Ala Arg Ser Ala Phe Phe Leu Val Asn
            435                440                445

Asp Trp Leu Ser Val Glu Thr Glu Ala Asn Gly Gly Leu Val Glu Lys
 450                      455                  460

Glu Val Leu Ala Ala Ser Asp Ala Ala Leu Leu Arg Phe Arg Arg Leu
465                  470                  475                  480

Leu Val Ala Glu Leu Gln Arg Gly Phe Phe Asp Lys His Ile Trp Leu
              485                490                495

Ser Ile Trp Asp Arg Pro Pro Arg Ser Arg Phe Thr Arg Ile Gln Arg
         500                  505                510

Ala Thr Cys Cys Val Leu Leu Ile Cys Leu Phe Leu Gly Ala Asn Ala
            515                520                525

-continued

```
Val Trp Tyr Gly Ala Val Gly Asp Ser Ala Tyr Ser Thr Gly His Val
    530                 535                 540
Ser Arg Leu Ser Pro Leu Ser Val Asp Thr Val Ala Val Gly Leu Val
545                 550                 555                 560
Ser Ser Val Val Val Tyr Pro Val Tyr Leu Ala Ile Leu Phe Leu Phe
                565                 570                 575
Arg Met Ser Arg Ser Lys Val Ala Gly Ser Pro Ser Pro Thr Pro Ala
            580                 585                 590
Gly Gln Gln Val Leu Asp Ile Asp Ser Cys Leu Asp Ser Ser Val Leu
        595                 600                 605
Asp Ser Ser Phe Leu Thr Phe Ser Gly Leu His Ala Glu Ala Phe Val
    610                 615                 620
Gly Gln Met Lys Ser Asp Leu Phe Leu Asp Asp Ser Lys Ser Leu Val
625                 630                 635                 640
Cys Trp Pro Ser Gly Glu Gly Thr Leu Ser Trp Pro Asp Leu Leu Ser
                645                 650                 655
Asp Pro Ser Ile Val Gly Ser Asn Leu Arg Gln Leu Ala Arg Gly Gln
            660                 665                 670
Ala Gly His Gly Leu Gly Pro Glu Glu Asp Gly Phe Ser Leu Ala Ser
        675                 680                 685
Pro Tyr Ser Pro Ala Lys Ser Phe Ser Ala Ser Asp Glu Asp Leu Ile
    690                 695                 700
Gln Gln Val Leu Ala Glu Gly Val Ser Ser Pro Ala Pro Thr Gln Asp
705                 710                 715                 720
Thr His Met Glu Thr Asp Leu Leu Ser Ser Leu Ser Ser Thr Pro Gly
                725                 730                 735
Glu Lys Thr Glu Thr Leu Ala Leu Gln Arg Leu Gly Glu Leu Gly Pro
            740                 745                 750
Pro Ser Pro Gly Leu Asn Trp Glu Gln Pro Gln Ala Ala Arg Leu Ser
        755                 760                 765
Arg Thr Gly Leu Val Glu Gly Leu Arg Lys Arg Leu Leu Pro Ala Trp
    770                 775                 780
Cys Ala Ser Leu Ala His Gly Leu Ser Leu Leu Leu Val Ala Val Ala
785                 790                 795                 800
Val Ala Val Ser Gly Trp Val Gly Ala Ser Phe Pro Pro Gly Val Ser
                805                 810                 815
Val Ala Trp Leu Leu Ser Ser Ser Ala Ser Phe Leu Ala Ser Phe Leu
            820                 825                 830
Gly Trp Glu Pro Leu Lys Val Leu Leu Glu Ala Leu Tyr Phe Ser Leu
        835                 840                 845
Val Ala Lys Arg Leu His Pro Asp Glu Asp Asp Thr Leu Val Glu Ser
    850                 855                 860
Pro Ala Val Thr Pro Val Ser Ala Arg Val Pro Arg Val Arg Pro Pro
865                 870                 875                 880
His Gly Phe Ala Leu Phe Leu Ala Lys Glu Glu Ala Arg Lys Val Lys
                885                 890                 895
Arg Leu His Gly Met Leu Arg Ser Leu Leu Val Tyr Met Leu Phe Leu
            900                 905                 910
Leu Val Thr Leu Leu Ala Ser Tyr Gly Asp Ala Ser Cys His Gly His
        915                 920                 925
Ala Tyr Arg Leu Gln Ser Ala Ile Lys Gln Glu Leu His Ser Arg Ala
    930                 935                 940
```

```
Phe Leu Ala Ile Thr Arg Ser Glu Glu Leu Trp Pro Trp Met Ala His
945                 950                 955                 960

Val Leu Leu Pro Tyr Val His Gly Asn Gln Ser Ser Pro Glu Leu Gly
            965                 970                 975

Pro Pro Arg Leu Arg Gln Val Arg Leu Gln Glu Ala Leu Tyr Pro Asp
            980                 985                 990

Pro Pro Gly Pro Arg Val His Thr Cys Ser Ala Ala Gly Gly Phe Ser
            995                 1000                1005

Thr Ser Asp Tyr Asp Val Gly Trp Glu Ser Pro His Asn Gly Ser Gly
    1010                1015                1020

Thr Trp Ala Tyr Ser Ala Pro Asp Leu Leu Gly Ala Trp Ser Trp Gly
1025                1030                1035                1040

Ser Cys Ala Val Tyr Asp Ser Gly Gly Tyr Val Gln Glu Leu Gly Leu
                1045                1050                1055

Ser Leu Glu Glu Ser Arg Asp Arg Leu Arg Phe Leu Gln Leu His Asn
                1060                1065                1070

Trp Leu Asp Asn Arg Ser Arg Ala Val Phe Leu Glu Leu Thr Arg Tyr
        1075                1080                1085

Ser Pro Ala Val Gly Leu His Ala Ala Val Thr Leu Arg Leu Glu Phe
    1090                1095                1100

Pro Ala Ala Gly Arg Ala Leu Ala Leu Ser Val Arg Pro Phe Ala
1105                1110                1115                1120

Leu Arg Arg Leu Ser Ala Gly Leu Ser Leu Pro Leu Leu Thr Ser Val
                1125                1130                1135

Cys Leu Leu Leu Phe Ala Val His Phe Ala Val Ala Glu Ala Arg Thr
                1140                1145                1150

Trp His Arg Glu Gly Arg Trp Arg Val Leu Arg Leu Gly Ala Trp Ala
        1155                1160                1165

Arg Trp Leu Leu Val Ala Leu Thr Ala Ala Thr Ala Leu Val Arg Leu
    1170                1175                1180

Ala Gln Leu Gly Ala Ala Asp Arg Gln Trp Thr Arg Phe Val Arg Gly
1185                1190                1195                1200

Arg Pro Arg Arg Phe Thr Ser Phe Asp Gln Val Ala His Val Ser Ser
                1205                1210                1215

Ala Ala Arg Gly Leu Ala Ala Ser Leu Leu Phe Leu Leu Leu Val Lys
            1220                1225                1230

Ala Ala Gln His Val Arg Phe Val Arg Gln Trp Ser Val Phe Gly Lys
        1235                1240                1245

Thr Leu Cys Arg Ala Leu Pro Glu Leu Leu Gly Val Thr Leu Gly Leu
    1250                1255                1260

Val Val Leu Gly Val Ala Tyr Ala Gln Leu Ala Ile Leu Leu Val Ser
1265                1270                1275                1280

Ser Cys Val Asp Ser Leu Trp Ser Val Ala Gln Ala Leu Leu Val Leu
            1285                1290                1295

Cys Pro Gly Thr Gly Leu Ser Thr Leu Cys Pro Ala Glu Ser Trp His
                1300                1305                1310

Leu Ser Pro Leu Leu Cys Val Gly Leu Trp Ala Leu Arg Leu Trp Gly
    1315                1320                1325

Ala Leu Arg Leu Gly Ala Val Ile Leu Arg Trp Arg Tyr His Ala Leu
            1330                1335                1340

Arg Gly Glu Leu Tyr Arg Pro Ala Trp Glu Pro Gln Asp Tyr Glu Met
1345                1350                1355                1360

Val Glu Leu Phe Leu Arg Arg Leu Arg Leu Trp Met Gly Leu Ser Lys
```

-continued

```
                    1365              1370              1375
Val Lys Glu Phe Arg His Lys Val Arg Phe Glu Gly Met Glu Pro Leu
            1380              1385              1390

Pro Ser Arg Ser Ser Arg Gly Ser Lys Val Ser Asp Val Pro Pro
        1395              1400              1405

Pro Ser Ala Gly Ser Asp Ala Ser His Pro Ser Thr Ser Ser Ser Gln
    1410              1415              1420

Leu Asp Gly Leu Ser Val Ser Leu Gly Arg Leu Gly Thr Arg Cys Glu
1425              1430              1435              1440

Pro Glu Pro Ser Arg Leu Gln Ala Val Phe Glu Ala Leu Leu Thr Gln
                1445              1450              1455

Phe Asp Arg Leu Asn Gln Ala Thr Glu Asp Val Tyr Gln Leu Glu Gln
            1460              1465              1470

Gln Leu His Ser Leu Gln Gly Arg Arg Ser Ser Arg Ala Pro Ala Gly
        1475              1480              1485

Ser Ser Arg Gly Pro Ser Pro Gly Leu Arg Pro Ala Leu Pro Ser Arg
    1490              1495              1500

Leu Ala Arg Ala Ser Arg Gly Val Asp Leu Ala Thr Gly Pro Ser Arg
1505              1510              1515              1520

Thr Pro Ser Gly Gln Glu Gln Gly Pro Pro Gln Gln His Leu Val Leu
                1525              1530              1535

Leu Pro Gly Gly Gly Gly Pro Trp Ser Arg Ser Gly His Arg Ser Val
            1540              1545              1550

Leu Leu Ser Ala Ala Val Lys Ala Glu Gly Gln Ala Glu Trp Leu His
        1555              1560              1565

Val Gly Ser Pro Glu Ser Arg Gln Gly His Leu Ser Val Cys Gly Leu
    1570              1575              1580

Gln His Phe Lys Glu Ala Val Trp Pro Thr Arg Thr Gln Gly Pro Leu
1585              1590              1595              1600

Pro Ser Ser Leu Gly Lys Asp Thr Ala Val Leu Asp Gly Phe
                1605              1610
```

(2) INFORMATION FOR SEQ ID NO: 3:

(i) SEQUENCE CHARACTERISTICS:
        (A) LENGTH: 553 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: misc_feature
        (B) LOCATION:1..533
        (D) OTHER INFORMATION:/function= "1A1 H.6 probe"

(xi) SEQUENCE DESCRIPTION: SEQ ID NO: 3:

```
AGCTTGGCAC CATCAAGGGC CAGTTCAACT TTGTCCACGT GATCGTCACC CCGCTGGACT    60

ACGAGTGCAA CCTGGTGTCC CTGCAGTGCA GGAAAGACAT GGAGGGCCTT GTGGACACCA   120

GCGTGGCCAA GATCGTGTCT GACCGCAACC TGCCCTTCGT GGCCCGCCAG ATGGCCCTGC   180

ACGCAAATAT GGCCTCACAG GTGCATCATA GCCGCTCCAA CCCCACCGAT ATCTACCCCT   240

CCAAGTGGAT TGCCCGGCTC CGCCACATCA AGCGGCTCCG CCAGCGGATC TGCGAGGAAG   300

CCGCCTACTC CAACCCCAGC CTACCTCTGG TGCACCCTCC GTCCCATAGC AAAGCCCCTG   360
```

```
CACAGACTCC AGCCGAGCCC ACACCTGGCT ATGAGGTGGG CCAGCGGAAG CGCCTCATCT      420

CCTCGGTGGA GGACTTCACC GAGTTTGTGT GAGGCCGGGG CCCTCCCTCC TGCACTGGCC      480

TTGGACGGTA TTGCCTGTCA GTGAAATAAA TAAAGTCCTG ACCCCAGTGC ACAGACATAG      540

AGGCACAGAT TGC                                                        553
```

(2) INFORMATION FOR SEQ ID NO: 4:

(i) SEQUENCE CHARACTERISTICS:
        (A) LENGTH: 517 base pairs
        (B) TYPE: nucleic acid
        (C) STRANDEDNESS: unknown
        (D) TOPOLOGY: unknown (ii) MOLECULE TYPE: DNA (genomic)

(vi) ORIGINAL SOURCE:
        (A) ORGANISM: Homo sapiens (ix) FEATURE:
        (A) NAME/KEY: misc_feature
        (B) LOCATION:1..517
        (D) OTHER INFORMATION:/function= "CW10 probe"

(xi) SEQUENCE DESCRIPTION: SEQ ID NO: 4:

```
CTGGTGTGTG TGAGACGTGC GGGGCTGGGA AGTGTTGGCA GAGCCGCGAG TACCGTCCTC       60

ACTCCTTTTG TTCTTTTGAC GTAAGCTGGC GAGTGGCACT GCCTGAGTTC CGCTCAGTGC      120

CCGCCCTGAT GTGCGGACCC CGCTGCATTC TTGCTGTTAG GTGGTGGCGG TGTGCGCTGT      180

CGCTGGTGGG CACCGAGAGT CTTTGGGAGC TTTGGGGAGG TTGTGCCAAG CCTGAGCCTC      240

GACGTCCCCC TTCCCGGCTT TCTGTTGGCT CTTCTGAGGC CAGGGCATCT CTATGAGGGC      300

CTCCTGCTGG AGCCGTCTCT GTGGATCTCC TCTGCCATCC TGGCCCATGA GTGGGTGATG      360

CGCTGGCCAC CATCTGGTGA CAGTGGCCGG GCACCGCTGC CAAATGTGGG TCCCGCATCT      420

GCAAGCCCCT CCCTGGGTCC CCTAGGGTAT GGGGTGGTTC TGCCACTGCC CTCGCTCCCC      480

CACCTTGGGG TGCCTCTCCC CCTGCTCGTG GGGAGA                                517
```

(2) INFORMATION FOR SEQ ID NO: 5:

(i) SEQUENCE CHARACTERISTICS:
        (A) LENGTH: 13807 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: CDS
        (B) LOCATION:2..13018

(ix) FEATURE:
        (A) NAME/KEY: misc_feature
        (B) LOCATION:7295..8184
        (D) OTHER INFORMATION:/function= "g alpha 22 fragment"

(ix) FEATURE:
        (A) NAME/KEY: misc_feature
        (B) LOCATION:6422..7294
        (D) OTHER INFORMATION:/function= "GAP GAMMA PETER
            fragment"

(ix) FEATURE:
        (A) NAME/KEY: misc_feature (B) LOCATION:3697..6421
            (D) OTHER INFORMATION:/function= "JH8 fragment"

(ix) FEATURE:
            (A) NAME/KEY: misc_feature
            (B) LOCATION:1373..1701
            (D) OTHER INFORMATION:/function= "S3/S4 PETER fragment"

(ix) FEATURE:
            (A) NAME/KEY: misc_feature
            (B) LOCATION:2176..2962
            (D) OTHER INFORMATION:/function= "S3/S4 CON2 PETER
                fragment"

(ix) FEATURE:
            (A) NAME/KEY: misc_feature
            (B) LOCATION:2963..3696
            (D) OTHER INFORMATION:/function= "S1/S3 PETER fragment"

(ix) FEATURE:
            (A) NAME/KEY: misc_feature
            (B) LOCATION:118..1372
            (D) OTHER INFORMATION:/function= "S4/JH13 fragment"

(ix) FEATURE:
            (A) NAME/KEY: misc_feature
            (B) LOCATION:1..85
            (D) OTHER INFORMATION:/function= "5' COMPLETE [Split]
                fragment"

(ix) FEATURE:
            (A) NAME/KEY: misc_feature
            (B) LOCATION:87..3696
            (D) OTHER INFORMATION:/function= "5' COMPLETE [Split]
                fragment"

(ix) FEATURE:
            (A) NAME/KEY: misc_feature
            (B) LOCATION:1..85
            (D) OTHER INFORMATION:/function= "6 (5) R cDNA [Split]
                fragment"

(ix) FEATURE:
            (A) NAME/KEY: misc_feature
            (B) LOCATION:87..117
            (D) OTHER INFORMATION:/product= "6 (5) R cDNA [Split]
                fragment"

(xi) SEQUENCE DESCRIPTION: SEQ ID NO: 5:

```
C GGC GCC GCC TGC CGC GTC AAC TGC TCG GGC CGC GGG CTG CGG ACG         46
  Gly Ala Ala Cys Arg Val Asn Cys Ser Gly Arg Gly Leu Arg Thr
  1615                1620                1625

CTC GGT CCC GCG CTG CGC ATC CCC GCG GAC GCC ACA GCG CTA GAC GTC       94
Leu Gly Pro Ala Leu Arg Ile Pro Ala Asp Ala Thr Ala Leu Asp Val
1630                1635                1640                1645

TCC CAC AAC CTG CTC CGG GCG CTG GAC GTT GGG CTC CTG GCG AAC CTC      142
Ser His Asn Leu Leu Arg Ala Leu Asp Val Gly Leu Leu Ala Asn Leu
                1650                1655                1660

TCG GCG CTG GCA GAG CTG GAT ATA AGC AAC AAC AAG ATT TCT ACG TTA      190
Ser Ala Leu Ala Glu Leu Asp Ile Ser Asn Asn Lys Ile Ser Thr Leu
                1665                1670                1675

GAA GAA GGA ATA TTT GCT AAT TTA TTT AAT TTA AGT GAA ATA AAC CTG      238
Glu Glu Gly Ile Phe Ala Asn Leu Phe Asn Leu Ser Glu Ile Asn Leu
                1680                1685                1690

AGT GGG AAC CCG TTT GAG TGT GAC TGT GGC CTG GCG TGG CTG CCG CGA      286
Ser Gly Asn Pro Phe Glu Cys Asp Cys Gly Leu Ala Trp Leu Pro Arg
                1695                1700                1705

TGG GCG GAG GAG CAG CAG GTG CGG GTG GTG CAG CCC GAG GCA GCC ACG      334
Trp Ala Glu Glu Gln Gln Val Arg Val Val Gln Pro Glu Ala Ala Thr
1710                1715                1720                1725

TGT GCT GGG CCT GGC TCC CTG GCT GGC CAG CCT CTG CTT GGC ATC CCC      382
```

```
                                                         -continued

Cys Ala Gly Pro Gly Ser Leu Ala Gly Gln Pro Leu Leu Gly Ile Pro
            1730                1735                1740

TTG CTG GAC AGT GGC TGT GGT GAG GAG TAT GTC GCC TGC CTC CCT GAC        430
Leu Leu Asp Ser Gly Cys Gly Glu Glu Tyr Val Ala Cys Leu Pro Asp
            1745                1750                1755

AAC AGC TCA GGC ACC GTG GCA GCA GTG TCC TTT TCA GCT GCC CAC GAA        478
Asn Ser Ser Gly Thr Val Ala Ala Val Ser Phe Ser Ala Ala His Glu
            1760                1765                1770

GGC CTG CTT CAG CCA GAG GCC TGC AGC GCC TTC TGC TTC TCC ACC GGC        526
Gly Leu Leu Gln Pro Glu Ala Cys Ser Ala Phe Cys Phe Ser Thr Gly
        1775                1780                1785

CAG GGC CTC GCA GCC CTC TCG GAG CAG GGC TGG TGC CTG TGT GGG GCG        574
Gln Gly Leu Ala Ala Leu Ser Glu Gln Gly Trp Cys Leu Cys Gly Ala
1790                1795                1800                1805

GCC CAG CCC TCC AGT GCC TCC TTT GCC TGC CTG TCC CTC TGC TCC GGC        622
Ala Gln Pro Ser Ser Ala Ser Phe Ala Cys Leu Ser Leu Cys Ser Gly
            1810                1815                1820

CCC CCG CCA CCT CCT GCC CCC ACC TGT AGG GGC CCC ACC CTC CTC CAG        670
Pro Pro Pro Pro Pro Ala Pro Thr Cys Arg Gly Pro Thr Leu Leu Gln
            1825                1830                1835

CAC GTC TTC CCT GCC TCC CCA GGG GCC ACC CTG GTG GGG CCC CAC GGA        718
His Val Phe Pro Ala Ser Pro Gly Ala Thr Leu Val Gly Pro His Gly
            1840                1845                1850

CCT CTG GCC TCT GGC CAG CTA GCA GCC TTC CAC ATC GCT GCC CCG CTC        766
Pro Leu Ala Ser Gly Gln Leu Ala Ala Phe His Ile Ala Ala Pro Leu
        1855                1860                1865

CCT GTC ACT GCC ACA CGC TGG GAC TTC GGA GAC GGC TCC GCC GAG GTG        814
Pro Val Thr Ala Thr Arg Trp Asp Phe Gly Asp Gly Ser Ala Glu Val
1870                1875                1880                1885

GAT GCC GCT GGG CCG GCT GCC TCG CAT CGC TAT GTG CTG CCT GGG CGC        862
Asp Ala Ala Gly Pro Ala Ala Ser His Arg Tyr Val Leu Pro Gly Arg
            1890                1895                1900

TAT CAC GTG ACG GCC GTG CTG GCC CTG GGG GCC GGC TCA GCC CTG CTG        910
Tyr His Val Thr Ala Val Leu Ala Leu Gly Ala Gly Ser Ala Leu Leu
            1905                1910                1915

GGG ACA GAC GTG CAG GTG GAA GCG GCA CCT GCC GCC CTG GAG CTC GTG        958
Gly Thr Asp Val Gln Val Glu Ala Ala Pro Ala Ala Leu Glu Leu Val
        1920                1925                1930

TGC CCG TCC TCG GTG CAG AGT GAC GAG AGC CTT GAC CTC AGC ATC CAG       1006
Cys Pro Ser Ser Val Gln Ser Asp Glu Ser Leu Asp Leu Ser Ile Gln
        1935                1940                1945

AAC CGC GGT GGT TCA GGC CTG GAG GCC GCC TAC AGC ATC GTG GCC CTG       1054
Asn Arg Gly Gly Ser Gly Leu Glu Ala Ala Tyr Ser Ile Val Ala Leu
1950                1955                1960                1965

GGC GAG GAG CCG GCC CGA GCG GTG CAC CCG CTC TGC CCC TCG GAC ACG       1102
Gly Glu Glu Pro Ala Arg Ala Val His Pro Leu Cys Pro Ser Asp Thr
            1970                1975                1980

GAG ATC TTC CCT GGC AAC GGG CAC TGC TAC CGC CTG GTG GTG GAG AAG       1150
Glu Ile Phe Pro Gly Asn Gly His Cys Tyr Arg Leu Val Val Glu Lys
        1985                1990                1995

GCG GCC TGG CTG CAG GCG CAG GAG CAG TGT CAG GCC TGG GCC GGG GCC       1198
Ala Ala Trp Leu Gln Ala Gln Glu Gln Cys Gln Ala Trp Ala Gly Ala
        2000                2005                2010

GCC CTG GCA ATG GTG GAC AGT CCC GCC GTG CAG CGC TTC CTG GTC TCC       1246
Ala Leu Ala Met Val Asp Ser Pro Ala Val Gln Arg Phe Leu Val Ser
        2015                2020                2025

CGG GTC ACC AGG AGC CTA GAC GTG TGG ATC GGC TTC TCG ACT GTG CAG       1294
Arg Val Thr Arg Ser Leu Asp Val Trp Ile Gly Phe Ser Thr Val Gln
2030                2035                2040                2045
```

```
GGG GTG GAG GTG GGC CCA GCG CCG CAG GGC GAG GCC TTC AGC CTG GAG      1342
Gly Val Glu Val Gly Pro Ala Pro Gln Gly Glu Ala Phe Ser Leu Glu
                2050                2055                2060

AGC TGC CAG AAC TGG CTG CCC GGG GAG CCA CAC CCA GCC ACA GCC GAG      1390
Ser Cys Gln Asn Trp Leu Pro Gly Glu Pro His Pro Ala Thr Ala Glu
                2065                2070                2075

CAC TGC GTC CGG CTC GGG CCC ACC GGG TGG TGT AAC ACC GAC CTG TGC      1438
His Cys Val Arg Leu Gly Pro Thr Gly Trp Cys Asn Thr Asp Leu Cys
                2080                2085                2090

TCA GCG CCG CAC AGC TAC GTC TGC GAG CTG CAG CCC GGA GGC CCA GTG      1486
Ser Ala Pro His Ser Tyr Val Cys Glu Leu Gln Pro Gly Gly Pro Val
                2095                2100                2105

CAG GAT GCC GAG AAC CTC CTC GTG GGA GCG CCC AGT GGG GAC CTG CAG      1534
Gln Asp Ala Glu Asn Leu Leu Val Gly Ala Pro Ser Gly Asp Leu Gln
2110                2115                2120                2125

GGA CCC CTG ACG CCT CTG GCA CAG CAG GAC GGC CTC TCA GCC CCG CAC      1582
Gly Pro Leu Thr Pro Leu Ala Gln Gln Asp Gly Leu Ser Ala Pro His
                2130                2135                2140

GAG CCC GTG GAG GTC ATG GTA TTC CCG GGC CTG CGT CTG AGC CGT GAA      1630
Glu Pro Val Glu Val Met Val Phe Pro Gly Leu Arg Leu Ser Arg Glu
                2145                2150                2155

GCC TTC CTC ACC ACG GCC GAA TTT GGG ACC CAG GAG CTC CGG CGG CCC      1678
Ala Phe Leu Thr Thr Ala Glu Phe Gly Thr Gln Glu Leu Arg Arg Pro
                2160                2165                2170

GCC CAG CTG CGG CTG CAG GTG TAC CGG CTC CTC AGC ACA GCA GGG ACC      1726
Ala Gln Leu Arg Leu Gln Val Tyr Arg Leu Leu Ser Thr Ala Gly Thr
                2175                2180                2185

CCG GAG AAC GGC AGC GAG CCT GAG AGC AGG TCC CCG GAC AAC AGG ACC      1774
Pro Glu Asn Gly Ser Glu Pro Glu Ser Arg Ser Pro Asp Asn Arg Thr
2190                2195                2200                2205

CAG CTG GCC CCC GCG TGC ATG CCA GGG GGA CGC TGG TGC CCT GGA GCC      1822
Gln Leu Ala Pro Ala Cys Met Pro Gly Gly Arg Trp Cys Pro Gly Ala
                2210                2215                2220

AAC ATC TGC TTG CCG CTG GAC GCC TCT TGC CAC CCC CAG GCC TGC GCC      1870
Asn Ile Cys Leu Pro Leu Asp Ala Ser Cys His Pro Gln Ala Cys Ala
                2225                2230                2235

AAT GGC TGC ACG TCA GGG CCA GGG CTA CCC GGG GCC CCC TAT GCG CTA      1918
Asn Gly Cys Thr Ser Gly Pro Gly Leu Pro Gly Ala Pro Tyr Ala Leu
                2240                2245                2250

TGG AGA GAG TTC CTC TTC TCC GTT GCC GCG GGG CCC CCC GCG CAG TAC      1966
Trp Arg Glu Phe Leu Phe Ser Val Ala Ala Gly Pro Pro Ala Gln Tyr
                2255                2260                2265

TCG GTC ACC CTC CAC GGC CAG GAT GTC CTC ATG CTC CCT GGT GAC CTC      2014
Ser Val Thr Leu His Gly Gln Asp Val Leu Met Leu Pro Gly Asp Leu
2270                2275                2280                2285

GTT GGC TTG CAG CAC GAC GCT GGC CCT GGC GCC CTC CTG CAC TGC TCG      2062
Val Gly Leu Gln His Asp Ala Gly Pro Gly Ala Leu Leu His Cys Ser
                2290                2295                2300

CCG GCT CCC GGC CAC CCT GGT CCC CAG GCC CCG TAC CTC TCC GCC AAC      2110
Pro Ala Pro Gly His Pro Gly Pro Gln Ala Pro Tyr Leu Ser Ala Asn
                2305                2310                2315

GCC TCG TCA TGG CTG CCC CAC TTG CCA GCC AGC TG GAG GGC ACT TGG       2158
Ala Ser Ser Trp Leu Pro His Leu Pro Ala Ser Leu Glu Gly Thr Trp
                2320                2325                2330

GCC TGC CCT GCC TGT GCC CTG CGG CTG CTT GCA GCC ACG GAA CAG CTC      2206
Ala Cys Pro Ala Cys Ala Leu Arg Leu Leu Ala Ala Thr Glu Gln Leu
                2335                2340                2345

ACC GTG CTG CTG GGC TTG AGG CCC AAC CCT GGA CTG CGG ATG CCT GGG      2254
Thr Val Leu Leu Gly Leu Arg Pro Asn Pro Gly Leu Arg Met Pro Gly
2350                2355                2360                2365
```

```
CGC TAT GAG GTC CGG GCA GAG GTG GGC AAT GGC GTG TCC AGG CAC AAC        2302
Arg Tyr Glu Val Arg Ala Glu Val Gly Asn Gly Val Ser Arg His Asn
                2370            2375                2380

CTC TCC TGC AGC TTT GAC GTG GTC TCC CCA GTG GCT GGG CTG CGG GTC        2350
Leu Ser Cys Ser Phe Asp Val Val Ser Pro Val Ala Gly Leu Arg Val
                2385            2390                2395

ATC TAC CCT GCC CCC CGC GAC GGC CGC CTC TAC GTG CCC ACC AAC GGC        2398
Ile Tyr Pro Ala Pro Arg Asp Gly Arg Leu Tyr Val Pro Thr Asn Gly
                2400            2405                2410

TCA GCC TTG GTG CTC CAG GTG GAC TCT GGT GCC AAC GCC ACG GCC ACG        2446
Ser Ala Leu Val Leu Gln Val Asp Ser Gly Ala Asn Ala Thr Ala Thr
                2415            2420                2425

GCT CGC TGG CCT GGG GGC AGT GTC AGC GCC CGC TTT GAG AAT GTC TGC        2494
Ala Arg Trp Pro Gly Gly Ser Val Ser Ala Arg Phe Glu Asn Val Cys
2430            2435            2440                2445

CCT GCC CTG GTG GCC ACC TTC GTG CCC GGC TGC CCC TGG GAG ACC AAC        2542
Pro Ala Leu Val Ala Thr Phe Val Pro Gly Cys Pro Trp Glu Thr Asn
                2450            2455                2460

GAT ACC CTG TTC TCA GTG GTA GCA CTG CCG TGG CTC AGT GAG GGG GAG        2590
Asp Thr Leu Phe Ser Val Val Ala Leu Pro Trp Leu Ser Glu Gly Glu
                2465            2470                2475

CAC GTG GTG GAC GTG GTG GTG GAA AAC AGC GCC AGC CGG GCC AAC CTC        2638
His Val Val Asp Val Val Val Glu Asn Ser Ala Ser Arg Ala Asn Leu
                2480            2485                2490

AGC CTG CGG GTG ACG GCG GAG GAG CCC ATC TGT GGC CTC CGC GCC ACG        2686
Ser Leu Arg Val Thr Ala Glu Glu Pro Ile Cys Gly Leu Arg Ala Thr
                2495            2500                2505

CCC AGC CCC GAG GCC CGT GTA CTG CAG GGA GTC CTA GTG AGG TAC AGC        2734
Pro Ser Pro Glu Ala Arg Val Leu Gln Gly Val Leu Val Arg Tyr Ser
2510            2515            2520                2525

CCC GTG GTG GAG GCC GGC TCG GAC ATG GTC TTC CGG TGG ACC ATC AAC        2782
Pro Val Val Glu Ala Gly Ser Asp Met Val Phe Arg Trp Thr Ile Asn
                2530            2535                2540

GAC AAG CAG TCC CTG ACC TTC CAG AAC GTG GTC TTC AAT GTC ATT TAT        2830
Asp Lys Gln Ser Leu Thr Phe Gln Asn Val Val Phe Asn Val Ile Tyr
                2545            2550                2555

CAG AGC GCG GCG GTC TTC AAG CTC TCA CTG ACG GCC TCC AAC CAC GTG        2878
Gln Ser Ala Ala Val Phe Lys Leu Ser Leu Thr Ala Ser Asn His Val
                2560            2565                2570

AGC AAC GTC ACC GTG AAC TAC AAC GTA ACC GTG GAG CGG ATG AAC AGG        2926
Ser Asn Val Thr Val Asn Tyr Asn Val Thr Val Glu Arg Met Asn Arg
                2575            2580                2585

ATG CAG GGT CTG CAG GTC TCC ACA GTG CCG GCC GTG CTG TCC CCC AAT        2974
Met Gln Gly Leu Gln Val Ser Thr Val Pro Ala Val Leu Ser Pro Asn
2590            2595            2600                2605

GCC ACA CTG GTA CTG ACG GGT GGT GTG CTG GTG GAC TCA GCT GTG GAG        3022
Ala Thr Leu Val Leu Thr Gly Gly Val Leu Val Asp Ser Ala Val Glu
                2610            2615                2620

GTG GCC TTC CTG TGG AAC TTT GGG GAT GGG GAG CAG GCC CTC CAC CAG        3070
Val Ala Phe Leu Trp Asn Phe Gly Asp Gly Glu Gln Ala Leu His Gln
                2625            2630                2635

TTC CAG CCT CCG TAC AAC GAG TCC TTC CCG GTT CCA GAC CCC TCG GTG        3118
Phe Gln Pro Pro Tyr Asn Glu Ser Phe Pro Val Pro Asp Pro Ser Val
                2640            2645                2650

GCC CAG GTG CTG GTG GAG CAC AAT GTC ATG CAC ACC TAC GCT GCC CCA        3166
Ala Gln Val Leu Val Glu His Asn Val Met His Thr Tyr Ala Ala Pro
                2655            2660                2665

GGT GAG TAC CTC CTG ACC GTG CTG GCA TCT AAT GCC TTC GAG AAC CTG        3214
Gly Glu Tyr Leu Leu Thr Val Leu Ala Ser Asn Ala Phe Glu Asn Leu
```

```
                 2670                2675                2680                2685

ACG CAG CAG GTG CCT GTG AGC GTG CGC GCC TCC CTG CCC TCC GTG GCT       3262
Thr Gln Gln Val Pro Val Ser Val Arg Ala Ser Leu Pro Ser Val Ala
                2690                2695                2700

GTG GGT GTG AGT GAC GGC GTC CTG GTG GCC GGC CGG CCC GTC ACC TTC       3310
Val Gly Val Ser Asp Gly Val Leu Val Ala Gly Arg Pro Val Thr Phe
                2705                2710                2715

TAC CCG CAC CCG CTG CCC TCG CCT GGG GGT GTT CTT TAC ACG TGG GAC       3358
Tyr Pro His Pro Leu Pro Ser Pro Gly Gly Val Leu Tyr Thr Trp Asp
                2720                2725                2730

TTC GGG GAC GGC TCC CCT GTC CTG ACC CAG AGC CAG CCG GCT GCC AAC       3406
Phe Gly Asp Gly Ser Pro Val Leu Thr Gln Ser Gln Pro Ala Ala Asn
                2735                2740                2745

CAC ACC TAT GCC TCG AGG GGC ACC TAC CAC GTG CGC CTG GAG GTC AAC       3454
His Thr Tyr Ala Ser Arg Gly Thr Tyr His Val Arg Leu Glu Val Asn
2750                2755                2760                2765

AAC ACG GTG AGC GGT GCG GCG GCC CAG GCG GAT GTG CGC GTC TTT GAG       3502
Asn Thr Val Ser Gly Ala Ala Ala Gln Ala Asp Val Arg Val Phe Glu
                2770                2775                2780

GAG CTC CGC GGA CTC AGC GTG GAC ATG AGC CTG GCC GTG GAG CAG GGC       3550
Glu Leu Arg Gly Leu Ser Val Asp Met Ser Leu Ala Val Glu Gln Gly
                2785                2790                2795

GCC CCC GTG GTG GTC AGC GCC GCG GTG CAG ACG GGC GAC AAC ATC ACG       3598
Ala Pro Val Val Val Ser Ala Ala Val Gln Thr Gly Asp Asn Ile Thr
                2800                2805                2810

TGG ACC TTC GAC ATG GGG GAC GGC ACC GTG CTG TCG GGC CCG GAG GCA       3646
Trp Thr Phe Asp Met Gly Asp Gly Thr Val Leu Ser Gly Pro Glu Ala
                2815                2820                2825

ACA GTG GAG CAT GTG TAC CTG CGG GCA CAG AAC TGC ACA GTG ACC GTG       3694
Thr Val Glu His Val Tyr Leu Arg Ala Gln Asn Cys Thr Val Thr Val
2830                2835                2840                2845

GGT GCG GCC AGC CCC GCC GGC CAC CTG GCC CGG AGC CTG CAC GTG CTG       3742
Gly Ala Ala Ser Pro Ala Gly His Leu Ala Arg Ser Leu His Val Leu
                2850                2855                2860

GTC TTC GTC CTG GAG GTG CTG CGC GTT GAA CCC GCC GCC TGC ATC CCC       3790
Val Phe Val Leu Glu Val Leu Arg Val Glu Pro Ala Ala Cys Ile Pro
                2865                2870                2875

ACG CAG CCT GAC GCG CGG CTC ACG GCC TAC GTC ACC GGG AAC CCG GCC       3838
Thr Gln Pro Asp Ala Arg Leu Thr Ala Tyr Val Thr Gly Asn Pro Ala
                2880                2885                2890

CAC TAC CTC TTC GAC TGG ACC TTC GGG GAT GGC TCC TCC AAC ACG ACC       3886
His Tyr Leu Phe Asp Trp Thr Phe Gly Asp Gly Ser Ser Asn Thr Thr
                2895                2900                2905

GTG CGG GGG TGC CCG ACG GTG ACA CAC AAC TTC ACG CGG AGC GGC ACG       3934
Val Arg Gly Cys Pro Thr Val Thr His Asn Phe Thr Arg Ser Gly Thr
2910                2915                2920                2925

TTC CCC CTG GCG CTG GTG CTG TCC AGC CGC GTG AAC AGG GCG CAT TAC       3982
Phe Pro Leu Ala Leu Val Leu Ser Ser Arg Val Asn Arg Ala His Tyr
                2930                2935                2940

TTC ACC AGC ATC TGC GTG GAG CCA GAG GTG GGC AAC GTC ACC CTG CAG       4030
Phe Thr Ser Ile Cys Val Glu Pro Glu Val Gly Asn Val Thr Leu Gln
                2945                2950                2955

CCA GAG AGG CAG TTT GTG CAG CTC GGG GAC GAG GCC TGG CTG GTG GCA       4078
Pro Glu Arg Gln Phe Val Gln Leu Gly Asp Glu Ala Trp Leu Val Ala
                2960                2965                2970

TGT GCC TGG CCC CCG TTC CCC TAC CGC TAC ACC TGG GAC TTT GGC ACC       4126
Cys Ala Trp Pro Pro Phe Pro Tyr Arg Tyr Thr Trp Asp Phe Gly Thr
                2975                2980                2985

GAG GAA GCC GCC CCC ACC CGT GCC AGG GGC CCT GAG GTG ACG TTC ATC       4174
```

```
Glu Glu Ala Ala Pro Thr Arg Ala Arg Gly Pro Glu Val Thr Phe Ile
2990                2995                3000                3005

TAC CGA GAC CCA GGC TCC TAT CTT GTG ACA GTC ACC GCG TCC AAC AAC      4222
Tyr Arg Asp Pro Gly Ser Tyr Leu Val Thr Val Thr Ala Ser Asn Asn
                3010                3015                3020

ATC TCT GCT GCC AAT GAC TCA GCC CTG GTG GAG GTG CAG GAG CCC GTG      4270
Ile Ser Ala Ala Asn Asp Ser Ala Leu Val Glu Val Gln Glu Pro Val
                3025                3030                3035

CTG GTC ACC AGC ATC AAG GTC AAT GGC TCC CTT GGG CTG GAG CTG CAG      4318
Leu Val Thr Ser Ile Lys Val Asn Gly Ser Leu Gly Leu Glu Leu Gln
                3040                3045                3050

CAG CCG TAC CTG TTC TCT GCT GTG GGC CGT GGG CGC CCC GCC AGC TAC      4366
Gln Pro Tyr Leu Phe Ser Ala Val Gly Arg Gly Arg Pro Ala Ser Tyr
                3055                3060                3065

CTG TGG GAT CTG GGG GAC GGT GGG TGG CTC GAG GGT CCG GAG GTC ACC      4414
Leu Trp Asp Leu Gly Asp Gly Gly Trp Leu Glu Gly Pro Glu Val Thr
3070                3075                3080                3085

CAC GCT TAC AAC AGC ACA GGT GAC TTC ACC GTT AGG GTG GCC GGC TGG      4462
His Ala Tyr Asn Ser Thr Gly Asp Phe Thr Val Arg Val Ala Gly Trp
                3090                3095                3100

AAT GAG GTG AGC CGC AGC GAG GCC TGG CTC AAT GTG ACG GTG AAG CGG      4510
Asn Glu Val Ser Arg Ser Glu Ala Trp Leu Asn Val Thr Val Lys Arg
                3105                3110                3115

CGC GTG CGG GGG CTC GTC GTC AAT GCA AGC CGC ACG GTG GTG CCC CTG      4558
Arg Val Arg Gly Leu Val Val Asn Ala Ser Arg Thr Val Val Pro Leu
                3120                3125                3130

AAT GGG AGC GTG AGC TTC AGC ACG TCG CTG GAG GCC GGC AGT GAT GTG      4606
Asn Gly Ser Val Ser Phe Ser Thr Ser Leu Glu Ala Gly Ser Asp Val
                3135                3140                3145

CGC TAT TCC TGG GTG CTC TGT GAC CGC TGC ACG CCC ATC CCT GGG GGT      4654
Arg Tyr Ser Trp Val Leu Cys Asp Arg Cys Thr Pro Ile Pro Gly Gly
3150                3155                3160                3165

CCT ACC ATC TCT TAC ACC TTC CGC TCC GTG GGC ACC TTC AAT ATC ATC      4702
Pro Thr Ile Ser Tyr Thr Phe Arg Ser Val Gly Thr Phe Asn Ile Ile
                3170                3175                3180

GTC ACG GCT GAG AAC GAG GTG GGC TCC GCC CAG GAC AGC ATC TTC GTC      4750
Val Thr Ala Glu Asn Glu Val Gly Ser Ala Gln Asp Ser Ile Phe Val
                3185                3190                3195

TAT GTC CTG CAG CTC ATA GAG GGG CTG CAG GTG GTG GGC GGT GGC CGC      4798
Tyr Val Leu Gln Leu Ile Glu Gly Leu Gln Val Val Gly Gly Gly Arg
                3200                3205                3210

TAC TTC CCC ACC AAC CAC ACG GTA CAG CTG CAG GCC GTG GTT AGG GAT      4846
Tyr Phe Pro Thr Asn His Thr Val Gln Leu Gln Ala Val Val Arg Asp
                3215                3220                3225

GGC ACC AAC GTC TCC TAC AGC TGG ACT GCC TGG AGG GAC AGG GGC CCG      4894
Gly Thr Asn Val Ser Tyr Ser Trp Thr Ala Trp Arg Asp Arg Gly Pro
3230                3235                3240                3245

GCC CTG GCC GGC AGC GGC AAA GGC TTC TCG CTC ACC GTG CTC GAG GCC      4942
Ala Leu Ala Gly Ser Gly Lys Gly Phe Ser Leu Thr Val Leu Glu Ala
                3250                3255                3260

GGC ACC TAC CAT GTG CAG CTG CGG GCC ACC AAC ATG CTG GGC AGC GCC      4990
Gly Thr Tyr His Val Gln Leu Arg Ala Thr Asn Met Leu Gly Ser Ala
                3265                3270                3275

TGG GCC GAC TGC ACC ATG GAC TTC GTG GAG CCT GTG GGG TGG CTG ATG      5038
Trp Ala Asp Cys Thr Met Asp Phe Val Glu Pro Val Gly Trp Leu Met
                3280                3285                3290

GTG ACC GCC TCC CCG AAC CCA GCT GCC GTC AAC ACA AGC GTC ACC CTC      5086
Val Thr Ala Ser Pro Asn Pro Ala Ala Val Asn Thr Ser Val Thr Leu
                3295                3300                3305
```

```
AGT GCC GAG CTG GCT GGT GGC AGT GGT GTC GTA TAC ACT TGG TCC TTG      5134
Ser Ala Glu Leu Ala Gly Gly Ser Gly Val Val Tyr Thr Trp Ser Leu
3310                3315                3320                3325

GAG GAG GGG CTG AGC TGG GAG ACC TCC GAG CCA TTT ACC ACC CAT AGC      5182
Glu Glu Gly Leu Ser Trp Glu Thr Ser Glu Pro Phe Thr Thr His Ser
            3330                3335                3340

TTC CCC ACA CCC GGC CTG CAC TTG GTC ACC ATG ACG GCA GGG AAC CCG      5230
Phe Pro Thr Pro Gly Leu His Leu Val Thr Met Thr Ala Gly Asn Pro
                3345                3350                3355

CTG GGC TCA GCC AAC GCC ACC GTG GAA GTG GAT GTG CAG GTG CCT GTG      5278
Leu Gly Ser Ala Asn Ala Thr Val Glu Val Asp Val Gln Val Pro Val
                    3360                3365                3370

AGT GGC CTC AGC ATC AGG GCC AGC GAG CCC GGA GGC AGC TTC GTG GCG      5326
Ser Gly Leu Ser Ile Arg Ala Ser Glu Pro Gly Gly Ser Phe Val Ala
3375                3380                3385

GCC GGG TCC TCT GTG CCC TTT TGG GGG CAG CTG GCC ACG GGC ACC AAT      5374
Ala Gly Ser Ser Val Pro Phe Trp Gly Gln Leu Ala Thr Gly Thr Asn
        3390                3395                3400                3405

GTG AGC TGG TGC TGG GCT GTG CCC GGC GGC AGC AGC AAG CGT GGC CCT      5422
Val Ser Trp Cys Trp Ala Val Pro Gly Gly Ser Ser Lys Arg Gly Pro
            3410                3415                3420

CAT GTC ACC ATG GTC TTC CCG GAT GCT GGC ACC TTC TCC ATC CGG CTC      5470
His Val Thr Met Val Phe Pro Asp Ala Gly Thr Phe Ser Ile Arg Leu
                3425                3430                3435

AAT GCC TCC AAC GCA GTC AGC TGG GTC TCA GCC ACG TAC AAC CTC ACG      5518
Asn Ala Ser Asn Ala Val Ser Trp Val Ser Ala Thr Tyr Asn Leu Thr
                    3440                3445                3450

GCG GAG GAG CCC ATC GTG GGC CTG GTG CTG TGG GCC AGC AGC AAG GTG      5566
Ala Glu Glu Pro Ile Val Gly Leu Val Leu Trp Ala Ser Ser Lys Val
3455                3460                3465

GTG GCG CCC GGG CAG CTG GTC CAT TTT CAG ATC CTG CTG GCT GCC GGC      5614
Val Ala Pro Gly Gln Leu Val His Phe Gln Ile Leu Leu Ala Ala Gly
        3470                3475                3480                3485

TCA GCT GTC ACC TTC CGC CTG CAG GTC GGC GGG GCC AAC CCC GAG GTG      5662
Ser Ala Val Thr Phe Arg Leu Gln Val Gly Gly Ala Asn Pro Glu Val
            3490                3495                3500

CTC CCC GGG CCC CGT TTC TCC CAC AGC TTC CCC CGC GTC GGA GAC CAC      5710
Leu Pro Gly Pro Arg Phe Ser His Ser Phe Pro Arg Val Gly Asp His
                3505                3510                3515

GTG GTG AGC GTG CGG GGC AAA AAC CAC GTG AGC TGG GCC CAG GCG CAG      5758
Val Val Ser Val Arg Gly Lys Asn His Val Ser Trp Ala Gln Ala Gln
                    3520                3525                3530

GTG CGC ATC GTG GTG CTG GAG GCC GTG AGT GGG CTG CAG ATG CCC AAC      5806
Val Arg Ile Val Val Leu Glu Ala Val Ser Gly Leu Gln Met Pro Asn
3535                3540                3545

TGC TGC GAG CCT GGC ATC GCC ACG GGC ACT GAG AGG AAC TTC ACA GCC      5854
Cys Cys Glu Pro Gly Ile Ala Thr Gly Thr Glu Arg Asn Phe Thr Ala
        3550                3555                3560                3565

CGC GTG CAG CGC GGC TCT CGG GTC GCC TAC GCC TGG TAC TTC TCG CTG      5902
Arg Val Gln Arg Gly Ser Arg Val Ala Tyr Ala Trp Tyr Phe Ser Leu
            3570                3575                3580

CAG AAG GTC CAG GGC GAC TCG CTG GTC ATC CTG TCG GGC CGC GAC GTC      5950
Gln Lys Val Gln Gly Asp Ser Leu Val Ile Leu Ser Gly Arg Asp Val
                3585                3590                3595

ACC TAC ACG CCC GTG GCC GCG GGG CTG TTG GAG ATC CAG GTG CGC GCC      5998
Thr Tyr Thr Pro Val Ala Ala Gly Leu Leu Glu Ile Gln Val Arg Ala
                    3600                3605                3610

TTC AAC GCC CTG GGC AGT GAG AAC CGC ACG CTG GTG CTG GAG GTT CAG      6046
Phe Asn Ala Leu Gly Ser Glu Asn Arg Thr Leu Val Leu Glu Val Gln
3615                3620                3625
```

-continued

```
GAC GCC GTC CAG TAT GTG GCC CTG CAG AGC GGC CCC TGC TTC ACC AAC       6094
Asp Ala Val Gln Tyr Val Ala Leu Gln Ser Gly Pro Cys Phe Thr Asn
3630              3635              3640              3645

CGC TCG GCG CAG TTT GAG GCC GCC ACC AGC CCC AGC CCC CGG CGT GTG       6142
Arg Ser Ala Gln Phe Glu Ala Ala Thr Ser Pro Ser Pro Arg Arg Val
              3650              3655              3660

GCC TAC CAC TGG GAC TTT GGG GAT GGG TCG CCA GGG CAG GAC ACA GAT       6190
Ala Tyr His Trp Asp Phe Gly Asp Gly Ser Pro Gly Gln Asp Thr Asp
3665              3670              3675

GAG CCC AGG GCC GAG CAC TCC TAC CTG AGG CCT GGG GAC TAC CGC GTG       6238
Glu Pro Arg Ala Glu His Ser Tyr Leu Arg Pro Gly Asp Tyr Arg Val
3680              3685              3690

CAG GTG AAC GCC TCC AAC CTG GTG AGC TTC TTC GTG GCG CAG GCC ACG       6286
Gln Val Asn Ala Ser Asn Leu Val Ser Phe Phe Val Ala Gln Ala Thr
     3695              3700              3705

GTG ACC GTC CAG GTG CTG GCC TGC CGG GAG CCG GAG GTG GAC GTG GTC       6334
Val Thr Val Gln Val Leu Ala Cys Arg Glu Pro Glu Val Asp Val Val
3710              3715              3720              3725

CTG CCC CTG CAG GTG CTG ATG CGG CGA TCA CAG CGC AAC TAC TTG GAG       6382
Leu Pro Leu Gln Val Leu Met Arg Arg Ser Gln Arg Asn Tyr Leu Glu
              3730              3735              3740

GCC CAC GTT GAC CTG CGC GAC TGC GTC ACC TAC CAG ACT GAG TAC CGC       6430
Ala His Val Asp Leu Arg Asp Cys Val Thr Tyr Gln Thr Glu Tyr Arg
          3745              3750              3755

TGG GAG GTG TAT CGC ACC GCC AGC TGC CAG CGG CCG GGG CGC CCA GCG       6478
Trp Glu Val Tyr Arg Thr Ala Ser Cys Gln Arg Pro Gly Arg Pro Ala
     3760              3765              3770

CGT GTG GCC CTG CCC GGC GTG GAC GTG AGC CGG CCT CGG CTG GTG CTG       6526
Arg Val Ala Leu Pro Gly Val Asp Val Ser Arg Pro Arg Leu Val Leu
3775              3780              3785

CCG CGG CTG GCG CTG CCT GTG GGG CAC TAC TGC TTT GTG TTT GTC GTG       6574
Pro Arg Leu Ala Leu Pro Val Gly His Tyr Cys Phe Val Phe Val Val
3790              3795              3800              3805

TCA TTT GGG GAC ACG CCA CTG ACA CAG AGC ATC CAG GCC AAT GTG ACG       6622
Ser Phe Gly Asp Thr Pro Leu Thr Gln Ser Ile Gln Ala Asn Val Thr
              3810              3815              3820

GTG GCC CCC GAG CGC CTG GTG CCC ATC ATT GAG GGT GGC TCA TAC CGC       6670
Val Ala Pro Glu Arg Leu Val Pro Ile Ile Glu Gly Gly Ser Tyr Arg
          3825              3830              3835

GTG TGG TCA GAC ACA CGG GAC CTG GTG CTG GAT GGG AGC GAG TCC TAC       6718
Val Trp Ser Asp Thr Arg Asp Leu Val Leu Asp Gly Ser Glu Ser Tyr
     3840              3845              3850

GAC CCC AAC CTG GAG GAC GGC GAC CAG ACG CCG CTC AGT TTC CAC TGG       6766
Asp Pro Asn Leu Glu Asp Gly Asp Gln Thr Pro Leu Ser Phe His Trp
3855              3860              3865

GCC TGT GTG GCT TCG ACA CAG AGG GAG GCT GGC GGG TGT GCG CTG AAC       6814
Ala Cys Val Ala Ser Thr Gln Arg Glu Ala Gly Gly Cys Ala Leu Asn
3870              3875              3880              3885

TTT GGG CCC CGC GGG AGC AGC ACG GTC ACC ATT CCA CGG GAG CGG CTG       6862
Phe Gly Pro Arg Gly Ser Ser Thr Val Thr Ile Pro Arg Glu Arg Leu
              3890              3895              3900

GCG GCT GGC GTG GAG TAC ACC TTC AGC CTG ACC GTG TGG AAG GCC GGC       6910
Ala Ala Gly Val Glu Tyr Thr Phe Ser Leu Thr Val Trp Lys Ala Gly
          3905              3910              3915

CGC AAG GAG GAG GCC ACC AAC CAG ACG GTG CTG ATC CGG AGT GGC CGG       6958
Arg Lys Glu Glu Ala Thr Asn Gln Thr Val Leu Ile Arg Ser Gly Arg
     3920              3925              3930

GTG CCC ATT GTG TCC TTG GAG TGT GTG TCC TGC AAG GCA CAG GCC GTG       7006
Val Pro Ile Val Ser Leu Glu Cys Val Ser Cys Lys Ala Gln Ala Val
```

```
              3935                3940                3945
TAC GAA GTG AGC CGC AGC TCC TAC GTG TAC TTG GAG GGC CGC TGC CTC   7054
Tyr Glu Val Ser Arg Ser Ser Tyr Val Tyr Leu Glu Gly Arg Cys Leu
3950                3955                3960                3965

AAT TGC AGC AGC GGC TCC AAG CGA GGG CGG TGG GCT GCA CGT ACG TTC   7102
Asn Cys Ser Ser Gly Ser Lys Arg Gly Arg Trp Ala Ala Arg Thr Phe
            3970                3975                3980

AGC AAC AAG ACG CTG GTG CTG GAT GAG ACC ACC ACA TCC ACG GGC AGT   7150
Ser Asn Lys Thr Leu Val Leu Asp Glu Thr Thr Thr Ser Thr Gly Ser
        3985                3990                3995

GCA GGC ATG CGA CTG GTG CTG CGG CGG GGC GTG CTG CGG GAC GGC GAG   7198
Ala Gly Met Arg Leu Val Leu Arg Arg Gly Val Leu Arg Asp Gly Glu
    4000                4005                4010

GGA TAC ACC TTC ACG CTC ACG GTG CTG GGC CGC TCT GGC GAG GAG GAG   7246
Gly Tyr Thr Phe Thr Leu Thr Val Leu Gly Arg Ser Gly Glu Glu Glu
    4015                4020                4025

GGC TGC GCC TCC ATC CGC CTG TCC CCC AAC CGC CCG CCG CTG GGG GGC   7294
Gly Cys Ala Ser Ile Arg Leu Ser Pro Asn Arg Pro Pro Leu Gly Gly
4030                4035                4040                4045

TCT TGC CGC CTC TTC CCA CTG GGC GCT GTG CAC GCC CTC ACC ACC AAG   7342
Ser Cys Arg Leu Phe Pro Leu Gly Ala Val His Ala Leu Thr Thr Lys
            4050                4055                4060

GTG CAC TTC GAA TGC ACG GGC TGG CAT GAC GCG GAG GAT GCT GGC GCC   7390
Val His Phe Glu Cys Thr Gly Trp His Asp Ala Glu Asp Ala Gly Ala
        4065                4070                4075

CCG CTG GTG TAC GCC CTG CTG CTG CGG CGC TGT CGC CAG GGC CAC TGC   7438
Pro Leu Val Tyr Ala Leu Leu Leu Arg Arg Cys Arg Gln Gly His Cys
    4080                4085                4090

GAG GAG TTC TGT GTC TAC AAG GGC AGC CTC TCC AGC TAC GGA GCC GTG   7486
Glu Glu Phe Cys Val Tyr Lys Gly Ser Leu Ser Ser Tyr Gly Ala Val
    4095                4100                4105

CTG CCC CCG GGT TTC AGG CCA CAC TTC GAG GTG GGC CTG GCC GTG GTG   7534
Leu Pro Pro Gly Phe Arg Pro His Phe Glu Val Gly Leu Ala Val Val
4110                4115                4120                4125

GTG CAG GAC CAG CTG GGA GCC GCT GTG GTC GCC CTC AAC AGG TCT TTG   7582
Val Gln Asp Gln Leu Gly Ala Ala Val Val Ala Leu Asn Arg Ser Leu
            4130                4135                4140

GCC ATC ACC CTC CCA GAG CCC AAC GGC AGC GCA ACG GGG CTC ACA GTC   7630
Ala Ile Thr Leu Pro Glu Pro Asn Gly Ser Ala Thr Gly Leu Thr Val
        4145                4150                4155

TGG CTG CAC GGG CTC ACC GCT AGT GTG CTC CCA GGG CTG CTG CGG CAG   7678
Trp Leu His Gly Leu Thr Ala Ser Val Leu Pro Gly Leu Leu Arg Gln
    4160                4165                4170

GCC GAT CCC CAG CAC GTC ATC GAG TAC TCG TTG GCC CTG GTC ACC GTG   7726
Ala Asp Pro Gln His Val Ile Glu Tyr Ser Leu Ala Leu Val Thr Val
    4175                4180                4185

CTG AAC GAG TAC GAG CGG GCC CTG GAC GTG GCG GCA GAG CCC AAG CAC   7774
Leu Asn Glu Tyr Glu Arg Ala Leu Asp Val Ala Ala Glu Pro Lys His
4190                4195                4200                4205

GAG CGG CAG CAC CGA GCC CAG ATA CGC AAG AAC ATC ACG GAG ACT CTG   7822
Glu Arg Gln His Arg Ala Gln Ile Arg Lys Asn Ile Thr Glu Thr Leu
            4210                4215                4220

GTG TCC CTG AGG GTC CAC ACT GTG GAT GAC ATC CAG CAG ATC GCT GCT   7870
Val Ser Leu Arg Val His Thr Val Asp Asp Ile Gln Gln Ile Ala Ala
        4225                4230                4235

GCG CTG GCC CAG TGC ATG GGG CCC AGC AGG GAG CTC GTA TGC CGC TCG   7918
Ala Leu Ala Gln Cys Met Gly Pro Ser Arg Glu Leu Val Cys Arg Ser
    4240                4245                4250

TGC CTG AAG CAG ACG CTG CAC AAG CTG GAG GCC ATG ATG CTC ATC CTG   7966
```

```
Cys Leu Lys Gln Thr Leu His Lys Leu Glu Ala Met Met Leu Ile Leu
    4255                4260                4265

CAG GCA GAG ACC ACC GCG GGC ACC GTG ACG CCC ACC GCC ATC GGA GAC    8014
Gln Ala Glu Thr Thr Ala Gly Thr Val Thr Pro Thr Ala Ile Gly Asp
4270            4275                4280                4285

AGC ATC CTC AAC ATC ACA GGA GAC CTC ATC CAC CTG GCC AGC TCG GAC    8062
Ser Ile Leu Asn Ile Thr Gly Asp Leu Ile His Leu Ala Ser Ser Asp
                4290                4295                4300

GTG CGG GCA CCA CAG CCC TCA GAG CTG GGA GCC GAG TCA CCA TCT CGG    8110
Val Arg Ala Pro Gln Pro Ser Glu Leu Gly Ala Glu Ser Pro Ser Arg
            4305                4310                4315

ATG GTG GCG TCC CAG GCC TAC AAC CTG ACC TCT GCC CTC ATG CGC ATC    8158
Met Val Ala Ser Gln Ala Tyr Asn Leu Thr Ser Ala Leu Met Arg Ile
        4320                4325                4330

CTC ATG CGC TCC CGC GTG CTC AAC GAG GAG CCC CTG ACG CTG GCG GGC    8206
Leu Met Arg Ser Arg Val Leu Asn Glu Glu Pro Leu Thr Leu Ala Gly
    4335                4340                4345

GAG GAG ATC GTG GCC CAG GGC AAG CGC TCG GAC CCG CGG AGC CTG CTG    8254
Glu Glu Ile Val Ala Gln Gly Lys Arg Ser Asp Pro Arg Ser Leu Leu
4350            4355                4360                4365

TGC TAT GGC GGC GCC CCA GGG CCT GGC TGC CAC TTC TCC ATC CCC GAG    8302
Cys Tyr Gly Gly Ala Pro Gly Pro Gly Cys His Phe Ser Ile Pro Glu
                4370                4375                4380

GCT TTC AGC GGG GCC CTG GCC AAC CTC AGT GAC GTG GTG CAG CTC ATC    8350
Ala Phe Ser Gly Ala Leu Ala Asn Leu Ser Asp Val Val Gln Leu Ile
            4385                4390                4395

TTT CTG GTG GAC TCC AAT CCC TTT CCC TTT GGC TAT ATC AGC AAC TAC    8398
Phe Leu Val Asp Ser Asn Pro Phe Pro Phe Gly Tyr Ile Ser Asn Tyr
        4400                4405                4410

ACC GTC TCC ACC AAG GTG GCC TCG ATG GCA TTC CAG ACA CAG GCC GGC    8446
Thr Val Ser Thr Lys Val Ala Ser Met Ala Phe Gln Thr Gln Ala Gly
    4415                4420                4425

GCC CAG ATC CCC ATC GAG CGG CTG GCC TCA GAG CGC GCC ATC ACC GTG    8494
Ala Gln Ile Pro Ile Glu Arg Leu Ala Ser Glu Arg Ala Ile Thr Val
4430            4435                4440                4445

AAG GTG CCC AAC AAC TCG GAC TGG GCT GCC CGG GGC CAC CGC AGC TCC    8542
Lys Val Pro Asn Asn Ser Asp Trp Ala Ala Arg Gly His Arg Ser Ser
                4450                4455                4460

GCC AAC TCC GCC AAC TCC GTT GTG GTC CAG CCC CAG GCC TCC GTC GGT    8590
Ala Asn Ser Ala Asn Ser Val Val Val Gln Pro Gln Ala Ser Val Gly
            4465                4470                4475

GCT GTG GTC ACC CTG GAC AGC AGC AAC CCT GCG GCC GGG CTG CAT CTG    8638
Ala Val Val Thr Leu Asp Ser Ser Asn Pro Ala Ala Gly Leu His Leu
        4480                4485                4490

CAG CTC AAC TAT ACG CTG CTG GAC GGC CAC TAC CTG TCT GAG GAA CCT    8686
Gln Leu Asn Tyr Thr Leu Leu Asp Gly His Tyr Leu Ser Glu Glu Pro
    4495                4500                4505

GAG CCC TAC CTG GCA GTC TAC CTA CAC TCG GAG CCC CGG CCC AAT GAG    8734
Glu Pro Tyr Leu Ala Val Tyr Leu His Ser Glu Pro Arg Pro Asn Glu
4510            4515                4520                4525

CAC AAC TGC TCG GCT AGC AGG AGG ATC CGC CCA GAG TCA CTC CAG GGT    8782
His Asn Cys Ser Ala Ser Arg Arg Ile Arg Pro Glu Ser Leu Gln Gly
                4530                4535                4540

GCT GAC CAC CGG CCC TAC ACC TTC TTC ATT TCC CCG GGG AGC AGA GAC    8830
Ala Asp His Arg Pro Tyr Thr Phe Phe Ile Ser Pro Gly Ser Arg Asp
            4545                4550                4555

CCA GCG GGG AGT TAC CAT CTG AAC CTC TCC AGC CAC TTC CGC TGG TCG    8878
Pro Ala Gly Ser Tyr His Leu Asn Leu Ser Ser His Phe Arg Trp Ser
        4560                4565                4570
```

```
GCG CTG CAG GTG TCC GTG GGC CTG TAC ACG TCC CTG TGC CAG TAC TTC        8926
Ala Leu Gln Val Ser Val Gly Leu Tyr Thr Ser Leu Cys Gln Tyr Phe
    4575                4580                4585

AGC GAG GAG GAC ATG GTG TGG CGG ACA GAG GGG CTG CTG CCC CTG GAG        8974
Ser Glu Glu Asp Met Val Trp Arg Thr Glu Gly Leu Leu Pro Leu Glu
4590                4595                4600                4605

GAG ACC TCG CCC CGC CAG GCC GTC TGC CTC ACC CGC CAC CTC ACC GCC        9022
Glu Thr Ser Pro Arg Gln Ala Val Cys Leu Thr Arg His Leu Thr Ala
            4610                4615                4620

TTC GGC GCC AGC CTC TTC GTG CCC CCA AGC CAT GTC CGC TTT GTG TTT        9070
Phe Gly Ala Ser Leu Phe Val Pro Pro Ser His Val Arg Phe Val Phe
                4625                4630                4635

CCT GAG CCG ACA GCG GAT GTA AAC TAC ATC GTC ATG CTG ACA TGT GCT        9118
Pro Glu Pro Thr Ala Asp Val Asn Tyr Ile Val Met Leu Thr Cys Ala
                    4640                4645                4650

GTG TGC CTG GTG ACC TAC ATG GTC ATG GCC GCC ATC CTG CAC AAG CTG        9166
Val Cys Leu Val Thr Tyr Met Val Met Ala Ala Ile Leu His Lys Leu
        4655                4660                4665

GAC CAG TTG GAT GCC AGC CGG GGC CGC GCC ATC CCT TTC TGT GGG CAG        9214
Asp Gln Leu Asp Ala Ser Arg Gly Arg Ala Ile Pro Phe Cys Gly Gln
4670                4675                4680                4685

CGG GGC CGC TTC AAG TAC GAG ATC CTC GTC AAG ACA GGC TGG GGC CGG        9262
Arg Gly Arg Phe Lys Tyr Glu Ile Leu Val Lys Thr Gly Trp Gly Arg
            4690                4695                4700

GGC TCA GGT ACC ACG GCC CAC GTG GGC ATC ATG CTG TAT GGG GTG GAC        9310
Gly Ser Gly Thr Thr Ala His Val Gly Ile Met Leu Tyr Gly Val Asp
                4705                4710                4715

AGC CGG AGC GGC CAC CGG CAC CTG GAC GGC GAC AGA GCC TTC CAC CGC        9358
Ser Arg Ser Gly His Arg His Leu Asp Gly Asp Arg Ala Phe His Arg
                    4720                4725                4730

AAC AGC CTG GAC ATC TTC CGG ATC GCC ACC CCG CAC AGC CTG GGT AGC        9406
Asn Ser Leu Asp Ile Phe Arg Ile Ala Thr Pro His Ser Leu Gly Ser
        4735                4740                4745

GTG TGG AAG ATC CGA GTG TGG CAC GAC AAC AAA GGG CTC AGC CCT GCC        9454
Val Trp Lys Ile Arg Val Trp His Asp Asn Lys Gly Leu Ser Pro Ala
4750                4755                4760                4765

TGG TTC CTG CAG CAC GTC ATC GTC AGG GAC CTG CAG ACG GCA CGC AGC        9502
Trp Phe Leu Gln His Val Ile Val Arg Asp Leu Gln Thr Ala Arg Ser
            4770                4775                4780

GCC TTC TTC CTG GTC AAT GAC TGG CTT TCG GTG GAG ACG GAG GCC AAC        9550
Ala Phe Phe Leu Val Asn Asp Trp Leu Ser Val Glu Thr Glu Ala Asn
                4785                4790                4795

GGG GGC CTG GTG GAG AAG GAG GTG CTG GCC GCG AGC GAC GCA GCC CTT        9598
Gly Gly Leu Val Glu Lys Glu Val Leu Ala Ala Ser Asp Ala Ala Leu
                    4800                4805                4810

TTG CGC TTC CGG CGC CTG CTG GTG GCT GAG CTG CAG CGT GGC TTC TTT        9646
Leu Arg Phe Arg Arg Leu Leu Val Ala Glu Leu Gln Arg Gly Phe Phe
        4815                4820                4825

GAC AAG CAC ATC TGG CTC TCC ATA TGG GAC CGG CCG CCT CGT AGC CGT        9694
Asp Lys His Ile Trp Leu Ser Ile Trp Asp Arg Pro Pro Arg Ser Arg
4830                4835                4840                4845

TTC ACT CGC ATC CAG AGG GCC ACC TGC TGC GTT CTC CTC ATC TGC CTC        9742
Phe Thr Arg Ile Gln Arg Ala Thr Cys Cys Val Leu Leu Ile Cys Leu
            4850                4855                4860

TTC CTG GGC GCC AAC GCC GTG TGG TAC GGG GCT GTT GGC GAC TCT GCC        9790
Phe Leu Gly Ala Asn Ala Val Trp Tyr Gly Ala Val Gly Asp Ser Ala
                4865                4870                4875

TAC AGC ACG GGG CAT GTG TCC AGG CTG AGC CCG CTG AGC GTC GAC ACA        9838
Tyr Ser Thr Gly His Val Ser Arg Leu Ser Pro Leu Ser Val Asp Thr
                    4880                4885                4890
```

```
GTC GCT GTT GGC CTG GTG TCC AGC GTG GTT GTC TAT CCC GTC TAC CTG        9886
Val Ala Val Gly Leu Val Ser Ser Val Val Val Tyr Pro Val Tyr Leu
        4895                4900                4905

GCC ATC CTT TTT CTC TTC CGG ATG TCC CGG AGC AAG GTG GCT GGG AGC        9934
Ala Ile Leu Phe Leu Phe Arg Met Ser Arg Ser Lys Val Ala Gly Ser
4910            4915                4920                    4925

CCG AGC CCC ACA CCT GCC GGG CAG CAG GTG CTG GAC ATC GAC AGC TGC        9982
Pro Ser Pro Thr Pro Ala Gly Gln Gln Val Leu Asp Ile Asp Ser Cys
                4930                4935                4940

CTG GAC TCG TCC GTG CTG GAC AGC TCC TTC CTC ACG TTC TCA GGC CTC       10030
Leu Asp Ser Ser Val Leu Asp Ser Ser Phe Leu Thr Phe Ser Gly Leu
            4945                4950                4955

CAC GCT GAG GCC TTT GTT GGA CAG ATG AAG AGT GAC TTG TTT CTG GAT       10078
His Ala Glu Ala Phe Val Gly Gln Met Lys Ser Asp Leu Phe Leu Asp
        4960                4965                4970

GAT TCT AAG AGT CTG GTG TGC TGG CCC TCC GGC GAG GGA ACG CTC AGT       10126
Asp Ser Lys Ser Leu Val Cys Trp Pro Ser Gly Glu Gly Thr Leu Ser
    4975                4980                4985

TGG CCG GAC CTG CTC AGT GAC CCG TCC ATT GTG GGT AGC AAT CTG CGG       10174
Trp Pro Asp Leu Leu Ser Asp Pro Ser Ile Val Gly Ser Asn Leu Arg
4990            4995                5000                    5005

CAG CTG GCA CGG GGC CAG GCG GGC CAT GGG CTG GGC CCA GAG GAG GAC       10222
Gln Leu Ala Arg Gly Gln Ala Gly His Gly Leu Gly Pro Glu Glu Asp
                5010                5015                5020

GGC TTC TCC CTG GCC AGC CCC TAC TCG CCT GCC AAA TCC TTC TCA GCA       10270
Gly Phe Ser Leu Ala Ser Pro Tyr Ser Pro Ala Lys Ser Phe Ser Ala
            5025                5030                5035

TCA GAT GAA GAC CTG ATC CAG CAG GTC CTT GCC GAG GGG GTC AGC AGC       10318
Ser Asp Glu Asp Leu Ile Gln Gln Val Leu Ala Glu Gly Val Ser Ser
        5040                5045                5050

CCA GCC CCT ACC CAA GAC ACC CAC ATG GAA ACG GAC CTG CTC AGC AGC       10366
Pro Ala Pro Thr Gln Asp Thr His Met Glu Thr Asp Leu Leu Ser Ser
    5055                5060                5065

CTG TCC AGC ACT CCT GGG GAG AAG ACA GAG ACG CTG GCG CTG CAG AGG       10414
Leu Ser Ser Thr Pro Gly Glu Lys Thr Glu Thr Leu Ala Leu Gln Arg
5070            5075                5080                    5085

CTG GGG GAG CTG GGG CCA CCC AGC CCA GGC CTG AAC TGG GAA CAG CCC       10462
Leu Gly Glu Leu Gly Pro Pro Ser Pro Gly Leu Asn Trp Glu Gln Pro
                5090                5095                5100

CAG GCA GCG AGG CTG TCC AGG ACA GGA CTG GTG GAG GGT CTG CGG AAG       10510
Gln Ala Ala Arg Leu Ser Arg Thr Gly Leu Val Glu Gly Leu Arg Lys
            5105                5110                5115

CGC CTG CTG CCG GCC TGG TGT GCC TCC CTG GCC CAC GGG CTC AGC CTG       10558
Arg Leu Leu Pro Ala Trp Cys Ala Ser Leu Ala His Gly Leu Ser Leu
        5120                5125                5130

CTC CTG GTG GCT GTG GCT GTG GCT GTC TCA GGG TGG GTG GGT GCG AGC       10606
Leu Leu Val Ala Val Ala Val Ala Val Ser Gly Trp Val Gly Ala Ser
    5135                5140                5145

TTC CCC CCG GGC GTG AGT GTT GCG TGG CTC CTG TCC AGC AGC GCC AGC       10654
Phe Pro Pro Gly Val Ser Val Ala Trp Leu Leu Ser Ser Ser Ala Ser
5150            5155                5160                    5165

TTC CTG GCC TCA TTC CTC GGC TGG GAG CCA CTG AAG GTC TTG CTG GAA       10702
Phe Leu Ala Ser Phe Leu Gly Trp Glu Pro Leu Lys Val Leu Leu Glu
                5170                5175                5180

GCC CTG TAC TTC TCA CTG GTG GCC AAG CGG CTG CAC CCG GAT GAA GAT       10750
Ala Leu Tyr Phe Ser Leu Val Ala Lys Arg Leu His Pro Asp Glu Asp
            5185                5190                5195

GAC ACC CTG GTA GAG AGC CCG GCT GTG ACG CCT GTG AGC GCA CGT GTG       10798
Asp Thr Leu Val Glu Ser Pro Ala Val Thr Pro Val Ser Ala Arg Val
```

-continued

| | | |
|---|---|---|
| CCC CGC GTA CGG CCA CCC CAC GGC TTT GCA CTC TTC CTG GCC AAG GAA<br>Pro Arg Val Arg Pro Pro His Gly Phe Ala Leu Phe Leu Ala Lys Glu<br>    5215                         5220                      5225 | 10846 |
| GAA GCC CGC AAG GTC AAG AGG CTA CAT GGC ATG CTG CGG AGC CTC CTG<br>Glu Ala Arg Lys Val Lys Arg Leu His Gly Met Leu Arg Ser Leu Leu<br>5230                      5235                      5240                      5245 | 10894 |
| GTG TAC ATG CTT TTT CTG CTG GTG ACC CTG CTG GCC AGC TAT GGG GAT<br>Val Tyr Met Leu Phe Leu Leu Val Thr Leu Leu Ala Ser Tyr Gly Asp<br>              5250                      5255                      5260 | 10942 |
| GCC TCA TGC CAT GGG CAC GCC TAC CGT CTG CAA AGC GCC ATC AAG CAG<br>Ala Ser Cys His Gly His Ala Tyr Arg Leu Gln Ser Ala Ile Lys Gln<br>                  5265                      5270                      5275 | 10990 |
| GAG CTG CAC AGC CGG GCC TTC CTG GCC ATC ACG CGG TCT GAG GAG CTC<br>Glu Leu His Ser Arg Ala Phe Leu Ala Ile Thr Arg Ser Glu Glu Leu<br>        5280                      5285                      5290 | 11038 |
| TGG CCA TGG ATG GCC CAC GTG CTG CTG CCC TAC GTC CAC GGG AAC CAG<br>Trp Pro Trp Met Ala His Val Leu Leu Pro Tyr Val His Gly Asn Gln<br>    5295                      5300                      5305 | 11086 |
| TCC AGC CCA GAG CTG GGG CCC CCA CGG CTG CGG CAG GTG CGG CTG CAG<br>Ser Ser Pro Glu Leu Gly Pro Pro Arg Leu Arg Gln Val Arg Leu Gln<br>5310                      5315                      5320                      5325 | 11134 |
| GAA GCA CTC TAC CCA GAC CCT CCC GGC CCC AGG GTC CAC ACG TGC TCG<br>Glu Ala Leu Tyr Pro Asp Pro Pro Gly Pro Arg Val His Thr Cys Ser<br>                5330                      5335                      5340 | 11182 |
| GCC GCA GGA GGC TTC AGC ACC AGC GAT TAC GAC GTT GGC TGG GAG AGT<br>Ala Ala Gly Gly Phe Ser Thr Ser Asp Tyr Asp Val Gly Trp Glu Ser<br>            5345                      5350                      5355 | 11230 |
| CCT CAC AAT GGC TCG GGG ACG TGG GCC TAT TCA GCG CCG GAT CTG CTG<br>Pro His Asn Gly Ser Gly Thr Trp Ala Tyr Ser Ala Pro Asp Leu Leu<br>        5360                      5365                      5370 | 11278 |
| GGG GCA TGG TCC TGG GGC TCC TGT GCC GTG TAT GAC AGC GGG GGC TAC<br>Gly Ala Trp Ser Trp Gly Ser Cys Ala Val Tyr Asp Ser Gly Gly Tyr<br>    5375                      5380                      5385 | 11326 |
| GTG CAG GAG CTG GGC CTG AGC CTG GAG GAG AGC CGC GAC CGG CTG CGC<br>Val Gln Glu Leu Gly Leu Ser Leu Glu Glu Ser Arg Asp Arg Leu Arg<br>5390                      5395                      5400                      5405 | 11374 |
| TTC CTG CAG CTG CAC AAC TGG CTG GAC AAC AGG AGC CGC GCT GTG TTC<br>Phe Leu Gln Leu His Asn Trp Leu Asp Asn Arg Ser Arg Ala Val Phe<br>            5410                      5415                      5420 | 11422 |
| CTG GAG CTC ACG CGC TAC AGC CCG GCC GTG GGG CTG CAC GCC GCC GTC<br>Leu Glu Leu Thr Arg Tyr Ser Pro Ala Val Gly Leu His Ala Ala Val<br>        5425                      5430                      5435 | 11470 |
| ACG CTG CGC CTC GAG TTC CCG GCG GCC GGC CGC GCC CTG GCC GCC CTC<br>Thr Leu Arg Leu Glu Phe Pro Ala Ala Gly Arg Ala Leu Ala Ala Leu<br>            5440                      5445                      5450 | 11518 |
| AGC GTC CGC CCC TTT GCG CTG CGC CGC CTC AGC GCG GGC CTC TCG CTG<br>Ser Val Arg Pro Phe Ala Leu Arg Arg Leu Ser Ala Gly Leu Ser Leu<br>    5455                      5460                      5465 | 11566 |
| CCT CTG CTC ACC TCG GTG TGC CTG CTG CTG TTC GCC GTG CAC TTC GCC<br>Pro Leu Leu Thr Ser Val Cys Leu Leu Leu Phe Ala Val His Phe Ala<br>5470                      5475                      5480                      5485 | 11614 |
| GTG GCC GAG GCC CGT ACT TGG CAC AGG GAA GGG CGC TGG CGC GTG CTG<br>Val Ala Glu Ala Arg Thr Trp His Arg Glu Gly Arg Trp Arg Val Leu<br>                5490                      5495                      5500 | 11662 |
| CGG CTC GGA GCC TGG GCG CGG TGG CTG CTG GTG GCG CTG ACG GCG GCC<br>Arg Leu Gly Ala Trp Ala Arg Trp Leu Leu Val Ala Leu Thr Ala Ala<br>            5505                      5510                      5515 | 11710 |
| ACG GCA CTG GTA CGC CTC GCC CAG CTG GGT GCC GCT GAC CGC AGG TGG<br>  | 11758 |

```
Thr Ala Leu Val Arg Leu Ala Gln Leu Gly Ala Ala Asp Arg Gln Trp
        5520                5525                5530

ACC CGT TTC GTG CGC GGC CGC CCG CGC CGC TTC ACT AGC TTC GAC CAG          11806
Thr Arg Phe Val Arg Gly Arg Pro Arg Arg Phe Thr Ser Phe Asp Gln
    5535                5540                5545

GTG GCG CAC GTG AGC TCC GCA GCC CGT GGC CTG GCG GCC TCG CTG CTC          11854
Val Ala His Val Ser Ser Ala Ala Arg Gly Leu Ala Ala Ser Leu Leu
5550                5555                5560                5565

TTC CTG CTT TTG GTC AAG GCT GCC CAG CAC GTA CGC TTC GTG CGC CAG          11902
Phe Leu Leu Leu Val Lys Ala Ala Gln His Val Arg Phe Val Arg Gln
                5570                5575                5580

TGG TCC GTC TTT GGC AAG ACA TTA TGC CGA GCT CTG CCA GAG CTC CTG          11950
Trp Ser Val Phe Gly Lys Thr Leu Cys Arg Ala Leu Pro Glu Leu Leu
            5585                5590                5595

GGG GTC ACC TTG GGC CTG GTG GTG CTC GGG GTA GCC TAC GCC CAG CTG          11998
Gly Val Thr Leu Gly Leu Val Val Leu Gly Val Ala Tyr Ala Gln Leu
        5600                5605                5610

GCC ATC CTG CTC GTG TCT TCC TGT GTG GAC TCC CTC TGG AGC GTG GCC          12046
Ala Ile Leu Leu Val Ser Ser Cys Val Asp Ser Leu Trp Ser Val Ala
    5615                5620                5625

CAG GCC CTG TTG GTG CTG TGC CCT GGG ACT GGG CTC TCT ACC CTG TGT          12094
Gln Ala Leu Leu Val Leu Cys Pro Gly Thr Gly Leu Ser Thr Leu Cys
5630                5635                5640                5645

CCT GCC GAG TCC TGG CAC CTG TCA CCC CTG CTG TGT GTG GGG CTC TGG          12142
Pro Ala Glu Ser Trp His Leu Ser Pro Leu Leu Cys Val Gly Leu Trp
                5650                5655                5660

GCA CTG CGG CTG TGG GGC GCC CTA CGG CTG GGG GCT GTT ATT CTC CGC          12190
Ala Leu Arg Leu Trp Gly Ala Leu Arg Leu Gly Ala Val Ile Leu Arg
            5665                5670                5675

TGG CGC TAC CAC GCC TTG CGT GGA GAG CTG TAC CGG CCG GCC TGG GAG          12238
Trp Arg Tyr His Ala Leu Arg Gly Glu Leu Tyr Arg Pro Ala Trp Glu
        5680                5685                5690

CCC CAG GAC TAC GAG ATG GTG GAG TTG TTC CTG CGC AGG CTG CGC CTC          12286
Pro Gln Asp Tyr Glu Met Val Glu Leu Phe Leu Arg Arg Leu Arg Leu
    5695                5700                5705

TGG ATG GGC CTC AGC AAG GTC AAG GAG TTC CGC CAC AAA GTC CGC TTT          12334
Trp Met Gly Leu Ser Lys Val Lys Glu Phe Arg His Lys Val Arg Phe
5710                5715                5720                5725

GAA GGG ATG GAG CCG CTG CCC TCT CGC TCC TCC AGG GGC TCC AAG GTA          12382
Glu Gly Met Glu Pro Leu Pro Ser Arg Ser Ser Arg Gly Ser Lys Val
                5730                5735                5740

TCC CCG GAT GTG CCC CCA CCC AGC GCT GGC TCC GAT GCC TCG CAC CCC          12430
Ser Pro Asp Val Pro Pro Pro Ser Ala Gly Ser Asp Ala Ser His Pro
            5745                5750                5755

TCC ACC TCC TCC AGC CAG CTG GAT GGG CTG AGC GTG AGC CTG GGC CGG          12478
Ser Thr Ser Ser Ser Gln Leu Asp Gly Leu Ser Val Ser Leu Gly Arg
        5760                5765                5770

CTG GGG ACA AGG TGT GAG CCT GAG CCC TCC CGC CTC CAA GCC GTG TTC          12526
Leu Gly Thr Arg Cys Glu Pro Glu Pro Ser Arg Leu Gln Ala Val Phe
    5775                5780                5785

GAG GCC CTG CTC ACC CAG TTT GAC CGA CTC AAC CAG GCC ACA GAG GAC          12574
Glu Ala Leu Leu Thr Gln Phe Asp Arg Leu Asn Gln Ala Thr Glu Asp
5790                5795                5800                5805

GTC TAC CAG CTG GAG CAG CAG CTG CAC AGC CTG CAA GGC CGC AGG AGC          12622
Val Tyr Gln Leu Glu Gln Gln Leu His Ser Leu Gln Gly Arg Arg Ser
                5810                5815                5820

AGC CGG GCG CCC GCC GGA TCT TCC CGT GGC CCA TCC CCG GGC CTG CGG          12670
Ser Arg Ala Pro Ala Gly Ser Ser Arg Gly Pro Ser Pro Gly Leu Arg
            5825                5830                5835
```

```
CCA GCA CTG CCC AGC CGC CTT GCC CGG GCC AGT CGG GGT GTG GAC CTG        12718
Pro Ala Leu Pro Ser Arg Leu Ala Arg Ala Ser Arg Gly Val Asp Leu
        5840            5845                5850

GCC ACT GGC CCC AGC AGG ACA CCT TCG GGC CAA GAA CAA GGT CCA CCC        12766
Ala Thr Gly Pro Ser Arg Thr Pro Ser Gly Gln Glu Gln Gly Pro Pro
    5855                5860                5865

CAG CAG CAC TTA GTC CTC CTT CCT GGC GGG GGT GGG CCG TGG AGT CGG        12814
Gln Gln His Leu Val Leu Leu Pro Gly Gly Gly Pro Trp Ser Arg
5870                5875                5880                5885

AGT GGA CAC CGC TCA GTA TTA CTT TCT GCC GCT GTC AAG GCC GAG GGC        12862
Ser Gly His Arg Ser Val Leu Leu Ser Ala Ala Val Lys Ala Glu Gly
            5890                5895                5900

CAG GCA GAA TGG CTG CAC GTA GGT TCC CCA GAG AGC AGG CAG GGG CAT        12910
Gln Ala Glu Trp Leu His Val Gly Ser Pro Glu Ser Arg Gln Gly His
                5905                5910                5915

CTG TCT GTC TGT GGG CTT CAG CAC TTT AAA GAG GCT GTG TGG CCA ACC        12958
Leu Ser Val Cys Gly Leu Gln His Phe Lys Glu Ala Val Trp Pro Thr
            5920                5925                5930

AGG ACC CAG GGT CCC CTC CCC AGC TCC CTT GGG AAG GAC ACA GCA GTA        13006
Arg Thr Gln Gly Pro Leu Pro Ser Ser Leu Gly Lys Asp Thr Ala Val
        5935                5940                5945

TTG GAC GGT TTC TAGCCTCTGA GATGCTAATT TATTTCCCCG AGTCCTCAGG            13058
Leu Asp Gly Phe
5950

TACAGCGGGC TGTGCCCGGC CCCACCCCCT GGGCAGATGT CCCCCACTGC TAAGGCTGCT      13118

GGCTTCAGGG AGGGTTAGCC TGCACCGCCG CCACCCTGCC CCTAAGTTAT TACCTCTCCA      13178

GTTCCTACCG TACTCCCTGC ACCGTCTCAC TGTGTGTCTC GTGTCAGTAA TTTATATGGT      13238

GTTAAAATGT GTATATTTTT GTATGTCACT ATTTTCACTA GGGCTGAGGG GCCTGCGCCC      13298

AGAGCTGGCC TCCCCCAACA CCTGCTGCGC TTGGTAGGTG TGGTGGCGTT ATGGCAGCCC      13358

GGCTGCTGCT TGGATGCGAG CTTGGCCTTG GCCGGTGCT GGGGGCACAG CTGTCTGCCA       13418

GGCACTCTCA TCACCCCAGA GGCCTTGTCA TCCTCCCTTG CCCCAGGCCA GGTAGCAAGA     13478

GAGCAGCGCC CAGGCCTGCT GGCATCAGGT CTGGGCAAGT AGCAGGACTA GGCATGTCAG      13538

AGGACCCCAG GGTGGTTAGA GGAAAAGACT CCTCCTGGGG GCTGGCTCCC AGGGTGGAGG      13598

AAGGTGACTG TGTGTGTGTG TGTGTGCGCG CGCGACGCGC GAGTGTGCTG TATGGCCCAG      13658

GCAGCCTCAA GGCCCTCGGA GCTGGCTGTG CCTGCTTCTG TGTACCACTT CTGTGGGCAT     13718

GGCCGCTTCT AGAGCCTCGA CACCCCCCA ACCCCCGCAC CAAGCAGACA AAGTCAATAA      13778

AAGAGCTGTC TGACTGCAAA AAAAAAAA                                        13807

(2) INFORMATION FOR SEQ ID NO: 6:

(i) SEQUENCE CHARACTERISTICS:
        (A) LENGTH: 4339 amino acids
        (B) TYPE: amino acid
        (D) TOPOLOGY: linear (ii) MOLECULE TYPE: protein (xi) SEQUENCE DESCRIPTION: SEQ ID NO: 6:

Gly Ala Ala Cys Arg Val Asn Cys Ser Gly Arg Gly Leu Arg Thr Leu
 1               5                  10                  15

Gly Pro Ala Leu Arg Ile Pro Ala Asp Ala Thr Ala Leu Asp Val Ser
            20                  25                  30

His Asn Leu Leu Arg Ala Leu Asp Val Gly Leu Leu Ala Asn Leu Ser
        35                  40                  45
```

-continued

```
Ala Leu Ala Glu Leu Asp Ile Ser Asn Asn Lys Ile Ser Thr Leu Glu
 50                  55                  60

Glu Gly Ile Phe Ala Asn Leu Phe Asn Leu Ser Glu Ile Asn Leu Ser
 65                  70                  75                  80

Gly Asn Pro Phe Glu Cys Asp Cys Gly Leu Ala Trp Leu Pro Arg Trp
                 85                  90                  95

Ala Glu Glu Gln Gln Val Arg Val Gln Pro Glu Ala Ala Thr Cys
                100                 105                 110

Ala Gly Pro Gly Ser Leu Ala Gly Gln Pro Leu Leu Gly Ile Pro Leu
            115                 120                 125

Leu Asp Ser Gly Cys Gly Glu Glu Tyr Val Ala Cys Leu Pro Asp Asn
            130                 135                 140

Ser Ser Gly Thr Val Ala Ala Val Ser Phe Ser Ala Ala His Glu Gly
145                 150                 155                 160

Leu Leu Gln Pro Glu Ala Cys Ser Ala Phe Cys Phe Ser Thr Gly Gln
                165                 170                 175

Gly Leu Ala Ala Leu Ser Glu Gln Gly Trp Cys Leu Cys Gly Ala Ala
            180                 185                 190

Gln Pro Ser Ser Ala Ser Phe Ala Cys Leu Ser Leu Cys Ser Gly Pro
        195                 200                 205

Pro Pro Pro Ala Pro Thr Cys Arg Gly Pro Thr Leu Leu Gln His
    210                 215                 220

Val Phe Pro Ala Ser Pro Gly Ala Thr Leu Val Gly Pro His Gly Pro
225                 230                 235                 240

Leu Ala Ser Gly Gln Leu Ala Ala Phe His Ile Ala Ala Pro Leu Pro
                245                 250                 255

Val Thr Ala Thr Arg Trp Asp Phe Gly Asp Gly Ser Ala Glu Val Asp
            260                 265                 270

Ala Ala Gly Pro Ala Ala Ser His Arg Tyr Val Leu Pro Gly Arg Tyr
            275                 280                 285

His Val Thr Ala Val Leu Ala Leu Gly Ala Gly Ser Ala Leu Leu Gly
        290                 295                 300

Thr Asp Val Gln Val Glu Ala Ala Pro Ala Ala Leu Glu Leu Val Cys
305                 310                 315                 320

Pro Ser Ser Val Gln Ser Asp Glu Ser Leu Asp Leu Ser Ile Gln Asn
                325                 330                 335

Arg Gly Gly Ser Gly Leu Glu Ala Ala Tyr Ser Ile Val Ala Leu Gly
            340                 345                 350

Glu Glu Pro Ala Arg Ala Val His Pro Leu Cys Pro Ser Asp Thr Glu
        355                 360                 365

Ile Phe Pro Gly Asn Gly His Cys Tyr Arg Leu Val Val Glu Lys Ala
    370                 375                 380

Ala Trp Leu Gln Ala Gln Glu Gln Cys Gln Ala Trp Ala Gly Ala Ala
385                 390                 395                 400

Leu Ala Met Val Asp Ser Pro Ala Val Gln Arg Phe Leu Val Ser Arg
                405                 410                 415

Val Thr Arg Ser Leu Asp Val Trp Ile Gly Phe Ser Thr Val Gln Gly
            420                 425                 430

Val Glu Val Gly Pro Ala Pro Gln Gly Glu Ala Phe Ser Leu Glu Ser
        435                 440                 445

Cys Gln Asn Trp Leu Pro Gly Glu Pro His Pro Ala Thr Ala Glu His
    450                 455                 460

Cys Val Arg Leu Gly Pro Thr Gly Trp Cys Asn Thr Asp Leu Cys Ser
```

-continued

```
465                 470                 475                 480
Ala Pro His Ser Tyr Val Cys Glu Leu Gln Pro Gly Gly Pro Val Gln
            485                 490                 495
Asp Ala Glu Asn Leu Leu Val Gly Ala Pro Ser Gly Asp Leu Gln Gly
            500                 505                 510
Pro Leu Thr Pro Leu Ala Gln Gln Asp Gly Leu Ser Ala Pro His Glu
            515                 520                 525
Pro Val Glu Val Met Val Phe Pro Gly Leu Arg Leu Ser Arg Glu Ala
            530                 535                 540
Phe Leu Thr Thr Ala Glu Phe Gly Thr Gln Glu Leu Arg Arg Pro Ala
545                 550                 555                 560
Gln Leu Arg Leu Gln Val Tyr Arg Leu Leu Ser Thr Ala Gly Thr Pro
            565                 570                 575
Glu Asn Gly Ser Glu Pro Glu Ser Arg Ser Pro Asp Asn Arg Thr Gln
            580                 585                 590
Leu Ala Pro Ala Cys Met Pro Gly Gly Arg Trp Cys Pro Gly Ala Asn
            595                 600                 605
Ile Cys Leu Pro Leu Asp Ala Ser Cys His Pro Gln Ala Cys Ala Asn
            610                 615                 620
Gly Cys Thr Ser Gly Pro Gly Leu Pro Gly Ala Pro Tyr Ala Leu Trp
625                 630                 635                 640
Arg Glu Phe Leu Phe Ser Val Ala Ala Gly Pro Pro Ala Gln Tyr Ser
            645                 650                 655
Val Thr Leu His Gly Gln Asp Val Leu Met Leu Pro Gly Asp Leu Val
            660                 665                 670
Gly Leu Gln His Asp Ala Gly Pro Gly Ala Leu Leu His Cys Ser Pro
            675                 680                 685
Ala Pro Gly His Pro Gly Pro Gln Ala Pro Tyr Leu Ser Ala Asn Ala
            690                 695                 700
Ser Ser Trp Leu Pro His Leu Pro Ala Gln Leu Glu Gly Thr Trp Ala
705                 710                 715                 720
Cys Pro Ala Cys Ala Leu Arg Leu Leu Ala Thr Glu Gln Leu Thr
            725                 730                 735
Val Leu Leu Gly Leu Arg Pro Asn Pro Gly Leu Arg Met Pro Gly Arg
            740                 745                 750
Tyr Glu Val Arg Ala Glu Val Gly Asn Gly Val Ser Arg His Asn Leu
            755                 760                 765
Ser Cys Ser Phe Asp Val Val Ser Pro Val Ala Gly Leu Arg Val Ile
            770                 775                 780
Tyr Pro Ala Pro Arg Asp Gly Arg Leu Tyr Val Pro Thr Asn Gly Ser
785                 790                 795                 800
Ala Leu Val Leu Gln Val Asp Ser Gly Ala Asn Ala Thr Ala Thr Ala
            805                 810                 815
Arg Trp Pro Gly Gly Ser Val Ser Ala Arg Phe Glu Asn Val Cys Pro
            820                 825                 830
Ala Leu Val Ala Thr Phe Val Pro Gly Cys Pro Trp Glu Thr Asn Asp
            835                 840                 845
Thr Leu Phe Ser Val Val Ala Leu Pro Trp Leu Ser Glu Gly Glu His
            850                 855                 860
Val Val Asp Val Val Val Glu Asn Ser Ala Ser Arg Ala Asn Leu Ser
865                 870                 875                 880
Leu Arg Val Thr Ala Glu Glu Pro Ile Cys Gly Leu Arg Ala Thr Pro
            885                 890                 895
```

-continued

```
Ser Pro Glu Ala Arg Val Leu Gln Gly Val Leu Val Arg Tyr Ser Pro
                900                 905                 910
Val Val Glu Ala Gly Ser Asp Met Val Phe Arg Trp Thr Ile Asn Asp
            915                 920                 925
Lys Gln Ser Leu Thr Phe Gln Asn Val Phe Asn Val Ile Tyr Gln
        930                 935                 940
Ser Ala Ala Val Phe Lys Leu Ser Leu Thr Ala Ser Asn His Val Ser
945                 950                 955                 960
Asn Val Thr Val Asn Tyr Asn Val Thr Val Glu Arg Met Asn Arg Met
                965                 970                 975
Gln Gly Leu Gln Val Ser Thr Val Pro Ala Val Leu Ser Pro Asn Ala
            980                 985                 990
Thr Leu Val Leu Thr Gly Gly Val Leu Val Asp Ser Ala Val Glu Val
        995                 1000                1005
Ala Phe Leu Trp Asn Phe Gly Asp Gly Glu Gln Ala Leu His Gln Phe
    1010                1015                1020
Gln Pro Pro Tyr Asn Glu Ser Phe Pro Val Pro Asp Pro Ser Val Ala
1025                1030                1035                1040
Gln Val Leu Val Glu His Asn Val Met His Thr Tyr Ala Ala Pro Gly
            1045                1050                1055
Glu Tyr Leu Leu Thr Val Leu Ala Ser Asn Ala Phe Glu Asn Leu Thr
        1060                1065                1070
Gln Gln Val Pro Val Ser Val Arg Ala Ser Leu Pro Ser Val Ala Val
        1075                1080                1085
Gly Val Ser Asp Gly Val Leu Val Ala Gly Arg Pro Val Thr Phe Tyr
    1090                1095                1100
Pro His Pro Leu Pro Ser Pro Gly Gly Val Leu Tyr Thr Trp Asp Phe
1105                1110                1115                1120
Gly Asp Gly Ser Pro Val Leu Thr Gln Ser Gln Pro Ala Ala Asn His
            1125                1130                1135
Thr Tyr Ala Ser Arg Gly Thr Tyr His Val Arg Leu Glu Val Asn Asn
        1140                1145                1150
Thr Val Ser Gly Ala Ala Ala Gln Ala Asp Val Arg Val Phe Glu Glu
    1155                1160                1165
Leu Arg Gly Leu Ser Val Asp Met Ser Leu Ala Val Glu Gln Gly Ala
    1170                1175                1180
Pro Val Val Ser Ala Ala Val Gln Thr Gly Asp Asn Ile Thr Trp
1185                1190                1195                1200
Thr Phe Asp Met Gly Asp Gly Thr Val Leu Ser Gly Pro Glu Ala Thr
            1205                1210                1215
Val Glu His Val Tyr Leu Arg Ala Gln Asn Cys Thr Val Thr Val Gly
        1220                1225                1230
Ala Ala Ser Pro Ala Gly His Leu Ala Arg Ser Leu His Val Leu Val
    1235                1240                1245
Phe Val Leu Glu Val Leu Arg Val Glu Pro Ala Ala Cys Ile Pro Thr
    1250                1255                1260
Gln Pro Asp Ala Arg Leu Thr Ala Tyr Val Thr Gly Asn Pro Ala His
1265                1270                1275                1280
Tyr Leu Phe Asp Trp Thr Phe Gly Asp Gly Ser Ser Asn Thr Thr Val
            1285                1290                1295
Arg Gly Cys Pro Thr Val Thr His Asn Phe Thr Arg Ser Gly Thr Phe
        1300                1305                1310
```

```
Pro Leu Ala Leu Val Leu Ser Ser Arg Val Asn Arg Ala His Tyr Phe
        1315                1320                1325
Thr Ser Ile Cys Val Glu Pro Glu Val Gly Asn Val Thr Leu Gln Pro
        1330                1335                1340
Glu Arg Gln Phe Val Gln Leu Gly Asp Glu Ala Trp Leu Val Ala Cys
1345                1350                1355                1360
Ala Trp Pro Pro Phe Pro Tyr Arg Tyr Thr Trp Asp Phe Gly Thr Glu
            1365                1370                1375
Glu Ala Ala Pro Thr Arg Ala Arg Gly Pro Glu Val Thr Phe Ile Tyr
            1380                1385                1390
Arg Asp Pro Gly Ser Tyr Leu Val Thr Val Thr Ala Ser Asn Asn Ile
            1395                1400                1405
Ser Ala Ala Asn Asp Ser Ala Leu Val Glu Val Gln Glu Pro Val Leu
        1410                1415                1420
Val Thr Ser Ile Lys Val Asn Gly Ser Leu Gly Leu Glu Leu Gln Gln
1425                1430                1435                1440
Pro Tyr Leu Phe Ser Ala Val Gly Arg Gly Arg Pro Ala Ser Tyr Leu
            1445                1450                1455
Trp Asp Leu Gly Asp Gly Gly Trp Leu Glu Gly Pro Glu Val Thr His
            1460                1465                1470
Ala Tyr Asn Ser Thr Gly Asp Phe Thr Val Arg Val Ala Gly Trp Asn
            1475                1480                1485
Glu Val Ser Arg Ser Glu Ala Trp Leu Asn Val Thr Val Lys Arg Arg
        1490                1495                1500
Val Arg Gly Leu Val Val Asn Ala Ser Arg Thr Val Val Pro Leu Asn
1505                1510                1515                1520
Gly Ser Val Ser Phe Ser Thr Ser Leu Glu Ala Gly Ser Asp Val Arg
            1525                1530                1535
Tyr Ser Trp Val Leu Cys Asp Arg Cys Thr Pro Ile Pro Gly Gly Pro
            1540                1545                1550
Thr Ile Ser Tyr Thr Phe Arg Ser Val Gly Thr Phe Asn Ile Ile Val
            1555                1560                1565
Thr Ala Glu Asn Glu Val Gly Ser Ala Gln Asp Ser Ile Phe Val Tyr
1570                1575                1580
Val Leu Gln Leu Ile Glu Gly Leu Gln Val Gly Gly Gly Arg Tyr
1585                1590                1595                1600
Phe Pro Thr Asn His Thr Val Gln Leu Gln Ala Val Val Arg Asp Gly
            1605                1610                1615
Thr Asn Val Ser Tyr Ser Trp Thr Ala Trp Arg Asp Arg Gly Pro Ala
            1620                1625                1630
Leu Ala Gly Ser Gly Lys Gly Phe Ser Leu Thr Val Leu Glu Ala Gly
            1635                1640                1645
Thr Tyr His Val Gln Leu Arg Ala Thr Asn Met Leu Gly Ser Ala Trp
        1650                1655                1660
Ala Asp Cys Thr Met Asp Phe Val Glu Pro Val Gly Trp Leu Met Val
1665                1670                1675                1680
Thr Ala Ser Pro Asn Pro Ala Ala Val Asn Thr Ser Val Thr Leu Ser
            1685                1690                1695
Ala Glu Leu Ala Gly Gly Ser Gly Val Val Tyr Thr Trp Ser Leu Glu
            1700                1705                1710
Glu Gly Leu Ser Trp Glu Thr Ser Glu Pro Phe Thr Thr His Ser Phe
            1715                1720                1725
Pro Thr Pro Gly Leu His Leu Val Thr Met Thr Ala Gly Asn Pro Leu
```

-continued

```
            1730                1735                1740
Gly Ser Ala Asn Ala Thr Val Glu Val Asp Val Gln Val Pro Val Ser
1745                1750                1755                1760
Gly Leu Ser Ile Arg Ala Ser Glu Pro Gly Ser Phe Val Ala Ala
                1765                1770                1775
Gly Ser Ser Val Pro Phe Trp Gly Gln Leu Ala Thr Gly Thr Asn Val
                1780                1785                1790
Ser Trp Cys Trp Ala Val Pro Gly Gly Ser Ser Lys Arg Gly Pro His
            1795                1800                1805
Val Thr Met Val Phe Pro Asp Ala Gly Thr Phe Ser Ile Arg Leu Asn
            1810                1815                1820
Ala Ser Asn Ala Val Ser Trp Val Ser Ala Thr Tyr Asn Leu Thr Ala
1825                1830                1835                1840
Glu Glu Pro Ile Val Gly Leu Val Leu Trp Ala Ser Ser Lys Val Val
                1845                1850                1855
Ala Pro Gly Gln Leu Val His Phe Gln Ile Leu Leu Ala Ala Gly Ser
                1860                1865                1870
Ala Val Thr Phe Arg Leu Gln Val Gly Gly Ala Asn Pro Glu Val Leu
            1875                1880                1885
Pro Gly Pro Arg Phe Ser His Ser Phe Pro Arg Val Gly Asp His Val
            1890                1895                1900
Val Ser Val Arg Gly Lys Asn His Val Ser Trp Ala Gln Ala Gln Val
1905                1910                1915                1920
Arg Ile Val Val Leu Glu Ala Val Ser Gly Leu Gln Met Pro Asn Cys
                1925                1930                1935
Cys Glu Pro Gly Ile Ala Thr Gly Thr Glu Arg Asn Phe Thr Ala Arg
                1940                1945                1950
Val Gln Arg Gly Ser Arg Val Ala Tyr Ala Trp Tyr Phe Ser Leu Gln
                1955                1960                1965
Lys Val Gln Gly Asp Ser Leu Val Ile Leu Ser Gly Arg Asp Val Thr
            1970                1975                1980
Tyr Thr Pro Val Ala Ala Gly Leu Leu Glu Ile Gln Val Arg Ala Phe
1985                1990                1995                2000
Asn Ala Leu Gly Ser Glu Asn Arg Thr Leu Val Leu Glu Val Gln Asp
                2005                2010                2015
Ala Val Gln Tyr Val Ala Leu Gln Ser Gly Pro Cys Phe Thr Asn Arg
                2020                2025                2030
Ser Ala Gln Phe Glu Ala Ala Thr Ser Pro Ser Pro Arg Arg Val Ala
                2035                2040                2045
Tyr His Trp Asp Phe Gly Asp Gly Ser Pro Gly Gln Asp Thr Asp Glu
            2050                2055                2060
Pro Arg Ala Glu His Ser Tyr Leu Arg Pro Gly Asp Tyr Arg Val Gln
2065                2070                2075                2080
Val Asn Ala Ser Asn Leu Val Ser Phe Phe Val Ala Gln Ala Thr Val
                2085                2090                2095
Thr Val Gln Val Leu Ala Cys Arg Glu Pro Glu Val Asp Val Val Leu
                2100                2105                2110
Pro Leu Gln Val Leu Met Arg Arg Ser Gln Arg Asn Tyr Leu Glu Ala
                2115                2120                2125
His Val Asp Leu Arg Asp Cys Val Thr Tyr Gln Thr Glu Tyr Arg Trp
            2130                2135                2140
Glu Val Tyr Arg Thr Ala Ser Cys Gln Arg Pro Gly Arg Pro Ala Arg
2145                2150                2155                2160
```

-continued

```
Val Ala Leu Pro Gly Val Asp Val Ser Arg Pro Arg Leu Val Leu Pro
            2165                2170                2175
Arg Leu Ala Leu Pro Val Gly His Tyr Cys Phe Val Phe Val Val Ser
            2180                2185                2190
Phe Gly Asp Thr Pro Leu Thr Gln Ser Ile Gln Ala Asn Val Thr Val
            2195                2200                2205
Ala Pro Glu Arg Leu Val Pro Ile Ile Glu Gly Ser Tyr Arg Val
            2210                2215            2220
Trp Ser Asp Thr Arg Asp Leu Val Leu Asp Gly Ser Glu Ser Tyr Asp
2225            2230                2235                2240
Pro Asn Leu Glu Asp Gly Asp Gln Thr Pro Leu Ser Phe His Trp Ala
            2245                2250                2255
Cys Val Ala Ser Thr Gln Arg Glu Ala Gly Gly Cys Ala Leu Asn Phe
            2260                2265                2270
Gly Pro Arg Gly Ser Ser Thr Val Thr Ile Pro Arg Glu Arg Leu Ala
            2275                2280                2285
Ala Gly Val Glu Tyr Thr Phe Ser Leu Thr Val Trp Lys Ala Gly Arg
            2290                2295                2300
Lys Glu Glu Ala Thr Asn Gln Thr Val Leu Ile Arg Ser Gly Arg Val
2305            2310                2315                2320
Pro Ile Val Ser Leu Glu Cys Val Ser Cys Lys Ala Gln Ala Val Tyr
            2325                2330                2335
Glu Val Ser Arg Ser Ser Tyr Val Tyr Leu Glu Gly Arg Cys Leu Asn
            2340                2345                2350
Cys Ser Ser Gly Ser Lys Arg Gly Arg Trp Ala Ala Arg Thr Phe Ser
            2355                2360                2365
Asn Lys Thr Leu Val Leu Asp Glu Thr Thr Thr Ser Thr Gly Ser Ala
            2370                2375                2380
Gly Met Arg Leu Val Leu Arg Arg Gly Val Leu Arg Asp Gly Glu Gly
2385            2390                2395                2400
Tyr Thr Phe Thr Leu Thr Val Leu Gly Arg Ser Gly Glu Glu Glu Gly
            2405                2410                2415
Cys Ala Ser Ile Arg Leu Ser Pro Asn Arg Pro Pro Leu Gly Gly Ser
            2420                2425                2430
Cys Arg Leu Phe Pro Leu Gly Ala Val His Ala Leu Thr Thr Lys Val
            2435                2440                2445
His Phe Glu Cys Thr Gly Trp His Asp Ala Glu Asp Ala Gly Ala Pro
            2450                2455                2460
Leu Val Tyr Ala Leu Leu Leu Arg Arg Cys Arg Gln Gly His Cys Glu
2465            2470                2475                2480
Glu Phe Cys Val Tyr Lys Gly Ser Leu Ser Ser Tyr Gly Ala Val Leu
            2485                2490                2495
Pro Pro Gly Phe Arg Pro His Phe Glu Val Gly Leu Ala Val Val Val
            2500                2505                2510
Gln Asp Gln Leu Gly Ala Ala Val Val Ala Leu Asn Arg Ser Leu Ala
            2515                2520                2525
Ile Thr Leu Pro Glu Pro Asn Gly Ser Ala Thr Gly Leu Thr Val Trp
            2530                2535                2540
Leu His Gly Leu Thr Ala Ser Val Leu Pro Gly Leu Leu Arg Gln Ala
2545            2550                2555                2560
Asp Pro Gln His Val Ile Glu Tyr Ser Leu Ala Leu Val Thr Val Leu
            2565                2570                2575
```

-continued

```
Asn Glu Tyr Glu Arg Ala Leu Asp Val Ala Ala Glu Pro Lys His Glu
            2580                2585                2590

Arg Gln His Arg Ala Gln Ile Arg Lys Asn Ile Thr Glu Thr Leu Val
            2595                2600                2605

Ser Leu Arg Val His Thr Val Asp Asp Ile Gln Gln Ile Ala Ala Ala
            2610                2615                2620

Leu Ala Gln Cys Met Gly Pro Ser Arg Glu Leu Val Cys Arg Ser Cys
2625                2630                2635                2640

Leu Lys Gln Thr Leu His Lys Leu Glu Ala Met Met Leu Ile Leu Gln
            2645                2650                2655

Ala Glu Thr Thr Ala Gly Thr Val Thr Pro Thr Ala Ile Gly Asp Ser
            2660                2665                2670

Ile Leu Asn Ile Thr Gly Asp Leu Ile His Leu Ala Ser Ser Asp Val
            2675                2680                2685

Arg Ala Pro Gln Pro Ser Glu Leu Gly Ala Glu Ser Pro Ser Arg Met
            2690                2695                2700

Val Ala Ser Gln Ala Tyr Asn Leu Thr Ser Ala Leu Met Arg Ile Leu
2705                2710                2715                2720

Met Arg Ser Arg Val Leu Asn Glu Glu Pro Leu Thr Leu Ala Gly Glu
            2725                2730                2735

Glu Ile Val Ala Gln Gly Lys Arg Ser Asp Pro Arg Ser Leu Leu Cys
            2740                2745                2750

Tyr Gly Gly Ala Pro Gly Pro Gly Cys His Phe Ser Ile Pro Glu Ala
            2755                2760                2765

Phe Ser Gly Ala Leu Ala Asn Leu Ser Asp Val Val Gln Leu Ile Phe
            2770                2775                2780

Leu Val Asp Ser Asn Pro Phe Pro Phe Gly Tyr Ile Ser Asn Tyr Thr
2785                2790                2795                2800

Val Ser Thr Lys Val Ala Ser Met Ala Phe Gln Thr Gln Ala Gly Ala
            2805                2810                2815

Gln Ile Pro Ile Glu Arg Leu Ala Ser Glu Arg Ala Ile Thr Val Lys
            2820                2825                2830

Val Pro Asn Asn Ser Asp Trp Ala Ala Arg Gly His Arg Ser Ser Ala
            2835                2840                2845

Asn Ser Ala Asn Ser Val Val Gln Pro Gln Ala Ser Val Gly Ala
            2850                2855                2860

Val Val Thr Leu Asp Ser Ser Asn Pro Ala Ala Gly Leu His Leu Gln
2865                2870                2875                2880

Leu Asn Tyr Thr Leu Leu Asp Gly His Tyr Leu Ser Glu Glu Pro Glu
            2885                2890                2895

Pro Tyr Leu Ala Val Tyr Leu His Ser Glu Pro Arg Pro Asn Glu His
            2900                2905                2910

Asn Cys Ser Ala Ser Arg Arg Ile Arg Pro Glu Ser Leu Gln Gly Ala
            2915                2920                2925

Asp His Arg Pro Tyr Thr Phe Phe Ile Ser Pro Gly Ser Arg Asp Pro
            2930                2935                2940

Ala Gly Ser Tyr His Leu Asn Leu Ser Ser His Phe Arg Trp Ser Ala
2945                2950                2955                2960

Leu Gln Val Ser Val Gly Leu Tyr Thr Ser Leu Cys Gln Tyr Phe Ser
            2965                2970                2975

Glu Glu Asp Met Val Trp Arg Thr Glu Gly Leu Leu Pro Leu Glu Glu
            2980                2985                2990

Thr Ser Pro Arg Gln Ala Val Cys Leu Thr Arg His Leu Thr Ala Phe
```

-continued

```
            2995                3000                  3005
Gly Ala Ser Leu Phe Val Pro Pro Ser His Val Arg Phe Val Phe Pro
            3010                3015               3020
Glu Pro Thr Ala Asp Val Asn Tyr Ile Val Met Leu Thr Cys Ala Val
3025                3030                3035                3040
Cys Leu Val Thr Tyr Met Val Met Ala Ala Ile Leu His Lys Leu Asp
                3045                3050                3055
Gln Leu Asp Ala Ser Arg Gly Arg Ala Ile Pro Phe Cys Gly Gln Arg
            3060                3065                3070
Gly Arg Phe Lys Tyr Glu Ile Leu Val Lys Thr Gly Trp Gly Arg Gly
            3075                3080                3085
Ser Gly Thr Thr Ala His Val Gly Ile Met Leu Tyr Gly Val Asp Ser
            3090                3095                3100
Arg Ser Gly His Arg His Leu Asp Gly Asp Arg Ala Phe His Arg Asn
3105                3110                3115                3120
Ser Leu Asp Ile Phe Arg Ile Ala Thr Pro His Ser Leu Gly Ser Val
                3125                3130                3135
Trp Lys Ile Arg Val Trp His Asp Asn Lys Gly Leu Ser Pro Ala Trp
            3140                3145                3150
Phe Leu Gln His Val Ile Val Arg Asp Leu Gln Thr Ala Arg Ser Ala
            3155                3160                3165
Phe Phe Leu Val Asn Asp Trp Leu Ser Val Glu Thr Glu Ala Asn Gly
            3170                3175                3180
Gly Leu Val Glu Lys Glu Val Leu Ala Ala Ser Asp Ala Ala Leu Leu
3185                3190                3195                3200
Arg Phe Arg Arg Leu Leu Val Ala Glu Leu Gln Arg Gly Phe Phe Asp
            3205                3210                3215
Lys His Ile Trp Leu Ser Ile Trp Asp Arg Pro Pro Arg Ser Arg Phe
            3220                3225                3230
Thr Arg Ile Gln Arg Ala Thr Cys Cys Val Leu Leu Ile Cys Leu Phe
            3235                3240                3245
Leu Gly Ala Asn Ala Val Trp Tyr Gly Ala Val Gly Asp Ser Ala Tyr
            3250                3255                3260
Ser Thr Gly His Val Ser Arg Leu Ser Pro Leu Ser Val Asp Thr Val
3265                3270                3275                3280
Ala Val Gly Leu Val Ser Ser Val Val Tyr Pro Val Tyr Leu Ala
                3285                3290                3295
Ile Leu Phe Leu Phe Arg Met Ser Arg Ser Lys Val Ala Gly Ser Pro
                3300                3305                3310
Ser Pro Thr Pro Ala Gly Gln Gln Val Leu Asp Ile Asp Ser Cys Leu
            3315                3320                3325
Asp Ser Ser Val Leu Asp Ser Ser Phe Leu Thr Phe Ser Gly Leu His
            3330                3335                3340
Ala Glu Ala Phe Val Gly Gln Met Lys Ser Asp Leu Phe Leu Asp Asp
3345                3350                3355                3360
Ser Lys Ser Leu Val Cys Trp Pro Ser Gly Glu Gly Thr Leu Ser Trp
                3365                3370                3375
Pro Asp Leu Leu Ser Asp Pro Ser Ile Val Gly Ser Asn Leu Arg Gln
            3380                3385                3390
Leu Ala Arg Gly Gln Ala Gly His Gly Leu Gly Pro Glu Glu Asp Gly
            3395                3400                3405
Phe Ser Leu Ala Ser Pro Tyr Ser Pro Ala Lys Ser Phe Ser Ala Ser
            3410                3415                3420
```

```
Asp Glu Asp Leu Ile Gln Gln Val Leu Ala Glu Gly Val Ser Ser Pro
3425                3430                3435                3440

Ala Pro Thr Gln Asp Thr His Met Glu Thr Asp Leu Leu Ser Ser Leu
            3445                3450                3455

Ser Ser Thr Pro Gly Glu Lys Thr Glu Thr Leu Ala Leu Gln Arg Leu
            3460                3465                3470

Gly Glu Leu Gly Pro Pro Ser Pro Gly Leu Asn Trp Glu Gln Pro Gln
            3475                3480                3485

Ala Ala Arg Leu Ser Arg Thr Gly Leu Val Glu Gly Leu Arg Lys Arg
            3490                3495                3500

Leu Leu Pro Ala Trp Cys Ala Ser Leu Ala His Gly Leu Ser Leu Leu
3505                3510                3515                3520

Leu Val Ala Val Ala Val Ala Val Ser Gly Trp Val Gly Ala Ser Phe
            3525                3530                3535

Pro Pro Gly Val Ser Val Ala Trp Leu Leu Ser Ser Ser Ala Ser Phe
            3540                3545                3550

Leu Ala Ser Phe Leu Gly Trp Glu Pro Leu Lys Val Leu Leu Glu Ala
            3555                3560                3565

Leu Tyr Phe Ser Leu Val Ala Lys Arg Leu His Pro Asp Glu Asp Asp
            3570                3575                3580

Thr Leu Val Glu Ser Pro Ala Val Thr Pro Val Ser Ala Arg Val Pro
3585                3590                3595                3600

Arg Val Arg Pro Pro His Gly Phe Ala Leu Phe Leu Ala Lys Glu Glu
            3605                3610                3615

Ala Arg Lys Val Lys Arg Leu His Gly Met Leu Arg Ser Leu Leu Val
            3620                3625                3630

Tyr Met Leu Phe Leu Leu Val Thr Leu Leu Ala Ser Tyr Gly Asp Ala
            3635                3640                3645

Ser Cys His Gly His Ala Tyr Arg Leu Gln Ser Ala Ile Lys Gln Glu
            3650                3655                3660

Leu His Ser Arg Ala Phe Leu Ala Ile Thr Arg Ser Glu Glu Leu Trp
3665                3670                3675                3680

Pro Trp Met Ala His Val Leu Leu Pro Tyr Val His Gly Asn Gln Ser
            3685                3690                3695

Ser Pro Glu Leu Gly Pro Pro Arg Leu Arg Gln Val Arg Leu Gln Glu
            3700                3705                3710

Ala Leu Tyr Pro Asp Pro Pro Gly Pro Arg Val His Thr Cys Ser Ala
            3715                3720                3725

Ala Gly Gly Phe Ser Thr Ser Asp Tyr Asp Val Gly Trp Glu Ser Pro
            3730                3735                3740

His Asn Gly Ser Gly Thr Trp Ala Tyr Ser Ala Pro Asp Leu Leu Gly
3745                3750                3755                3760

Ala Trp Ser Trp Gly Ser Cys Ala Val Tyr Asp Ser Gly Gly Tyr Val
            3765                3770                3775

Gln Glu Leu Gly Leu Ser Leu Glu Glu Ser Arg Asp Arg Leu Arg Phe
            3780                3785                3790

Leu Gln Leu His Asn Trp Leu Asp Asn Arg Ser Arg Ala Val Phe Leu
            3795                3800                3805

Glu Leu Thr Arg Tyr Ser Pro Ala Val Gly Leu His Ala Ala Val Thr
            3810                3815                3820

Leu Arg Leu Glu Phe Pro Ala Ala Gly Arg Ala Leu Ala Ala Leu Ser
3825                3830                3835                3840
```

-continued

```
Val Arg Pro Phe Ala Leu Arg Arg Leu Ser Ala Gly Leu Ser Leu Pro
            3845                3850                3855

Leu Leu Thr Ser Val Cys Leu Leu Phe Ala Val His Phe Ala Val
            3860                3865                3870

Ala Glu Ala Arg Thr Trp His Arg Glu Gly Arg Trp Arg Val Leu Arg
            3875                3880                3885

Leu Gly Ala Trp Ala Arg Trp Leu Leu Val Ala Leu Thr Ala Ala Thr
            3890                3895                3900

Ala Leu Val Arg Leu Ala Gln Leu Gly Ala Ala Asp Arg Gln Trp Thr
3905                3910                3915                3920

Arg Phe Val Arg Gly Arg Pro Arg Arg Phe Thr Ser Phe Asp Gln Val
            3925                3930                3935

Ala His Val Ser Ser Ala Ala Arg Gly Leu Ala Ala Ser Leu Leu Phe
            3940                3945                3950

Leu Leu Leu Val Lys Ala Ala Gln His Val Arg Phe Val Arg Gln Trp
            3955                3960                3965

Ser Val Phe Gly Lys Thr Leu Cys Arg Ala Leu Pro Glu Leu Leu Gly
            3970                3975                3980

Val Thr Leu Gly Leu Val Val Leu Gly Val Ala Tyr Ala Gln Leu Ala
3985                3990                3995                4000

Ile Leu Leu Val Ser Ser Cys Val Asp Ser Leu Trp Ser Val Ala Gln
            4005                4010                4015

Ala Leu Leu Val Leu Cys Pro Gly Thr Gly Leu Ser Thr Leu Cys Pro
            4020                4025                4030

Ala Glu Ser Trp His Leu Ser Pro Leu Leu Cys Val Gly Leu Trp Ala
            4035                4040                4045

Leu Arg Leu Trp Gly Ala Leu Arg Leu Gly Ala Val Ile Leu Arg Trp
            4050                4055                4060

Arg Tyr His Ala Leu Arg Gly Glu Leu Tyr Arg Pro Ala Trp Glu Pro
4065                4070                4075                4080

Gln Asp Tyr Glu Met Val Glu Leu Phe Leu Arg Arg Leu Arg Leu Trp
            4085                4090                4095

Met Gly Leu Ser Lys Val Lys Glu Phe Arg His Lys Val Arg Phe Glu
            4100                4105                4110

Gly Met Glu Pro Leu Pro Ser Arg Ser Ser Arg Gly Ser Lys Val Ser
            4115                4120                4125

Pro Asp Val Pro Pro Ser Ala Gly Ser Asp Ala Ser His Pro Ser
            4130                4135                4140

Thr Ser Ser Ser Gln Leu Asp Gly Leu Ser Val Ser Leu Gly Arg Leu
4145                4150                4155                4160

Gly Thr Arg Cys Glu Pro Glu Pro Ser Arg Leu Gln Ala Val Phe Glu
            4165                4170                4175

Ala Leu Leu Thr Gln Phe Asp Arg Leu Asn Gln Ala Thr Glu Asp Val
            4180                4185                4190

Tyr Gln Leu Glu Gln Gln Leu His Ser Leu Gln Gly Arg Arg Ser Ser
            4195                4200                4205

Arg Ala Pro Ala Gly Ser Ser Arg Gly Pro Ser Pro Gly Leu Arg Pro
            4210                4215                4220

Ala Leu Pro Ser Arg Leu Ala Arg Ala Ser Arg Gly Val Asp Leu Ala
4225                4230                4235                4240

Thr Gly Pro Ser Arg Thr Pro Ser Gly Gln Glu Gln Gly Pro Pro Gln
            4245                4250                4255

Gln His Leu Val Leu Leu Pro Gly Gly Gly Pro Trp Ser Arg Ser
```

-continued

```
                    4260           4265           4270

Gly His Arg Ser Val Leu Leu Ser Ala Ala Val Lys Ala Glu Gly Gln
        4275           4280           4285

Ala Glu Trp Leu His Val Gly Ser Pro Glu Ser Arg Gln Gly His Leu
    4290           4295           4300

Ser Val Cys Gly Leu Gln His Phe Lys Glu Ala Val Trp Pro Thr Arg
4305           4310           4315           4320

Thr Gln Gly Pro Leu Pro Ser Ser Leu Gly Lys Asp Thr Ala Val Leu
            4325           4330           4335

Asp Gly Phe
```

(2) INFORMATION FOR SEQ ID NO: 7:

(i) SEQUENCE CHARACTERISTICS:
        (A) LENGTH: 14148 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: CDS
        (B) LOCATION:212..13117

(ix) FEATURE:
        (A) NAME/KEY: misc_feature
        (B) LOCATION:212..278
        (D) OTHER INFORMATION:/note= "Probable signal sequence"

(ix) FEATURE:
        (A) NAME/KEY: misc_feature
        (B) LOCATION:359..4574
        (D) OTHER INFORMATION:/note= "N-linked glycosylation
            sites at the following positions: 359, 476, 557, 572,    770

(ix) FEATURE:
        (A) NAME/KEY: misc_feature
        (B) LOCATION:4574..8144
        (D) OTHER INFORMATION:/note= "N-linked glycosylation
            sites at following locations: 4559, 4574, 4631, 4763,    483

(ix) FEATURE:
        (A) NAME/KEY: misc_feature
        (B) LOCATION:8363..11741
        (D) OTHER INFORMATION:/note= "N-linked glycosylation
            sites at following locations: 8471, 8663, 8732, 8843,    898

(ix) FEATURE:
        (A) NAME/KEY: misc_feature
        (B) LOCATION:7949..8009
        (D) OTHER INFORMATION:/note= "Predicted transmembrane
            domain"

(ix) FEATURE:
        (A) NAME/KEY: misc_feature
        (B) LOCATION:8288..8348
        (D) OTHER INFORMATION:/note= "Predicted transmembrane
            domain"

(ix) FEATURE:
        (A) NAME/KEY: misc_feature
        (B) LOCATION:9434..9494
        (D) OTHER INFORMATION:/note= "Predicted transmembrane
            domain"

(ix) FEATURE:
        (A) NAME/KEY: misc_feature
        (B) LOCATION:10052..10112
        (D) OTHER INFORMATION:/note= "Predicted transmembrane

```
     (ix) FEATURE:
           (A) NAME/KEY: misc_feature
           (B) LOCATION:10178..10238
           (D) OTHER INFORMATION:/note= "Predicted transmembrane
               domain"

(ix) FEATURE:
           (A) NAME/KEY: misc_feature
           (B) LOCATION:10886..10946
           (D) OTHER INFORMATION:/note= "Predicted transmembrane
               domain"

(ix) FEATURE:
           (A) NAME/KEY: misc_feature
           (B) LOCATION:10955..11015
           (D) OTHER INFORMATION:/note= "Predicted transmembrane
               domain"

(ix) FEATURE:
           (A) NAME/KEY: misc_feature
           (B) LOCATION:11216..11276
           (D) OTHER INFORMATION:/note= "Predicted transmembrane
               domain"

(ix) FEATURE:
           (A) NAME/KEY: misc_feature
           (B) LOCATION:11894..11954
           (D) OTHER INFORMATION:/note= "Predicted transmembrane
               domain"

(ix) FEATURE:
           (A) NAME/KEY: misc_feature
           (B) LOCATION:12293..12353
           (D) OTHER INFORMATION:/note= "Predicted transmembrane
               domain"

(ix) FEATURE:
           (A) NAME/KEY: misc_feature
           (B) LOCATION:12377..12437
           (D) OTHER INFORMATION:/note= "Predicted transmembrane
               domain"

(ix) FEATURE:
           (A) NAME/KEY: misc_feature
           (B) LOCATION:212..278
           (D) OTHER INFORMATION:/note= "Possible hinge sequence"

(ix) FEATURE:
           (A) NAME/KEY: misc_feature
           (B) LOCATION:279
           (D) OTHER INFORMATION:/note= "Cleavage site"

(xi) SEQUENCE DESCRIPTION: SEQ ID NO: 7:

GCACTGCAGC GCCAGCGTCC GAGCGGGCGG CCGAGCTCCC GGAGCGGCCT GGCCCCGAGC        60

CCCGAGCGGG CGTCGCTCAG CAGCAGGTCG CGGCCGCGCA GCCCCATCCA GCCCCGCGCC       120

CGCCATGCCG TCCGCGGGCC CCGCCTGAGC TGCGGTCTCC GCGCGCGGGC GGGCCTGGGG       180

ACGGCGGGGC CATGCGCGCG CTGCCCTAAC G ATG CCG CCC GCC GCG CCC GCC         232
                                 Met Pro Pro Ala Ala Pro Ala
                                 4340                4345

CGC CTG GCG CTG GCC CTG GGC CTG GGC CTG TGG CTC GGG GCG CTG GCG        280
Arg Leu Ala Leu Ala Leu Gly Leu Gly Leu Trp Leu Gly Ala Leu Ala
        4350            4355            4360

GGG GGC CCC GGG CGC GGC TGC GGG CCC TGC GAG CCC CCC TGC CTC TGC        328
Gly Gly Pro Gly Arg Gly Cys Gly Pro Cys Glu Pro Pro Cys Leu Cys
    4365            4370            4375

GGC CCA GCG CCC GGC GCC GCC TGC CGC GTC AAC TGC TCG GGC CGC GGG        376
Gly Pro Ala Pro Gly Ala Ala Cys Arg Val Asn Cys Ser Gly Arg Gly
    4380            4385            4390

CTG CGG ACG CTC GGT CCC GCG CTG CGC ATC CCC GCG GAC GCC ACA GCG        424
```

```
                                              -continued

Leu Arg Thr Leu Gly Pro Ala Leu Arg Ile Pro Ala Asp Ala Thr Ala
4395                4400                4405                4410

CTA GAC GTC TCC CAC AAC CTG CTC CGG GCG CTG GAC GTT GGG CTC CTG        472
Leu Asp Val Ser His Asn Leu Leu Arg Ala Leu Asp Val Gly Leu Leu
                4415                4420                4425

GCG AAC CTC TCG GCG CTG GCA GAG CTG GAT ATA AGC AAC AAC AAG ATT        520
Ala Asn Leu Ser Ala Leu Ala Glu Leu Asp Ile Ser Asn Asn Lys Ile
            4430                4435                4440

TCT ACG TTA GAA GAA GGA ATA TTT GCT AAT TTA TTT AAT TTA AGT GAA        568
Ser Thr Leu Glu Glu Gly Ile Phe Ala Asn Leu Phe Asn Leu Ser Glu
        4445                4450                4455

ATA AAC CTG AGT GGG AAC CCG TTT GAG TGT GAC TGT GGC CTG GCG TGG        616
Ile Asn Leu Ser Gly Asn Pro Phe Glu Cys Asp Cys Gly Leu Ala Trp
    4460                4465                4470

CTG CCG CGA TGG GCG GAG GAG CAG CAG GTG CGG GTG GTG CAG CCC GAG        664
Leu Pro Arg Trp Ala Glu Glu Gln Gln Val Arg Val Val Gln Pro Glu
4475                4480                4485                4490

GCA GCC ACG TGT GCT GGG CCT GGC TCC CTG GCT GGC CAG CCT CTG CTT        712
Ala Ala Thr Cys Ala Gly Pro Gly Ser Leu Ala Gly Gln Pro Leu Leu
                4495                4500                4505

GGC ATC CCC TTG CTG GAC AGT GGC TGT GGT GAG GAG TAT GTC GCC TGC        760
Gly Ile Pro Leu Leu Asp Ser Gly Cys Gly Glu Glu Tyr Val Ala Cys
            4510                4515                4520

CTC CCT GAC AAC AGC TCA GGC ACC GTG GCA GCA GTG TCC TTT TCA GCT        808
Leu Pro Asp Asn Ser Ser Gly Thr Val Ala Ala Val Ser Phe Ser Ala
        4525                4530                4535

GCC CAC GAA GGC CTG CTT CAG CCA GAG GCC TGC AGC GCC TTC TGC TTC        856
Ala His Glu Gly Leu Leu Gln Pro Glu Ala Cys Ser Ala Phe Cys Phe
    4540                4545                4550

TCC ACC GGC CAG GGC CTC GCA GCC CTC TCG GAG CAG GGC TGG TGC CTG        904
Ser Thr Gly Gln Gly Leu Ala Ala Leu Ser Glu Gln Gly Trp Cys Leu
4555                4560                4565                4570

TGT GGG GCG GCC CAG CCC TCC AGT GCC TCC TTT GCC TGC CTG TCC CTC        952
Cys Gly Ala Ala Gln Pro Ser Ser Ala Ser Phe Ala Cys Leu Ser Leu
                4575                4580                4585

TGC TCC GGC CCC CCG CCA CCT CCT GCC CCC ACC TGT AGG GGC CCC ACC       1000
Cys Ser Gly Pro Pro Pro Pro Pro Ala Pro Thr Cys Arg Gly Pro Thr
            4590                4595                4600

CTC CTC CAG CAC GTC TTC CCT GCC TCC CCA GGG GCC ACC CTG GTG GGG       1048
Leu Leu Gln His Val Phe Pro Ala Ser Pro Gly Ala Thr Leu Val Gly
        4605                4610                4615

CCC CAC GGA CCT CTG GCC TCT GGC CAG CTA GCA GCC TTC CAC ATC GCT       1096
Pro His Gly Pro Leu Ala Ser Gly Gln Leu Ala Ala Phe His Ile Ala
    4620                4625                4630

GCC CCG CTC CCT GTC ACT GCC ACA CGC TGG GAC TTC GGA GAC GGC TCC       1144
Ala Pro Leu Pro Val Thr Ala Thr Arg Trp Asp Phe Gly Asp Gly Ser
4635                4640                4645                4650

GCC GAG GTG GAT GCC GCT GGG CCG GCT GCC TCG CAT CGC TAT GTG CTG       1192
Ala Glu Val Asp Ala Ala Gly Pro Ala Ala Ser His Arg Tyr Val Leu
                4655                4660                4665

CCT GGG CGC TAT CAC GTG ACG GCC GTG CTG GCC CTG GGG GCC GGC TCA       1240
Pro Gly Arg Tyr His Val Thr Ala Val Leu Ala Leu Gly Ala Gly Ser
            4670                4675                4680

GCC CTG CTG GGG ACA GAC GTG CAG GTG GAA GCG GCA CCT GCC GCC CTG       1288
Ala Leu Leu Gly Thr Asp Val Gln Val Glu Ala Ala Pro Ala Ala Leu
        4685                4690                4695

GAG CTC GTG TGC CCG TCC TCG GTG CAG AGT GAC GAG AGC CTT GAC CTC       1336
Glu Leu Val Cys Pro Ser Ser Val Gln Ser Asp Glu Ser Leu Asp Leu
    4700                4705                4710
```

```
AGC ATC CAG AAC CGC GGT GGT TCA GGC CTG GAG GCC GCC TAC AGC ATC    1384
Ser Ile Gln Asn Arg Gly Gly Ser Gly Leu Glu Ala Ala Tyr Ser Ile
4715            4720            4725            4730

GTG GCC CTG GGC GAG GAG CCG GCC CGA GCG GTG CAC CCG CTC TGC CCC    1432
Val Ala Leu Gly Glu Glu Pro Ala Arg Ala Val His Pro Leu Cys Pro
        4735            4740            4745

TCG GAC ACG GAG ATC TTC CCT GGC AAC GGG CAC TGC TAC CGC CTG GTG    1480
Ser Asp Thr Glu Ile Phe Pro Gly Asn Gly His Cys Tyr Arg Leu Val
                4750            4755            4760

GTG GAG AAG GCG GCC TGG CTG CAG GCG CAG GAG CAG TGT CAG GCC TGG    1528
Val Glu Lys Ala Ala Trp Leu Gln Ala Gln Glu Gln Cys Gln Ala Trp
        4765            4770            4775

GCC GGG GCC GCC CTG GCA ATG GTG GAC AGT CCC GCC GTG CAG CGC TTC    1576
Ala Gly Ala Ala Leu Ala Met Val Asp Ser Pro Ala Val Gln Arg Phe
            4780            4785            4790

CTG GTC TCC CGG GTC ACC AGG AGC CTA GAC GTG TGG ATC GGC TTC TCG    1624
Leu Val Ser Arg Val Thr Arg Ser Leu Asp Val Trp Ile Gly Phe Ser
4795            4800            4805            4810

ACT GTG CAG GGG GTG GAG GTG GGC CCA GCG CCG CAG GGC GAG GCC TTC    1672
Thr Val Gln Gly Val Glu Val Gly Pro Ala Pro Gln Gly Glu Ala Phe
                4815            4820            4825

AGC CTG GAG AGC TGC CAG AAC TGG CTG CCC GGG GAG CCA CAC CCA GCC    1720
Ser Leu Glu Ser Cys Gln Asn Trp Leu Pro Gly Glu Pro His Pro Ala
        4830            4835            4840

ACA GCC GAG CAC TGC GTC CGG CTC GGG CCC ACC GGG TGG TGT AAC ACC    1768
Thr Ala Glu His Cys Val Arg Leu Gly Pro Thr Gly Trp Cys Asn Thr
            4845            4850            4855

GAC CTG TGC TCA GCG CCG CAC AGC TAC GTC TGC GAG CTG CAG CCC GGA    1816
Asp Leu Cys Ser Ala Pro His Ser Tyr Val Cys Glu Leu Gln Pro Gly
4860            4865            4870

GGC CCA GTG CAG GAT GCC GAG AAC CTC CTC GTG GGA GCG CCC AGT GGG    1864
Gly Pro Val Gln Asp Ala Glu Asn Leu Leu Val Gly Ala Pro Ser Gly
4875            4880            4885            4890

GAC CTG CAG GGA CCC CTG ACG CCT CTG GCA CAG CAG GAC GGC CTC TCA    1912
Asp Leu Gln Gly Pro Leu Thr Pro Leu Ala Gln Gln Asp Gly Leu Ser
            4895            4900            4905

GCC CCG CAC GAG CCC GTG GAG GTC ATG GTA TTC CCG GGC CTG CGT CTG    1960
Ala Pro His Glu Pro Val Glu Val Met Val Phe Pro Gly Leu Arg Leu
        4910            4915            4920

AGC CGT GAA GCC TTC CTC ACC ACG GCC GAA TTT GGG ACC CAG GAG CTC    2008
Ser Arg Glu Ala Phe Leu Thr Thr Ala Glu Phe Gly Thr Gln Glu Leu
            4925            4930            4935

CGG CGG CCC GCC CAG CTG CGG CTG CAG GTG TAC CGG CTC CTC AGC ACA    2056
Arg Arg Pro Ala Gln Leu Arg Leu Gln Val Tyr Arg Leu Leu Ser Thr
        4940            4945            4950

GCA GGG ACC CCG GAG AAC GGC AGC GAG CCT GAG AGC AGG TCC CCG GAC    2104
Ala Gly Thr Pro Glu Asn Gly Ser Glu Pro Glu Ser Arg Ser Pro Asp
4955            4960            4965            4970

AAC AGG ACC CAG CTG GCC CCC GCG TGC ATG CCA GGG GGA CGC TGG TGC    2152
Asn Arg Thr Gln Leu Ala Pro Ala Cys Met Pro Gly Gly Arg Trp Cys
            4975            4980            4985

CCT GGA GCC AAC ATC TGC TTG CCG CTG GAC GCC TCT TGC CAC CCC CAG    2200
Pro Gly Ala Asn Ile Cys Leu Pro Leu Asp Ala Ser Cys His Pro Gln
            4990            4995            5000

GCC TGC GCC AAT GGC TGC ACG TCA GGG CCA GGG CTA CCC GGG GCC CCC    2248
Ala Cys Ala Asn Gly Cys Thr Ser Gly Pro Gly Leu Pro Gly Ala Pro
        5005            5010            5015

TAT GCG CTA TGG AGA GAG TTC CTC TTC TCC GTT GCC GCG GGG CCC CCC    2296
Tyr Ala Leu Trp Arg Glu Phe Leu Phe Ser Val Ala Ala Gly Pro Pro
            5020            5025            5030
```

```
GCG CAG TAC TCG GTC ACC CTC CAC GGC CAG GAT GTC CTC ATG CTC CCT      2344
Ala Gln Tyr Ser Val Thr Leu His Gly Gln Asp Val Leu Met Leu Pro
5035             5040             5045             5050

GGT GAC CTC GTT GGC TTG CAG CAC GAC GCT GGC CCT GGC GCC CTC CTG      2392
Gly Asp Leu Val Gly Leu Gln His Asp Ala Gly Pro Gly Ala Leu Leu
         5055             5060             5065

CAC TGC TCG CCG GCT CCC GGC CAC CCT GGT CCC CAG GCC CCG TAC CTC      2440
His Cys Ser Pro Ala Pro Gly His Pro Gly Pro Gln Ala Pro Tyr Leu
             5070             5075             5080

TCC GCC AAC GCC TCG TCA TGG CTG CCC CAC TTG CCA GCC CAG CTG GAG      2488
Ser Ala Asn Ala Ser Ser Trp Leu Pro His Leu Pro Ala Gln Leu Glu
         5085             5090             5095

GGC ACT TGG GCC TGC CCT GCC TGT GCC CTG CGG CTG CTT GCA GCC ACG      2536
Gly Thr Trp Ala Cys Pro Ala Cys Ala Leu Arg Leu Leu Ala Ala Thr
             5100             5105             5110

GAA CAG CTC ACC GTG CTG CTG GGC TTG AGG CCC AAC CCT GGA CTG CGG      2584
Glu Gln Leu Thr Val Leu Leu Gly Leu Arg Pro Asn Pro Gly Leu Arg
5115             5120             5125             5130

ATG CCT GGG CGC TAT GAG GTC CGG GCA GAG GTG GGC AAT GGC GTG TCC      2632
Met Pro Gly Arg Tyr Glu Val Arg Ala Glu Val Gly Asn Gly Val Ser
             5135             5140             5145

AGG CAC AAC CTC TCC TGC AGC TTT GAC GTG GTC TCC CCA GTG GCT GGG      2680
Arg His Asn Leu Ser Cys Ser Phe Asp Val Val Ser Pro Val Ala Gly
             5150             5155             5160

CTG CGG GTC ATC TAC CCT GCC CCC CGC GAC GGC CGC CTC TAC GTG CCC      2728
Leu Arg Val Ile Tyr Pro Ala Pro Arg Asp Gly Arg Leu Tyr Val Pro
             5165             5170             5175

ACC AAC GGC TCA GCC TTG GTG CTC CAG GTG GAC TCT GGT GCC AAC GCC      2776
Thr Asn Gly Ser Ala Leu Val Leu Gln Val Asp Ser Gly Ala Asn Ala
             5180             5185             5190

ACG GCC ACG GCT CGC TGG CCT GGG GGC AGT GTC AGC GCC CGC TTT GAG      2824
Thr Ala Thr Ala Arg Trp Pro Gly Gly Ser Val Ser Ala Arg Phe Glu
5195             5200             5205             5210

AAT GTC TGC CCT GCC CTG GTG GCC ACC TTC GTG CCC GGC TGC CCC TGG      2872
Asn Val Cys Pro Ala Leu Val Ala Thr Phe Val Pro Gly Cys Pro Trp
             5215             5220             5225

GAG ACC AAC GAT ACC CTG TTC TCA GTG GTA GCA CTG CCG TGG CTC AGT      2920
Glu Thr Asn Asp Thr Leu Phe Ser Val Val Ala Leu Pro Trp Leu Ser
             5230             5235             5240

GAG GGG GAG CAC GTG GTG GAC GTG GTG GTG GAA AAC AGC GCC AGC CGG      2968
Glu Gly Glu His Val Val Asp Val Val Val Glu Asn Ser Ala Ser Arg
             5245             5250             5255

GCC AAC CTC AGC CTG CGG GTG ACG GCG GAG GAG CCC ATC TGT GGC CTC      3016
Ala Asn Leu Ser Leu Arg Val Thr Ala Glu Glu Pro Ile Cys Gly Leu
         5260             5265             5270

CGC GCC ACG CCC AGC CCC GAG GCC CGT GTA CTG CAG GGA GTC CTA GTG      3064
Arg Ala Thr Pro Ser Pro Glu Ala Arg Val Leu Gln Gly Val Leu Val
5275             5280             5285             5290

AGG TAC AGC CCC GTG GTG GAG GCC GGC TCG GAC ATG GTC TTC CGG TGG      3112
Arg Tyr Ser Pro Val Val Glu Ala Gly Ser Asp Met Val Phe Arg Trp
             5295             5300             5305

ACC ATC AAC GAC AAG CAG TCC CTG ACC TTC CAG AAC GTG GTC TTC AAT      3160
Thr Ile Asn Asp Lys Gln Ser Leu Thr Phe Gln Asn Val Val Phe Asn
             5310             5315             5320

GTC ATT TAT CAG AGC GCG GCG GTC TTC AAG CTC TCA CTG ACG GCC TCC      3208
Val Ile Tyr Gln Ser Ala Ala Val Phe Lys Leu Ser Leu Thr Ala Ser
             5325             5330             5335

AAC CAC GTG AGC AAC GTC ACC GTG AAC TAC AAC GTA ACC GTG GAG CGG      3256
Asn His Val Ser Asn Val Thr Val Asn Tyr Asn Val Thr Val Glu Arg
```

```
                5340                5345                5350
ATG AAC AGG ATG CAG GGT CTG CAG GTC TCC ACA GTG CCG GCC GTG CTG      3304
Met Asn Arg Met Gln Gly Leu Gln Val Ser Thr Val Pro Ala Val Leu
5355                5360                5365                5370

TCC CCC AAT GCC ACA CTG GTA CTG ACG GGT GGT GTG CTG GTG GAC TCA      3352
Ser Pro Asn Ala Thr Leu Val Leu Thr Gly Gly Val Leu Val Asp Ser
                5375                5380                5385

GCT GTG GAG GTG GCC TTC CTG TGG AAC TTT GGG GAT GGG GAG CAG GCC      3400
Ala Val Glu Val Ala Phe Leu Trp Asn Phe Gly Asp Gly Glu Gln Ala
            5390                5395                5400

CTC CAC CAG TTC CAG CCT CCG TAC AAC GAG TCC TTC CCG GTT CCA GAC      3448
Leu His Gln Phe Gln Pro Pro Tyr Asn Glu Ser Phe Pro Val Pro Asp
            5405                5410                5415

CCC TCG GTG GCC CAG GTG CTG GTG GAG CAC AAT GTC ATG CAC ACC TAC      3496
Pro Ser Val Ala Gln Val Leu Val Glu His Asn Val Met His Thr Tyr
        5420                5425                5430

GCT GCC CCA GGT GAG TAC CTC CTG ACC GTG CTG GCA TCT AAT GCC TTC      3544
Ala Ala Pro Gly Glu Tyr Leu Leu Thr Val Leu Ala Ser Asn Ala Phe
5435                5440                5445                5450

GAG AAC CTG ACG CAG CAG GTG CCT GTG AGC GTG CGC GCC TCC CTG CCC      3592
Glu Asn Leu Thr Gln Gln Val Pro Val Ser Val Arg Ala Ser Leu Pro
                5455                5460                5465

TCC GTG GCT GTG GGT GTG AGT GAC GGC GTC CTG GTG GCC GGC CGG CCC      3640
Ser Val Ala Val Gly Val Ser Asp Gly Val Leu Val Ala Gly Arg Pro
                5470                5475                5480

GTC ACC TTC TAC CCG CAC CCG CTG CCC TCG CCT GGG GGT GTT CTT TAC      3688
Val Thr Phe Tyr Pro His Pro Leu Pro Ser Pro Gly Gly Val Leu Tyr
            5485                5490                5495

ACG TGG GAC TTC GGG GAC GGC TCC CCT GTC CTG ACC CAG AGC CAG CCG      3736
Thr Trp Asp Phe Gly Asp Gly Ser Pro Val Leu Thr Gln Ser Gln Pro
        5500                5505                5510

GCT GCC AAC CAC ACC TAT GCC TCG AGG GGC ACC TAC CAC GTG CGC CTG      3784
Ala Ala Asn His Thr Tyr Ala Ser Arg Gly Thr Tyr His Val Arg Leu
5515                5520                5525                5530

GAG GTC AAC AAC ACG GTG AGC GGT GCG GCG GCC CAG GCG GAT GTG CGC      3832
Glu Val Asn Asn Thr Val Ser Gly Ala Ala Ala Gln Ala Asp Val Arg
                5535                5540                5545

GTC TTT GAG GAG CTC CGC GGA CTC AGC GTG GAC ATG AGC CTG GCC GTG      3880
Val Phe Glu Glu Leu Arg Gly Leu Ser Val Asp Met Ser Leu Ala Val
            5550                5555                5560

GAG CAG GGC GCC CCC GTG GTG GTC AGC GCC GCG GTG CAG ACG GGC GAC      3928
Glu Gln Gly Ala Pro Val Val Val Ser Ala Ala Val Gln Thr Gly Asp
        5565                5570                5575

AAC ATC ACG TGG ACC TTC GAC ATG GGG GAC GGC ACC GTG CTG TCG GGC      3976
Asn Ile Thr Trp Thr Phe Asp Met Gly Asp Gly Thr Val Leu Ser Gly
    5580                5585                5590

CCG GAG GCA ACA GTG GAG CAT GTG TAC CTG CGG GCA CAG AAC TGC ACA      4024
Pro Glu Ala Thr Val Glu His Val Tyr Leu Arg Ala Gln Asn Cys Thr
5595                5600                5605                5610

GTG ACC GTG GGT GCG GCC AGC CCC GCC GGC CAC CTG GCC CGG AGC CTG      4072
Val Thr Val Gly Ala Ala Ser Pro Ala Gly His Leu Ala Arg Ser Leu
                5615                5620                5625

CAC GTG CTG GTC TTC GTC CTG GAG GTG CTG CGC GTT GAA CCC GCC GCC      4120
His Val Leu Val Phe Val Leu Glu Val Leu Arg Val Glu Pro Ala Ala
            5630                5635                5640

TGC ATC CCC ACG CAG CCT GAC GCG CGG CTC ACG GCC TAC GTC ACC GGG      4168
Cys Ile Pro Thr Gln Pro Asp Ala Arg Leu Thr Ala Tyr Val Thr Gly
            5645                5650                5655

AAC CCG GCC CAC TAC CTC TTC GAC TGG ACC TTC GGG GAT GGC TCC TCC      4216
```

```
                                                            -continued

Asn Pro Ala His Tyr Leu Phe Asp Trp Thr Phe Gly Asp Gly Ser Ser
    5660                5665                5670

AAC ACG ACC GTG CGG GGG TGC CCG ACG GTG ACA CAC AAC TTC ACG CGG      4264
Asn Thr Thr Val Arg Gly Cys Pro Thr Val Thr His Asn Phe Thr Arg
5675            5680                5685                5690

AGC GGC ACG TTC CCC CTG GCG CTG GTG CTG TCC AGC CGC GTG AAC AGG      4312
Ser Gly Thr Phe Pro Leu Ala Leu Val Leu Ser Ser Arg Val Asn Arg
                5695                5700                5705

GCG CAT TAC TTC ACC AGC ATC TGC GTG GAG CCA GAG GTG GGC AAC GTC      4360
Ala His Tyr Phe Thr Ser Ile Cys Val Glu Pro Glu Val Gly Asn Val
                    5710                5715                5720

ACC CTG CAG CCA GAG AGG CAG TTT GTG CAG CTC GGG GAC GAG GCC TGG      4408
Thr Leu Gln Pro Glu Arg Gln Phe Val Gln Leu Gly Asp Glu Ala Trp
                        5725                5730                5735

CTG GTG GCA TGT GCC TGG CCC CCG TTC CCC TAC CGC TAC ACC TGG GAC      4456
Leu Val Ala Cys Ala Trp Pro Pro Phe Pro Tyr Arg Tyr Thr Trp Asp
            5740                5745                5750

TTT GGC ACC GAG GAA GCC GCC CCC ACC CGT GCC AGG GGC CCT GAG GTG      4504
Phe Gly Thr Glu Glu Ala Ala Pro Thr Arg Ala Arg Gly Pro Glu Val
5755                5760                5765                5770

ACG TTC ATC TAC CGA GAC CCA GGC TCC TAT CTT GTG ACA GTC ACC GCG      4552
Thr Phe Ile Tyr Arg Asp Pro Gly Ser Tyr Leu Val Thr Val Thr Ala
                5775                5780                5785

TCC AAC AAC ATC TCT GCT GCC AAT GAC TCA GCC CTG GTG GAG GTG CAG      4600
Ser Asn Asn Ile Ser Ala Ala Asn Asp Ser Ala Leu Val Glu Val Gln
                    5790                5795                5800

GAG CCC GTG CTG GTC ACC AGC ATC AAG GTC AAT GGC TCC CTT GGG CTG      4648
Glu Pro Val Leu Val Thr Ser Ile Lys Val Asn Gly Ser Leu Gly Leu
                        5805                5810                5815

GAG CTG CAG CAG CCG TAC CTG TTC TCT GCT GTG GGC CGT GGG CGC CCC      4696
Glu Leu Gln Gln Pro Tyr Leu Phe Ser Ala Val Gly Arg Gly Arg Pro
            5820                5825                5830

GCC AGC TAC CTG TGG GAT CTG GGG GAC GGT GGG TGG CTC GAG GGT CCG      4744
Ala Ser Tyr Leu Trp Asp Leu Gly Asp Gly Gly Trp Leu Glu Gly Pro
5835                5840                5845                5850

GAG GTC ACC CAC GCT TAC AAC AGC ACA GGT GAC TTC ACC GTT AGG GTG      4792
Glu Val Thr His Ala Tyr Asn Ser Thr Gly Asp Phe Thr Val Arg Val
                5855                5860                5865

GCC GGC TGG AAT GAG GTG AGC CGC AGC GAG GCC TGG CTC AAT GTG ACG      4840
Ala Gly Trp Asn Glu Val Ser Arg Ser Glu Ala Trp Leu Asn Val Thr
                    5870                5875                5880

GTG AAG CGG CGT GTG CGG GGG CTC GTC GTC AAT GCA AGC CGC ACG GTG      4888
Val Lys Arg Arg Val Arg Gly Leu Val Val Asn Ala Ser Arg Thr Val
                        5885                5890                5895

GTG CCC CTG AAT GGG AGC GTG AGC TTC AGC ACG TCG CTG GAG GCC GGC      4936
Val Pro Leu Asn Gly Ser Val Ser Phe Ser Thr Ser Leu Glu Ala Gly
            5900                5905                5910

AGT GAT GTG CGC TAT TCC TGG GTG CTC TGT GAC CGC TGC ACG CCC ATC      4984
Ser Asp Val Arg Tyr Ser Trp Val Leu Cys Asp Arg Cys Thr Pro Ile
5915                5920                5925                5930

CCT GGG GGT CCT ACC ATC TCT TAC ACC TTC CGC TCC GTG GGC ACC TTC      5032
Pro Gly Gly Pro Thr Ile Ser Tyr Thr Phe Arg Ser Val Gly Thr Phe
                5935                5940                5945

AAT ATC ATC GTC ACG GCT GAG AAC GAG GTG GGC TCC GCC CAG GAC AGC      5080
Asn Ile Ile Val Thr Ala Glu Asn Glu Val Gly Ser Ala Gln Asp Ser
                    5950                5955                5960

ATC TTC GTC TAT GTC CTG CAG CTC ATA GAG GGG CTG CAG GTG GTG GGC      5128
Ile Phe Val Tyr Val Leu Gln Leu Ile Glu Gly Leu Gln Val Val Gly
                        5965                5970                5975
```

-continued

```
GGT GGC CGC TAC TTC CCC ACC AAC CAC ACG GTA CAG CTG CAG GCC GTG         5176
Gly Gly Arg Tyr Phe Pro Thr Asn His Thr Val Gln Leu Gln Ala Val
        5980                5985                5990

GTT AGG GAT GGC ACC AAC GTC TCC TAC AGC TGG ACT GCC TGG AGG GAC         5224
Val Arg Asp Gly Thr Asn Val Ser Tyr Ser Trp Thr Ala Trp Arg Asp
5995                6000                6005                6010

AGG GGC CCG GCC CTG GCC GGC AGC GGC AAA GGC TTC TCG CTC ACC GTG         5272
Arg Gly Pro Ala Leu Ala Gly Ser Gly Lys Gly Phe Ser Leu Thr Val
                6015                6020                6025

CTC GAG GCC GGC ACC TAC CAT GTG CAG CTG CGG GCC ACC AAC ATG CTG         5320
Leu Glu Ala Gly Thr Tyr His Val Gln Leu Arg Ala Thr Asn Met Leu
        6030                6035                6040

GGC AGC GCC TGG GCC GAC TGC ACC ATG GAC TTC GTG GAG CCT GTG GGG         5368
Gly Ser Ala Trp Ala Asp Cys Thr Met Asp Phe Val Glu Pro Val Gly
        6045                6050                6055

TGG CTG ATG GTG ACC GCC TCC CCG AAC CCA GCT GCC GTC AAC ACA AGC         5416
Trp Leu Met Val Thr Ala Ser Pro Asn Pro Ala Ala Val Asn Thr Ser
        6060                6065                6070

GTC ACC CTC AGT GCC GAG CTG GCT GGT GGC AGT GGT GTC GTA TAC ACT         5464
Val Thr Leu Ser Ala Glu Leu Ala Gly Gly Ser Gly Val Val Tyr Thr
6075                6080                6085                6090

TGG TCC TTG GAG GAG GGG CTG AGC TGG GAG ACC TCC GAG CCA TTT ACC         5512
Trp Ser Leu Glu Glu Gly Leu Ser Trp Glu Thr Ser Glu Pro Phe Thr
                6095                6100                6105

ACC CAT AGC TTC CCC ACA CCC GGC CTG CAC TTG GTC ACC ATG ACG GCA         5560
Thr His Ser Phe Pro Thr Pro Gly Leu His Leu Val Thr Met Thr Ala
        6110                6115                6120

GGG AAC CCG CTG GGC TCA GCC AAC GCC ACC GTG GAA GTG GAT GTG CAG         5608
Gly Asn Pro Leu Gly Ser Ala Asn Ala Thr Val Glu Val Asp Val Gln
        6125                6130                6135

GTG CCT GTG AGT GGC CTC AGC ATC AGG GCC AGC GAG CCC GGA GGC AGC         5656
Val Pro Val Ser Gly Leu Ser Ile Arg Ala Ser Glu Pro Gly Gly Ser
        6140                6145                6150

TTC GTG GCG GCC GGG TCC TCT GTG CCC TTT TGG GGG CAG CTG GCC ACG         5704
Phe Val Ala Ala Gly Ser Ser Val Pro Phe Trp Gly Gln Leu Ala Thr
6155                6160                6165                6170

GGC ACC AAT GTG AGC TGG TGC TGG GCT GTG CCC GGC GGC AGC AGC AAG         5752
Gly Thr Asn Val Ser Trp Cys Trp Ala Val Pro Gly Gly Ser Ser Lys
                6175                6180                6185

CGT GGC CCT CAT GTC ACC ATG GTC TTC CCG GAT GCT GGC ACC TTC TCC         5800
Arg Gly Pro His Val Thr Met Val Phe Pro Asp Ala Gly Thr Phe Ser
        6190                6195                6200

ATC CGG CTC AAT GCC TCC AAC GCA GTC AGC TGG GTC TCA GCC ACG TAC         5848
Ile Arg Leu Asn Ala Ser Asn Ala Val Ser Trp Val Ser Ala Thr Tyr
        6205                6210                6215

AAC CTC ACG GCG GAG GAG CCC ATC GTG GGC CTG GTG CTG TGG GCC AGC         5896
Asn Leu Thr Ala Glu Glu Pro Ile Val Gly Leu Val Leu Trp Ala Ser
        6220                6225                6230

AGC AAG GTG GTG GCG CCC GGG CAG CTG GTC CAT TTT CAG ATC CTG CTG         5944
Ser Lys Val Val Ala Pro Gly Gln Leu Val His Phe Gln Ile Leu Leu
6235                6240                6245                6250

GCT GCC GGC TCA GCT GTC ACC TTC CGC CTG CAG GTC GGC GGG GCC AAC         5992
Ala Ala Gly Ser Ala Val Thr Phe Arg Leu Gln Val Gly Gly Ala Asn
                6255                6260                6265

CCC GAG GTG CTC CCC GGG CCC CGT TTC TCC CAC AGC TTC CCC CGC GTC         6040
Pro Glu Val Leu Pro Gly Pro Arg Phe Ser His Ser Phe Pro Arg Val
        6270                6275                6280

GGA GAC CAC GTG GTG AGC GTG CGG GGC AAA AAC CAC GTG AGC TGG GCC         6088
Gly Asp His Val Val Ser Val Arg Gly Lys Asn His Val Ser Trp Ala
        6285                6290                6295
```

-continued

| | |
|---|---|
| CAG GCG CAG GTG CGC ATC GTG GTG CTG GAG GCC GTG AGT GGG CTG CAG<br>Gln Ala Gln Val Arg Ile Val Val Leu Glu Ala Val Ser Gly Leu Gln<br>      6300                6305              6310 | 6136 |
| ATG CCC AAC TGC TGC GAG CCT GGC ATC GCC ACG GGC ACT GAG AGG AAC<br>Met Pro Asn Cys Cys Glu Pro Gly Ile Ala Thr Gly Thr Glu Arg Asn<br>6315              6320               6325            6330 | 6184 |
| TTC ACA GCC CGC GTG CAG CGC GGC TCT CGG GTC GCC TAC GCC TGG TAC<br>Phe Thr Ala Arg Val Gln Arg Gly Ser Arg Val Ala Tyr Ala Trp Tyr<br>      6335              6340              6345 | 6232 |
| TTC TCG CTG CAG AAG GTC CAG GGC GAC TCG CTG GTC ATC CTG TCG GGC<br>Phe Ser Leu Gln Lys Val Gln Gly Asp Ser Leu Val Ile Leu Ser Gly<br>      6350              6355              6360 | 6280 |
| CGC GAC GTC ACC TAC ACG CCC GTG GCC GCG GGG CTG TTG GAG ATC CAG<br>Arg Asp Val Thr Tyr Thr Pro Val Ala Ala Gly Leu Leu Glu Ile Gln<br>6365              6370               6375 | 6328 |
| GTG CGC GCC TTC AAC GCC CTG GGC AGT GAG AAC CGC ACG CTG GTG CTG<br>Val Arg Ala Phe Asn Ala Leu Gly Ser Glu Asn Arg Thr Leu Val Leu<br>      6380              6385              6390 | 6376 |
| GAG GTT CAG GAC GCC GTC CAG TAT GTG GCC CTG CAG AGC GGC CCC TGC<br>Glu Val Gln Asp Ala Val Gln Tyr Val Ala Leu Gln Ser Gly Pro Cys<br>6395              6400               6405            6410 | 6424 |
| TTC ACC AAC CGC TCG GCG CAG TTT GAG GCC GCC ACC AGC CCC AGC CCC<br>Phe Thr Asn Arg Ser Ala Gln Phe Glu Ala Ala Thr Ser Pro Ser Pro<br>      6415              6420              6425 | 6472 |
| CGG CGT GTG GCC TAC CAC TGG GAC TTT GGG GAT GGG TCG CCA GGG CAG<br>Arg Arg Val Ala Tyr His Trp Asp Phe Gly Asp Gly Ser Pro Gly Gln<br>      6430              6435              6440 | 6520 |
| GAC ACA GAT GAG CCC AGG GCC GAG CAC TCC TAC CTG AGG CCT GGG GAC<br>Asp Thr Asp Glu Pro Arg Ala Glu His Ser Tyr Leu Arg Pro Gly Asp<br>      6445              6450              6455 | 6568 |
| TAC CGC GTG CAG GTG AAC GCC TCC AAC CTG GTG AGC TTC TTC GTG GCG<br>Tyr Arg Val Gln Val Asn Ala Ser Asn Leu Val Ser Phe Phe Val Ala<br>      6460              6465              6470 | 6616 |
| CAG GCC ACG GTG ACC GTC CAG GTG CTG GCC TGC CGG GAG CCG GAG GTG<br>Gln Ala Thr Val Thr Val Gln Val Leu Ala Cys Arg Glu Pro Glu Val<br>6475              6480               6485            6490 | 6664 |
| GAC GTG GTC CTG CCC CTG CAG GTG CTG ATG CGG CGA TCA CAG CGC AAC<br>Asp Val Val Leu Pro Leu Gln Val Leu Met Arg Arg Ser Gln Arg Asn<br>      6495              6500              6505 | 6712 |
| TAC TTG GAG GCC CAC GTT GAC CTG CGC GAC TGC GTC ACC TAC CAG ACT<br>Tyr Leu Glu Ala His Val Asp Leu Arg Asp Cys Val Thr Tyr Gln Thr<br>      6510              6515              6520 | 6760 |
| GAG TAC CGC TGG GAG GTG TAT CGC ACC GCC AGC TGC CAG CGG CCG GGG<br>Glu Tyr Arg Trp Glu Val Tyr Arg Thr Ala Ser Cys Gln Arg Pro Gly<br>      6525              6530              6535 | 6808 |
| CGC CCA GCG CGT GTG GCC CTG CCC GGC GTG GAC GTG AGC CGG CCT CGG<br>Arg Pro Ala Arg Val Ala Leu Pro Gly Val Asp Val Ser Arg Pro Arg<br>      6540              6545              6550 | 6856 |
| CTG GTG CTG CCG CGG CTG GCG CTG CCT GTG GGG CAC TAC TGC TTT GTG<br>Leu Val Leu Pro Arg Leu Ala Leu Pro Val Gly His Tyr Cys Phe Val<br>6555              6560               6565            6570 | 6904 |
| TTT GTC GTG TCA TTT GGG GAC ACG CCA CTG ACA CAG AGC ATC CAG GCC<br>Phe Val Val Ser Phe Gly Asp Thr Pro Leu Thr Gln Ser Ile Gln Ala<br>      6575              6580              6585 | 6952 |
| AAT GTG ACG GTG GCC CCC GAG CGC CTG GTG CCC ATC ATT GAG GGT GGC<br>Asn Val Thr Val Ala Pro Glu Arg Leu Val Pro Ile Ile Glu Gly Gly<br>      6590              6595              6600 | 7000 |
| TCA TAC CGC GTG TGG TCA GAC ACA CGG GAC CTG GTG CTG GAT GGG AGC<br>Ser Tyr Arg Val Trp Ser Asp Thr Arg Asp Leu Val Leu Asp Gly Ser | 7048 |

```
                  6605                6610                6615
GAG TCC TAC GAC CCC AAC CTG GAG GAC GGC GAC CAG ACG CCG CTC AGT       7096
Glu Ser Tyr Asp Pro Asn Leu Glu Asp Gly Asp Gln Thr Pro Leu Ser
        6620                6625                6630

TTC CAC TGG GCC TGT GTG GCT TCG ACA CAG AGG GAG GCT GGC GGG TGT       7144
Phe His Trp Ala Cys Val Ala Ser Thr Gln Arg Glu Ala Gly Gly Cys
6635                6640                6645                6650

GCG CTG AAC TTT GGG CCC CGC GGG AGC AGC ACG GTC ACC ATT CCA CGG       7192
Ala Leu Asn Phe Gly Pro Arg Gly Ser Ser Thr Val Thr Ile Pro Arg
                6655                6660                6665

GAG CGG CTG GCG GCT GGC GTG GAG TAC ACC TTC AGC CTG ACC GTG TGG       7240
Glu Arg Leu Ala Ala Gly Val Glu Tyr Thr Phe Ser Leu Thr Val Trp
            6670                6675                6680

AAG GCC GGC CGC AAG GAG GAG GCC ACC AAC CAG ACG GTG CTG ATC CGG       7288
Lys Ala Gly Arg Lys Glu Glu Ala Thr Asn Gln Thr Val Leu Ile Arg
                6685                6690                6695

AGT GGC CGG GTG CCC ATT GTG TCC TTG GAG TGT GTG TCC TGC AAG GCA       7336
Ser Gly Arg Val Pro Ile Val Ser Leu Glu Cys Val Ser Cys Lys Ala
        6700                6705                6710

CAG GCC GTG TAC GAA GTG AGC CGC AGC TCC TAC GTG TAC TTG GAG GGC       7384
Gln Ala Val Tyr Glu Val Ser Arg Ser Ser Tyr Val Tyr Leu Glu Gly
6715                6720                6725                6730

CGC TGC CTC AAT TGC AGC AGC GGC TCC AAG CGA GGG CGG TGG GCT GCA       7432
Arg Cys Leu Asn Cys Ser Ser Gly Ser Lys Arg Gly Arg Trp Ala Ala
                6735                6740                6745

CGT ACG TTC AGC AAC AAG ACG CTG GTG CTG GAT GAG ACC ACC ACA TCC       7480
Arg Thr Phe Ser Asn Lys Thr Leu Val Leu Asp Glu Thr Thr Thr Ser
            6750                6755                6760

ACG GGC AGT GCA GGC ATG CGA CTG GTG CTG CGG CGG GGC GTG CTG CGG       7528
Thr Gly Ser Ala Gly Met Arg Leu Val Leu Arg Arg Gly Val Leu Arg
            6765                6770                6775

GAC GGC GAG GGA TAC ACC TTC ACG CTC ACG GTG CTG GGC CGC TCT GGC       7576
Asp Gly Glu Gly Tyr Thr Phe Thr Leu Thr Val Leu Gly Arg Ser Gly
        6780                6785                6790

GAG GAG GAG GGC TGC GCC TCC ATC CGC CTG TCC CCC AAC CGC CCG CCG       7624
Glu Glu Glu Gly Cys Ala Ser Ile Arg Leu Ser Pro Asn Arg Pro Pro
6795                6800                6805                6810

CTG GGG GGC TCT TGC CGC CTC TTC CCA CTG GGC GCT GTG CAC GCC CTC       7672
Leu Gly Gly Ser Cys Arg Leu Phe Pro Leu Gly Ala Val His Ala Leu
                6815                6820                6825

ACC ACC AAG GTG CAC TTC GAA TGC ACG GGC TGG CAT GAC GCG GAG GAT       7720
Thr Thr Lys Val His Phe Glu Cys Thr Gly Trp His Asp Ala Glu Asp
            6830                6835                6840

GCT GGC GCC CCG CTG GTG TAC GCC CTG CTG CTG CGG CGC TGT CGC CAG       7768
Ala Gly Ala Pro Leu Val Tyr Ala Leu Leu Leu Arg Arg Cys Arg Gln
        6845                6850                6855

GGC CAC TGC GAG GAG TTC TGT GTC TAC AAG GGC AGC CTC TCC AGC TAC       7816
Gly His Cys Glu Glu Phe Cys Val Tyr Lys Gly Ser Leu Ser Ser Tyr
        6860                6865                6870

GGA GCC GTG CTG CCC CCG GGT TTC AGG CCA CAC TTC GAG GTG GGC CTG       7864
Gly Ala Val Leu Pro Pro Gly Phe Arg Pro His Phe Glu Val Gly Leu
6875                6880                6885                6890

GCC GTG GTG GTG CAG GAC CAG CTG GGA GCC GCT GTG GTC GCC CTC AAC       7912
Ala Val Val Val Gln Asp Gln Leu Gly Ala Ala Val Val Ala Leu Asn
                6895                6900                6905

AGG TCT TTG GCC ATC ACC CTC CCA GAG CCC AAC GGC AGC GCA ACG GGG       7960
Arg Ser Leu Ala Ile Thr Leu Pro Glu Pro Asn Gly Ser Ala Thr Gly
            6910                6915                6920

CTC ACA GTC TGG CTG CAC GGG CTC ACC GCT AGT GTG CTC CCA GGG CTG       8008
```

```
Leu Thr Val Trp Leu His Gly Leu Thr Ala Ser Val Leu Pro Gly Leu
            6925                6930                6935

CTG CGG CAG GCC GAT CCC CAG CAC GTC ATC GAG TAC TCG TTG GCC CTG         8056
Leu Arg Gln Ala Asp Pro Gln His Val Ile Glu Tyr Ser Leu Ala Leu
            6940                6945                6950

GTC ACC GTG CTG AAC GAG TAC GAG CGG GCC CTG GAC GTG GCG GCA GAG         8104
Val Thr Val Leu Asn Glu Tyr Glu Arg Ala Leu Asp Val Ala Ala Glu
6955                6960                6965                6970

CCC AAG CAC GAG CGG CAG CAC CGA GCC CAG ATA CGC AAG AAC ATC ACG         8152
Pro Lys His Glu Arg Gln His Arg Ala Gln Ile Arg Lys Asn Ile Thr
            6975                6980                6985

GAG ACT CTG GTG TCC CTG AGG GTC CAC ACT GTG GAT GAC ATC CAG CAG         8200
Glu Thr Leu Val Ser Leu Arg Val His Thr Val Asp Asp Ile Gln Gln
            6990                6995                7000

ATC GCT GCT GCG CTG GCC CAG TGC ATG GGG CCC AGC AGG GAG CTC GTA         8248
Ile Ala Ala Ala Leu Ala Gln Cys Met Gly Pro Ser Arg Glu Leu Val
            7005                7010                7015

TGC CGC TCG TGC CTG AAG CAG ACG CTG CAC AAG CTG GAG GCC ATG ATG         8296
Cys Arg Ser Cys Leu Lys Gln Thr Leu His Lys Leu Glu Ala Met Met
            7020                7025                7030

CTC ATC CTG CAG GCA GAG ACC ACC GCG GGC ACC GTG ACG CCC ACC GCC         8344
Leu Ile Leu Gln Ala Glu Thr Thr Ala Gly Thr Val Thr Pro Thr Ala
7035                7040                7045                7050

ATC GGA GAC AGC ATC CTC AAC ATC ACA GGA GAC CTC ATC CAC CTG GCC         8392
Ile Gly Asp Ser Ile Leu Asn Ile Thr Gly Asp Leu Ile His Leu Ala
            7055                7060                7065

AGC TCG GAC GTG CGG GCA CCA CAG CCC TCA GAG CTG GGA GCC GAG TCA         8440
Ser Ser Asp Val Arg Ala Pro Gln Pro Ser Glu Leu Gly Ala Glu Ser
            7070                7075                7080

CCA TCT CGG ATG GTG GCG TCC CAG GCC TAC AAC CTG ACC TCT GCC CTC         8488
Pro Ser Arg Met Val Ala Ser Gln Ala Tyr Asn Leu Thr Ser Ala Leu
            7085                7090                7095

ATG CGC ATC CTC ATG CGC TCC CGC GTG CTC AAC GAG GAG CCC CTG ACG         8536
Met Arg Ile Leu Met Arg Ser Arg Val Leu Asn Glu Glu Pro Leu Thr
            7100                7105                7110

CTG GCG GGC GAG GAG ATC GTG GCC CAG GGC AAG CGC TCG GAC CCG CGG         8584
Leu Ala Gly Glu Glu Ile Val Ala Gln Gly Lys Arg Ser Asp Pro Arg
7115                7120                7125                7130

AGC CTG CTG TGC TAT GGC GGC GCC CCA GGG CCT GGC TGC CAC TTC TCC         8632
Ser Leu Leu Cys Tyr Gly Gly Ala Pro Gly Pro Gly Cys His Phe Ser
            7135                7140                7145

ATC CCC GAG GCT TTC AGC GGG GCC CTG GCC AAC CTC AGT GAC GTG GTG         8680
Ile Pro Glu Ala Phe Ser Gly Ala Leu Ala Asn Leu Ser Asp Val Val
            7150                7155                7160

CAG CTC ATC TTT CTG GTG GAC TCC AAT CCC TTT CCC TTT GGC TAT ATC         8728
Gln Leu Ile Phe Leu Val Asp Ser Asn Pro Phe Pro Phe Gly Tyr Ile
            7165                7170                7175

AGC AAC TAC ACC GTC TCC ACC AAG GTG GCC TCG ATG GCA TTC CAG ACA         8776
Ser Asn Tyr Thr Val Ser Thr Lys Val Ala Ser Met Ala Phe Gln Thr
            7180                7185                7190

CAG GCC GGC GCC CAG ATC CCC ATC GAG CGG CTG GCC TCA GAG CGC GCC         8824
Gln Ala Gly Ala Gln Ile Pro Ile Glu Arg Leu Ala Ser Glu Arg Ala
7195                7200                7205                7210

ATC ACC GTG AAG GTG CCC AAC AAC TCG GAC TGG GCT GCC CGG GGC CAC         8872
Ile Thr Val Lys Val Pro Asn Asn Ser Asp Trp Ala Ala Arg Gly His
            7215                7220                7225

CGC AGC TCC GCC AAC TCC GCC AAC TCC GTT GTG GTC CAG CCC CAG GCC         8920
Arg Ser Ser Ala Asn Ser Ala Asn Ser Val Val Val Gln Pro Gln Ala
            7230                7235                7240
```

```
TCC GTC GGT GCT GTG GTC ACC CTG GAC AGC AGC AAC CCT GCG GCC GGG    8968
Ser Val Gly Ala Val Val Thr Leu Asp Ser Ser Asn Pro Ala Ala Gly
        7245                7250                7255

CTG CAT CTG CAG CTC AAC TAT ACG CTG CTG GAC GGC CAC TAC CTG TCT    9016
Leu His Leu Gln Leu Asn Tyr Thr Leu Leu Asp Gly His Tyr Leu Ser
    7260                7265                7270

GAG GAA CCT GAG CCC TAC CTG GCA GTC TAC CTA CAC TCG GAG CCC CGG    9064
Glu Glu Pro Glu Pro Tyr Leu Ala Val Tyr Leu His Ser Glu Pro Arg
7275                7280                7285                7290

CCC AAT GAG CAC AAC TGC TCG GCT AGC AGG AGG ATC CGC CCA GAG TCA    9112
Pro Asn Glu His Asn Cys Ser Ala Ser Arg Arg Ile Arg Pro Glu Ser
            7295                7300                7305

CTC CAG GGT GCT GAC CAC CGG CCC TAC ACC TTC TTC ATT TCC CCG GGG    9160
Leu Gln Gly Ala Asp His Arg Pro Tyr Thr Phe Phe Ile Ser Pro Gly
        7310                7315                7320

AGC AGA GAC CCA GCG GGG AGT TAC CAT CTG AAC CTC TCC AGC CAC TTC    9208
Ser Arg Asp Pro Ala Gly Ser Tyr His Leu Asn Leu Ser Ser His Phe
    7325                7330                7335

CGC TGG TCG GCG CTG CAG GTG TCC GTG GGC CTG TAC ACG TCC CTG TGC    9256
Arg Trp Ser Ala Leu Gln Val Ser Val Gly Leu Tyr Thr Ser Leu Cys
7340                7345                7350

CAG TAC TTC AGC GAG GAG GAC ATG GTG TGG CGG ACA GAG GGG CTG CTG    9304
Gln Tyr Phe Ser Glu Glu Asp Met Val Trp Arg Thr Glu Gly Leu Leu
7355                7360                7365                7370

CCC CTG GAG GAG ACC TCG CCC CGC CAG GCC GTC TGC CTC ACC CGC CAC    9352
Pro Leu Glu Glu Thr Ser Pro Arg Gln Ala Val Cys Leu Thr Arg His
            7375                7380                7385

CTC ACC GCC TTC GGC GCC AGC CTC TTC GTG CCC CCA AGC CAT GTC CGC    9400
Leu Thr Ala Phe Gly Ala Ser Leu Phe Val Pro Pro Ser His Val Arg
        7390                7395                7400

TTT GTG TTT CCT GAG CCG ACA GCG GAT GTA AAC TAC ATC GTC ATG CTG    9448
Phe Val Phe Pro Glu Pro Thr Ala Asp Val Asn Tyr Ile Val Met Leu
    7405                7410                7415

ACA TGT GCT GTG TGC CTG GTG ACC TAC ATG GTC ATG GCC GCC ATC CTG    9496
Thr Cys Ala Val Cys Leu Val Thr Tyr Met Val Met Ala Ala Ile Leu
7420                7425                7430

CAC AAG CTG GAC CAG TTG GAT GCC AGC CGG GGC CGC GCC ATC CCT TTC    9544
His Lys Leu Asp Gln Leu Asp Ala Ser Arg Gly Arg Ala Ile Pro Phe
7435                7440                7445                7450

TGT GGG CAG CGG GGC CGC TTC AAG TAC GAG ATC CTC GTC AAG ACA GGC    9592
Cys Gly Gln Arg Gly Arg Phe Lys Tyr Glu Ile Leu Val Lys Thr Gly
            7455                7460                7465

TGG GGC CGG GGC TCA GGT ACC ACG GCC CAC GTG GGC ATC ATG CTG TAT    9640
Trp Gly Arg Gly Ser Gly Thr Thr Ala His Val Gly Ile Met Leu Tyr
        7470                7475                7480

GGG GTG GAC AGC CGG AGC GGC CAC CGG CAC CTG GAC GGC GAC AGA GCC    9688
Gly Val Asp Ser Arg Ser Gly His Arg His Leu Asp Gly Asp Arg Ala
    7485                7490                7495

TTC CAC CGC AAC AGC CTG GAC ATC TTC CGG ATC GCC ACC CCG CAC AGC    9736
Phe His Arg Asn Ser Leu Asp Ile Phe Arg Ile Ala Thr Pro His Ser
7500                7505                7510

CTG GGT AGC GTG TGG AAG ATC CGA GTG TGG CAC GAC AAC AAA GGG CTC    9784
Leu Gly Ser Val Trp Lys Ile Arg Val Trp His Asp Asn Lys Gly Leu
7515                7520                7525                7530

AGC CCT GCC TGG TTC CTG CAG CAC GTC ATC GTC AGG GAC CTG CAG ACG    9832
Ser Pro Ala Trp Phe Leu Gln His Val Ile Val Arg Asp Leu Gln Thr
            7535                7540                7545

GCA CGC AGC GCC TTC TTC CTG GTC AAT GAC TGG CTT TCG GTG GAG ACG    9880
Ala Arg Ser Ala Phe Phe Leu Val Asn Asp Trp Leu Ser Val Glu Thr
        7550                7555                7560
```

| | | | | | | | | | | | | | | | | |
|---|---|---|---|---|---|---|---|---|---|---|---|---|---|---|---|---|
|GAG|GCC|AAC|GGG|GGC|CTG|GTG|GAG|AAG|GAG|GTG|CTG|GCC|GCG|AGC|GAC|9928|
|Glu|Ala|Asn|Gly|Gly|Leu|Val|Glu|Lys|Glu|Val|Leu|Ala|Ala|Ser|Asp||
| | |7565| | |7570| | | |7575| | | | | | | |

| | | | | | | | | | | | | | | | | |
|---|---|---|---|---|---|---|---|---|---|---|---|---|---|---|---|---|
|GCA|GCC|CTT|TTG|CGC|TTC|CGG|CGC|CTG|CTG|GTG|GCT|GAG|CTG|CAG|CGT|9976|
|Ala|Ala|Leu|Leu|Arg|Phe|Arg|Arg|Leu|Leu|Val|Ala|Glu|Leu|Gln|Arg||
| |7580| | | | |7585| | | | |7590| | | | | |

| | | | | | | | | | | | | | | | | |
|---|---|---|---|---|---|---|---|---|---|---|---|---|---|---|---|---|
|GGC|TTC|TTT|GAC|AAG|CAC|ATC|TGG|CTC|TCC|ATA|TGG|GAC|CGG|CCG|CCT|10024|
|Gly|Phe|Phe|Asp|Lys|His|Ile|Trp|Leu|Ser|Ile|Trp|Asp|Arg|Pro|Pro||
|7595| | | | |7600| | | | |7605| | | | |7610| |

| | | | | | | | | | | | | | | | | |
|---|---|---|---|---|---|---|---|---|---|---|---|---|---|---|---|---|
|CGT|AGC|CGT|TTC|ACT|CGC|ATC|CAG|AGG|GCC|ACC|TGC|TGC|GTT|CTC|CTC|10072|
|Arg|Ser|Arg|Phe|Thr|Arg|Ile|Gln|Arg|Ala|Thr|Cys|Cys|Val|Leu|Leu||
| | | | |7615| | | | |7620| | | | |7625| | |

| | | | | | | | | | | | | | | | | |
|---|---|---|---|---|---|---|---|---|---|---|---|---|---|---|---|---|
|ATC|TGC|CTC|TTC|CTG|GGC|GCC|AAC|GCC|GTG|TGG|TAC|GGG|GCT|GTT|GGC|10120|
|Ile|Cys|Leu|Phe|Leu|Gly|Ala|Asn|Ala|Val|Trp|Tyr|Gly|Ala|Val|Gly||
| | | | |7630| | | | |7635| | | | |7640| | |

| | | | | | | | | | | | | | | | | |
|---|---|---|---|---|---|---|---|---|---|---|---|---|---|---|---|---|
|GAC|TCT|GCC|TAC|AGC|ACG|GGG|CAT|GTG|TCC|AGG|CTG|AGC|CCG|CTG|AGC|10168|
|Asp|Ser|Ala|Tyr|Ser|Thr|Gly|His|Val|Ser|Arg|Leu|Ser|Pro|Leu|Ser||
| | | |7645| | | | |7650| | | | |7655| | | |

| | | | | | | | | | | | | | | | | |
|---|---|---|---|---|---|---|---|---|---|---|---|---|---|---|---|---|
|GTC|GAC|ACA|GTC|GCT|GTT|GGC|CTG|GTG|TCC|AGC|GTG|GTT|GTC|TAT|CCC|10216|
|Val|Asp|Thr|Val|Ala|Val|Gly|Leu|Val|Ser|Ser|Val|Val|Val|Tyr|Pro||
| | |7660| | | | |7665| | | | |7670| | | | |

| | | | | | | | | | | | | | | | | |
|---|---|---|---|---|---|---|---|---|---|---|---|---|---|---|---|---|
|GTC|TAC|CTG|GCC|ATC|CTT|TTT|CTC|TTC|CGG|ATG|TCC|CGG|AGC|AAG|GTG|10264|
|Val|Tyr|Leu|Ala|Ile|Leu|Phe|Leu|Phe|Arg|Met|Ser|Arg|Ser|Lys|Val||
|7675| | | |7680| | | | |7685| | | | |7690| | |

| | | | | | | | | | | | | | | | | |
|---|---|---|---|---|---|---|---|---|---|---|---|---|---|---|---|---|
|GCT|GGG|AGC|CCG|AGC|CCC|ACA|CCT|GCC|GGG|CAG|CAG|GTG|CTG|GAC|ATC|10312|
|Ala|Gly|Ser|Pro|Ser|Pro|Thr|Pro|Ala|Gly|Gln|Gln|Val|Leu|Asp|Ile||
| | | |7695| | | | |7700| | | | |7705| | | |

| | | | | | | | | | | | | | | | | |
|---|---|---|---|---|---|---|---|---|---|---|---|---|---|---|---|---|
|GAC|AGC|TGC|CTG|GAC|TCG|TCC|GTG|CTG|GAC|AGC|TCC|TTC|CTC|ACG|TTC|10360|
|Asp|Ser|Cys|Leu|Asp|Ser|Ser|Val|Leu|Asp|Ser|Ser|Phe|Leu|Thr|Phe||
| | | |7710| | | | |7715| | | | |7720| | | |

| | | | | | | | | | | | | | | | | |
|---|---|---|---|---|---|---|---|---|---|---|---|---|---|---|---|---|
|TCA|GGC|CTC|CAC|GCT|GAG|GCC|TTT|GTT|GGA|CAG|ATG|AAG|AGT|GAC|TTG|10408|
|Ser|Gly|Leu|His|Ala|Glu|Ala|Phe|Val|Gly|Gln|Met|Lys|Ser|Asp|Leu||
| | |7725| | | | |7730| | | | |7735| | | | |

| | | | | | | | | | | | | | | | | |
|---|---|---|---|---|---|---|---|---|---|---|---|---|---|---|---|---|
|TTT|CTG|GAT|GAT|TCT|AAG|AGT|CTG|GTG|TGC|TGG|CCC|TCC|GGC|GAG|GGA|10456|
|Phe|Leu|Asp|Asp|Ser|Lys|Ser|Leu|Val|Cys|Trp|Pro|Ser|Gly|Glu|Gly||
| | |7740| | | | |7745| | | | |7750| | | | |

| | | | | | | | | | | | | | | | | |
|---|---|---|---|---|---|---|---|---|---|---|---|---|---|---|---|---|
|ACG|CTC|AGT|TGG|CCG|GAC|CTG|CTC|AGT|GAC|CCG|TCC|ATT|GTG|GGT|AGC|10504|
|Thr|Leu|Ser|Trp|Pro|Asp|Leu|Leu|Ser|Asp|Pro|Ser|Ile|Val|Gly|Ser||
|7755| | | |7760| | | | |7765| | | | |7770| | |

| | | | | | | | | | | | | | | | | |
|---|---|---|---|---|---|---|---|---|---|---|---|---|---|---|---|---|
|AAT|CTG|CGG|CAG|CTG|GCA|CGG|GGC|CAG|GCG|GGC|CAT|GGG|CTG|GGC|CCA|10552|
|Asn|Leu|Arg|Gln|Leu|Ala|Arg|Gly|Gln|Ala|Gly|His|Gly|Leu|Gly|Pro||
| | | |7775| | | | |7780| | | | |7785| | | |

| | | | | | | | | | | | | | | | | |
|---|---|---|---|---|---|---|---|---|---|---|---|---|---|---|---|---|
|GAG|GAG|GAC|GGC|TTC|TCC|CTG|GCC|AGC|CCC|TAC|TCG|CCT|GCC|AAA|TCC|10600|
|Glu|Glu|Asp|Gly|Phe|Ser|Leu|Ala|Ser|Pro|Tyr|Ser|Pro|Ala|Lys|Ser||
| | | |7790| | | | |7795| | | | |7800| | | |

| | | | | | | | | | | | | | | | | |
|---|---|---|---|---|---|---|---|---|---|---|---|---|---|---|---|---|
|TTC|TCA|GCA|TCA|GAT|GAA|GAC|CTG|ATC|CAG|CAG|GTC|CTT|GCC|GAG|GGG|10648|
|Phe|Ser|Ala|Ser|Asp|Glu|Asp|Leu|Ile|Gln|Gln|Val|Leu|Ala|Glu|Gly||
| | |7805| | | | |7810| | | | |7815| | | | |

| | | | | | | | | | | | | | | | | |
|---|---|---|---|---|---|---|---|---|---|---|---|---|---|---|---|---|
|GTC|AGC|AGC|CCA|GCC|CCT|ACC|CAA|GAC|ACC|CAC|ATG|GAA|ACG|GAC|CTG|10696|
|Val|Ser|Ser|Pro|Ala|Pro|Thr|Gln|Asp|Thr|His|Met|Glu|Thr|Asp|Leu||
| | |7820| | | | |7825| | | | |7830| | | | |

| | | | | | | | | | | | | | | | | |
|---|---|---|---|---|---|---|---|---|---|---|---|---|---|---|---|---|
|CTC|AGC|AGC|CTG|TCC|AGC|ACT|CCT|GGG|GAG|AAG|ACA|GAG|ACG|CTG|GCG|10744|
|Leu|Ser|Ser|Leu|Ser|Ser|Thr|Pro|Gly|Glu|Lys|Thr|Glu|Thr|Leu|Ala||
|7835| | | |7840| | | | |7845| | | | |7850| | |

| | | | | | | | | | | | | | | | | |
|---|---|---|---|---|---|---|---|---|---|---|---|---|---|---|---|---|
|CTG|CAG|AGG|CTG|GGG|GAG|CTG|GGG|CCA|CCC|AGC|CCA|GGC|CTG|AAC|TGG|10792|
|Leu|Gln|Arg|Leu|Gly|Glu|Leu|Gly|Pro|Pro|Ser|Pro|Gly|Leu|Asn|Trp||
| | | |7855| | | | |7860| | | | |7865| | | |

| | | | | | | | | | | | | | | | | |
|---|---|---|---|---|---|---|---|---|---|---|---|---|---|---|---|---|
|GAA|CAG|CCC|CAG|GCA|GCG|AGG|CTG|TCC|AGG|ACA|GGA|CTG|GTG|GAG|GGT|10840|
|Glu|Gln|Pro|Gln|Ala|Ala|Arg|Leu|Ser|Arg|Thr|Gly|Leu|Val|Glu|Gly||

-continued

```
                    7870                  7875                  7880
CTG CGG AAG CGC CTG CTG CCG GCC TGG TGT GCC TCC CTG GCC CAC GGG         10888
Leu Arg Lys Arg Leu Leu Pro Ala Trp Cys Ala Ser Leu Ala His Gly
            7885                  7890                  7895

CTC AGC CTG CTC CTG GTG GCT GTG GCT GTG GCT GTC TCA GGG TGG GTG         10936
Leu Ser Leu Leu Leu Val Ala Val Ala Val Ala Val Ser Gly Trp Val
        7900                  7905                  7910

GGT GCG AGC TTC CCC CCG GGC GTG AGT GTT GCG TGG CTC CTG TCC AGC         10984
Gly Ala Ser Phe Pro Pro Gly Val Ser Val Ala Trp Leu Leu Ser Ser
7915                  7920                  7925                  7930

AGC GCC AGC TTC CTG GCC TCA TTC CTC GGC TGG GAG CCA CTG AAG GTC         11032
Ser Ala Ser Phe Leu Ala Ser Phe Leu Gly Trp Glu Pro Leu Lys Val
            7935                  7940                  7945

TTG CTG GAA GCC CTG TAC TTC TCA CTG GTG GCC AAG CGG CTG CAC CCG         11080
Leu Leu Glu Ala Leu Tyr Phe Ser Leu Val Ala Lys Arg Leu His Pro
        7950                  7955                  7960

GAT GAA GAT GAC ACC CTG GTA GAG AGC CCG GCT GTG ACG CCT GTG AGC         11128
Asp Glu Asp Asp Thr Leu Val Glu Ser Pro Ala Val Thr Pro Val Ser
        7965                  7970                  7975

GCA CGT GTG CCC CGC GTA CGG CCA CCC CAC GGC TTT GCA CTC TTC CTG         11176
Ala Arg Val Pro Arg Val Arg Pro Pro His Gly Phe Ala Leu Phe Leu
    7980                  7985                  7990

GCC AAG GAA GAA GCC CGC AAG GTC AAG AGG CTA CAT GGC ATG CTG CGG         11224
Ala Lys Glu Glu Ala Arg Lys Val Lys Arg Leu His Gly Met Leu Arg
7995                  8000                  8005                  8010

AGC CTC CTG GTG TAC ATG CTT TTT CTG CTG GTG ACC CTG CTG GCC AGC         11272
Ser Leu Leu Val Tyr Met Leu Phe Leu Leu Val Thr Leu Leu Ala Ser
            8015                  8020                  8025

TAT GGG GAT GCC TCA TGC CAT GGG CAC GCC TAC CGT CTG CAA AGC GCC         11320
Tyr Gly Asp Ala Ser Cys His Gly His Ala Tyr Arg Leu Gln Ser Ala
        8030                  8035                  8040

ATC AAG CAG GAG CTG CAC AGC CGG GCC TTC CTG GCC ATC ACG CGG TCT         11368
Ile Lys Gln Glu Leu His Ser Arg Ala Phe Leu Ala Ile Thr Arg Ser
        8045                  8050                  8055

GAG GAG CTC TGG CCA TGG ATG GCC CAC GTG CTG CTG CCC TAC GTC CAC         11416
Glu Glu Leu Trp Pro Trp Met Ala His Val Leu Leu Pro Tyr Val His
    8060                  8065                  8070

GGG AAC CAG TCC AGC CCA GAG CTG GGG CCC CCA CGG CTG CGG CAG GTG         11464
Gly Asn Gln Ser Ser Pro Glu Leu Gly Pro Pro Arg Leu Arg Gln Val
8075                  8080                  8085                  8090

CGG CTG CAG GAA GCA CTC TAC CCA GAC CCT CCC GGC CCC AGG GTC CAC         11512
Arg Leu Gln Glu Ala Leu Tyr Pro Asp Pro Pro Gly Pro Arg Val His
            8095                  8100                  8105

ACG TGC TCG GCC GCA GGA GGC TTC AGC ACC AGC GAT TAC GAC GTT GGC         11560
Thr Cys Ser Ala Ala Gly Gly Phe Ser Thr Ser Asp Tyr Asp Val Gly
        8110                  8115                  8120

TGG GAG AGT CCT CAC AAT GGC TCG GGG ACG TGG GCC TAT TCA GCG CCG         11608
Trp Glu Ser Pro His Asn Gly Ser Gly Thr Trp Ala Tyr Ser Ala Pro
        8125                  8130                  8135

GAT CTG CTG GGG GCA TGG TCC TGG GGC TCC TGT GCC GTG TAT GAC AGC         11656
Asp Leu Leu Gly Ala Trp Ser Trp Gly Ser Cys Ala Val Tyr Asp Ser
    8140                  8145                  8150

GGG GGC TAC GTG CAG GAG CTG GGC CTG AGC CTG GAG GAG AGC CGC GAC         11704
Gly Gly Tyr Val Gln Glu Leu Gly Leu Ser Leu Glu Glu Ser Arg Asp
8155                  8160                  8165                  8170

CGG CTG CGC TTC CTG CAG CTG CAC AAC TGG CTG GAC AAC AGG AGC CGC         11752
Arg Leu Arg Phe Leu Gln Leu His Asn Trp Leu Asp Asn Arg Ser Arg
            8175                  8180                  8185

GCT GTG TTC CTG GAG CTC ACG CGC TAC AGC CCG GCC GTG GGG CTG CAC         11800
```

-continued

```
Ala Val Phe Leu Glu Leu Thr Arg Tyr Ser Pro Ala Val Gly Leu His
        8190                8195            8200

GCC GCC GTC ACG CTG CGC CTC GAG TTC CCG GCG GCC GGC CGC GCC CTG    11848
Ala Ala Val Thr Leu Arg Leu Glu Phe Pro Ala Ala Gly Arg Ala Leu
        8205                8210            8215

GCC GCC CTC AGC GTC CGC CCC TTT GCG CTG CGC CGC CTC AGC GCG GGC    11896
Ala Ala Leu Ser Val Arg Pro Phe Ala Leu Arg Arg Leu Ser Ala Gly
        8220                8225            8230

CTC TCG CTG CCT CTG CTC ACC TCG GTG TGC CTG CTG CTG TTC GCC GTG    11944
Leu Ser Leu Pro Leu Leu Thr Ser Val Cys Leu Leu Leu Phe Ala Val
8235                8240            8245                8250

CAC TTC GCC GTG GCC GAG GCC CGT ACT TGG CAC AGG GAA GGG CGC TGG    11992
His Phe Ala Val Ala Glu Ala Arg Thr Trp His Arg Glu Gly Arg Trp
        8255                8260            8265

CGC GTG CTG CGG CTC GGA GCC TGG GCG CGG TGG CTG CTG GTG GCG CTG    12040
Arg Val Leu Arg Leu Gly Ala Trp Ala Arg Trp Leu Leu Val Ala Leu
        8270                8275            8280

ACG GCG GCC ACG GCA CTG GTA CGC CTC GCC CAG CTG GGT GCC GCT GAC    12088
Thr Ala Ala Thr Ala Leu Val Arg Leu Ala Gln Leu Gly Ala Ala Asp
        8285                8290            8295

CGC CAG TGG ACC CGT TTC GTG CGC GGC CGC CCG CGC CGC TTC ACT AGC    12136
Arg Gln Trp Thr Arg Phe Val Arg Gly Arg Pro Arg Arg Phe Thr Ser
        8300                8305            8310

TTC GAC CAG GTG GCG CAC GTG AGC TCC GCA GCC CGT GGC CTG GCG GCC    12184
Phe Asp Gln Val Ala His Val Ser Ser Ala Ala Arg Gly Leu Ala Ala
8315                8320            8325                8330

TCG CTG CTC TTC CTG CTT TTG GTC AAG GCT GCC CAG CAC GTA CGC TTC    12232
Ser Leu Leu Phe Leu Leu Leu Val Lys Ala Ala Gln His Val Arg Phe
        8335                8340            8345

GTG CGC CAG TGG TCC GTC TTT GGC AAG ACA TTA TGC CGA GCT CTG CCA    12280
Val Arg Gln Trp Ser Val Phe Gly Lys Thr Leu Cys Arg Ala Leu Pro
        8350                8355            8360

GAG CTC CTG GGG GTC ACC TTG GGC CTG GTG GTG CTC GGG GTA GCC TAC    12328
Glu Leu Leu Gly Val Thr Leu Gly Leu Val Val Leu Gly Val Ala Tyr
        8365                8370            8375

GCC CAG CTG GCC ATC CTG CTC GTG TCT TCC TGT GTG GAC TCC CTC TGG    12376
Ala Gln Leu Ala Ile Leu Leu Val Ser Ser Cys Val Asp Ser Leu Trp
        8380                8385            8390

AGC GTG GCC CAG GCC CTG TTG GTG CTG TGC CCT GGG ACT GGG CTC TCT    12424
Ser Val Ala Gln Ala Leu Leu Val Leu Cys Pro Gly Thr Gly Leu Ser
8395                8400            8405                8410

ACC CTG TGT CCT GCC GAG TCC TGG CAC CTG TCA CCC CTG CTG TGT GTG    12472
Thr Leu Cys Pro Ala Glu Ser Trp His Leu Ser Pro Leu Leu Cys Val
        8415                8420            8425

GGG CTC TGG GCA CTG CGG CTG TGG GGC GCC CTA CGG CTG GGG GCT GTT    12520
Gly Leu Trp Ala Leu Arg Leu Trp Gly Ala Leu Arg Leu Gly Ala Val
        8430                8435            8440

ATT CTC CGC TGG CGC TAC CAC GCC TTG CGT GGA GAG CTG TAC CGG CCG    12568
Ile Leu Arg Trp Arg Tyr His Ala Leu Arg Gly Glu Leu Tyr Arg Pro
        8445                8450            8455

GCC TGG GAG CCC CAG GAC TAC GAG ATG GTG GAG TTG TTC CTG CGC AGG    12616
Ala Trp Glu Pro Gln Asp Tyr Glu Met Val Glu Leu Phe Leu Arg Arg
        8460                8465            8470

CTG CGC CTC TGG ATG GGC CTC AGC AAG GTC AAG GAG TTC CGC CAC AAA    12664
Leu Arg Leu Trp Met Gly Leu Ser Lys Val Lys Glu Phe Arg His Lys
8475                8480            8485                8490

GTC CGC TTT GAA GGG ATG GAG CCG CTG CCC TCT CGC TCC TCC AGG GGC    12712
Val Arg Phe Glu Gly Met Glu Pro Leu Pro Ser Arg Ser Ser Arg Gly
        8495                8500            8505
```

| | | |
|---|---|---|
| TCC AAG GTA TCC CCG GAT GTG CCC CCA CCC AGC GCT GGC TCC GAT GCC<br>Ser Lys Val Ser Pro Asp Val Pro Pro Pro Ser Ala Gly Ser Asp Ala<br>          8510                       8515                     8520 | 12760 |
| TCG CAC CCC TCC ACC TCC TCC AGC CAG CTG GAT GGG CTG AGC GTG AGC<br>Ser His Pro Ser Thr Ser Ser Ser Gln Leu Asp Gly Leu Ser Val Ser<br>        8525                       8530                      8535 | 12808 |
| CTG GGC CGG CTG GGG ACA AGG TGT GAG CCT GAG CCC TCC CGC CTC CAA<br>Leu Gly Arg Leu Gly Thr Arg Cys Glu Pro Glu Pro Ser Arg Leu Gln<br>       8540                       8545                     8550 | 12856 |
| GCC GTG TTC GAG GCC CTG CTC ACC CAG TTT GAC CGA CTC AAC CAG GCC<br>Ala Val Phe Glu Ala Leu Leu Thr Gln Phe Asp Arg Leu Asn Gln Ala<br>8555                       8560                     8565                     8570 | 12904 |
| ACA GAG GAC GTC TAC CAG CTG GAG CAG CAG CTG CAC AGC CTG CAA GGC<br>Thr Glu Asp Val Tyr Gln Leu Glu Gln Gln Leu His Ser Leu Gln Gly<br>                8575                       8580                     8585 | 12952 |
| CGC AGG AGC AGC CGG GCG CCC GCC GGA TCT TCC CGT GGC CCA TCC CCG<br>Arg Arg Ser Ser Arg Ala Pro Ala Gly Ser Ser Arg Gly Pro Ser Pro<br>       8590                       8595                     8600 | 13000 |
| GGC CTG CGG CCA GCA CTG CCC AGC CGC CTT GCC CGG GCC AGT CGG GGT<br>Gly Leu Arg Pro Ala Leu Pro Ser Arg Leu Ala Arg Ala Ser Arg Gly<br>       8605                       8610                     8615 | 13048 |
| GTG GAC CTG GCC ACT GGC CCC AGC AGG ACA CCC CTT CGG GCC AAG AAC<br>Val Asp Leu Ala Thr Gly Pro Ser Arg Thr Pro Leu Arg Ala Lys Asn<br>8620                       8625                     8630 | 13096 |
| AAG GTC CAC CCC AGC AGC ACT TAGTCCTCCT TCCTGGCGGG GGTGGGCCGT<br>Lys Val His Pro Ser Ser Thr<br>8635                  8640 | 13147 |
| GGAGTCGGAG TGGACACCGC TCAGTATTAC TTTCTGCCGC TGTCAAGGCC GAGGGCCAGG | 13207 |
| CAGAATGGCT GCACGTAGGT TCCCCAGAGA GCAGGCAGGG GCATCTGTCT GTCTGTGGGC | 13267 |
| TTCAGCACTT TAAAGAGGCT GTGTGGCCAA CCAGGACCCA GGGTCCCCTC CCCAGCTCCC | 13327 |
| TTGGGAAGGA CACAGCAGTA TTGGACGGTT CTAGCCTCT GAGATGCTAA TTTATTTCCC | 13387 |
| CGAGTCCTCA GGTACAGCGG GCTGTGCCCG GCCCCACCCC CTGGGCAGAT GTCCCCCACT | 13447 |
| GCTAAGGCTG CTGGCTTCAG GGAGGGTTAG CCTGCACCGC CGCCACCCTG CCCTAAGTT | 13507 |
| ATTACCTCTC CAGTTCCTAC CGTACTCCCT GCACCGTCTC ACTGTGTGTC TCGTGTCAGT | 13567 |
| AATTTATATG GTGTTAAAAT GTGTATATTT TTGTATGTCA CTATTTTCAC TAGGGCTGAG | 13627 |
| GGGCCTGCGC CCAGAGCTGG CCTCCCCCAA CACCTGCTGC GCTTGGTAGG TGTGGTGGCG | 13687 |
| TTATGGCAGC CCGGCTGCTG CTTGGATGCG AGCTTGGCCT TGGGCCGGTG CTGGGGGCAC | 13747 |
| AGCTGTCTGC CAGGCACTCT CATCACCCCA GAGGCCTTGT CATCCTCCCT TGCCCCAGGC | 13807 |
| CAGGTAGCAA GAGAGCAGCG CCCAGGCCTG CTGGCATCAG GTCTGGGCAA GTAGCAGGAC | 13867 |
| TAGGCATGTC AGAGGACCCC AGGGTGGTTA GAGGAAAAGA CTCCTCCTGG GGGCTGGCTC | 13927 |
| CCAGGGTGGA GGAAGGTGAC TGTGTGTGTG TGTGTGTGCG CGCGCGACGC GCGAGTGTGC | 13987 |
| TGTATGGCCC AGGCAGCCTC AAGGCCCTCG GAGCTGGCTG TGCCTGCTTC TGTGTACCAC | 14047 |
| TTCTGTGGGC ATGGCCGCTT CTAGAGCCTC GACACCCCCC CAACCCCCGC ACCAAGCAGA | 14107 |
| CAAAGTCAAT AAAAGAGCTG TCTGACTGCA AAAAAAAAA A | 14148 |

(2) INFORMATION FOR SEQ ID NO: 8:

(i) SEQUENCE CHARACTERISTICS:
        (A) LENGTH: 4302 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Pro Pro Ala Ala Pro Ala Arg Leu Ala Leu Ala Leu Gly Leu Gly
 1               5                  10                  15

Leu Trp Leu Gly Ala Leu Ala Gly Gly Pro Gly Arg Gly Cys Gly Pro
                20                  25                  30

Cys Glu Pro Pro Cys Leu Cys Gly Pro Ala Pro Gly Ala Ala Cys Arg
            35                  40                  45

Val Asn Cys Ser Gly Arg Gly Leu Arg Thr Leu Gly Pro Ala Leu Arg
        50                  55                  60

Ile Pro Ala Asp Ala Thr Ala Leu Asp Val Ser His Asn Leu Leu Arg
 65                  70                  75                  80

Ala Leu Asp Val Gly Leu Leu Ala Asn Leu Ser Ala Leu Ala Glu Leu
                85                  90                  95

Asp Ile Ser Asn Asn Lys Ile Ser Thr Leu Glu Glu Gly Ile Phe Ala
                100                 105                 110

Asn Leu Phe Asn Leu Ser Glu Ile Asn Leu Ser Gly Asn Pro Phe Glu
            115                 120                 125

Cys Asp Cys Gly Leu Ala Trp Leu Pro Arg Trp Ala Glu Glu Gln Gln
        130                 135                 140

Val Arg Val Val Gln Pro Glu Ala Ala Thr Cys Ala Gly Pro Gly Ser
145                 150                 155                 160

Leu Ala Gly Gln Pro Leu Leu Gly Ile Pro Leu Leu Asp Ser Gly Cys
                165                 170                 175

Gly Glu Glu Tyr Val Ala Cys Leu Pro Asp Asn Ser Ser Gly Thr Val
            180                 185                 190

Ala Ala Val Ser Phe Ser Ala His Glu Gly Leu Leu Gln Pro Glu
        195                 200                 205

Ala Cys Ser Ala Phe Cys Phe Ser Thr Gly Gln Gly Leu Ala Ala Leu
        210                 215                 220

Ser Glu Gln Gly Trp Cys Leu Cys Gly Ala Ala Gln Pro Ser Ser Ala
225                 230                 235                 240

Ser Phe Ala Cys Leu Ser Leu Cys Ser Gly Pro Pro Pro Pro Pro Ala
                245                 250                 255

Pro Thr Cys Arg Gly Pro Thr Leu Leu Gln His Val Phe Pro Ala Ser
            260                 265                 270

Pro Gly Ala Thr Leu Val Gly Pro His Gly Pro Leu Ala Ser Gly Gln
        275                 280                 285

Leu Ala Ala Phe His Ile Ala Ala Pro Leu Pro Val Thr Ala Thr Arg
    290                 295                 300

Trp Asp Phe Gly Asp Gly Ser Ala Glu Val Asp Ala Ala Gly Pro Ala
305                 310                 315                 320

Ala Ser His Arg Tyr Val Leu Pro Gly Arg Tyr His Val Thr Ala Val
                325                 330                 335

Leu Ala Leu Gly Ala Gly Ser Ala Leu Leu Gly Thr Asp Val Gln Val
            340                 345                 350

Glu Ala Ala Pro Ala Ala Leu Glu Leu Val Cys Pro Ser Ser Val Gln
        355                 360                 365

Ser Asp Glu Ser Leu Asp Leu Ser Ile Gln Asn Arg Gly Gly Ser Gly
        370                 375                 380

Leu Glu Ala Ala Tyr Ser Ile Val Ala Leu Gly Glu Glu Pro Ala Arg
385                 390                 395                 400

Ala Val His Pro Leu Cys Pro Ser Asp Thr Glu Ile Phe Pro Gly Asn
```

-continued

```
                405                 410                 415
Gly His Cys Tyr Arg Leu Val Val Glu Lys Ala Ala Trp Leu Gln Ala
            420                 425                 430
Gln Glu Gln Cys Gln Ala Trp Ala Gly Ala Ala Leu Ala Met Val Asp
        435                 440                 445
Ser Pro Ala Val Gln Arg Phe Leu Val Ser Arg Val Thr Arg Ser Leu
    450                 455                 460
Asp Val Trp Ile Gly Phe Ser Thr Val Gln Gly Val Glu Val Gly Pro
465                 470                 475                 480
Ala Pro Gln Gly Glu Ala Phe Ser Leu Glu Ser Cys Gln Asn Trp Leu
                485                 490                 495
Pro Gly Glu Pro His Pro Ala Thr Ala Glu His Cys Val Arg Leu Gly
            500                 505                 510
Pro Thr Gly Trp Cys Asn Thr Asp Leu Cys Ser Ala Pro His Ser Tyr
        515                 520                 525
Val Cys Glu Leu Gln Pro Gly Gly Pro Val Gln Asp Ala Glu Asn Leu
    530                 535                 540
Leu Val Gly Ala Pro Ser Gly Asp Leu Gln Gly Pro Leu Thr Pro Leu
545                 550                 555                 560
Ala Gln Gln Asp Gly Leu Ser Ala Pro His Glu Pro Val Glu Val Met
                565                 570                 575
Val Phe Pro Gly Leu Arg Leu Ser Arg Glu Ala Phe Leu Thr Thr Ala
            580                 585                 590
Glu Phe Gly Thr Gln Glu Leu Arg Arg Pro Ala Gln Leu Arg Leu Gln
        595                 600                 605
Val Tyr Arg Leu Leu Ser Thr Ala Gly Thr Pro Glu Asn Gly Ser Glu
    610                 615                 620
Pro Glu Ser Arg Ser Pro Asp Asn Arg Thr Gln Leu Ala Pro Ala Cys
625                 630                 635                 640
Met Pro Gly Gly Arg Trp Cys Pro Gly Ala Asn Ile Cys Leu Pro Leu
                645                 650                 655
Asp Ala Ser Cys His Pro Gln Ala Cys Ala Asn Gly Cys Thr Ser Gly
            660                 665                 670
Pro Gly Leu Pro Gly Ala Pro Tyr Ala Leu Trp Arg Glu Phe Leu Phe
        675                 680                 685
Ser Val Ala Ala Gly Pro Pro Ala Gln Tyr Ser Val Thr Leu His Gly
    690                 695                 700
Gln Asp Val Leu Met Leu Pro Gly Asp Leu Val Gly Leu Gln His Asp
705                 710                 715                 720
Ala Gly Pro Gly Ala Leu Leu His Cys Ser Pro Ala Pro Gly His Pro
                725                 730                 735
Gly Pro Gln Ala Pro Tyr Leu Ser Ala Asn Ala Ser Ser Trp Leu Pro
            740                 745                 750
His Leu Pro Ala Gln Leu Glu Gly Thr Trp Ala Cys Pro Ala Cys Ala
        755                 760                 765
Leu Arg Leu Leu Ala Ala Thr Glu Gln Leu Thr Val Leu Leu Gly Leu
    770                 775                 780
Arg Pro Asn Pro Gly Leu Arg Met Pro Gly Arg Tyr Glu Val Arg Ala
785                 790                 795                 800
Glu Val Gly Asn Gly Val Ser Arg His Asn Leu Ser Cys Ser Phe Asp
                805                 810                 815
Val Val Ser Pro Val Ala Gly Leu Arg Val Ile Tyr Pro Ala Pro Arg
            820                 825                 830
```

-continued

```
Asp Gly Arg Leu Tyr Val Pro Thr Asn Gly Ser Ala Leu Val Leu Gln
        835                 840                 845
Val Asp Ser Gly Ala Asn Ala Thr Ala Thr Ala Arg Trp Pro Gly Gly
850                 855                 860
Ser Val Ser Ala Arg Phe Glu Asn Val Cys Pro Ala Leu Val Ala Thr
865                 870                 875                 880
Phe Val Pro Gly Cys Pro Trp Glu Thr Asn Asp Thr Leu Phe Ser Val
                885                 890                 895
Val Ala Leu Pro Trp Leu Ser Glu Gly Glu His Val Val Asp Val Val
            900                 905                 910
Val Glu Asn Ser Ala Ser Arg Ala Asn Leu Ser Leu Arg Val Thr Ala
            915                 920                 925
Glu Glu Pro Ile Cys Gly Leu Arg Ala Thr Pro Ser Pro Glu Ala Arg
            930                 935                 940
Val Leu Gln Gly Val Leu Val Arg Tyr Ser Pro Val Val Glu Ala Gly
945                 950                 955                 960
Ser Asp Met Val Phe Arg Trp Thr Ile Asn Asp Lys Gln Ser Leu Thr
                965                 970                 975
Phe Gln Asn Val Val Phe Asn Val Ile Tyr Gln Ser Ala Ala Val Phe
            980                 985                 990
Lys Leu Ser Leu Thr Ala Ser Asn His Val Ser Asn Val Thr Val Asn
            995                 1000                1005
Tyr Asn Val Thr Val Glu Arg Met Asn Arg Met Gln Gly Leu Gln Val
            1010                1015                1020
Ser Thr Val Pro Ala Val Leu Ser Pro Asn Ala Thr Leu Val Leu Thr
1025                1030                1035                1040
Gly Gly Val Leu Val Asp Ser Ala Val Glu Val Ala Phe Leu Trp Asn
                1045                1050                1055
Phe Gly Asp Gly Glu Gln Ala Leu His Gln Phe Gln Pro Pro Tyr Asn
            1060                1065                1070
Glu Ser Phe Pro Val Pro Asp Pro Ser Val Ala Gln Val Leu Val Glu
            1075                1080                1085
His Asn Val Met His Thr Tyr Ala Ala Pro Gly Glu Tyr Leu Leu Thr
            1090                1095                1100
Val Leu Ala Ser Asn Ala Phe Glu Asn Leu Thr Gln Gln Val Pro Val
1105                1110                1115                1120
Ser Val Arg Ala Ser Leu Pro Ser Val Ala Val Gly Val Ser Asp Gly
            1125                1130                1135
Val Leu Val Ala Gly Arg Pro Val Thr Phe Tyr Pro His Pro Leu Pro
            1140                1145                1150
Ser Pro Gly Gly Val Leu Tyr Thr Trp Asp Phe Gly Asp Gly Ser Pro
            1155                1160                1165
Val Leu Thr Gln Ser Gln Pro Ala Ala Asn His Thr Tyr Ala Ser Arg
            1170                1175                1180
Gly Thr Tyr His Val Arg Leu Gly Val Asn Asn Thr Val Ser Gly Ala
1185                1190                1195                1200
Ala Ala Gln Ala Asp Val Arg Val Phe Glu Glu Leu Arg Gly Leu Ser
            1205                1210                1215
Val Asp Met Ser Leu Ala Val Glu Gln Gly Ala Pro Val Val Val Ser
            1220                1225                1230
Ala Ala Val Gln Thr Gly Asp Asn Ile Thr Trp Thr Phe Asp Met Gly
            1235                1240                1245
```

-continued

Asp Gly Thr Val Leu Ser Gly Pro Glu Ala Thr Val Glu His Val Tyr
    1250                1255                1260

Leu Arg Ala Gln Asn Cys Thr Val Thr Val Gly Ala Ala Ser Pro Ala
1265            1270                1275                1280

Gly His Leu Ala Arg Ser Leu His Val Leu Val Phe Val Leu Glu Val
                1285                1290                1295

Leu Arg Val Glu Pro Ala Ala Cys Ile Pro Thr Gln Pro Asp Ala Arg
            1300                1305                1310

Leu Thr Ala Tyr Val Thr Gly Asn Pro Ala His Tyr Leu Phe Asp Trp
        1315                1320                1325

Thr Phe Gly Asp Gly Ser Ser Asn Thr Thr Val Arg Gly Cys Pro Thr
    1330                1335                1340

Val Thr His Asn Phe Thr Arg Ser Gly Thr Phe Pro Leu Ala Leu Val
1345                1350                1355                1360

Leu Ser Ser Arg Val Asn Arg Ala His Tyr Phe Thr Ser Ile Cys Val
                1365                1370                1375

Glu Pro Glu Val Gly Asn Val Thr Leu Gln Pro Glu Arg Gln Phe Val
            1380                1385                1390

Gln Leu Gly Asp Glu Ala Trp Leu Val Ala Cys Ala Trp Pro Pro Phe
        1395                1400                1405

Pro Tyr Arg Tyr Thr Trp Asp Phe Gly Thr Glu Ala Ala Pro Thr
    1410                1415                1420

Arg Ala Arg Gly Pro Glu Val Thr Phe Ile Tyr Arg Asp Pro Gly Ser
1425            1430                1435                1440

Tyr Leu Val Thr Val Thr Ala Ser Asn Asn Ile Ser Ala Ala Asn Asp
                1445                1450                1455

Ser Ala Leu Val Glu Val Gln Glu Pro Val Leu Val Thr Ser Ile Lys
            1460                1465                1470

Val Asn Gly Ser Leu Gly Leu Glu Leu Gln Gln Pro Tyr Leu Phe Ser
        1475                1480                1485

Ala Val Gly Arg Gly Arg Pro Ala Ser Tyr Leu Trp Asp Leu Gly Asp
    1490                1495                1500

Gly Gly Trp Leu Glu Gly Pro Glu Val Thr His Ala Tyr Asn Ser Thr
1505            1510                1515                1520

Gly Asp Phe Thr Val Arg Val Ala Gly Trp Asn Glu Val Ser Arg Ser
                1525                1530                1535

Glu Ala Trp Leu Asn Val Thr Val Lys Arg Arg Val Arg Gly Leu Val
            1540                1545                1550

Val Asn Ala Ser Arg Thr Val Val Pro Leu Asn Gly Ser Val Ser Phe
        1555                1560                1565

Ser Thr Ser Leu Glu Ala Gly Ser Asp Val Arg Tyr Ser Trp Val Leu
    1570                1575                1580

Cys Asp Arg Cys Thr Pro Ile Pro Gly Gly Pro Thr Ile Ser Tyr Thr
1585                1590                1595                1600

Phe Arg Ser Val Gly Thr Phe Asn Ile Ile Val Thr Ala Glu Asn Glu
                1605                1610                1615

Val Gly Ser Ala Gln Asp Ser Ile Phe Val Tyr Val Leu Gln Leu Ile
            1620                1625                1630

Glu Gly Leu Gln Val Val Gly Gly Gly Arg Tyr Phe Pro Thr Asn His
        1635                1640                1645

Thr Val Gln Leu Gln Ala Val Val Arg Asp Gly Thr Asn Val Ser Tyr
    1650                1655                1660

Ser Trp Thr Ala Trp Arg Asp Arg Gly Pro Ala Leu Ala Gly Ser Gly

```
                1665              1670              1675              1680
Lys Gly Phe Ser Leu Thr Val Leu Glu Ala Gly Thr Tyr His Val Gln
                1685              1690              1695

Leu Arg Ala Thr Asn Met Leu Gly Ser Ala Trp Ala Asp Cys Thr Met
                1700              1705              1710

Asp Phe Val Glu Pro Val Gly Trp Leu Met Val Thr Ala Ser Pro Asn
        1715              1720              1725

Pro Ala Ala Val Asn Thr Ser Val Thr Leu Ser Ala Glu Leu Ala Gly
        1730              1735              1740

Gly Ser Gly Val Val Tyr Thr Trp Ser Leu Glu Glu Gly Leu Ser Trp
1745              1750              1755              1760

Glu Thr Ser Glu Pro Phe Thr Thr His Ser Phe Pro Thr Pro Gly Leu
                1765              1770              1775

His Leu Val Thr Met Thr Ala Gly Asn Pro Leu Gly Ser Ala Asn Ala
                1780              1785              1790

Thr Val Glu Val Asp Val Gln Val Pro Val Ser Gly Leu Ser Ile Arg
        1795              1800              1805

Ala Ser Glu Pro Gly Gly Ser Phe Val Ala Ala Gly Ser Ser Val Pro
        1810              1815              1820

Phe Trp Gly Gln Leu Ala Thr Gly Thr Asn Val Ser Trp Cys Trp Ala
1825              1830              1835              1840

Val Pro Gly Gly Ser Ser Lys Arg Gly Pro His Val Thr Met Val Phe
                1845              1850              1855

Pro Asp Ala Gly Thr Phe Ser Ile Arg Leu Asn Ala Ser Asn Ala Val
                1860              1865              1870

Ser Trp Val Ser Ala Thr Tyr Asn Leu Thr Ala Glu Glu Pro Ile Val
        1875              1880              1885

Gly Leu Val Leu Trp Ala Ser Ser Lys Val Val Ala Pro Gly Gln Leu
        1890              1895              1900

Val His Phe Gln Ile Leu Leu Ala Ala Gly Ser Ala Val Thr Phe Arg
1905              1910              1915              1920

Leu Gln Val Gly Gly Ala Asn Pro Glu Val Leu Pro Gly Pro Arg Phe
                1925              1930              1935

Ser His Ser Phe Pro Arg Val Gly Asp His Val Val Ser Val Arg Gly
                1940              1945              1950

Lys Asn His Val Ser Trp Ala Gln Ala Gln Val Arg Ile Val Val Leu
        1955              1960              1965

Glu Ala Val Ser Gly Leu Gln Met Pro Asn Cys Cys Glu Pro Gly Ile
        1970              1975              1980

Ala Thr Gly Thr Glu Arg Asn Phe Thr Ala Arg Val Gln Arg Gly Ser
1985              1990              1995              2000

Arg Val Ala Tyr Ala Trp Tyr Phe Ser Leu Gln Lys Val Gln Gly Asp
                2005              2010              2015

Ser Leu Val Ile Leu Ser Gly Arg Asp Val Thr Tyr Thr Pro Val Ala
                2020              2025              2030

Ala Gly Leu Leu Glu Ile Gln Val Arg Ala Phe Asn Ala Leu Gly Ser
        2035              2040              2045

Glu Asn Arg Thr Leu Val Leu Glu Val Gln Asp Ala Val Gln Tyr Val
        2050              2055              2060

Ala Leu Gln Ser Gly Pro Cys Phe Thr Asn Arg Ser Ala Gln Phe Glu
2065              2070              2075              2080

Ala Ala Thr Ser Pro Ser Pro Arg Arg Val Ala Tyr His Trp Asp Phe
                2085              2090              2095
```

-continued

```
Gly Asp Gly Ser Pro Gly Gln Asp Thr Asp Glu Pro Arg Ala Glu His
            2100                2105                2110
Ser Tyr Leu Arg Pro Gly Asp Tyr Arg Val Gln Val Asn Ala Ser Asn
        2115                2120                2125
Leu Val Ser Phe Phe Val Ala Gln Ala Thr Val Thr Val Gln Val Leu
    2130                2135                2140
Ala Cys Arg Glu Pro Glu Val Asp Val Val Leu Pro Leu Gln Val Leu
2145                2150                2155                2160
Met Arg Arg Ser Gln Arg Asn Tyr Leu Glu Ala His Val Asp Leu Arg
            2165                2170                2175
Asp Cys Val Thr Tyr Gln Thr Glu Tyr Arg Trp Glu Val Tyr Arg Thr
        2180                2185                2190
Ala Ser Cys Gln Arg Pro Gly Arg Pro Ala Arg Val Ala Leu Pro Gly
        2195                2200                2205
Val Asp Val Ser Arg Pro Arg Leu Val Leu Pro Arg Leu Ala Leu Pro
        2210                2215                2220
Val Gly His Tyr Cys Phe Val Phe Val Val Ser Phe Gly Asp Thr Pro
2225                2230                2235                2240
Leu Thr Gln Ser Ile Gln Ala Asn Val Thr Val Ala Pro Glu Arg Leu
            2245                2250                2255
Val Pro Ile Ile Glu Gly Gly Ser Tyr Arg Val Trp Ser Asp Thr Arg
            2260                2265                2270
Asp Leu Val Leu Asp Gly Ser Glu Ser Tyr Asp Pro Asn Leu Glu Asp
            2275                2280                2285
Gly Asp Gln Thr Pro Leu Ser Phe His Trp Ala Cys Val Ala Ser Thr
        2290                2295                2300
Gln Arg Glu Ala Gly Gly Cys Ala Leu Asn Phe Gly Pro Arg Gly Ser
2305                2310                2315                2320
Ser Thr Val Thr Ile Pro Arg Glu Arg Leu Ala Ala Gly Val Glu Tyr
            2325                2330                2335
Thr Phe Ser Leu Thr Val Trp Lys Ala Gly Arg Lys Glu Glu Ala Thr
            2340                2345                2350
Asn Gln Thr Val Leu Ile Arg Ser Gly Arg Val Pro Ile Val Ser Leu
        2355                2360                2365
Glu Cys Val Ser Cys Lys Ala Gln Ala Val Tyr Glu Val Ser Arg Ser
    2370                2375                2380
Ser Tyr Val Tyr Leu Glu Gly Arg Cys Leu Asn Cys Ser Ser Gly Ser
2385                2390                2395                2400
Lys Arg Gly Arg Trp Ala Ala Arg Thr Phe Ser Asn Lys Thr Leu Val
            2405                2410                2415
Leu Asp Glu Thr Thr Thr Ser Thr Gly Ser Ala Gly Met Arg Leu Val
            2420                2425                2430
Leu Arg Arg Gly Val Leu Arg Asp Gly Glu Gly Tyr Thr Phe Thr Leu
        2435                2440                2445
Thr Val Leu Gly Arg Ser Gly Glu Glu Glu Gly Cys Ala Ser Ile Arg
    2450                2455                2460
Leu Ser Pro Asn Arg Pro Pro Leu Gly Gly Ser Cys Arg Leu Phe Pro
2465                2470                2475                2480
Leu Gly Ala Val His Ala Leu Thr Thr Lys Val His Phe Glu Cys Thr
            2485                2490                2495
Gly Trp His Asp Ala Glu Asp Ala Gly Ala Pro Leu Val Tyr Ala Leu
            2500                2505                2510
```

-continued

Leu Leu Arg Arg Cys Arg Gln Gly His Cys Glu Glu Phe Cys Val Tyr
        2515                2520                2525

Lys Gly Ser Leu Ser Ser Tyr Gly Ala Val Leu Pro Pro Gly Phe Arg
        2530                2535                2540

Pro His Phe Glu Val Gly Leu Ala Val Val Gln Asp Gln Leu Gly
2545                2550                2555                2560

Ala Ala Val Val Ala Leu Asn Arg Ser Leu Ala Ile Thr Leu Pro Glu
        2565                2570                2575

Pro Asn Gly Ser Ala Thr Gly Leu Thr Val Trp Leu His Gly Leu Thr
        2580                2585                2590

Ala Ser Val Leu Pro Gly Leu Leu Arg Gln Ala Asp Pro Gln His Val
        2595                2600                2605

Ile Glu Tyr Ser Leu Ala Leu Val Thr Val Leu Asn Glu Tyr Glu Arg
        2610                2615                2620

Ala Leu Asp Val Ala Ala Glu Pro Lys His Glu Arg Gln His Arg Ala
2625                2630                2635                2640

Gln Ile Arg Lys Asn Ile Thr Glu Thr Leu Val Ser Leu Arg Val His
        2645                2650                2655

Thr Val Asp Asp Ile Gln Gln Ile Ala Ala Ala Leu Ala Gln Cys Met
        2660                2665                2670

Gly Pro Ser Arg Glu Leu Val Cys Arg Ser Cys Leu Lys Gln Thr Leu
        2675                2680                2685

His Lys Leu Glu Ala Met Met Leu Ile Leu Gln Ala Glu Thr Thr Ala
        2690                2695                2700

Gly Thr Val Thr Pro Thr Ala Ile Gly Asp Ser Ile Leu Asn Ile Thr
2705                2710                2715                2720

Gly Asp Leu Ile His Leu Ala Ser Ser Asp Val Arg Ala Pro Gln Pro
        2725                2730                2735

Ser Glu Leu Gly Ala Glu Ser Pro Ser Arg Met Val Ala Ser Gln Ala
        2740                2745                2750

Tyr Asn Leu Thr Ser Ala Leu Met Arg Ile Leu Met Arg Ser Arg Val
        2755                2760                2765

Leu Asn Glu Glu Pro Leu Thr Leu Ala Gly Glu Glu Ile Val Ala Gln
        2770                2775                2780

Gly Lys Arg Ser Asp Pro Arg Ser Leu Leu Cys Tyr Gly Gly Ala Pro
2785                2790                2795                2800

Gly Pro Gly Cys His Phe Ser Ile Pro Glu Ala Phe Ser Gly Ala Leu
        2805                2810                2815

Ala Asn Leu Ser Asp Val Val Gln Leu Ile Phe Leu Val Asp Ser Asn
        2820                2825                2830

Pro Phe Pro Phe Gly Tyr Ile Ser Asn Tyr Thr Val Ser Thr Lys Val
        2835                2840                2845

Ala Ser Met Ala Phe Gln Thr Gln Ala Gly Ala Gln Ile Pro Ile Glu
        2850                2855                2860

Arg Leu Ala Ser Glu Arg Ala Ile Thr Val Lys Val Pro Asn Asn Ser
2865                2870                2875                2880

Asp Trp Ala Ala Arg Gly His Arg Ser Ser Ala Asn Ser Ala Asn Ser
        2885                2890                2895

Val Val Val Gln Pro Gln Ala Ser Val Gly Ala Val Val Thr Leu Asp
        2900                2905                2910

Ser Ser Asn Pro Ala Ala Gly Leu His Leu Gln Leu Asn Tyr Thr Leu
        2915                2920                2925

Leu Asp Gly His Tyr Leu Ser Glu Glu Pro Glu Pro Tyr Leu Ala Val

-continued

```
            2930                2935                2940
Tyr Leu His Ser Glu Pro Arg Pro Asn Glu His Asn Cys Ser Ala Ser
2945                2950                2955                2960
Arg Arg Ile Arg Pro Glu Ser Leu Gln Gly Ala Asp His Arg Pro Tyr
            2965                2970                2975
Thr Phe Phe Ile Ser Pro Gly Ser Arg Asp Pro Ala Gly Ser Tyr His
            2980                2985                2990
Leu Asn Leu Ser Ser His Phe Arg Trp Ser Ala Leu Gln Val Ser Val
            2995                3000                3005
Gly Leu Tyr Thr Ser Leu Cys Gln Tyr Phe Ser Glu Glu Asp Met Val
            3010                3015                3020
Trp Arg Thr Glu Gly Leu Leu Pro Leu Glu Glu Thr Ser Pro Arg Gln
3025                3030                3035                3040
Ala Val Cys Leu Thr Arg His Leu Thr Ala Phe Gly Ala Ser Leu Phe
            3045                3050                3055
Val Pro Pro Ser His Val Arg Phe Val Phe Pro Glu Pro Thr Ala Asp
            3060                3065                3070
Val Asn Tyr Ile Val Met Leu Thr Cys Ala Val Cys Leu Val Thr Tyr
            3075                3080                3085
Met Val Met Ala Ala Ile Leu His Lys Leu Asp Gln Leu Asp Ala Ser
            3090                3095                3100
Arg Gly Arg Ala Ile Pro Phe Cys Gly Gln Arg Gly Arg Phe Lys Tyr
3105                3110                3115                3120
Glu Ile Leu Val Lys Thr Gly Trp Gly Arg Gly Ser Gly Thr Thr Ala
            3125                3130                3135
His Val Gly Ile Met Leu Tyr Gly Val Asp Ser Arg Ser Gly His Arg
            3140                3145                3150
His Leu Asp Gly Asp Arg Ala Phe His Arg Asn Ser Leu Asp Ile Phe
            3155                3160                3165
Arg Ile Ala Thr Pro His Ser Leu Gly Ser Val Trp Lys Ile Arg Val
            3170                3175                3180
Trp His Asp Asn Lys Gly Leu Ser Pro Ala Trp Phe Leu Gln His Val
3185                3190                3195                3200
Ile Val Arg Asp Leu Gln Thr Ala Arg Ser Ala Phe Phe Leu Val Asn
            3205                3210                3215
Asp Trp Leu Ser Val Glu Thr Glu Ala Asn Gly Gly Leu Val Glu Lys
            3220                3225                3230
Glu Val Leu Ala Ala Ser Asp Ala Ala Leu Leu Arg Phe Arg Arg Leu
            3235                3240                3245
Leu Val Ala Glu Leu Gln Arg Gly Phe Phe Asp Lys His Ile Trp Leu
            3250                3255                3260
Ser Ile Trp Asp Arg Pro Pro Arg Ser Arg Phe Thr Arg Ile Gln Arg
3265                3270                3275                3280
Ala Thr Cys Cys Val Leu Leu Ile Cys Leu Phe Leu Gly Ala Asn Ala
            3285                3290                3295
Val Trp Tyr Gly Ala Val Gly Asp Ser Ala Tyr Ser Thr Gly His Val
            3300                3305                3310
Ser Arg Leu Ser Pro Leu Ser Val Asp Thr Val Ala Val Gly Leu Val
            3315                3320                3325
Ser Ser Val Val Val Tyr Pro Val Tyr Leu Ala Ile Leu Phe Leu Phe
            3330                3335                3340
Arg Met Ser Arg Ser Lys Val Ala Gly Ser Pro Ser Pro Thr Pro Ala
3345                3350                3355                3360
```

-continued

```
Gly Gln Gln Val Leu Asp Ile Asp Ser Cys Leu Asp Ser Ser Val Leu
                3365                3370                3375

Asp Ser Ser Phe Leu Thr Phe Ser Gly Leu His Ala Glu Ala Phe Val
                3380                3385                3390

Gly Gln Met Lys Ser Asp Leu Phe Leu Asp Asp Ser Lys Ser Leu Val
                3395                3400                3405

Cys Trp Pro Ser Gly Glu Gly Thr Leu Ser Trp Pro Asp Leu Leu Ser
                3410                3415                3420

Asp Pro Ser Ile Val Gly Ser Asn Leu Arg Gln Leu Ala Arg Gly Gln
3425                3430                3435                3440

Ala Gly His Gly Leu Gly Pro Glu Glu Asp Gly Phe Ser Leu Ala Ser
                3445                3450                3455

Pro Tyr Ser Pro Ala Lys Ser Phe Ser Ala Ser Asp Glu Asp Leu Ile
                3460                3465                3470

Gln Gln Val Leu Ala Glu Gly Val Ser Ser Pro Ala Pro Thr Gln Asp
                3475                3480                3485

Thr His Met Glu Thr Asp Leu Leu Ser Ser Leu Ser Ser Thr Pro Gly
                3490                3495                3500

Glu Lys Thr Glu Thr Leu Ala Leu Gln Arg Leu Gly Glu Leu Gly Pro
3505                3510                3515                3520

Pro Ser Pro Gly Leu Asn Trp Glu Gln Pro Gln Ala Ala Arg Leu Ser
                3525                3530                3535

Arg Thr Gly Leu Val Glu Gly Leu Arg Lys Arg Leu Leu Pro Ala Trp
                3540                3545                3550

Cys Ala Ser Leu Ala His Gly Leu Ser Leu Leu Leu Val Ala Val Ala
                3555                3560                3565

Val Ala Val Ser Gly Trp Val Gly Ala Ser Phe Pro Pro Gly Val Ser
                3570                3575                3580

Val Ala Trp Leu Leu Ser Ser Ser Ala Ser Phe Leu Ala Ser Phe Leu
3585                3590                3595                3600

Gly Trp Glu Pro Leu Lys Val Leu Leu Glu Ala Leu Tyr Phe Ser Leu
                3605                3610                3615

Val Ala Lys Arg Leu His Pro Asp Glu Asp Asp Thr Leu Val Glu Ser
                3620                3625                3630

Pro Ala Val Thr Pro Val Ser Ala Arg Val Pro Arg Val Arg Pro Pro
                3635                3640                3645

His Gly Phe Ala Leu Phe Leu Ala Lys Glu Glu Ala Arg Lys Val Lys
                3650                3655                3660

Arg Leu His Gly Met Leu Arg Ser Leu Leu Val Tyr Met Leu Phe Leu
3665                3670                3675                3680

Leu Val Thr Leu Leu Ala Ser Tyr Gly Asp Ala Ser Cys His Gly His
                3685                3690                3695

Ala Tyr Arg Leu Gln Ser Ala Ile Lys Gln Glu Leu His Ser Arg Ala
                3700                3705                3710

Phe Leu Ala Ile Thr Arg Ser Glu Glu Leu Trp Pro Trp Met Ala His
                3715                3720                3725

Val Leu Leu Pro Tyr Val His Gly Asn Gln Ser Ser Pro Glu Leu Gly
                3730                3735                3740

Pro Pro Arg Leu Arg Gln Val Arg Leu Gln Glu Ala Leu Tyr Pro Asp
3745                3750                3755                3760

Pro Pro Gly Pro Arg Val His Thr Cys Ser Ala Ala Gly Gly Phe Ser
                3765                3770                3775
```

-continued

```
Thr Ser Asp Tyr Asp Val Gly Trp Glu Ser Pro His Asn Gly Ser Gly
            3780                3785                3790

Thr Trp Ala Tyr Ser Ala Pro Asp Leu Leu Gly Ala Trp Ser Trp Gly
            3795                3800                3805

Ser Cys Ala Val Tyr Asp Ser Gly Gly Tyr Val Gln Glu Leu Gly Leu
            3810                3815                3820

Ser Leu Glu Glu Ser Arg Asp Arg Leu Arg Phe Leu Gln Leu His Asn
3825                3830                3835                3840

Trp Leu Asp Asn Arg Ser Arg Ala Val Phe Leu Glu Leu Thr Arg Tyr
            3845                3850                3855

Ser Pro Ala Val Gly Leu His Ala Ala Val Thr Leu Arg Leu Glu Phe
            3860                3865                3870

Pro Ala Ala Gly Arg Ala Leu Ala Ala Leu Ser Val Arg Pro Phe Ala
            3875                3880                3885

Leu Arg Arg Leu Ser Ala Gly Leu Ser Leu Pro Leu Leu Thr Ser Val
            3890                3895                3900

Cys Leu Leu Leu Phe Ala Val His Phe Ala Val Ala Glu Ala Arg Thr
3905                3910                3915                3920

Trp His Arg Glu Gly Arg Trp Arg Val Leu Arg Leu Gly Ala Trp Ala
            3925                3930                3935

Arg Trp Leu Leu Val Ala Leu Thr Ala Ala Thr Ala Leu Val Arg Leu
            3940                3945                3950

Ala Gln Leu Gly Ala Ala Asp Arg Gln Trp Thr Arg Phe Val Arg Gly
            3955                3960                3965

Arg Pro Arg Arg Phe Thr Ser Phe Asp Gln Val Ala His Val Ser Ser
            3970                3975                3980

Ala Ala Arg Gly Leu Ala Ala Ser Leu Leu Phe Leu Leu Leu Val Lys
3985                3990                3995                4000

Ala Ala Gln His Val Arg Phe Val Arg Gln Trp Ser Val Phe Gly Lys
            4005                4010                4015

Thr Leu Cys Arg Ala Leu Pro Glu Leu Leu Gly Val Thr Leu Gly Leu
            4020                4025                4030

Val Val Leu Gly Val Ala Tyr Ala Gln Leu Ala Ile Leu Leu Val Ser
            4035                4040                4045

Ser Cys Val Asp Ser Leu Trp Ser Val Ala Gln Ala Leu Leu Val Leu
            4050                4055                4060

Cys Pro Gly Thr Gly Leu Ser Thr Leu Cys Pro Ala Glu Ser Trp His
4065                4070                4075                4080

Leu Ser Pro Leu Leu Cys Val Gly Leu Trp Ala Leu Arg Leu Trp Gly
            4085                4090                4095

Ala Leu Arg Leu Gly Ala Val Ile Leu Arg Trp Arg Tyr His Ala Leu
            4100                4105                4110

Arg Gly Glu Leu Tyr Arg Pro Ala Trp Glu Pro Gln Asp Tyr Glu Met
            4115                4120                4125

Val Glu Leu Phe Leu Arg Arg Leu Arg Leu Trp Met Gly Leu Ser Lys
            4130                4135                4140

Val Lys Glu Phe Arg His Lys Val Arg Phe Glu Gly Met Glu Pro Leu
4145                4150                4155                4160

Pro Ser Arg Ser Ser Arg Gly Ser Lys Val Ser Pro Asp Val Pro Pro
            4165                4170                4175

Pro Ser Ala Gly Ser Asp Ala Ser His Pro Ser Thr Ser Ser Ser Gln
            4180                4185                4190

Leu Asp Gly Leu Ser Val Ser Leu Gly Arg Leu Gly Thr Arg Cys Glu
```

```
                    4195              4200              4205
Pro Glu Pro Ser Arg Leu Gln Ala Val Phe Glu Ala Leu Leu Thr Gln
        4210              4215              4220

Phe Asp Arg Leu Asn Gln Ala Thr Glu Asp Val Tyr Gln Leu Glu Gln
4225              4230              4235              4240

Gln Leu His Ser Leu Gln Gly Arg Arg Ser Ser Arg Ala Pro Ala Gly
                    4245              4250              4255

Ser Ser Arg Gly Pro Ser Pro Gly Leu Arg Pro Ala Leu Pro Ser Arg
            4260              4265              4270

Leu Ala Arg Ala Ser Arg Gly Val Asp Leu Ala Thr Gly Pro Ser Arg
                4275              4280              4285

Thr Pro Leu Arg Ala Lys Asn Lys Val His Pro Ser Ser Thr
        4290              4295              4300
```

(2) INFORMATION FOR SEQ ID NO: 9:

(i) SEQUENCE CHARACTERISTICS:
        (A) LENGTH: 23 base pairs
        (B) TYPE: nucleic acid
        (C) STRANDEDNESS: single
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: misc_feature
        (B) LOCATION:1..23
        (D) OTHER INFORMATION:/function= "AH3 F9 primer"

(xi) SEQUENCE DESCRIPTION: SEQ ID NO: 9:

```
TTTGACAAGC ACATCTGGCT CTC                                    23
```

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: misc_feature
        (B) LOCATION:1..20
        (D) OTHER INFORMATION:/function= "AH3 B7 primer"

(xi) SEQUENCE DESCRIPTION: SEQ ID NO: 10:

```
TACACCAGGA GGCTCCGCAG                                        20
```

(2) INFORMATION FOR SEQ ID NO: 11:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: cDNA (vi) ORIGINAL SOURCE:
        (A) ORGANISM: Homo sapiens (ix) FEATURE:
         (A) NAME/KEY: misc_feature
         (B) LOCATION:1..21
         (D) OTHER INFORMATION:/function= "3A3 C1 primer"

(xi) SEQUENCE DESCRIPTION: SEQ ID NO: 11:

CGCCGCTTCA CTAGCTTCGA C                                            21

(2) INFORMATION FOR SEQ ID NO: 12:

(i) SEQUENCE CHARACTERISTICS:
         (A) LENGTH: 20 base pairs
         (B) TYPE: nucleic acid
         (C) STRANDEDNESS: single
         (D) TOPOLOGY: unknown (ii) MOLECULE TYPE: cDNA (vi) ORIGINAL SOURCE:
         (A) ORGANISM: Homo sapiens (ix) FEATURE:
         (A) NAME/KEY: misc_feature
         (B) LOCATION:1..20
         (D) OTHER INFORMATION:/function= "3A3 C2 primer"

(xi) SEQUENCE DESCRIPTION: SEQ ID NO: 12:

ACGCTCCAGA GGGAGTCCAC                                              20

(2) INFORMATION FOR SEQ ID NO: 13:

(i) SEQUENCE CHARACTERISTICS:
         (A) LENGTH: 20 base pairs
         (B) TYPE: nucleic acid
         (C) STRANDEDNESS: single
         (D) TOPOLOGY: unknown (ii) MOLECULE TYPE: cDNA (vi) ORIGINAL SOURCE:
         (A) ORGANISM: Homo sapiens (ix) FEATURE:
         (A) NAME/KEY: misc_feature
         (B) LOCATION:1..20
         (D) OTHER INFORMATION:/function= "AH4F2 primer"

(xi) SEQUENCE DESCRIPTION: SEQ ID NO: 13:

GGGCAAGGGA GGATGACAAG                                              20

(2) INFORMATION FOR SEQ ID NO: 14:

(i) SEQUENCE CHARACTERISTICS:
         (A) LENGTH: 21 base pairs
         (B) TYPE: nucleic acid
         (C) STRANDEDNESS: single
         (D) TOPOLOGY: unknown (ii) MOLECULE TYPE: DNA (genomic)

(vi) ORIGINAL SOURCE:
         (A) ORGANISM: Homo sapiens (ix) FEATURE:
         (A) NAME/KEY: misc_feature
         (B) LOCATION:1..21
         (D) OTHER INFORMATION:/function= "JH14B3 primer"

(xi) SEQUENCE DESCRIPTION: SEQ ID NO: 14:

GGGTTTATCA GCAGCAAGCG G                                            21

(2) INFORMATION FOR SEQ ID NO: 15:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: misc_feature
        (B) LOCATION:1..30
        (D) OTHER INFORMATION:/function= "N2765 primer"

(xi) SEQUENCE DESCRIPTION: SEQ ID NO: 15:

GGCGCGGCGG GCGGCATCGT TAGGGCAGCG                            30

(2) INFORMATION FOR SEQ ID NO: 16:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: misc_feature
        (B) LOCATION:1..30
        (D) OTHER INFORMATION:/function= "N5496 primer"

(xi) SEQUENCE DESCRIPTION: SEQ ID NO: 16:

GGCGGGCGGC ATCGTTAGGG CAGCGCGCGC                            30

(2) INFORMATION FOR SEQ ID NO: 17:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: misc_feature
        (B) LOCATION:1..30
        (D) OTHER INFORMATION:/function= "N5495 primer"

(xi) SEQUENCE DESCRIPTION: SEQ ID NO: 17:

ACCTGCTGCT GAGCGACGCC CGCTCGGGGC                            30

(2) INFORMATION FOR SEQ ID NO: 18:

(i) SEQUENCE CHARACTERISTICS:
        (A) LENGTH: 54 base pairs
        (B) TYPE: nucleic acid
        (C) STRANDEDNESS: unknown
        (D) TOPOLOGY: unknown (ii) MOLECULE TYPE: genomic DNA (vi) ORIGINAL SOURCE:
    (A) ORGANISM: Homo sapiens (xi) SEQUENCE DESCRIPTION: SEQ ID NO: 18:

TTTTGGTCAA GGTGAGGGCT GGGCCGGTGG GCGCGGGGCT GGGCGCACAC CCCA          54

(2) INFORMATION FOR SEQ ID NO: 19:

(i) SEQUENCE CHARACTERISTICS:
        (A) LENGTH: 554 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Homo sapiens (ix) FEATURE:
        (A) NAME/KEY: misc_feature
        (D) OTHER INFORMATION:/function= "1A1H0.6 probe"

(xi) SEQUENCE DESCRIPTION: SEQ ID NO: 19:

AAGCTTGGCA CCATCAAGGG CCAGTTCAAC TTTGTCCACG TGATCGTCAC CCCGCTGGAC     60

TACGAGTGCA ACCTGGTGTC CCTGCAGTGC AGGAAAGACA TGGAGGGCCT TGTGGACACC    120

AGCGTGGCCA AGATCGTGTC TGACCGCAAC CTGCCCTTCG TGGCCCGCCA GATGGCCCTG    180

CACGCAAATA TGGCCTCACA GGTGCATCAT AGCCGCTCCA ACCCCACCGA TATCTACCCC    240

TCCAAGTGGA TTGCCCGGCT CCGCCACATC AAGCGGCTCC GCCAGCGGAT CTGCGAGGAA    300

GCCGCCTACT CCAACCCCAG CCTACCTCTG GTGCACCCTC CGTCCCATAG CAAAGCCCCT    360

GCACAGACTC CAGCCGAGCC CACACCTGGC TATGAGGTGG GCCAGCGGAA GCGCCTCATC    420

TCCTCGGTGG AGGACTTCAC CGAGTTTGTG TGAGGCCGGG GCCCTCCCTC CTGCACTGGC    480

CTTGGACGGT ATTGCCTGTC AGTGAAATAA ATAAAGTCCT GACCCCAGTG CACAGACATA    540

GAGGCACAGA TTGC                                                     554

(2) INFORMATION FOR SEQ ID NO: 20:

(i) SEQUENCE CHARACTERISTICS:
        (A) LENGTH: 192 base pairs
        (B) TYPE: nucleic acid
        (C) STRANDEDNESS: unknown
        (D) TOPOLOGY: unknown (ii) MOLECULE TYPE: other nucleic acid (vi) ORIGINAL SOURCE:
        (A) ORGANISM: Homo sapiens (ix) FEATURE:
        (A) NAME/KEY: misc_feature
        (D) OTHER INFORMATION:/function= "CW10F probe"

(xi) SEQUENCE DESCRIPTION: SEQ ID NO: 20:

GTCCGCGGTC GCACGTACGC TTCTGGTGTG TGTGAGACGT GCGGGCTGG GAAGTGTTGG      60

CAGACGGCGA GTACGTCCTC ACTCCTTTTG TTCTTTTGAC CTAAGCTGGC GAGTGGCACT    120

GCTGAGTTCC GCTCAGTGCC CGCCCTGATG TGCGACCCCC GTGCATTCTT GCTGTTAGGT    180

GGTGGCGGTG TG                                                       192

(2) INFORMATION FOR SEQ ID NO: 21:

-continued

```
        (i) SEQUENCE CHARACTERISTICS:
            (A) LENGTH: 41 base pairs
            (B) TYPE: nucleic acid
            (C) STRANDEDNESS: unknown
            (D) TOPOLOGY: unknown (ii) MOLECULE TYPE: other nucleic acid (vi) ORIGINAL SOURCE:
            (A) ORGANISM: Homo sapiens (ix) FEATURE:
            (A) NAME/KEY: misc_feature
            (D) OTHER INFORMATION:/function= "CW10R probe"

(xi) SEQUENCE DESCRIPTION: SEQ ID NO: 21:

AGGCAGGTCT CCCCCACGAC CAGGGGAGAG GCACCCAAGG T                               41

(2) INFORMATION FOR SEQ ID NO: 22:

(i) SEQUENCE CHARACTERISTICS:
            (A) LENGTH: 31 base pairs
            (B) TYPE: nucleic acid
            (C) STRANDEDNESS: unknown
            (D) TOPOLOGY: unknown (ii) MOLECULE TYPE: other nucleic acid (vi) ORIGINAL SOURCE:
            (A) ORGANISM: Homo sapiens (xi) SEQUENCE DESCRIPTION: SEQ ID NO: 22:

AGTCAGTAAT TTATATGGTG TTAAAATGTG A                                          31

(2) INFORMATION FOR SEQ ID NO: 23:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: protein (vi) ORIGINAL SOURCE:
            (A) ORGANISM: Homo sapiens (xi) SEQUENCE DESCRIPTION: SEQ ID NO: 23:

Trp Asp Phe Gly Asp Ser
 1               5
```

```

# POLYCYSTIC KIDNEY DISEASE 12 GENE AND USES THEREOF

This application is a divisional of application Ser. No. 08/422,582, filed Apr. 14, 1995 now U.S. Pat. No. 6,485,960.

BACKGROUND TO THE INVENTION

In humans, one of the commonest of all genetic disorders is autosomal dominant polycystic kidney disease (ADPKD) also termed adult polycystic kidney disease (APKD), affecting approximately 1/1000 individuals (Dalgaard, 1957). ADPKD is a progressive disease of cyst formation and enlargement typically leading to end stage renal disease (ESRD) in late middle age. The major cause of morbidity in ADPKD is progressive renal disease characterized by the formation and enlargement of fluid filled cysts, resulting in grossly enlarged kidneys. Renal function deteriorates as normal tissue is compromised by cystic growth, resulting in end stage renal disease (ESRD) in more than 50% of patients by the age of 60 years (Gabow, et al., 1992). ADPKD accounts for 8–10% of all renal transplantation and dialysis patients in Europe and the USA (Gabow, 1993).

ADPKD also causes cystic growth in other organs (reviewed in Gabow, 1990) and occasionally presents in childhood (Fink, et al., 1993; Zerres, et al., 1993). Extrarenal manifestations include liver cysts (Milutinovic, et al., 1980), and more rarely cysts of the pancreas (Gabow, 1993) and other organs. Intracranial aneurysms occur in approximately 5% of patients and are a significant cause of morbidity and mortality due to subarachnoid haemorrhage (Chapman, et al., 1992). ADPKD is associated with a higher prevalence of various connective tissue disorders. An increased prevalence of heart valve defects (Hossack, et al., 1988), hernia (Gabow, 1990) and colonic diverticulae (Scheff, et al., 1980) have been reported.

Considerable progress has been made in the last few years in understanding the pathophysiology of ADPKD (and other animal models of cystic disease). Cysts in ADPKD are known to develop from outpouchings of descending or ascending kidney tubules and the early stages are characterized by a thickening and disorganization of the basement membrane, accompanied by a de-differentiation of tubular epithelial cells. Several of the characteristics of ADPKD epithelia: altered growth responses, abnormal expression of various proteins and reversal of polarity, may be a sign of this de-differentiation and important in cyst expansion. The nature of the primary defect which triggers these changes is, however, unknown and consequently much effort has been devoted to identifying the causative agent by genetic means.

The first step towards positional cloning of an ADPKD gene was the demonstration of linkage of one locus now designated the polycystic kidney disease 1 (PKD1) locus to the a globin cluster on the short arm of chromosome 16 (Reeders, et al., 1985). Subsequently, families with unlinked to markers on 16p were described (Kimberling, et al., 1988; Romeo, et al., 1988) and a second ADPKD locus (PKD2) has recently been assigned to chromosome region 4q13-q23 (Kimberling, et al., 1993; Peter, et al., 1993). It is estimated that approximately 85% of ADPKD is due to PKD1 (Peters and Sankuijl, 1992) with PKD2 accounting for most of the remainder. PKD2 appears to be milder condition with a later age of onset and ESRD (Parfrey, et al., 1990; Gabow, et al., 1992; Ravine, et al., 1992).

The position of the PKD1 locus was refined to chromosome band 16p13.3 and many markers were isolated from that region (Breuning, et al., 1987; Reeders, et al., 1988; Breuning, et al., 1990; Germino, et al., 1990; Hyland, et al., 1990; Himmelbauer, et al., 1991). Their order, and the position of the PKD1 locus, has been determined by extensive linkage analysis in normal and PKD1 families and by the use of a panel of somatic cell hybrids (Reeders et al., 1988; Breuning, et al., 1990; Germino, et al., 1990). ADPKD is genetically heterogenous with loci mapped not only to 16p13.3 (PKD1), but also to chromosome 4 (DKD2). Although the phenotype of PKD1 and PKD2 are clearly similar, it is now well documented that PKD1 (which accounts for about 85% of ADPKD; (Peters, 1992) is a more severe disease with an average age at ESRD of about 56 years compared to about 71.5 years for PKD2 (Ravine, 1992). An accurate long range restriction map of the 16p13.3 region (Harris, et al., 1990; Germino, et al., 1992) has located the PKD1 locus in an interval of approximately 600 kb between the markers GGG1 and SM7 (Harris, et al., 1991; Somlo, et al., 1992) (see FIG. 1a). The density of CpG islands and identification of many mRNA transcripts indicated that this area is rich in gene sequences. Germino et al. (1992) estimated that the candidate region contains approximately 20 genes.

Identification of the PKD1 gene from within this area has thus proved difficult and other means to pinpoint the disease gene have been sought. Linkage disequilibrium has been demonstrated between PKD1 and the proximal marker VK5, in a Scottish population (Pound, et al., 1992) and between PKD1 and BLu24 (see FIG. 1a), in a Spanish population (Peral, et al., 1994). Studies with additional markers have shown evidence of a common ancestor in a proportion of each population (Peral, et al., 1994; Snarey, et al., 1994), but the association has not precisely positioned the PKD1 locus.

Disease associated genomic rearrangements, detected by cytogenetics or pulsed field gel electrophoresis (PFGE) have been instrumental in the identification of various genes associated with various genetic disorders. Hitherto, no such abnormalities related to PKD1 have been described. This situation contrasts with that for the tuberous sclerosis locus, which lies within 16p13.3 (TSC2). In that case, TSC associated deletions were detected by PFGE within the interval thought to contain the PKD1 gene and their characterisation was a significant step toward the rapid identification of the TSC2 gene (European Chromosome 16 Tuberous Sclerosis Consortium, 1993). The TSC2 gene therefore maps within the candidate region for the hitherto unidentified PKD1 gene; as polycystic kidneys are a feature common to TSC and ADPKD1 (Bernstein and Robbins, 1991) the possibility of an etiological link, as proposed by Kandt et al. (1992), was considered. A contiguous gene syndrome resulting from the disruption of PKD1 and the adjacent tuberous sclerosis 2 (TSC2) gene, which is associated with TSC and severe childhood onset polycystic kidney disease, has also been defined (Brook-Carter, et al. 1994).

We have now identified a pedigree in which the two distinct phenotypes, typical ADPKD or TSC, are seen in different members. In this family, the two individuals with ADPKD are carriers of a balanced chromosome translocation with a breakpoint within 16p13.3. We have located the chromosome 16 translocation breakpoint and a gene disrupted by this rearrangement has been defined; the discovery of additional mutations of that gene in other PKD1 patients shows that we have identified the PKD1 gene. Full characterisation of the PKD1 transcript has been significantly complicated because of the unusual genomic region containing most of the gene. All but 3.5 kb at the 3' end of the transcript (which is about 14 kb in total) is encoded by a region which is reiterated several times elsewhere on the same chromosome (in 16p13.1 and termed the HG area). The structure of the duplication is complex, with some regions copied more times than others, and the HG region encoding three large transcripts. The transcripts from the HG area are: HG-A (21 kb), HG-B (17 kb) and HG-C (8.5 kb) and although these have 3' ends which differ from PKD1, over most of their length they share substantial homology to the PKD1 transcript. Consequently, cloning and characterizing a bona fide PKD1 cDNA has proven difficult. To overcome the problem caused by duplication we have cloned cDNAs covering the entire transcript from a cell line which contains the PKD1 but not the HG loci. Characterisation of these cDNAs has enabled the PKD1 protein sequence to be predicted and led to the identification of several homologies with described motifs.

SUMMARY OF THE INVENTION

Accordingly, in one aspect, this invention provides an isolated, purified or recombinant nucleic acid sequence comprising:

(a) a PKD1-encoding nucleic acid or its complementary strand, (b) a sequence substantially homologous to, or capable of hybridizing to, a substantial portion of a molecule defined in (a) above, or (c) a fragment of a molecule defined in (a) or (b) above.

In particular, there is provided a sequence wherein the PKD1 gene has the nucleic acid sequence according to FIG. 15 (Seq. I.D. No. 7), or the partial sequence of FIGS. 7 (Seq. I.D. No. 1) or 10 (Seq. I.D. No. 5). The invention therefore includes a DNA molecule coding for a polypeptide having the amino acid sequence of FIG. 15 (Seq. I.D. No. 8), or a polypeptide fragment thereof; and genomic DNA corresponding to a molecule as in (a)–(c) above.

As used herein, "substantially homologous" refers to a nucleic acid strand that is sufficiently duplicative of the PKD1 sequence presented in FIG. 15 (Seq. I.D. No. 7) such that it is capable of hybridizing to that sequence under moderately stringent, and preferably stringent conditions, as defined herein below. Preferably, "substantially homologous" refers to a homology of between 97 and 100%. Further, such a strand will encode or be complementary to a strand that encodes PKD1 protein having the biological activity described below. As used herein, a "substantial portion of a molecule" refers to at least 60%, preferably 80% and most preferably 90% of the molecule in terms of its linear residue length or its molecular weight. "Nucleic acid" refers to both DNA and RNA.

The PKD1 gene described herein is a gene found on human chromosome 16, and the results of studies described herein form the basis for concluding that this PKD1 gene encodes a protein called PKD1 protein which has a role in the prevention or suppression of ADPKD. The PKD1 gene therefore includes the DNA sequences shown in FIG. 15 (Seq. I.D. No. 7), and all functional equivalents. By "functional equivalents", we mean nucleic acid sequences that are substantially homologous to the PKD1 nucleic acid sequence, as presented in FIG. 15 (Seq. I.D. No. 7), and encoding a protein that possesses one or more of the biological functions or activities of PKD1; i.e., that is involved in cell/cell adhesion, cell/cell recognition or cell/cell communication, for example to effect adhesion of cells to other cells or components of the extracellular matrix; effect communication and/or interaction between epithelial cells and the basal membrane (whether in kidneys or otherwise); assist in development of connective tissue such as assembly and/or maintenance of the basal membrane; in signal transduction between cells or cells and components of the extracellular matrix; and/or to promote binding of cells carrying proteins such as integrins or carbohydrates to target cells. The biological function of PKD1 of course includes maintaining a healthy physiological state; that is, the native protein's aberrations or absence results in ADPKD or an associated disorder.

The PKD1 gene may furthermore include regulatory regions which control the expression of the PKD1 coding sequence, including promoter, enhancer and terminator regions. Other DNA sequences such as introns spliced from the end-product PKD1 RNA transcript are also encompassed. Although work has been carried out in relation to the human gene, the corresponding genetic and functional sequences present in lower animals are also encompassed.

The present invention therefore further provides a PKD1 gene or its complementary strand having the sequence according to FIG. 15 (Seq. I.D. No. 7), which gene or strand is mutated in some ADPKD patients (more specifically, PKD1 patients). Therefore, the invention further provides a nucleic acid sequence comprising a mutant PKD1 gene as described herein, including wherein Intron 43 as defined hereinbelow has a deletion of 18 or 20 bp resulting in an intron of 55 or 57 bp.

As used herein, "PKD1 mutant" or "mutation" encompasses alterations of the native PKD1 nucleotide (Seq. I.D. No. 7), or amino acid sequence (Seq. I.D. No. 8), as defined by FIG. 15, i.e., substitutions, deletions or additions, and also encompasses deletion of DNA containing the entire PKD1 gene.

The invention further provides a nucleic acid sequence comprising a mutant PKD1 gene, especially one selected from a sequence comprising a partial sequence according to FIGS. 7 (Seq. I.D. No. 1) and/or 10 (Seq. I.D. No. 5), or the corresponding sequences disclosed in FIG. 15 (Seq. I.D. No. 7), when:

(a) [OX114] base pairs 1746–2192 as defined in FIG. 7 (Seq. I.D. No. 1) are deleted (446 bp);

(b) [OX32] base pairs 3696–3831 as defined in FIG. 7 (Seq. I.D. No. 1) are deleted by a splicing defect;

(c) [OX875] about 5.5 kb flanked by the two XbaI sites shown in FIG. 3a are deleted and the EcoR1 site separating the CW10 (41 kb) and JH1 (18 kb) sites is thereby absent (d) [WS53] about 100 kb extending between the JH1 and CW21 and the SM6 and JH17 sites shown in FIG. 6 and the PKD1 gene is thereby absent, the deletion lying proximally between SM6 and JH17

(e) [461] 18 bp are deleted in the 75 bp intron amplified by the primer pair 3A3C (Seq. I.D. Nos. 11 and 12) insert at position 3696 of the 3' sequence (Seq. I.D. No. 1) as shown in FIG. 11 (Seq. I.D. No. 18);

(f) [OX1054] 20 bp are deleted in the 75 bp intron amplified by the primer pair 3A3C (Seq. I.D. Nos. 11 and 12) insert at position 3696 of the 3' sequence (Seq. I.D. No. 1) as shown in FIG. 11 (Seq. I.D. No. 18);

(g) [WS212] about 75 kb are deleted between SM9-CW9 distally and the PKD1 3'UTR proximally as shown in FIG. 12;

(h) [WS-215] about 160 kb are deleted between CW20 and SM6-JH17 as shown in FIG. 12;

(i) [WS-227] about 50 kb are deleted between CW20 and JH11 as shown in FIG. 12;

(j) [WS-219] about 27 kb are deleted between JH1 and JH6 as shown in FIG. 12;

(k) [WS-250] about 160 kb are deleted between CW20 and Blu24 as shown in FIG. 12;

(l) [WS-194] about 65 kb is deleted between CW20 and CW10.

The invention therefore extends to RNA molecules comprising an RNA sequence corresponding to any of the DNA sequences set out above. Such molecule may be the transcript reference PBP and identifiable with respect to the restriction map of FIG. 3a and having a length of about 14 KB.

In another aspect, the invention provides a nucleic acid probe having a sequence as set out above; in particular, this invention extends to a purified nucleic acid probe which hybridizes to at least a portion of the DNA or RNA molecule of any of the preceding sequences. Preferably, the probe includes a label such as a radiolabel, for example, a $^{32}P$ label.

In another aspect, this invention provides a purified DNA or RNA coding for a protein comprising the amino acid sequence of FIG. 15 (Seq. I.D. No. 8), or a protein polypeptide having homologous properties with said protein, or having at least one functional domain or active site in common with said protein.

The DNA molecule defined above may be incorporated in a recombinant cloning vector for expressing a protein having the amino acid sequence of FIG. 15 (Seq. I.D. No. 8), or a protein or a polypeptide having at least one functional domain or active site in common with said protein. Such a vector may include any vector for expression in bacteria, e.g., *E. coli*; yeast, insect, or mammalian cells.

The invention also features a nucleic acid probe for detecting PKD1 nucleic acid comprising 10 consecutive nucleotides as presented in FIG. 15 (Seq. I.D. No. 7). Preferably, the probe may comprise 15, 20, 50, 100, 200, or 300, etc., consecutive nucleotides (nt) presented in FIG. 13, and may fall within the size range 15 nt–13 kb, 100 nt–5 kb, 150 nt–4 kb, 300 nt–2 kb, and 500 nt–1 kb.

Probes are used according to the invention in hybridization reactions to identify PKD1 sequences, whether they be native or mutated PKD1 DNA or RNA, as disclosed herein. Such probes are useful for identifying the PKD1 gene or a mutation thereof, as defined herein.

The invention also features a synthetic polypeptide corresponding in amino acid residue sequence to at least a portion of the sequence of naturally occurring PKD1, and having a molecular weight equal to less than that of the native protein. A synthetic polypeptide of the invention is useful for inducing the production of antibodies specific for the synthetic polypeptide and that bind to naturally occurring PKD1.

Preferred embodiments of this aspect of the invention include a group of synthetic polypeptides whose members correspond to a fragment of the PKD1 protein comprising a stretch of amino acids of at least 8, and preferably 15, 30, 50, or 100 residues in length from the sequence disclosed in FIG. 15 (Seq. I.D. No. 8).

In another aspect, the invention provides a polypeptide encoded by a sequence as set out above, or having the amino acid sequence according to the amino acid sequence of FIG. 15 (Seq. I.D. No. 8), or a protein or polypeptide having homologous properties with said protein, or having at least one functional domain or active site in common with said protein. In particular, there is provided an isolated, purified or recombinant polypeptide comprising a PKD1 protein or a mutant or variant thereof or encoded by a sequence set out above or a variant thereof having substantially the same activity as the PKD1 protein. The present invention may further comprise a polypeptide having 9 or 13 transmembrane pairs instead of 11 transmembrane domains as described hereinbelow. Further comprising this invention is a molecule which interacts with a polypeptide as herein described which molecule synergises, causes, enhances or is necessary for the functioning of the PKD1 protein as herein described.

The invention also encompasses recombinant expression vectors comprising a nucleic acid or isolated DNA encoding PKD1 and a process for preparing PKD1 polypeptide, comprising culturing a suitable host cell comprising the vector under conditions suitable for promoting expression of PKD1, and recovering said PKD1.

This invention also provides an in vitro method of determining whether an individual is likely to be affected with tuberous sclerosis, comprising assaying a biological sample from the individual to determine the presence and/or amount of PKD1 protein or polypeptide having the amino acid sequence of FIG. 15 (Seq. I.D. No. 8).

As used herein, "biological sample" includes any fluid or tissue sample from a mammal, preferably a human, including but not limited to blood, urine, saliva, any body organ tissue, cells from any body tissue, including blood cells.

Additionally or alternatively, a sample may be assayed to determine the presence and/or amount of mRNA coding for the protein or polypeptide having the amino acid sequence of FIG. 15 (Seq. I.D. No. 8), or to determine the fragment lengths of fragments of nucleotide sequences coding for the protein or polypeptide of FIG. 15 (Seq. I.D. No. 8), or to detect inactivating mutations in DNA coding for a protein having the amino acid sequence of FIG. 15 (Seq. I.D. No. 8) or a protein having homologous properties. The screening preferably includes applying a nucleic acid amplification process, as described herein in detail, to said sample to amplify a fragment of the DNA sequence. The nucleic acid amplification process advantageously utilizes at least one of the following sets of primers as identified herein: AH3 F9 (Seq. I.D. No. 9), : AH3 B7 (Seq. I.D. No. 10); 3A3 C1 (Seq. I.D. No. 11), : 3A3 C2 (Seq. I.D. No. 12); and AH4 F2(Seq. I.D. No. 13), : JH14 B3 (Seq. I.D. No. 14).

Alternatively, the screening method may comprise digesting the sample DNA to provide EcoRI fragments and hybridizing with a DNA probe which hybridizes to the EcoRI fragment identified (A) in FIG. 3(a), and the DNA probe may comprise the DNA probe CW10 (Seq. I.D. No. 4). identified herein.

Another screening method may comprise digesting the sample to provide BamHI fragments and hybridizing with a DNA probe which hybridizes to the BamHI fragment identified (B) in FIG. 3(a), and the DNA probe may comprise the DNA probe 1A1H.6 identified herein.

A method according to the present invention may comprise detecting a PKD1-associated disorder in a patient suspected of having or having predisposition to the disorder (i.e., a carrier), the method comprising detecting the presence of and/or evaluating the characteristics of PKD1 DNA, PKD1 mRNA and.or PKD1 protein in a sample taken from the patient. Such method may comprise detecting and/or evaluating whether the PKD1 DNA is deleted, missing, mutated, aberrant or not expressing normal PKD1 protein. One way of carrying out such a method comprises: A. taking a biological, tissue or biopsy sample from the patient; B. detecting the presence of and/or evaluating the characteristics of PKD1 DNA, PKD1 mRNA and/or PKD1 protein in the sample to obtain a first set of results; C. comparing the first set of results with a second set of results obtained using the same or similar methodology for an individual that is not suspected of having the disorder; and if the first and second sets of results differ in that the PKD1 DNA is deleted, missing, aberrant, mutated or not expressing PKD1 protein then that is indicative of the presence, predisposition or tendency of the patient to develop the disorder. As used herein, a "PKD1-associated disorder" refers to adult polycystic kidney disease, as described herein, and also refers to turberous sclerosis, as well as other disorders having symptoms such as cyst formation in common with these diseases.

A specific method according to the invention comprises extracting from a patient a sample of PKD1 DNA or DNA from the PKD1 locus purporting to be PKD1 DNA, cultivating the sample in vitro and analyzing the resulting protein, and comparing the resulting protein with normal PKD1 protein according to the well-established Protein Truncation Test. Less sensitive tests include analysis of RNA using RT PCR (reverse transcriptase polymerase chain reaction), and examination of genomic DNA.

Step C of the above method may be replaced by: comparing the first set of results with a second set of results obtained using the same or similar methodology in an individual that is known to have the or at least one of the disorder(s); and if the first and second sets of results are substantially identical, this indicates that the PKD1 DNA in the patient is deleted, mutated or not expressing normal PKD1 protein.

The invention further provides a method of characterizing a mutation in a subject suspected of having a mutation in the PKD1 gene, which method comprises: A. amplifying each of the exons in the PKD1 gene of the subject; B. denaturing the complementary strands of the amplified exons; C. diluting the denatured separate, complementary strands to allow each single-stranded DNA molecule to assume a secondary structural confirmation; D. subjecting the DNA molecule to electrophoresis under non-denaturing conditions; E. comparing the electrophoresis pattern of the single-stranded molecule with the electrophoresis pattern of a single-stranded molecule containing the same amplified exon from a control individual which has either a normal or PKD1 heterozygous genotype; and, F. sequencing any amplification product which has an electrophoretic pattern different from the pattern obtained from the DNA of the control individual.

The invention also extends to a diagnostic kit for carrying out a method as set out above, comprising nucleic acid primers for amplifying a fragment of the DNA or RNA sequences defined above, and packaging means therefore. The kit may optionally include written instructions stating that the primers are to be used for detection of disorders associated with the PKD1 gene. The nucleic acid primers may comprise at least one of the following sets: AH3 F9 (Seq. I.D. No. 9): AH3 B7 (Seq. I.D. No. 10): 3A3 C1 (Seq. I.D. No. 11): 3A3 C2 (Seq. I.D. No. 12): and AH4 F2 (Seq. I.D. No. 13): JH14 B3 (Seq. I.D. No. 14).

Another embodiment of kit may combine one or more substances for digesting a sample to provide EcoRI fragments and a DNA probe as previously defined. A further embodiment of kit may comprise one or more substances for digesting a sample to provide BamHI fragments and a DNA probe as previously defined.

A vector (such as Bluescript (available from Stratagene) comprising a nucleic acid sequence set out above; and a host cell (such as *E. coli* strain SL-1 Blue (available from Stratagene) transfected or transformed with the vector are also provided, together with the use of such a vector or a nucleic acid sequence set out above in gene therapy and/or in the preparation of an agent for treating or preventing a PKD1-associated disorder.

Therefore, there is further provided a method of treating or preventing a PKD1-associated disorder which method comprises administering to a patient in need thereof a functional PKD1 gene to affected cells in a manner that permits expression of PKD1 protein therein and/or a transcript produced from a mutated chromosome (such as the deleted WS-212 chromosome) which is capable of expressing functional-PKD1 protein therein.

As used herein, the term "hybridization" refers to conventional DNA/DNA or DNA/RNA hybridization conditions. For example, for a DNA or RNA probe of about 10–50 nucleotides, moderately stringent hybridization conditions are preferred and include 10×SSC, 5×Denhardts, 0.1% SDS, at 35–50 degrees for 15 hours; for a probe of about 50–300 nucleotides, "stringent" hybridization conditions are preferred and refer to hybridization in 6×SSC, 5×Denhardts, 0.1% SDS at 65 degrees for 15 hours.

The present invention further provides the use of PKD1 protein or polycystin or a mutant or variant thereof having substantially the same biological activity there as in therapy. In particular, to effect cell adhesion, recognition or communication for example to effect adhesion of cells to other cells or components of the extracellular matrix; effect communication and/or interaction between epithelial cells and the basal membrane (whether in kidneys or otherwise); assisting in development of connective tissue such as assembly and/or maintenance of the basal membrane; in signal transduction between cells or cells and components of the extracellular matrix; and/or to promote binding of cells carrying proteins such as integrins or carbohydrates to target cells.

Accordingly, where it is preferred to administer the polypeptide directly to a patient in need thereof, the invention further provides the use of a PKD1 protein or polycystin in the preparation of a medicament. Therefore, there is also provided a pharmaceutical formulation comprising a PKD1 protein, functional PKD1 gene and/or a transcript produced from a mutated chromosome which is capable of expressing functional PKD1 protein, in association with a pharmaceutically acceptable carrier therefor.

The invention also features an immunoglobin, i.e., a polyclonal or monoclonal antibody specific for an epitope of PKD1, which epitope is found in the amino acid sequence presented in FIG. 15 (Seq. I.D. No. 8).

The invention also features a method of assaying for the presence of PKD1 in a sample of mammalian, preferably human cells, comprising the steps of: (a) providing an antibody specific for said PKD1; and (b) assaying for the presence of PKD1 by admixing an aliquot from a sample of mammalian cells with antibody under conditions sufficient to allow for formation and detection of an immune complex of PKD1 and the antibody. Such method is useful for detecting disorders involving aberrant expression of the PKD1 gene or processing of the protein, as described herein.

Preferably, this method includes providing a monoclonal antibody specific for an epitope that is antigenically the same, as determined by Western blot assay, ELISA or immunocytochemical staining, and substantially corresponds in amino acid sequence to the amino acid sequence of a portion of PKD1 and having a molecular weight equal to less than that of PKD1.

The invention thus also features a kit for detecting PKD1, the kit including at least one package containing an antibody or idiotype-containing polyamide portion of an antibody raised to a synthetic polypeptide of this invention or to a conjugate of that polypeptide bound to a carrier. An indicating group or label is utilized to indicate the formation of an immune reaction between the antibody and PKD1 when the antibody is admixed with tissue or cells.

Further features will become more fully apparent in the following description of the embodiments of this invention and from the appended claims.

BRIEF DESCRIPTION OF THE DRAWINGS

Before describing preferred embodiments of the invention in detail, the drawings will briefly be described.

(bottom): A detailed map of the distal part of the PKD1 candidate region showing: the area of 16p13.3 duplicated in 16p13.1 (hatched); C, Cla I restriction sites; the breakpoints in the somatic cell hybrids, N—OH1 and P-MWH2A; DNA probes and the TSC2 gene. The limits of the position of the translocation breakpoint found in family 77 (see b), determined by evidence of heterozygosity (in 77-4) and PFGE (see c and text) is also indicated. The contig covering the 77 breakpoint region consists of the cosmids: 1, CW9D; 2, ZDS5; 3, JH2A; 4, REP59; 5, JC10.2B; 6, CW10III; 7, SM25A; 8, SMII; 9, NM17.

Figure 1A:
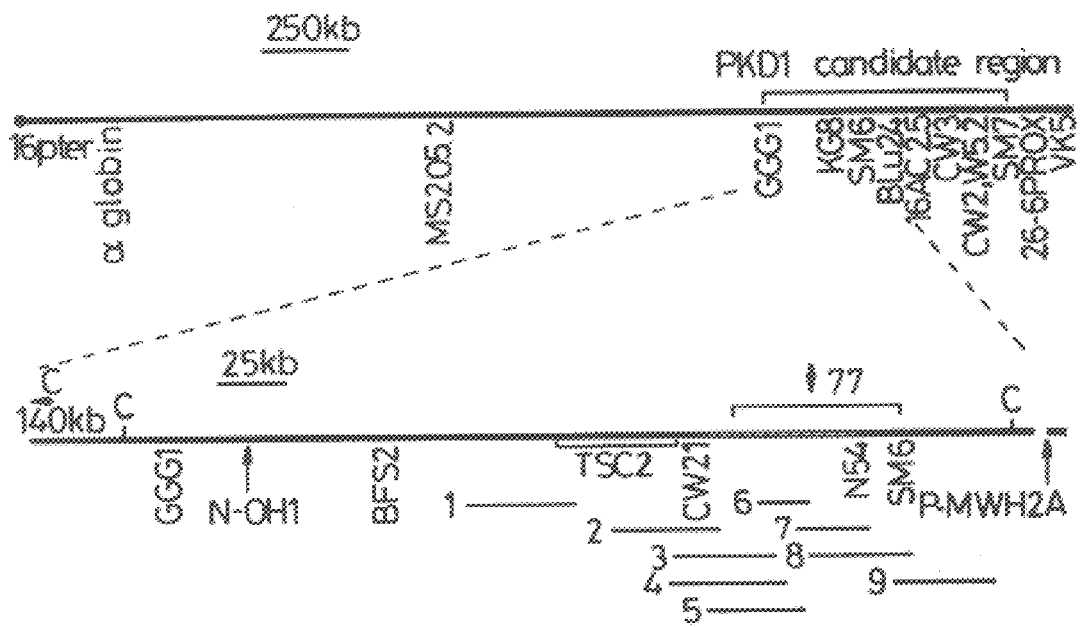
FIG. 1a (top): A long range map of the terminal region of the short arm of chromosome 16 showing the PKD1 candidate region defined by genetic linkage analysis. The positions of selected DNA probes and microsatellites used for haplotype, linkage or heterozygosity analyses are indicated. Markers previously described in linkage disequilibrium studies are shown in bold (from: Harris, et al., 1990; Harris, et al., 1991; Germino, et al., 1992; Somlo, et al., 1992; Peral, et al., 1994; Snarey, et al., 1994).
Figure 1B:
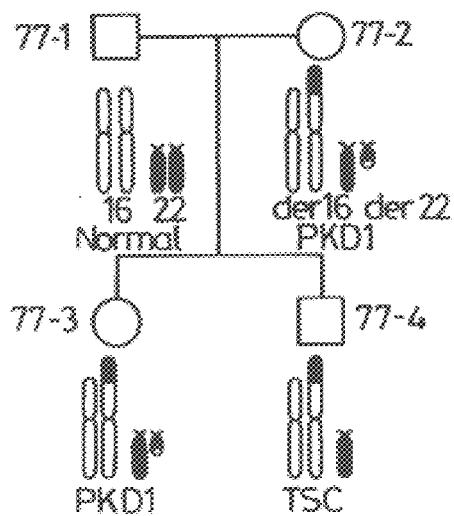

FIG. 1b: Pedigree of family 77 which segregates a 16;22 translocation; showing the chromosomal composition of each subject. Individuals 77-2 and 77-3 have the balanced products of the exchange—and have PKD1; 77-4 is monosomic for 16p13.3→16pter and 22q11.21→22pter—and has TSC.

Figure 1C:
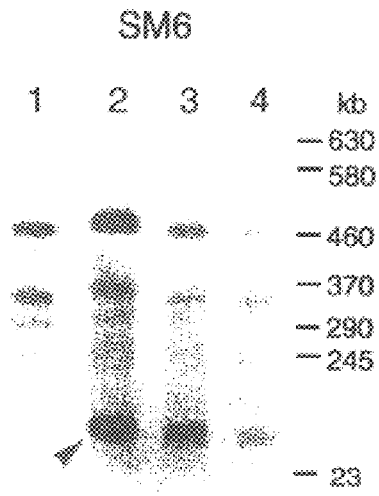

FIG. 1c: PFGE of DNA from members of the 77 family: 77-1 (1); 77-2 (2); 77-3 (3); 77-4 (4); digested with Cla I and hybridised with SM6. In addition to the normal fragments of 340 and partially digested fragment of 480 kb a proximal breakpoint fragment of approximately 100 kb (arrowed) is seen in individuals, 77-2, 77-3 and 77-4; concordant with segregation of the der(16) chromosome.

Figure 2:
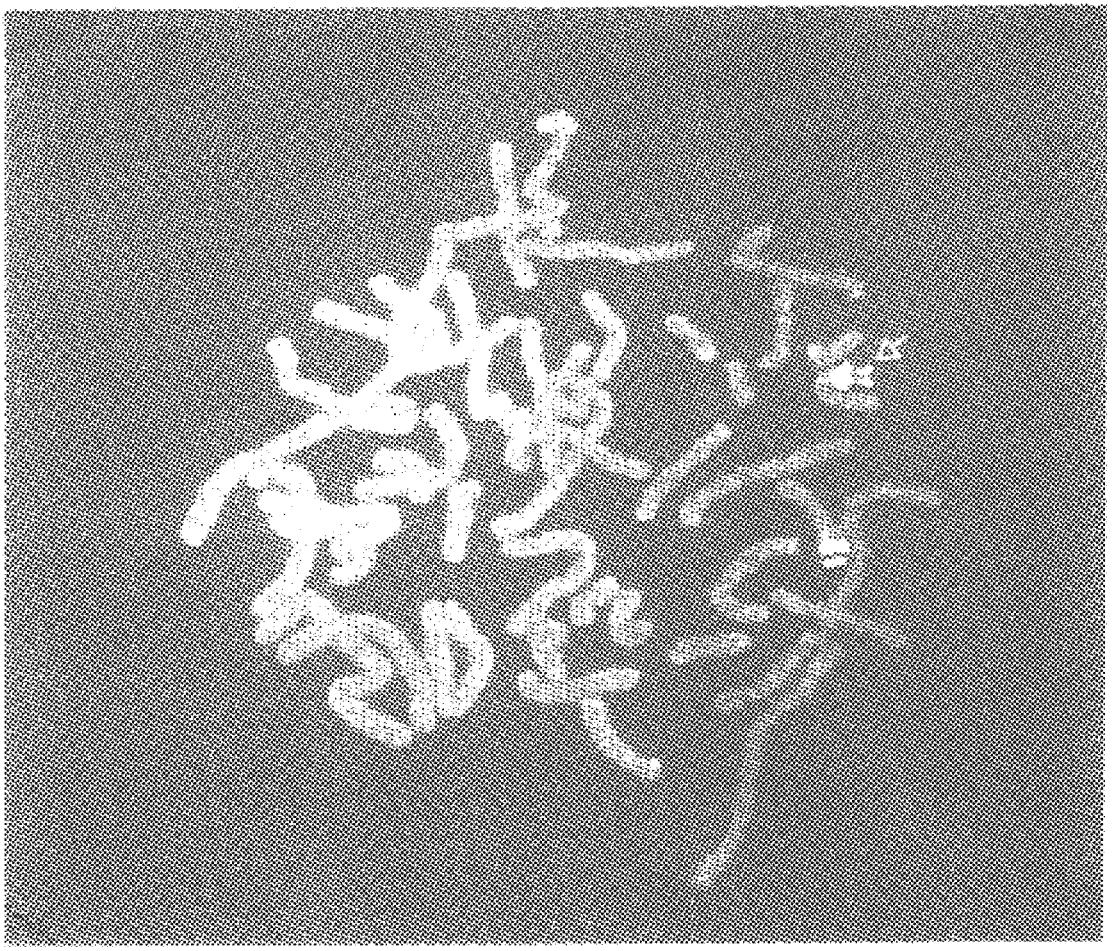

FIG. 2: FISH of the cosmid CW10III (cosmid 6; FIG. 1a) to a normal male metaphase. Duplication of this locus is illustrated with two sites of hybridisation on 16p; the distal site (the PKD1 region) is arrowed. The signal from the proximal site (16p13.1) is stronger than that from the distal, indicating that sequences homologous to CW10III are reiterated in 16p13.1.

Figure 3A:
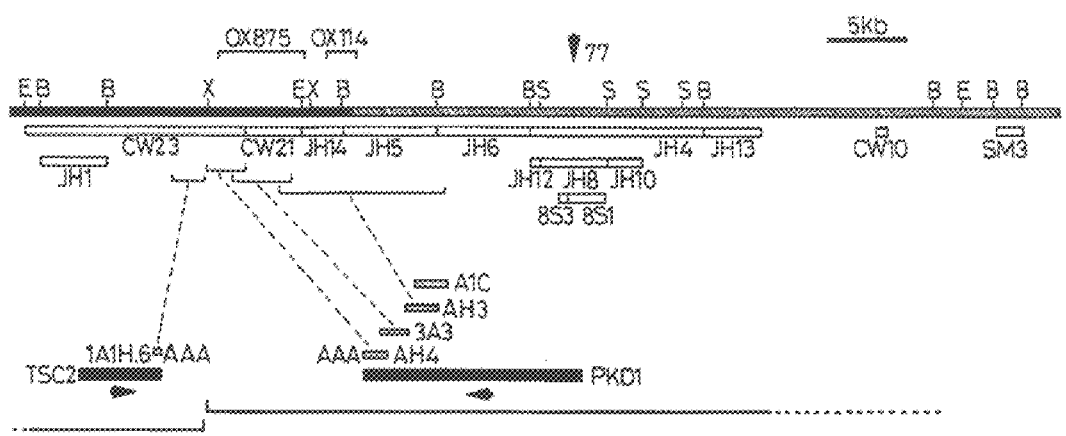

FIG. 3a: A detailed map of the 77 translocation region showing the precise localisation of the 77 breakpoint and the region that is duplicated in 16p13.1 (hatched). DNA probes (open boxes); the transcripts, PKD1 and TSC2 (filled boxes; with direction of transcription indicated by an arrow) and cDNAs (grey boxes) are shown below the genomic map. The known genomic extent of each gene is indicated at the bottom of the diagram and the approximate genomic locations of each cDNA is indicated under the genomic map. The positions of genomic deletions found in PKD1 patients, OX875 and OX114, are also indicated. Restriction sites for EcoR I (E) and incomplete maps for BamH I (B); Sac I (S) and Xba I (X) are shown. SM3 is a 2 kb BamH1 fragment shown at the 5' end of the gene.

Figure 3B:
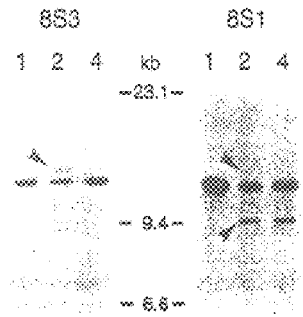

FIG. 3b: Southern blots of BamH I digested DNA from individuals: 77-1 (1); 77-2 (2); and 77-4 (4) hybridised with: left panel, 8S3 and right panel, 8S1 (see a). 8S3 detects a novel fragment on the telomeric side of the breakpoint (12 kb: arrowed) associated with the der(22) chromosome in 77-2, but not 77-4; 8S1 identifies a novel fragment on the centromeric side of the breakpoint (9 kb: arrowed)—associated with the der(16) chromosome—in 77-2 and 77-4. The telomeric breakpoint fragment is also seen weakly with 8S1 (arrowed) indicating that the breakpoint lies in the distal part of 8S1. The 8S3 and 8S1 loci are both duplicated; the normal BamH I fragment detected at the 16p13.3 site by these probes is 11 kb (see a), but a similar sized fragment is also detected at the 16p13.1 site. Consequently, the breakpoint fragments are much fainter than the normal (16p13.1 plus 16p13.3) band.

Figure 4A:
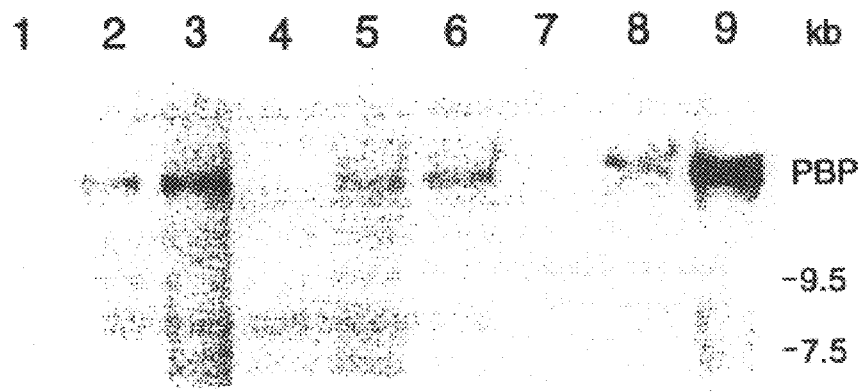

FIG. 4a: PBP cDNA, 3A3, hybridised to a Northern blot containing about 1 ug polyA selected mRNA per lane of the tissue specific cell lines: lane 1, MJ, EBV-transformed lymphocytes; lane 2, K562, erythroleukemia; lane 3, FS1, normal fibroblasts; lane 4, HeLa, cervical carcinoma; lane 5, G401, renal Wilm's tumour; lane 6, Hep3B, hepatoma; lane 7, HT29, colonic adenocarcinoma; lane 8, SW13, adrenal carcinoma; lane 9, G-CCM, astrocytoma. A single transcript of approximately 14 kb is seen; the highest level of expression is in fibroblasts and in the astrocytoma cell line, G-CCM. Although in this comparative experiment little expression is seen in lanes 1, 4 and 7, we have demonstrated at least a low level of expression in these cell lines on other Northern blots and by RT-PCR (see later).

Figure 4B:
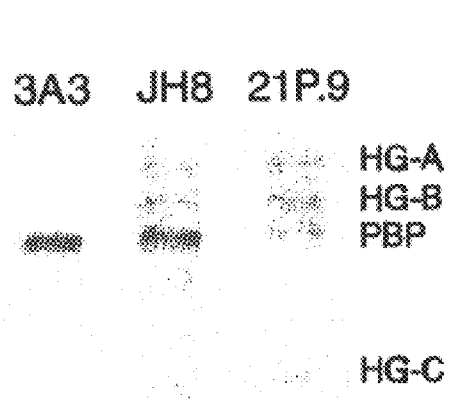

FIG. 4b: A Northern blot containing about 20 ug of total RNA from the cell line G-CCM hybridised with cDNAs or a genomic probe which identify various parts of the PBP gene. Left panel, a single about 14 kb transcript is seen with a cDNA from the single copy area, 3A3. Right panel, a cDNA, 21P.9, that is homologous to parts of the region that is duplicated (JH12, JH8 and JH10; see FIG. 3a) hybridises to the PBP transcript and three novel transcripts; HG-A (about 21 kb), HG-B (about 17 kb) and HG-C (8.5 kb). A similar pattern of transcripts is seen with cDNAs and genomic fragments that hybridise to the area between JH5 and JH13, with the exception of the JH8 area. Middle panel, JH8 hybridises to the transcripts PBP, HG-A and HG-B but not to HG-C.

Figure 4C:
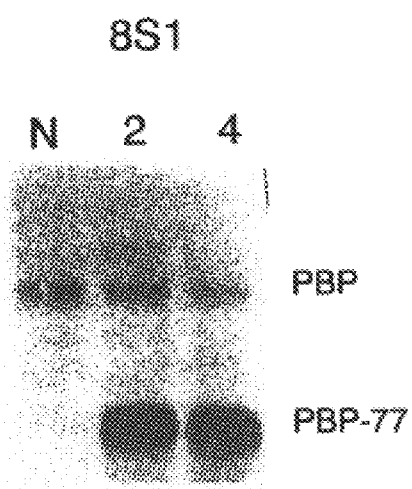

FIG. 4c: A Northern blot of 20 ug total fibroblast RNA from: normal control (N); 77-2 (2); 77-4 (4) hybridised with 8S1, which contains the 16;22 translocation breakpoint (see FIG. 3). A transcript of about 9 kb (PBP-77) is identified in the two patients with this translocation but not in the normal control. PBP-77 is a chimeric PBP transcript formed due to the translocation and is not seen in 77-2 or 77-4 RNA with probes which map distal to the breakpoint.

Figure 5A:
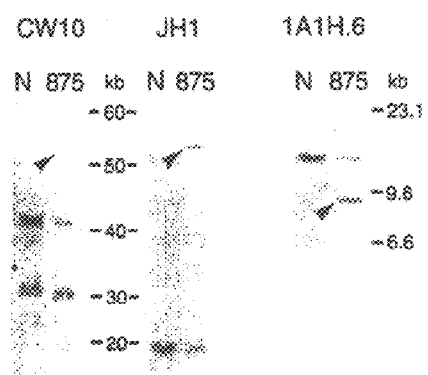

FIG. 5a: FIGE of DNA from: normal (N) and ADPKD patient OX875 (875), digested with EcoR I and hybridised with, left panel, CW10; middle panel, JH1. Normal fragments of 41 kb (plus a 31 kb fragment from the 16p13.1 site), CW10, and 18 kb, JHI, are identified with these probes; OX875 has an additional 53 kb band (arrowed). The EcoR I site separating these two fragments is removed by the deletion (see FIG 3a). The right panel shows a Southern blot of BamH I digested DNA (as above) hybridised with 1A1H.6. A novel fragment of 9.5 kb is seen in OX875 DNA, as well as the normal 15 kb fragment. These results indicate that OX875 has a 5.5 kb deletion; its position was determined more precisely by mapping relative to two Xba I sites which flank the deletion (see FIG. 3a).

Figure 5B:
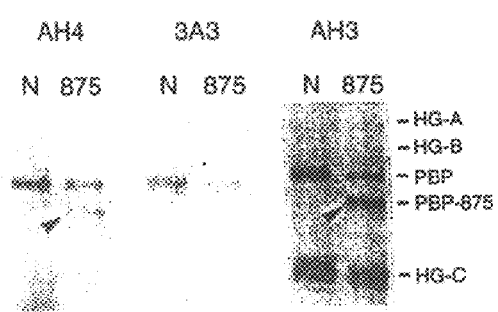

FIG. 5b: Northern blot of total fibroblast RNA, as (a), hybridised with the cDNAs, AH4, 3A3 and AH3. A novel transcript (PBP-875) of about 11 kb is seen with AH4 (the band is reduced in intensity because the probe is partly deleted) and AH3 (arrowed), which flank the deletion, but not 3A3 which is entirely deleted (see FIG. 3a). The transcripts HG-A, HG-B and HG-C, from the duplicated area, are seen with AH3 (see FIG. 4b).

Figure 5C:

FIG. 5c: Left panel; FIGE of DNA from: normal (N) and ADPKD patient OX114 (114), digested with EcoR I and hybridised with CW10; a novel fragment of 39 kb (arrowed) is seen in OX114. Middle panel; DNA, as above, plus the normal mother (M) and brother (B) of OX114 digested with BamH I and hybridised with CW21. A larger than normal fragment of 19 kb (arrowed) was detected in OX114 but not other family members due to deletion of a BamH I site; together these results are consistent with a 2 kb deletion (see FIG. 3a). Right panel; RT-PCR of RNA, as above, with primers flanking the OX114 deletion (see Experimental Procedures). A novel fragment of 810 bp (arrowed) is seen in OX114, indicating a deletion of 446 bp in the PBP transcript.

Figure 5D:
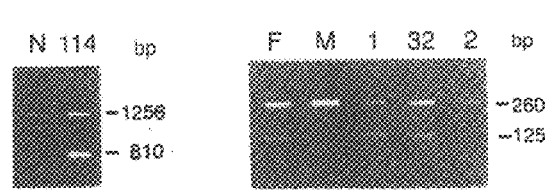

FIG. 5d: RT-PCR of RNA from: ADPKD patient OX32 (32) plus the probands, normal mother (M) and affected father (F) and sibs (1) and (2) using the C primer pair from 3A3 (Seq. I.D. Nos. 11 and 12) (see Experimental Procedures). A novel fragment of 125 bp is detected in each of the affected individuals.

Figure 6:
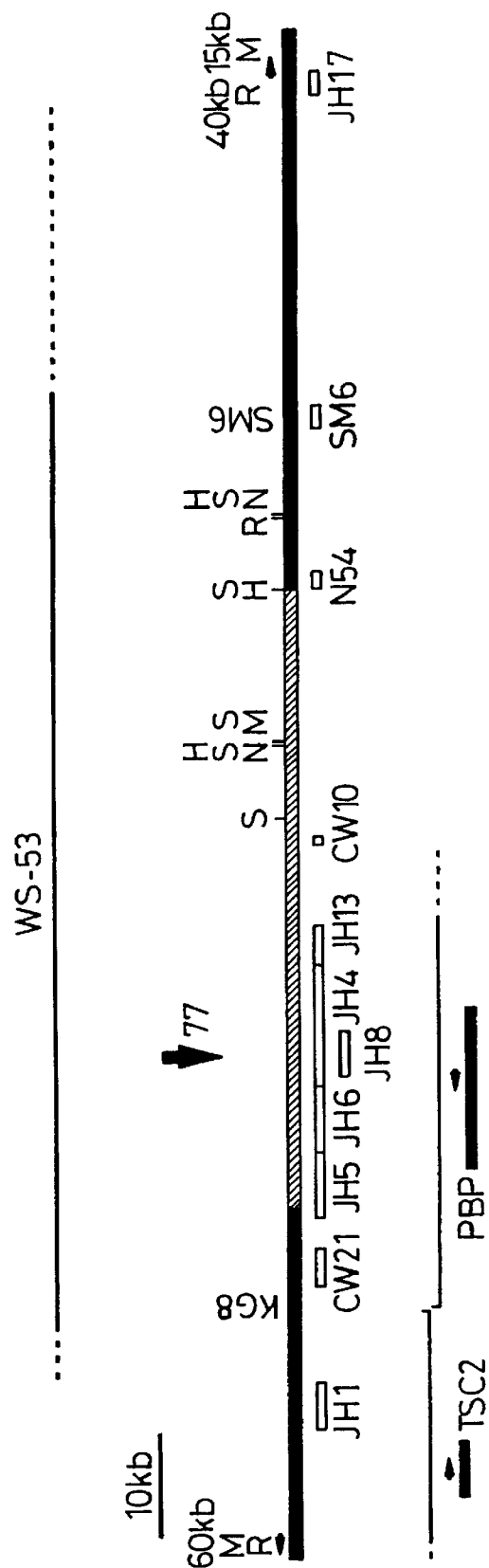

FIG. 6: Map of the region containing the TSC2 and PBP genes showing the area deleted in patient WS-53 and the position of the 77 translocation breakpoint. Localisation of the distal end of the WS-53 deletion was described (European Chromosome 16 Tuberous Sclerosis Consortium, 1993) and we have now localised the proximal end between SM6 and JH17. The size of the aberrant Mlu I fragment in WS-53, detected by JH1 and JH17, is 90 kb and these probes lie on adjacent Mlu I fragments of 120 kb and 70 kb, respectively. Therefore the WS-53 deletion is about 100 kb. Restriction sites for: Mlu I (M); Nru I (R); NOT I (N); and partial maps for Sac II (S) and BssH II (H) are shown. DNA probes (open boxes) and the TSC2 and PBP transcripts (filled boxes) are indicated below the line with their known genomic extents (brackets). The locations of the microsatellites KG8 and SM6 are also indicated.

FIG. 7: The partial nucleotide sequence (cDNA) of the PKD1 transcript extending 5631 bp to the 3' end of the gene (Seq. I.D. No. 1). The corresponding predicted protein (Seq. I.D. No. 2) is shown below the sequence and extends from the start of the nucleotide sequence. The GT-repeat, KG8, is in the 3' untranslated region between 5430–5448 bp. This sequence corresponds to GenBank Accession No. L33243.

FIG. 8: The sequence of the probe 1A1H0.6 (Seq. I.D. No. 19).

FIG. 9: The sequence of the probe CW10 (Seq. I.D. No. 4) which is about 0.5 kb. Also shown is the sequence of probe CW10R (Seq. I.D. No. 21).

Figure 10:
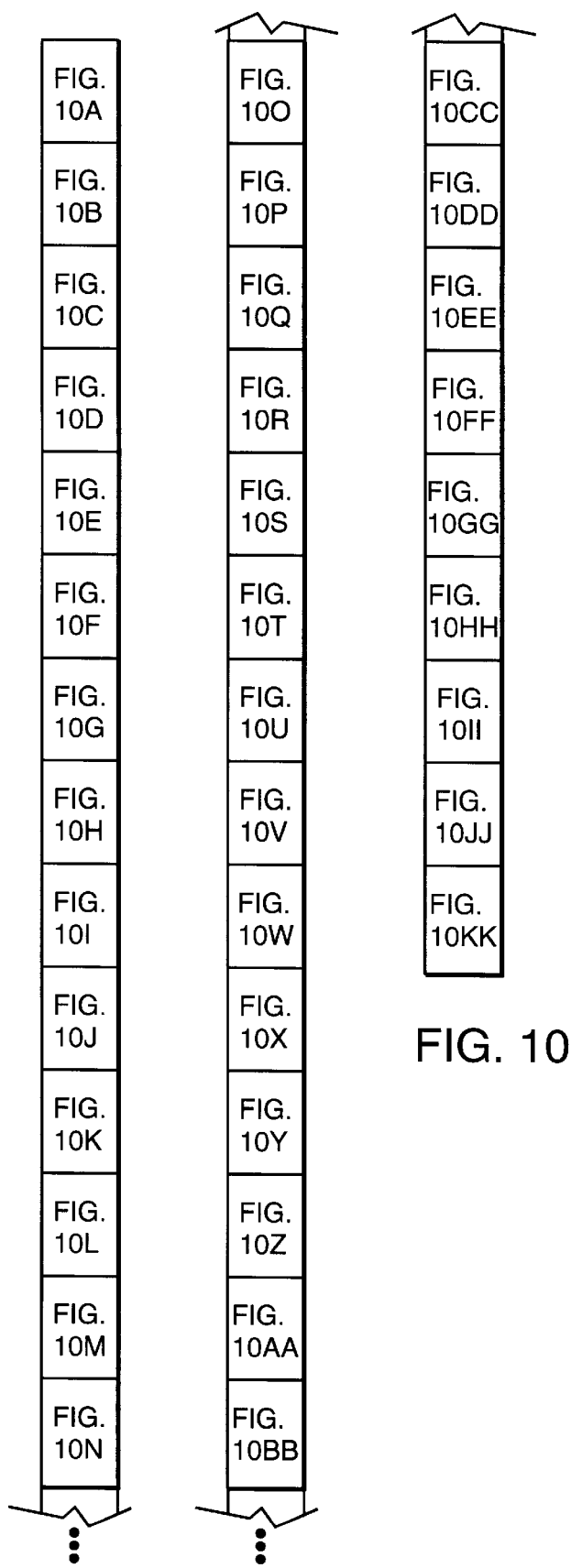

FIG. 10: Panels 10A—10A—10KK show the larger partial nucleotide sequence (Seq. I.D. No. 5) of the PKD1 transcript (cDNA) extending from bp 2 to 13807 bp to the 3' end of the gene together with the corresponding predicted protein also shown in Seq. I.D. No. 6. This larger partial sequence encompasses the (smaller) partial sequence of FIG. 7 from amino acid residue 2726 in Seq. I.D. No. 2 and relates to the entire PKD1 gene sequence (Seq. I.D. No. 7) apart from its extreme 5' end.

Figure 11:
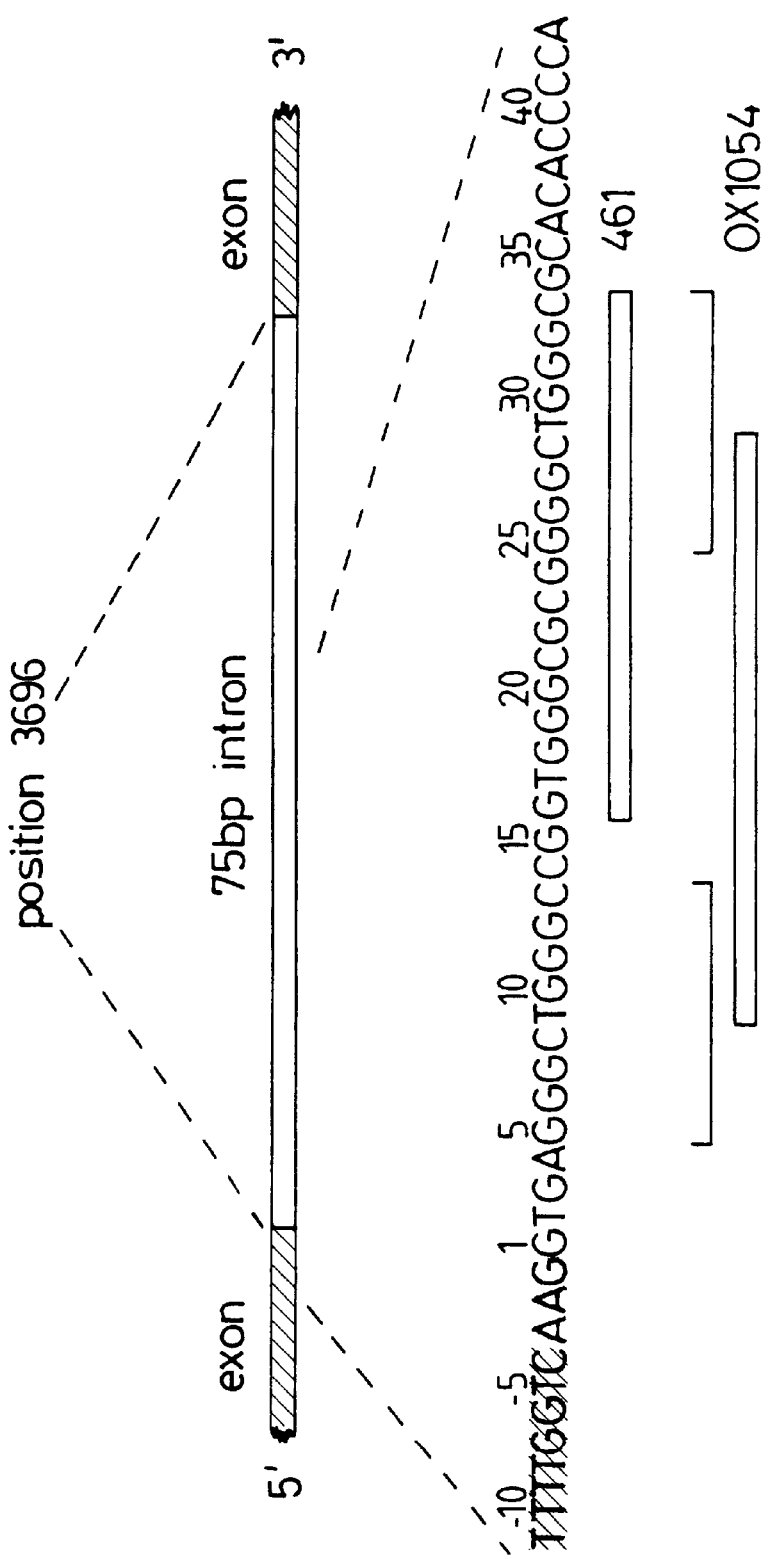

FIG. 11: A map of the 75 bp intron amplified by the primer set 3A3C (Seq. I.D. Nos. 11 and 12) insert (Seq. I.D. No. 18) at position 3696 of the 3' sequence (Seq. I.D. No. 1) showing the positions of genomic deletions found in PKD1 patients 461 and OX1054.

Figure 12:
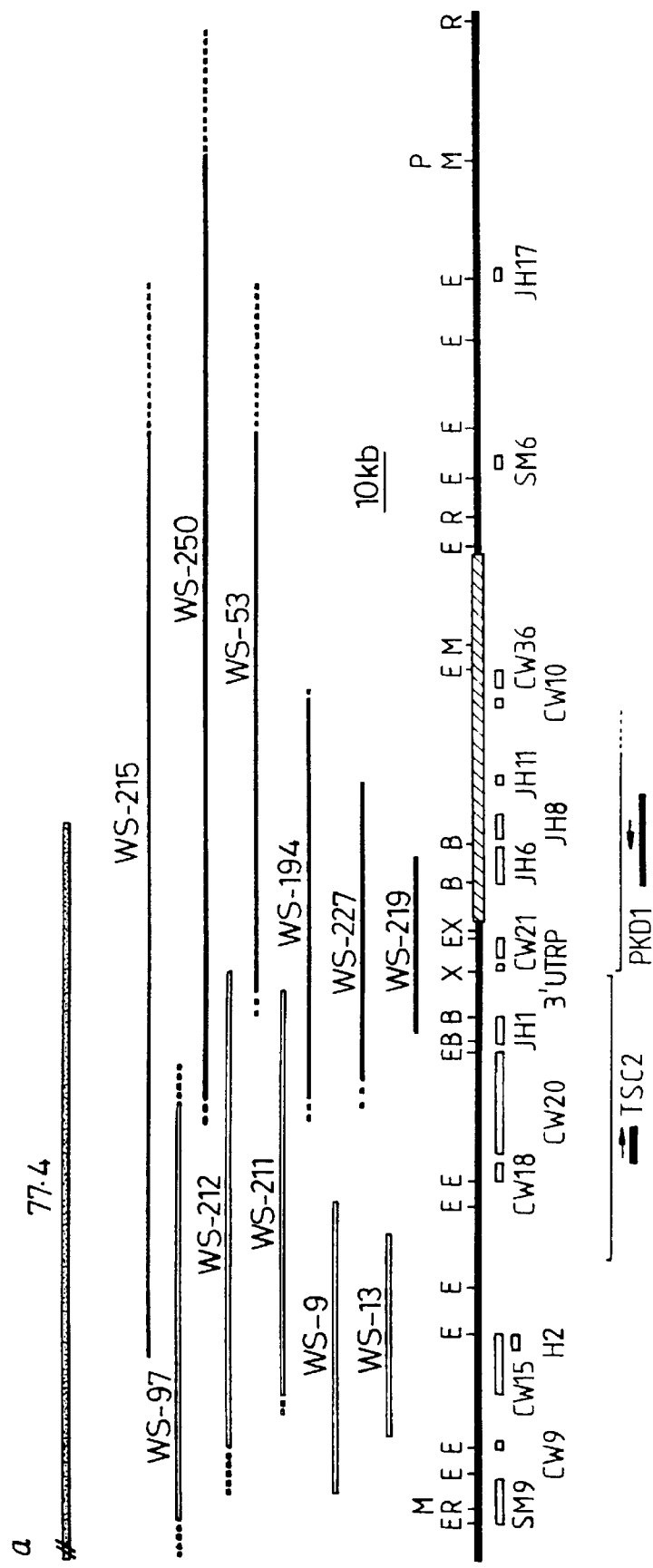

FIG. 12: A map of the region of chromosome 16 containing the TSC2 and PKD1 genes showing the areas affected in patients WS-215, WS-250, WS-212, WS-194, WS-227 and WS-219; also WS-53 (but cf. FIG. 6). Genomic sites for the enzymes Mlul (M), Clal (C), Pvul (P) and Nrul (R) are shown. Positions of single copy probes and cosmids used to screen for deletions are shown below the line which represents about 400 kb of genomic DNA. The genomic distribution of the approximately 45 kb TSC2 gene and known extent of the PKD1 gene are indicated above. The hatched area represents an about 50 kb region which is duplicated more proximally on chromosome 16p.

Figure 13:
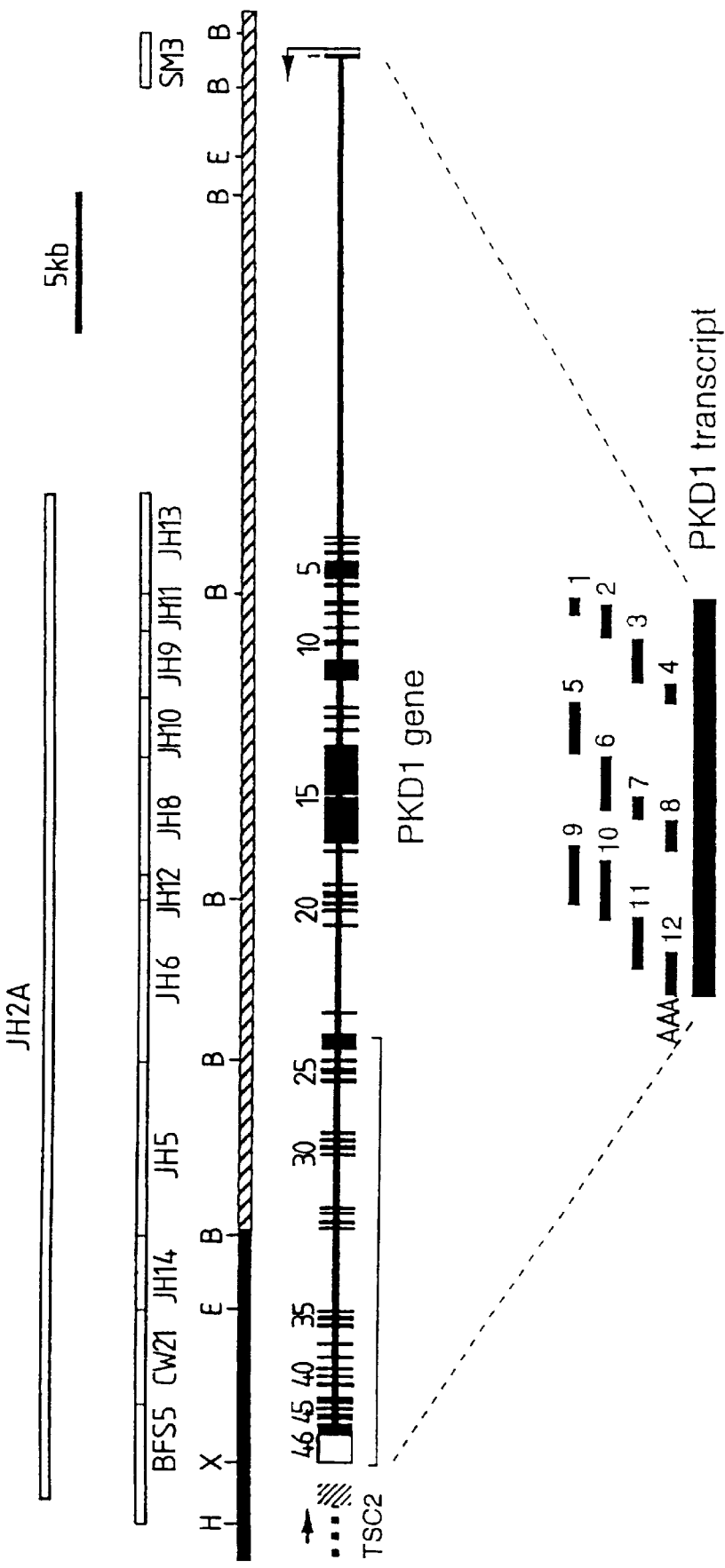

FIG. 13 is a genomic map of the PKD1 gene. (Top) A restriction map of the genomic area containing the PKD1 gene showing sites for Bam H1(B), EcoRI (E) and partial maps for Xbal (X) and Hind III(H), and the duplicated area (hatched). The position of genomic clones and the cosmid JH2A are shown above the map (open boxes). The positions of the 46 exons of the PKD1 gene are shown below the map (solid boxes, translated areas; open boxes, untranslated regions; UTRs). Each 5th exon is numbered and the direction of transcription arrowed. The area sequenced in FIGS. 7 and 10 is bracketed and the approximate location of the 3' end of the TSC2 gene is shown on the left (dashed line and hatched box). (Bottom) The cDNA contig covering the PKD1 transcript. The cDNAs are: 1, rev1; 2, S13;3, S3/4; 4, S1/3;5, GAP e; 6, GAP d; 7, GAP g; 8, GAP a (see table 2 for details); 9, A1C; 10, AH3; 11, 3A3; 12, AH4.

Figures 14A, 14B:
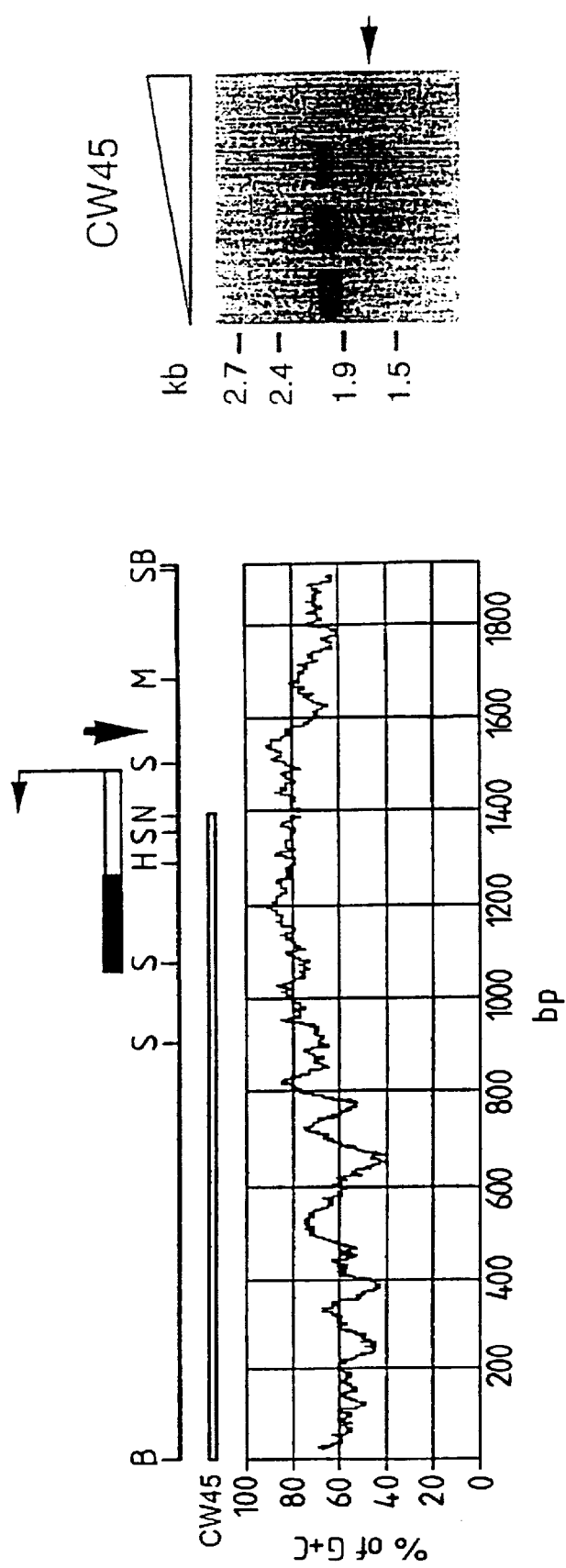

FIG. 14(a) (Top): Map of the genomic BamH I fragment, SM3 which contains the CpG island at the 5' end of the PKD1 gene, showing the probe CW45 (open box). Genomic restriction sites for the methylation sensitive enzymes: SacII (S), NotI (N), MluI (M) and BssHII (H) are illustrated. The approximate position of the DNase1 hypersensitive site is also shown (large arrow), plus the location of the first exon including the proposed transcription start site (small arrow), the 5'UTR (open box) and the translated region (solid bar). (Bottom) The GC content across the area is plotted with a window size of 50 nt. A peak of GC content of over 80% is seen in the area of the transcriptional start site and the first exon. A corresponding lack of CpG suppression was also found with an average CpG/GC ratio of 0.84 between 800–1,800 bp.

FIG. 14(b). Analysis of DNase I hypersensitivity at the PKD1 CpG island. DNA isolated from HeLa cells treated with an increasing amount of DNase I (left to right; first lane contains no DNase 1), digested with BamH I and hybridised with CW45. A fragment about 400 bp smaller than the restriction fragment is seen with increasing DNase 1, indicating a hypersensitive site as shown in (a). SM3 is within the duplicated area and so both the PKD1 and HG loci are assayed together. The degree of DNase1 digestion seen at the end of the assay indicates that cleavage occurs at the PKD1 and HG loci.

Figure 15:
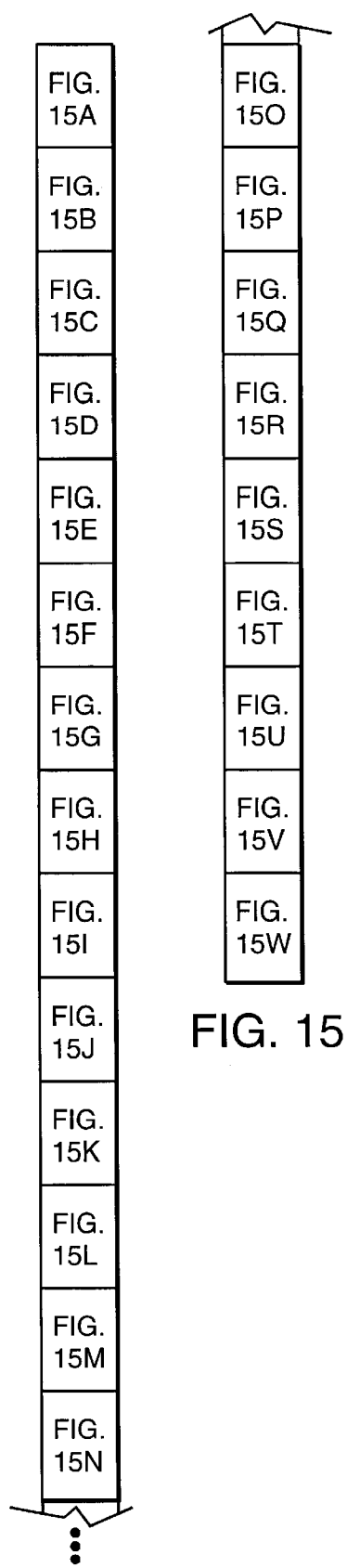

FIG. 15 provides the sequence of the PKD1 transcript (Seq. I.D. No. 7) and predicted protein (Seq. I.D. No. 8). The full sequence of 14,148 bp from the transcription start site to the poly A tail is shown. The probable signal sequence of 23 amino acids is shown after the first methionine (underlined) plus the cleavage site (arrow). The predicted transmembrane (TM) domains (double underlined and numbered) and N-linked glycosylation sites (asterisk) are indicated. The position of a possible hinge sequence is underlined and tyrosine kinase and protein kinase C phosphorylation sites marked with a box and circle, respectively.

FIG. 16(a). The leucine rich repeats (LRRs) found in the PKD1 protein (72–125aa) are compared with each other and to the LRR consensus (Rothberg, 1990; Kobe, 1994); a, aliphatic. A total of just over 2 full repeats are present in PKD1 but they have been arranged into 3 incomplete repeats to show their similarity to those found in slit (Rothberg, 1990). The black boxes show identity to the LRR consensus and shaded boxes other regions of similarity between the repeats which have also been noted in other LRRs (Kobe, 1994).

FIG. 16(b). The amino flanking region to the LRR in the PKD1 protein (33–71aa) is compared similar regions from a variety of other proteins. Black boxes shown identity with the consensus (adapted from [Rothberg, 1990 #1126]) and shaded boxes conserved amino acids. The different types of residue indicated in the consensus are: a, as above; p, polar or turn-like; h, hydrophobic. The listed proteins, with the species and Protein Identification Resource no. (PIR) shown in brackets, are: OMgp, oligodendrocyte myelin glycoprotein (Human, A34210); Slit (Drosophila; A36665); Chaoptin (Drosophila; A29943); GP-IB Beta, platelet glycoprotein 1bβ chain (Human; A31929); Pg1, proteoglycan-1 (mouse; 520811); Biglycan (Human; A40757); Trk (Human; A25184) and LH-CF, lutropinchoriogonadotrophin receptor (Rat; A41343).

FIG. 16(c). The carboxy flanking region of the LRR repeat from the PKD1 protein (126–180 aa) compared to similar regions in other proteins and a consensus accepted from [Rothberg, 1990 #1126]. The shading and amino acid types are as above. The proteins not described above are: Toll (Drosophila; A29943) and GP IX, platelet glycoprotein IX (Human; A46606).

FIG. 17 is a sequence comparison of the C-type lectin domain. The PKD1 lectin domain (403–532aa) is compared to those of: BRA3, acorn barnacle lectin (JC1503); Kupffer cell carbohydrate-binding receptor (Rat; A28166), CSP, cartilage specific protoglycan (Bovine; A27752); Agp; asialoglycoprotein receptor (Human; 55283), E-Selectin (Mouse; B42755) and glycoprotein gp120 (Human; A46274). Black squares show identify with the consensus and shaded boxes conserved residues. Amino acid types are: Very highly conserved residues are shown in bold in the consensus which is adapted from Drickamer 1987, Drickamer 1988.

FIG. 18 is a sequence analysis of the Ig-like repeat. The 16 copies of the PKD1 Ig-like repeat (PKDI 273–356 aa; PKDII–XVI, 851–2145aa) are compared to each other and to: V.a. colAi, and C.p. colA collagenases of Vibrio alginolyticus (S19658) and Clostridium perfringens (D13791), respectively; Pmel17, melanocyte specific glycoprotein (Human; A41234), FLT4, Ig repeat IV of fms-like tyrosine kinase 4 (Human; X68203), CaVPT, Ig repeat I of target protein of the calcium vector protein (CAVP) (amphioxius; PO5548). black boxes shown amino acids identical in more than 5 repeats and shaded boxes related residues. An Ig consensus determined from Harpaz et al. 1994 and Takagi et al. 1990 is shown in the symbols: a, aliphatic; h, hydrophobic; s, small and b, base with the predicted positions of the β-strands indicated below. The PKD repeat IV has an extra repetition of 20 aa in the centre of the repeat while all of the others are between 84–87 aa.

Figure 19B:
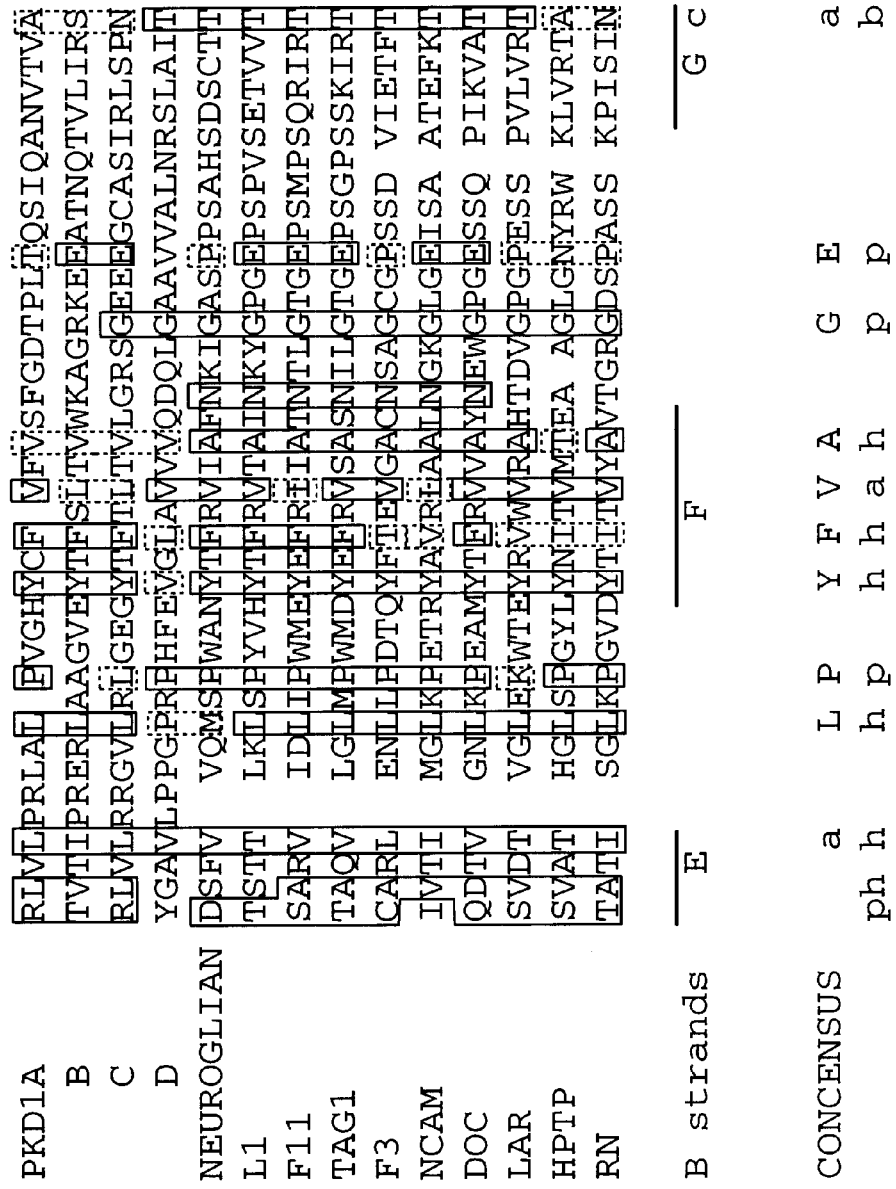

FIG. 19 reveals type III-related fibronectin domains. The four fibronectin-related domains from the PKD1 protein (2169–2573aa) are compared to similar domains in: Neuroglian (Drosophila; A32579); L1, neural recognition molecule L1 (X59847); F11, neural cell recognition molecule F11 (X14877); TAG 1, transiently expressed axonal surface glycoprotein-1 (Human; S28830); F3, Neuro-1 antigen (mouse; SO5944); NCAM, neural cell adhesion molecule (Rat; X06564); DCC, deleted in colorectal cancer (Human; X76132); LAR, Leukocyte-common antigen related molecule (Human; YOO815); HPTP, β protein tyrosine phosphate beta (Human; X54131) and FN, fibronectin (Human; X02761). The consensus sequence is compiled from Borh and Doolittle (1993), Kuma et al. (1993), Baron et al. (1992) and Borh and Doolittle (1992). Black boxes show identity to highly conserved residues and shaded boxes conserved changes or similarity in less highly conserved positions. The approximate positions of the β strands are illustrated. The fibronectin repeats in the PKD1 protein are linked by sequences of 27aa (A–B), 22aa (B–C) and 7aa (C–D) which are not shown.

Figure 20:
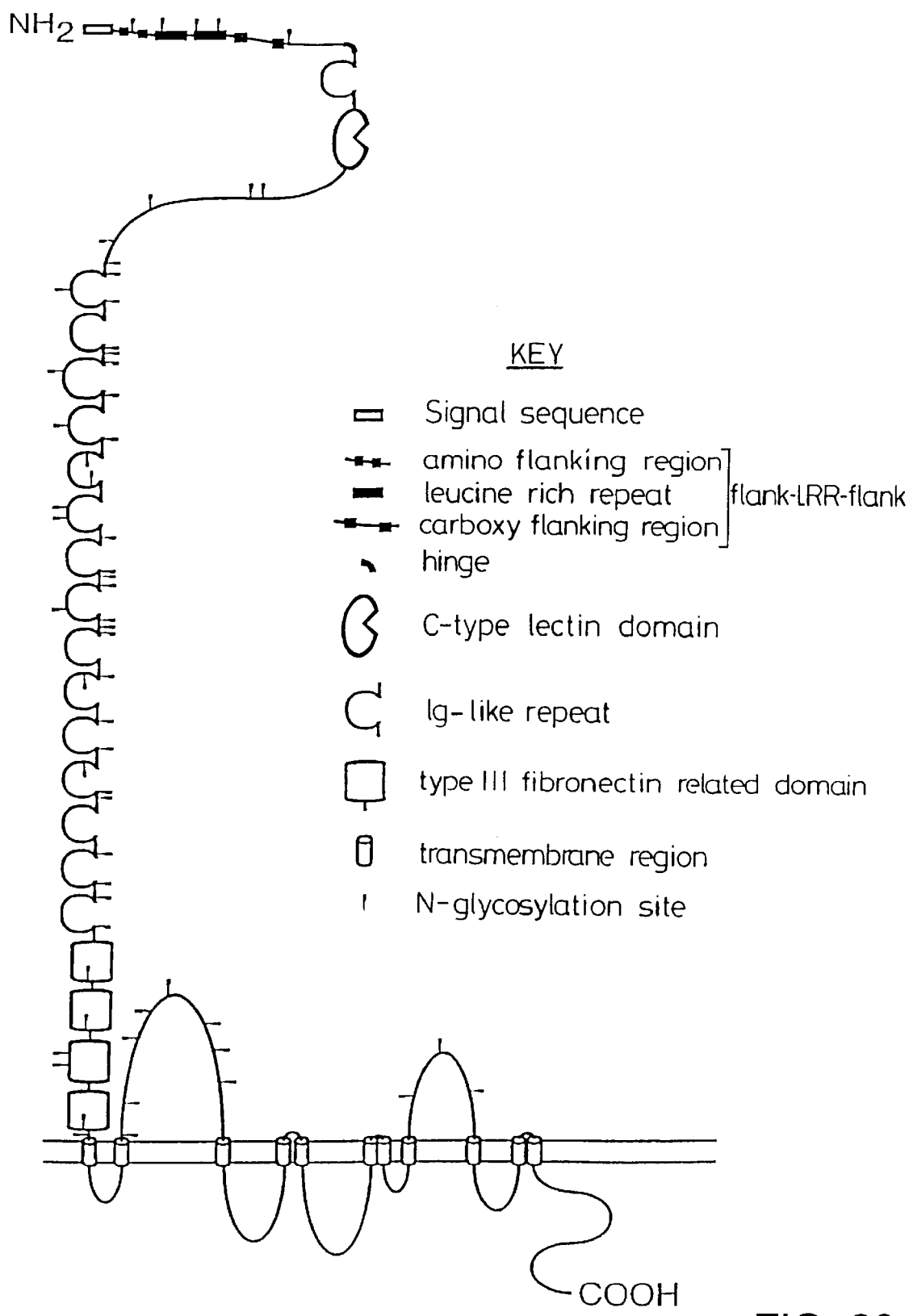

FIG. 20 presents a proposed model of the PKD1 protein, polycystin. The predicted structure of the PKD1 protein is shown.

DETAILED DESCRIPTION

All references mentioned herein are listed in full at the end of the description which are herein incorporated by reference in their entirety. Except where the context clearly indicates otherwise, references to the PBP gene, transcript, sequence, protein or the like can be read as referring to the PKD1 gene, transcript, sequence, protein or the like, respectively.

A Translocation Associated with ADPKD

A major pointer to the identity of the PKD1 gene was provided by a Portuguese pedigree (family 77) with both ADPKD and TSC (FIG. 1b). Cytogenetic analysis showed that the mother, 77-2, has a balanced translocation, 46XX t(16;22) (p13.3;q11.21) which was inherited by her daughter, 77-3. The son, 77-4, has the unbalanced karyotype, 45XY-16−22+der(16) (16qter→16p13.3:22q11.21→2qter) and consequently is monosomic for 16p13.3→16pter as well as for 22q11.21→22pter. This individual has the clinical phenotype of TSC (see Experimental Procedures); the most likely explanation is that the TSC2 locus located within 16p13.3 is deleted in the unbalanced karyotype.

Further analysis revealed that the mother (77-2), and the daughter (77-3) with the balanced translocation, have the clinical features of ADPKD (see Experimental Procedures), while the parents of 77-2 were cytogenetically normal, with no clinical features of TSC and no renal cysts on ultrasound examination (aged 67 and 82 years). Although kidney cysts can be a feature of TSC, no other clinical signs of TSC were identified in 77-2 or 77-3, making it unlikely that the polycystic kidneys were due to TSC. We therefore investigated the possibility that the translocation disrupted the PKD1 locus in 16p13.3 and proceeded to identify and clone the region containing the breakpoint.

The 77 family was analyzed with polymorphic markers from 16p13.3. Individual 77-4 was hemizygous for MS205.2 and GGG1, but heterozygous for SM6 and more proximal markers, locating the translocation breakpoint between GGG1 and SM6 (see FIG. 1a). Fluorescence in situ hybridization (FISH) of a cosmid from the TSC2 region, CW9D (cosmid 1 in FIG. 1a), to metaphase spreads showed that it hybridized to the der(22) chromosome of 77-2; placing the breakpoint proximal to CW9D and indicating that 77-4 was hemizygous for this region consistent with his TSC phenotype. DNA from members of the 77 family was digested with Cla I, separated by PFGE and hybridized with SM6; revealing a breakpoint fragment of about 100 kb in individuals with the der(16) chromosome (FIG. 1c). The small size of this novel fragment enabled the breakpoint to be localized distal to SM6 in a region of just 60 kb (FIG. 1a).

A cosmid contig covering this region was therefore constructed (see Experimental Procedures for details).

The Translocation Breakpoint Lies within a Region Duplicated Elsewhere on Chromosome 16p (16p13.1)

It is noted hereabove that the region between CW21 and N54 (FIG. 1a) was duplicated at a more proximal site on the short arm of chromosome 16 (Germino, et al., 1992; European Chromosome 16 Tuberous Sclerosis Consortium, 1993). FIG. 2 shows that a cosmid, CW10III, from the duplicated region hybridized to two points on 16p; the distal, PKD1 region and a proximal site positioned in 16p13.1. The structure of the duplicated area is complex with each fragment present once in 16p13.3 re-iterated two-four times in 16p13.1 (see FIG. 2). Cosmids spanning the duplicated area in 16p13.3 were subcloned (see FIG. 3a and Experimental Procedures for details) and a restriction map was generated. A genomic map of the PKD1 region was constructed using a radiation hybrid, Hy145.19 which contains the distal portion of 16p but not the duplicate site in 16p13.1.

To localize the 77 translocation breakpoint, subclones from the target region were hybridized to 77-2 DNA, digested with Cla I and separated by PFGE. Once probes mapping across the breakpoint were identified they were hybridized to conventional Southern blots of 77 family DNA. FIG. 3b shows that novel BamH I fragments were detected from the centromeric and telomeric side of the breakpoint, which was localized to the distal part of the probe 8S1 (FIG. 3a). Hence, the balanced translocation was not associated with a substantial deletion, and the breakpoint was located more than 20 kb proximal to the TSC2 locus (FIG. 3a). These results supported the hypothesis that polycystic kidney disease in individuals with the balanced translocation (77-2 and 77-3) was not due to disruption of the TSC2 gene, but indicated that a separate gene mapping just proximal to TSC2, was likely to be the PKD1 gene.

The Polycystic Breakpoint (PBP) Gene is Disrupted by the Translocation

Localization of the 77 breakpoint identified a precise region in which to look for a candidate or the PKD1 gene. During the search for the TSC2 gene we identified other transcripts not associated with TSC including a large transcript (about 14 kb) partially represented in the cDNAs 3A3 and AH4 which mapped to the genomic fragments CW23 and CW21 (FIG. 3a). The orientation of the gene encoding this transcript had been determined by the identification of a polyA tract in the cDNA, AH4: the 3' end of this gene lies very close to the TSC gene, in a tail to tail orientation (European Chromosome 16 Tuberous Sclerosis Consortium, 1993). To determine whether this gene crossed the translocation breakpoint genomic probes from within the duplicated area and flanking the breakpoint were hybridized to Northern blots. Probes from both sides of the breakpoint, between JH5 and JH13 identified the 14 kb transcript (FIG. 3a and see below for details). Therefore, this gene, called 3A3, but not designated the PBP gene extended over the 77 breakpoint and consequently was a candidate for the PKD1 gene. A walk was initiated to increase the extent of the PBP cDNA contig and several new cDNAs were identified using probes from the single copy (non-duplicated) region (see Experimental Procedures for details). A cDNA contig was constructed which extended about 5.7 kb, including about 2 kb into the area that is duplicated (FIG. 3a).

Expression of the PEP Gene

Initial studies of the expression pattern of the PBP gene were undertaken with cDNAs that map entirely within the single copy region (e.g. AH4 and 3A3). FIG. 4a shows that the about 14 kb transcript was identified by 3A3 in various tissue-specific cell lines. From this and other Northern blots we concluded that the PBP gene was expressed in all of the cell lines tested, although often at a low level. The two cell lines which showed the highest level of expression were fibroblasts and a cell line derived from an astrocytoma, G-CCM. Significant levels of expression were also obtained in cell lines derived from kidney (G401) and liver (Hep3B). Measuring the expression of the PBP gene in tissue samples by Northern blotting proved difficult because such a large transcript is. susceptible to minor RNA degradation. However, initial results with an RNAse protection assay, using a region of the gene located in the single copy area (see Experimental Procedures), showed a moderate level of expression of the PBP gene in tissue obtained from normal and polycystic kidney (data not shown). The widespread expression of the PBP is consistent with the systemic nature of ADPKD.

Identification of Transcripts that are Partially Homologous to the PBP Transcript New cDNAs were identified with the genomic fragments, JH4 and JH8, that map to the duplicated region (FIG. 3a and see Experimental Procedures). However, when these cDNAs were hybridized to Northern blots a more complex pattern than that seen with 3A3 was observed. As well as the ~14 kb PBP transcript, three other, partially homologous transcripts were identified designated homologous gene-A (HG-A; ~21 kb), HG-B (~17 kb) and HG-C (8.5 kb) FIG. 4b). There were two possible explanations for these results, either the HG transcripts were alternatively spliced forms of the PBP gene, or the HG transcripts were encoded by gene located in 16p13.1. To determine the genomic location of the HG loci a fragment from the 3' end of one HG cDNA (HG-4/1.1) was isolated. HG-4/1.1 hybridized to all three HG transcripts, but not to the PBP transcript and on a hybrid panel it mapped to 16p13.1 (not the PKD1 area). These results show that all the HG transcripts are related to each other outside the region of homology with the PBP transcript and that the HG loci map to the proximal site (16p13.1).

An Abnormal Transcript Associated with the 77 Translocation

As the PBP gene was transcribed across the region disrupted by the 77 translocation breakpoint, in a proximal to distal direction on the chromosome (see FIG. 3a) it was possible that a novel transcript originating from the PBP promotor would be found in this family. FIG. 4c shows that using a probe to the PBP transcript that mapped mainly proximal to the breakpoint, a novel transcript of approximately 9 kb (PBP-77) derived from the der(16) product of the translocation was detected. Interestingly, the PBP-77 transcript appears to be expressed at a higher level than the normal PBP product. These results confirmed that the 77 translocation disrupts the PBP gene and supports the hypothesis that this is the PKD1 gene.

Mutations of the PBP Gene in other ADPXD Patients

To prove that the PBP gene is the defective gene at the PKD1 locus, we analyzed this region for mutations in patients with typical ADPKD. The 3' end of the PBP gene was most accessible to study as it maps outside the duplicated area. To screen this region BamH I digests of DNA from 282 apparently unrelated ADPKD patients were hybridized with the probe 1A1H.6, (Seq. I.D. No. 3), (see FIG. 3a). In addition, a large EcoR I fragment (41 kb) which contains a significant proportion of the PBP gene was assayed by field inversion gel electrophoresis (FIGE) in 167 ADPKD patients, using the probe CW10 (Seq. I.D. No. 4). Two genomic rearrangements were identified in ADPKD patients by these procedures; each identified by both methods.

The first rearrangement was identified in patient OX875 (see Experimental Procedures for clinical details) who was shown to have a 5.5 kb genomic deletion without the 3' end of the PBP gene, producing a smaller transcript (PBP-875) (see FIGS. 5a, b and 3a for details). This genomic deletion results in a ~3 kb internal deletion of the transcript with the ~500 bp adjacent to the polyA tail intact. In this family linkage of ADPKD to chromosome 16 could not be proven because although OX875 has a positive family history of ADPKD there were no living, affected relatives. However, paraffin-embedded tissue from her affected father (now deceased) was available. We demonstrated that this individual has the same rearrangement as OX875 by PCR amplification of a 220 bp fragment spanning the deletion (data not shown). This result and analysis of two unaffected sibs of OX875, that did not have the deletion, showed that this mutation was transmitted with ADPKD.

The second rearrangement detected by hybridization was a 2 kb genomic deletion within the PBP gene, in ADPKD patient OX114 (see Experimental Procedures for clinical details and FIGS. 5c and 3a). No abnormal PBP transcript was identified by Northern blot analysis, but using primers flanking the deletion (see Experimental Procedures) a shortened product was detected by RT-PCR (FIG. 5c). This was cloned and sequenced and shown to have a frame-shift deletion of 446 bp (between base pair 1746 and 2192 of the sequence shown in FIG. 7 (Seq. I.D. No. 1)). OX114 is the only member of the family with ADPKD (she has no children) and ultrasound analysis of her parents at age 78 (father) and 73 years old (mother) showed no evidence of renal cysts. Somatic cell hybrids were produced from OX114 and the deleted chromosome was found to be of paternal origin by haplotype analysis. The father of OX114 (OX984) with seven microsatellite markers from the PKD1 region, as OX114. Renal ultrasound revealed no cysts in OX984 at age 53 and no deletion was detected by DNA analysis (FIG. 5c). Hence, the deletion in OX114 is a de novo event associated with the development of ADPKD. Although it is not possible to show that the ADPKD on chromosome 16-linked, the location of the PBP gene indicated that this is a de novo PKD1 mutation.

To identify more PKD1 associated mutations, single copy regions of the PBP gene were analyzed by RT-PCR using RNA isolated from lymphoblastoid cell lines established from ADPKD patients. cDNA from 48 unrelated patients was amplified with the primer pair 3A3 C (Seq. I.D. Nos. 11 and 12) (see Experimental Procedures) and the product of 260 bp was analyzed on an agarose gel. In one patient, OX32, an additional smaller product (125 bp) was identified, consistent with a deletion or splicing mutation. OX32 comes from a large family in which the disease can be traced through three generations. Analysis of RNA from two affected sibs of OX32 and his parents showed that the abnormal transcript segregates with PKD1 (FIG. 5d).

Amplification of normal genomic DNA with the 3A3 C primers (Seq. I.D. Nos. 11 and 12) generates a product of 418 bp; sequencing showed that this region contains two small introns (5', 75 bp and 3', 83 bp) flanking a 135 bp exon. The product amplified from OX32 genomic DNA was normal in size, excluding a genomic deletion. However, heteroduplex analysis of that DNA revealed larger heteroduplex bands, consistent with a mutation within that genomic interval. The abnormal OX32, RT-PCR product was cloned and sequenced: this demonstrated that, although present in genomic DNA, the 135 bp exon was missing from the abnormal transcript. Sequencing of OX32 genomic DNA demonstrated a G→C transition at +1 of the splice donor site following the 135 bp exon. This mutation was confirmed in all available affected family members by digesting amplified genomic DNA with the enzyme Bst NI: a site is destroyed by the base substitution. The splicing defect results in an in-frame deletion of 135 bp from the PBP transcript (3696 bp to 3831 bp of the sequence shown in FIG. 7 (Seq. I.D. No. 1)). Together, the three intragenic mutations confirm that the PBP gene is the defective gene at the PKD1 locus.

Deletions that Disrupt the TSC2 and the PKD1 Gene

The deletion called WS-53 disrupts both the TSC2 gene and the PKD1 gene (European Chromosome 16 Tuberous Sclerosis Consortium, 1993), although the full proximal extent of the deletion was not determined. Further study has shown that the deletion extends ~100 kb (see FIG. 6 for details) and deletes most if not all of the PKD1 gene. This patient has TSC but also has unusually severe polycystic disease of the kidneys. Other patients with a similar phenotype have also been under investigation. Deletions involving both TSC2 and PKD1 were identified and characterized in six patients in whom TSC was associated with infantile polycystic kidney disease. As well as the deletion in WS-53, those in WS-215 and WS-250 also extended proximally well beyond the known distribution of PKD1 and probably delete the entire gene. The deletion in WS-194 extended over the known extent of PKD1, but not much further proximally, while the proximal breakpoints in WS-219 and WS-227 lay within PKD1 itself. Northern analysis of case WS-227 lay within PKD1 itself. Northern analysis of case WS-219 with probe JH8, which lies outside the deletion, showed a reduced level of the PKD1 transcript but no evidence of an abnormally sized transcript (data not shown). Analysis of samples from the clinically unaffected parents of patients WS-53, WS-215, WS-219, WS-227 and WS-250 showed the deletions in these patients to be de novo. The father of WS-194 was unavailable for study.

In a further case (WS-212), renal ultrasound showed no cysts at four years of age but a deletion was identified which removed the entire TSC2 gene and deleted an XbaI site which is located 42 bp 5' to the polyadenylation signal of PKD1. To determine the precise position of the proximal breakpoint in PKD1, a 587 bp probe from the 3' untranslated region (3'UTR) was hybridized to XbaI digested DNA. A 15 kb XbaI breakpoint fragment was detected with an approximately equal intensity to the normal fragment of 6 kb, indicating that most of the PKD1 3'UTR was preserved on the mutant chromosome. Evidence that a PKD1 transcript is produced from the deleted chromosome in WS-212 was obtained by 3' rapid identification of cDNA ends (RACE) with a novel, smaller product generated from WS-212 cDNA. Characterization of this product showed that polyadenylation occurs 546 bp 5' to the normal position, within the 3'UTR of PKD1 (231 bp 3' to the stop codon at 5073 bp of the described PKD1 sequence[14] (Seq. I.D. No. 1)). A transcript with an intact open reading frame is thus produced from the deleted WS-212 chromosome. It is likely that a functional PKD1 protein in produced from this transcript, explaining the lack of cystic disease in this patient. The sequence preceding the novel site of polyA addition is: AGTCAGT<u>AATTTA</u>TATGGTGTTAAAATGTG(A)n (Seq. I.D. No. 22). Although not conforming precisely to the consensus of AATAAA, it is likely that part of this AT rich region acts as an alternative polyadenylation signal if, as in this case, the normal signal is deleted (a possible sequence is underlined).

The WS-212 deletion is 75 kb between SM9-CW9 distally and the PKD1 3'UTR proximally. The WS-215 deletion is 160 kb between CW15 and SM6-JH17. WS-194 has 65 kb deleted between CW20 and CW10-CW36. WS-227 has a 50 kb deletion between CW20 and JH11 and WS-219 has a 27 kb deletion between JH1 and JH6. The distal end of the WS-250 deletion is in CW20 but the precise location of the proximal end is not known. However, the same breakpoint fragment of 320 kb is seen with PvuI-digested DNA using probes on adjacent PvuI fragments, CE18 (which normally detects a 245 kb fragment) and Blu24 (235 kb). Hence this deletion can be estimated ~160 kb. b. PFGE analysis of the deletion in WS-219. MluI digested DNA from a normal control (N) and WS-219 probed with the clones H2, JH1, CW21 and CW10 (Seq. I.D. No. 4) which detect an ~130 kb fragment in normal individuals. CW10 (Seq. I.D. No. 4) also detects a much smaller fragment from the duplicated region situated more proximally on 16p. A novel fragment of ~100 kb is seen in WS-219 with probes H2 and CW10 (Seq. I.D. No. 4) which flank the deletion in this patient. JH1 is partially deleted but detects the novel band weakly. The aberrant fragment is not detected by CW-21, which is deleted on the mutant chromosome. BamHI digested DNA of normal control (N) and WS-219 separated by conventional gel electrophoresis and hybridized to probes JH1 and JH6 which flank the deletion. The same breakpoint fragment of ~3 kb is seen with both probes, consistent with a deletion of ~27 kb ending within the BamHI fragments seen by these probes.

Two Further Deletions

In addition we have characterized two further mutations of this gene which were identified in typical PKD1 families. In both cases the mutation is a deletion in the 75 bp intron amplified by the primer pair 3A3C (Seq. I.D. Nos. 11 and 12) (European Polycystic Kidney Disease Consortium, 1994). The deletions are of 18 bp and 20 bp, respectively, in the patients 461 and OX1054. Although these deletions do not disrupt the highly conserved sequences flanking the exon/intron boundaries, they do result in aberrant splicing of the transcript. In both cases, two abnormal mRNAs are produced, one larger and one smaller than normal. Sequencing of these cDNAs showed that the larger transcript includes the deleted intron, and so has an in-frame insertion of 57 bp in 461, while OX1054 has a frameshift insertion of 55 bp. The smaller transcript is due to activation of a cryptic splice site in the exon preceding the deleted intron and results in an in-frame deletion of 66 bp in both patients. The demonstration of two additional mutations of this gene in PKD1 patients further confirms that this is the PKD1 gene.

Partial Characterization of the PKD1 Gene

To characterize the PKD1 gene further, evolutionary conservation was analyzed by 'zoo blotting'. Using probes from the single copy, 3' region (3A3) and from the duplicated area (JH4, JH8) the PKD1 gene was conserved in other mammalian species, including horse, dog, pig and rodents (data not shown). No evidence of related sequences were seen in chicken, frog or drosophila by hybridization at normal stringency. The degree of conservation was similar when probes from the single copy of the duplicated region were employed.

Although the full genomic extent of the PKD1 gene was not yet known, results obtained by hybridization to Northern blots showed that it extended from at least as far as JH13. Several CpG islands were localized 5' of the known extent of the PKD1 gene (FIG. 6), although there was no direct evidence that any of these are associated with this gene.

The cDNA contig extending 5631 bp to the 3' end of the PKD1 transcript was sequenced; where possible more than one cDNA was analyzed and in all regions both strands were sequenced (FIG. 7) (Seq. I.D. No. 1). We estimated that this accounts for ~40% of the PKD1 transcript. An open reading frame was detected which runs from the 5' end of the region sequenced and spans 4842 bp, leaving a 3' untranslated region of 789 bp which contains the previously described microsatellite, KG8 (Peral, et al., 1994; Snarey, et al., 1994). A polyadenylation signal is present at nucleotides 5598–5603 and a polyA tail was detected in two independent cDNAs (AH4 and AH6) at position 5620. Comparison with the cDNAs HG-4 and 11BHS21, which are encoded by genes in the duplicate, 16p13.1 region, show that 1866 bp at the 5' end of the partial PKD1 sequence shown in FIG. 7 (Seq. I.D. No. 1) lies within the duplicated area. The predicted amino acid sequence from the available open reading frame extends 1614 residues, and is shown in FIG. 7 (Seq. I.D. No. 2). A search of the swissprot and NBRF data bases with the available protein sequence, using the Blast program (Altschul, et al., 1990) identified only short regions of similarity (notably, between amino-acids 690–770 and 1390–1530) to a diverse group of proteins; no highly significant areas of homology were recognized. The importance of the short regions of similarity is unclear as the search for protein motifs with the ProSite Program did not identify any recognized functional protein domains within the PKD1 gene.

The test of identifying and characterizing the PKD1 gene has been more difficult than for other disorders because more than three quarters of the gene is embedded in a region of DNA that is duplicated elsewhere on chromosome 16. This segment of 40–50 kb of DNA, present as a single copy in the PKD1 area (16p13.3), is reiterated as several divergent copies in the more proximal region, 16p13.1. This proximal site contains three gene loci (HG-A, -B and -C) that each produce polyadenylated mRNAs and share substantial homology to the PKD1 gene; it is not known whether these partially homologous transcripts are translated into functional proteins.

Although gene amplification is known as a major mechanism for creating protein diversity during evolution, the discovery of a human disease locus embedded within an area duplicated relatively recently is a new observation. In this case because of the recent nature of the reiteration the whole duplicated genomic region retains a high level of homology, not just the exons. The sequence of events leading to the duplication and which sequence represents the original gene locus are not yet clear. However, early evidence of homology of the 3' ends of the three HG transcripts which are different from the 3' end of the PKD1 gene indicated that the loci in 16p13.1 have probably arisen by further reiteration of sequences at this site, after it separated from the distal locus.

To try to overcome the duplication problem we employed an exon linking approach using RNA isolated from a radiation hybrid, HY145.19, that contains just the PKD1 part of chromosome 16, and not the duplicate site in 16p13.1. Hence, this hybrid produces transcripts from the PKD1 gene but not from the homologous genes (HG-A, HG-B and HG-C). We have also sequenced much of the genomic region containing the PKD1 gene, from the cosmid JH2A, and have sequenced a number of cDNAs from the HG locus. To determine the likely position of PKD1 exons in the genomic DNA we compared HG cDNAs, (HG-4 and HG-7) to the genomic sequence. We then designed primers with sequences corresponding to the genomic DNA, to regions identified by the HG exons and employing DNA generated from the hybrid HY145.19, we amplified sections of the PKD1 transcript. The polymerase Pfu was used to minimise incorporation errors. These amplified fragments were then cloned and sequenced. The PKD1 cDNA contig whose sequence is shown in FIG. 10 is made up of (3'-5') the original 5.7 kb of sequence shown in FIG. 7 (Seq. I.D. No. 1), and the cDNAs: gap α 22 (890 bp), gap gamma (872 bp), a section of genomic DNA from the clone JH8 (2,724 bp) which corresponds to a large exon, S1-S3 (733 bp), S3-S4 (1,589 bp) and S4-S13 (1,372 bp). Together these make a cDNA of 13,807 nt. When these cDNAs from the PKD1 contig were sequenced an open reading frame was found to run from the start of the contig to the stop codon, a region of 13,018 bp (Seq. I.D. No. 5). The predicted protein encoded by the PKD1 transcript is also shown in FIG. 10 (Seq. I.D. No. 6) and has 4,339 amino acid residues.

Cloning a Full Length PKD1 cDNA cDNAs known to originate from the PKD1 or HG transcripts show on average a sequence divergence of less than 3%. Consequently, although many cDNAs were identified by hybridisation of various PKD1 genomic probes to cDNA libraries, it proved difficult to differentiate genuine PKD1 clones from those of the HG transcripts. For this reason a novel strategy was employed to clone the PKD1 transcript.

To obtain a template of genomic sequence of the PKD1 gene, clones which contain the transcribed region, JH6 and JH8-JH13, were sequentially truncated and sequenced. These clones were isolated from the cosmid JH2A, which extends into the single copy area containing the 3' portion of the PKD1 gene (FIG. 13) and hence represents the PKD1 and not the HG loci. As a result of this analysis a contig of about 18 kb of genomic sequence was generated, which was ultimately found to encode >95% of the unsequenced portion of the PKD1 transcript.

A number of HG cDNA clones identified by the DNA probes JH8 or JH13 (including HG-4, HG-7C and 13A1) were sequenced. Clones identified by JH8 were chosen because this genomic area is duplicated fewer times than the surrounding DNA, with only the HG-A and HG-B transcripts (not HG-C) homologous to this region. The comparison of these cDNA and genomic sequences showed a characteristic intron/exon pattern and we concluded that the exons highlighted in the genomic sequence were likely to be exons of the PKD1 gene. To prove this, pairs of primers matching the sequence of the putative PKD1 exons and spaced 0.7–2 kb apart in the proposed transcript, were synthesised. Employing RNA from a radiation hybrid, HY145.19, that contains the PKD1 but not the HG loci, PKD1 specific cDNAs were amplified by RT-PCR and cloned (see Experimental Procedures for details). In this way, a number of overlapping cDNAs spanning the PKD1 transcript, for the cDNAs at the 3' end to those homologous to JH13 were cloned (FIG. 13).

Analysis of a further cDNA, HG-6 showed that a short region (~100 bp) of HG-6 lay 5' to the sequenced genomic region and this was located by hybridisation to the genomic clone SM3 (FIG. 13); SM3 was subsequently sequenced. The position of the cDNA in SM3 was identified and the possible 5' extent of this exon was determined in the genomic sequence; and in-frame stop codon was identified hear the 3' end of the exon. This exon lay at a CpG island (described hereinafter) suggesting, along with the presence of the stop codon, that this may be the first exon of the PKD1 gene. to determine the likely transcriptional start site the method of primer extension from three different oligos within the first exon was employed (see Experimental Procedures). In all cases, a transcriptional start was identified at the same G nucleotide and showed the first exon to be 426 bp. The structure of the PKD1 transcript was confirmed by a final exon link, rev1 which starts 3 bp 3' to the proposed transcriptional start (see FIG. 13 and Experimental Procedures for details).

The Intron/exon Structure of the PKD1 Gene

Sequencing the cDNA contig revealed a total sequence of 14,148 bp which extends over approximately 52 bp of genomic sequence from SM3 to BFS5 (FIG. 13). We were able to determine the intron/exon structure of much of the gene by direct comparison between the cDNA and genomic sequence. In the 3' region of the gene (JH5-BFS5), a partial genomic sequence was obtained at intron/exon borders by sequencing the corresponding genomic clone from exonic primer.

The PKD1 CpG Island

The 5' end of the gene lies at CpG island SM3. SM3 is located entirely within the duplicated region, but this clone was isolated from the cosmid SM11 which extends through the duplicated area into the proximal flanking single copy region and therefore is known to originate from this area. FIG. 14 shows a map of the PKD1 CpG island including genomic sites for several methylation sensitive enzymes, the location of the first exon and the GC content across the island. Evidence that the enzyme sites in the PKD1 region (and not just the HG area) digest, was obtained by pulsed field gel electrophoresis with the enzymes Mlul, Notl and BssHll using probes outside the duplicated area. Digestion of the Sacll sites and confirmation of the Notl site was made with a panel of somatic cell hybrids which either contain just the HG (P-MWH2A) or just the PKD1 locus (Hy145.19). These results showed that the Sacll and Notl sites digest in both sets of hybrids (data not shown), indicating that this region is a CpG island in the HG as well as the PKD1 area. Further proof that this is the likely position of a functional promoter was obtained by analysis for DNAase 1 hypersensitivity. A DNAase hypersensitive site in the region 5' to the transcription start site in SM3 was detected (FIGS. 14a and b).

Analysis of the PKD1 Transcript

Analysis of the sequence shows an open reading frame running from the start of the sequence to position 13,117 bp (FIG. 15) (Seq. I.D. No. 7). Detailed sequencing of the genomic region containing the 3' portion of the gene revealed two extra Cs at positions 13,081-2 (FIG. 15) (Seq. I.D. No. 7). An in-frame start codon which is consistent with the Kozak consensus was detected at position 212 bp; just 3' to the stop codon in the 5'UTR. Analysis for a signal sequence cleavage site using the von Hinge (von Hinge 1986) algorithm showed a high probability of a hydrophobic signal sequence with cleavage at amino acid 23 (see FIG. 15) (Seq. I.D. No. 8). The total length of the predicted protein is 4302 aa with a calculated molecular mass after excision of the signal peptide of 460 kD and an estimated isoelectric point of 6.26. However, this may be an underestimate of the total mass of the protein as many potential sites for N-linked glycosylation are present (FIG. 15) (Seq. I.D. No. 8).

Homologies with the PKD1 Protein

The predicted PKD1 protein was analysed for homologies with know proteins in the SwissProt and NBRF databases using the BLAST Altschul et al 1990) and FASTA algorithms. This analysis revealed two clear homologies and also a number of other potential similarities which were studied on detail.

Leucine Rich Repeat

Near the 5' end of the PKD1 protein is a region of leucine rich-repeats (LRRs). LRRs are a highly conserved motif usually of 24 residues with precisely spaced leucines (or other aliphatic amino acids) and an asparagine at position 19 (FIG. 16a and reviewed in Kobe and Reisenhofer (1994)). Two complete LRRs plus a partial repeat unit are found in the PKD1 protein, which have complete homology with the LRR consensus.

Surrounding the LRRs are distinctive cysteine-rich amino and carboxy flanking regions (FIGS. 16b and c). This flank-LRR-flank structure is exclusively found on proteins in extracellular locations and is thought to be involved in protein-protein interactions such as adhesion to other cells or to components of the extracellular matrix or as a receptor concerned with binding or signal transduction. The structure found in the PKD1 protein is similar to that found in the Drosophila protein, slit, which is important for normal central nervous system development (Rothberg, 1990). Although slit contains far more LRRs than the PKD1 protein, with four blocks each consisting of 4 or 5 repeat units, the structure of each block is similar as they finish on the amino and carboxy side with shortened LRRs which are immediately flanked by the cysteine rich regions. In the PKD1 protein two shortened LRRs surround one complete repeat unit and immediately abut the amino and carboxy flanking regions.

The amino flanking region consists of four invariant cysteines and a number of other highly conserved residues in an area of 30–40 amino acids; comparison of the PKD1 region to amino flanking motifs of other proteins is shown in FIG. 4b. The carboxy flanking region extends over an area of between 50–60 residues and consists of an invariant proline and four cysteines plus several other highly conserved amino acids. The similarity of the PKD1 region to carboxy flanking regions from other proteins is shown in FIG. 4c.

Some LRR proteins, such as slit (Rothberg 1990) and small proteoglycans are wholly extracellular but others including Toll (Hashimoto et al, 1990) and trkc (Lamballe 1991) have a single transmembrane sequence, while the LH-CRG receptor and related proteins have seven transmembrane segments and are involved in signal transduction.

C Type Lectin Domain

Analysis of the sequence from exons 6 and 7 showed a high level of homology with a C type lectin domain. C type lectins are found in a variety of proteins in extracellular locations where they bind specific carbohydrates in the presence of $Ca^{2+}$ ion (Drickamer 1987, 1988; Weiss 1992). FIG. 17 illustrates the similarity of the PKD1 lectin domain to those found in a number of proteins including: proteogylcans, which interact with collagens and other components of the extracellular matrix; endocytic receptors, and selecting which are involved in cell adhesion and recognition. Three different selecting have been identified: E-selectin (endothelium), P-selectin (platelets) and L-selectin (lymphocytes) and these work with other cell adhesion molecules to promote binding of the cell carrying the selectin to various other target cells.

Immunoglobulin-like Repeat Motif

Significant homologies were detected between a region of exon 5 and three regions of exon 15, with the same conserved sequence, WDFGDGS (Seq. I.D. No. 8), which is also found in a melanocyte-specific secreted glycoprotein, Pmel17 (Kwon et al, 1991) and three prokaryotic collagenases or proteinases (Ohara et al, 1989, Takeuchi et al, 1992 and Matsushita et al, 1994). Further analysis of the amino acid sequence of the PKD1 protein showed that a conserved region of approximately 85 bp could be discerned around this central sequence and that 16 copies of this repeat were present in the PKD1 protein; 1 in exon 5 and the other 15 as a tandem array in exons 11 to 15. FIG. 18 shows that a highly conserved structure is maintained between the repeats although in some cases less similarity is noted with the WDFGDGS (Seq. I.D. No. 8) sequence. Further analysis of the most conserved residues found in the repeat units showed similarity to various immunoglobulin (Ig) domains; two Ig repeats which show particular homology to the PKD1 protein are shown (FIG. 18). The repeat unit is most similar to that found in a number of cell adhesion and surface receptors which have recently been defined as the I set of Ig domains (Harpaz 1994). Ig repeats consist of 7–9 β strands of 5–10 residues linked by turns which are packed into two β sheets. The B, C, F and G β-strands of the I set are particularly similar to the PKD1 repeat, although the highly conserved cystine residues which stabilise the two β sheets through a disulphide bond are absent. The D and E β strands, however, seem less similar and in some cases are significantly shortened or apparently absent.

Further evidence that this PKD1 repeat has an Ig-like structure is found by analysis of the secondary structure with the predominant configuration found of β strands linked by turns. The WDFGDS (Seq. I.D. No. 23) area of the Ig molecule is one that often has a specific binding function (Jones et al., 1995) and this sequence may have a specific binding role in polycystin.

Type III Fibronectin-related Domains

Analysis of the secondary structure of the PKD1 protein beyond the carboxy end of the region of Ig-like repeats showed a continuation of the β stand and turn structure. No evidence of further Ig-like repeats could be found in this area but three pairs of evenly spaced (38–40aa) tryptophan and tyrosine residues was noted which are the most highly conserved positions of the type III fibronectin repeat which has a similar secondary structure to Ig domains. Further analysis and comparison with other type III fibronectin domains showed that in total four fibronectin repeats (one with leucine replacing the conserved tyrosine) could be recognised in this area with many of the most highly conserved residues of this domain found in the PKD1 repeat (FIG. 20).

A large number of proteins with Ig-like repeats have now been described which are involved in cell-cell interactions and cell adhesion (reviewed in Brummendork and Rathjen, 1994), while type III fibronectin (FNIII) domains are found on extracellular matrix molecules and adhesion proteins. A number of cell adhesion proteins which are located mainly on neural cells, have both Ig-like and FNIII-related domains. In these cases the FNIII repeats are always positioned C-terminal of the Ig-like units and close to a transmembrane domain; a similar pattern is seen in the proposed structure of polycystin. These Ig/FNIII containing proteins such as neuroglican and NrCAM are thought to be involved in neuron-neuron interactions and the patterning of the axonal network.

Many cell adhesion proteins of the Ig superfamily are also involved in communication and signal transduction mediated through their cytoplasmic tails. These cytoplasmic regions are known to bind to cytoskeletal proteins and other intracellular components, and phosphorylation of this part of the molecule is also thought to affect adhesive properties of the protein; potential phosphorylation sites are found in the cytoplasmic tail and one intracellular loop of polycystin (FIG. 20).

Transmembrane Regions

Analysis of hydrophobicity predicted that the deduced protein is an integral membrane protein with a signal peotide and multiple transmembrane (TM) domains located in the C-terminal region. From this analysis 11 regions (including the signal peptide) had a mean hydrophobicity indice higher than 1.4 and therefore were considered as certain membrane spanning domains (see Experimental Procedures for details). Three others with a mean hydrophobicity indice between 0.75–1.0 were considered as putative TM domains. The most likely topology of the protein was predicted using TopPed II programme (see Experimental Procedures for details) and the resulting model included one putative segment plus the 10 certain transmembrane domains and the signal peptide. According to this model the N-terminal end is extracellular and the (highly hydrophobic) carboxyterminal region is anchored to the membrane by 11 membrane-spanning segments, with the highly charged carboxy end located in the cytoplasm. This topology is supported by the study of N-glycosylation sites with all but one site, out of a total of 61 predicted, in an extracellular location according to the model, including 11 in the two large extracellular loops between TM regions.

However, if degree of hydrophobicity required to define a certain putative transmembrane region is altered within the model, the predicted number of such domains can change to 9 (excluding the most N-terminal pair) or 13 (with two new domains defined between TM7 and TM8). This can be ascertained by studies with specific antibodies.

Most transmembrane proteins containing the types of cell adhesion domain found on polycystin have a single transmembrane domain. The role of the multiple membrane spanning domains found in polycystin is not yet clear.

Proposed Structure of the PKD1 Protein

From the detailed analysis of the predicted PKD1 protein sequence a model of the likely structure of the protein can be formulated (FIG. 20). This model predicts an extracellular N-terminal region of approximately 2550 aa containing several distinctive extracellular domains and an intracellular C-terminus of approximately 225 aa. The intervening region of nearly 1500 aa is associated with the membrane with 11 transmembrane regions predicted and 10 variously sized extracellular and cytoplasmic loops (see FIG. 20). A proline rich hinge is found between the flank-LRR-flank region and the first Ig-like repeat. Two phosphorylation sites for tyrosine kinase and protein kinase C are found in cytoplasmic locations (FIG. 15 (Seq. I.D. No. 8) and 20).

Therefore, the PKD1 protein, named polycystin, has highlighted several clear domains, plus a reiterated motif that occupies over 30% of the protein.

Characterisation of the PKD1 gene has proven to be a uniquely difficult problem because most of the gene lies in a region which is reiterated elsewhere on the chromosome. The high degree of similarity between the two areas (>97%) both in exons and introns has meant that a novel approach has been required to clone the full length transcript; involving extensive genomic sequencing and generating cDNAs from a cell line with the PKD1 but not the HG loci. In this way a contig containing the entire PKD1 transcript has now been cloned.

Preliminary analysis shows that the HG genes are very similar to PKD1 both in terms of genomic structure and sequence over most of their length (apart from the novel 3' regions). The 5' end of the PKD1 gene is at a CpG island which lies within the duplicated area. Homologous areas to this island, in the HG region, also have cleavable sites for methylation sensitive enzymes; these duplicate islands probably lie at the 5' ends of the various HG genes. Analysis for DNAase hypersensitivity also inindicates that the HG, CpG islands probably contain active promoters. These results are consistent with the observation of polyadenylated mRNA from the HG genes on Northern blots and the similarity of the expression pattern of the HG and PKD1 genes in different tissue specific cell lines. The HG genes may have complete open reading frames and may encode functional proteins. Antibodies to their 'unique' 3' regions will be required to determine this. Although the PKD1 transcript is large, the overall size of the gene, at 52 kb, is not (the Duchenne muscular dystrophy (DMD) gene which encodes a slightly smaller transcript has a genomic size of over 2 Mb). Indeed, if the first intron of PKD1 is excluded from the analysis, 40.3% of the remainder of the gene is found in the mature mRNA. In the compact structure of the PKD1 gene, some of the introns are close to or smaller than the minimal size of 80 bp thought to be required for efficient splicing, although they are presumably excised effectively. We have shown that deletion of 18 or 10 bp from one small intron (intron 43), resulting in an intron of 55 or 57 bp, leads to aberrant splicing (Peral, 1995). Similar mutations may be found in the other small introns of this gene. The compact nature of the PKD1 gene probably reflects the GC rich area of the genome in which it is found (the PKD1 transcript has a total GC content of about 65%); a. similar organisation is seen in other genes from the area of chromosome 16 (Vyas, 1992) is in an AT rich genomic region.

It is clear that polycystin has many features of a cell adhesion or recognition molecule with multiple different extracellular domains. These various binding domains are likely to have different specificities so that it can be envisaged that it will bind to a variety of different proteins (and carbohydrates) both on other cells and possibly in the extracellular matrix. Although provisional evidence indicates a wide range of expression of polycystin in tissue specific cell lines, detailed analysis by in situ of the mRNA and with antibodies to determine the cells expressing this protein both in adult tissue and during development will provide further evidence.

Initial analysis has revealed little clear evidence of alternate splicing, although one cDNA (out of 6 studied) had an extra exon of 255 bp positioned in intron 16. This exon contains an in-frame stop codon and it is not known at this stage if this represents an incompletely spliced mRNA or a splice form of polycystin which terminates at this point. Truncation of the protein here would leave a secreted protein lacking all of the transmembrane and cytoplasmic regions. Interestingly, a similar secreted form of the neural adhesion protein, NCAM, which is normally attached to the cell membrane, is produced by alternate splicing by insertion of an exon containing a stop codon (Gower et al., 1988).

The initial changes that have been noted in ADPKD kidneys are abnormal thickening and splitting of the basement membrane (BM) and simultaneous de-differentiation of associated epithelial cells at the point of tubular dilation. Similar results have been noted in the heterozygote Han:SPRD rat (Schafer et al., 1994) which is a dominant model of PKD, although it is not known if it is a rat model of PKD1. Concurrent changes in cellular characteristics and the BM suggests that a disruption or alteration of communication between the cell and the BM may be the primary change in this disease. Polycystin could play an important role in interaction and communication between epithelial cells and the BM. It is known that signals are required from cells to the extracellular matrix (ECM) for normal BM development and also that communication from the ECM to cells is required for control of cellular differentiation. Communication between the ECM and cells occurs by several different means including through integrins and so polycystin may bind to integrins, although it may interact directly with components of the ECM. Although ADPKD is generally a disease of adulthood there is plenty of evidence that the cystic changes in the kidney may start much earlier (Milutinovic et al., 1970), even in utero (Reeders, 1986). Expression of polycystin during renal development may be when its major role occurs, perhaps in assembly of the BM and it is then that the errors, which later lead to cyst development, occur.

The plethora of connective tissue abnormalities associated with ADPKD indicate that the adhesion/communication roles of polycystin may be important for assembly and/or maintenance of the BM in many tissues, as well as the kidney. Hence, it is possible that disruption of normal cell adhesion and communication mediated by polycystin may explain the primary defects seen in the kidney and other organs in ADPKD. Clearly molecules that interact with polycystin or have a similar role are candidates for the other renal polycystic diseases of man.

A study of the mutations of the PKD1 gene highlight important functional regions of the protein. All of the mutations described so far in typical PKD1 families involve deletion or other disruption in the 3' end of gene. Two large deletions detected on Southern blots remove a large part of the protein (or make an out of frame product) including the last 6 transmembrane domains and the C-terminal end. The in-frame splicing change described in the same paper would remove most of TM10 and part of the preceding cytoplasmic loop. Two recently described splicing mutations (Peral, 1995) create three different products which either delete part of the cytoplasmic loop between TM7 and TM8 or a larger region of this loop including part of TM7 or insert an extra region into that loop. These mutated genes may make functional protein (they all produce abnormal mRNA) and it is interesting to note that, in each case, these proteins would have an intact extracellular region with disrupted cytoplasmic and transmembrane areas. Such proteins may bind to extracellular targets but are unable to communicate in a normal way.

A group of mutations of PKD1 which completely delete the gene and hence are clearly inactivating have been described (Brook-Carter, 1994). However, in each of these cases the deletions also disrupt the adjacent TSC2 gene making interpretation of these cases difficult (TSC2 mutations alone can cause the development of renal cysts). Nevertheless, the severity of the polycystic disease in these patients indicate that inactivation of one PKD1 allele does promote cyst development. Further more, all these children are often severely affected at birth, cyst formation must occur in utero in these cases and hence polycystin has an important developmental role. A second somatic hit in the target tissue may also be required in these cases (and normal PKD1 patients) before cyst development can occur.

PKD1 Gene and Polycystic Kidney Disease

We have therefore compelling evidence that mutations of the PKD1 gene give rise to the typical phenotype of ADPKD. The location of this gene within the PKD1 candidate region and the available genetic evidence from the families with mutations show that this is the PKD1 gene. The present invention therefore includes the complete PKD1 gene itself and the six PKD1—associated mutations which have been described: a de novo translocation, which was subsequently transmitted with the phenotype; two intragenic deletions (one a de novo event); two further deletions; and a splicing defect.

It has been argued that PKD1 could be recessive at the cellular level, with a second somatic mutation required to give rise to cystic epithelium (Reeders, 1992). This "two hit" process is thought to be the mutational mechanism giving rise to several dominant diseases, such as neurofibromatosis (Legius, et al., 1993) and tuberous sclerosis (Green, et al., 1994) which result from a defect in the control of cellular growth. If this were the case, however, we might expect that a proportion of constitutional PKD1 mutations would be inactivating deletions as seen in these other disorders.

The location of the PKD1 mutations may, however, reflect some ascertainment bias as it is this single copy area which has been screened most intensively for mutations. Nevertheless, no additional deletions were detected when a large part of the gene was screened by FIGE, and studies by PFGE showed no large deletions of this area in 75 PKD1 patients. It is possible that the mutations detected so far result in the production of an abnormal protein which causes disease through a gain of function. However, it is also possible that these mutations eliminate the production of functional protein from this chromosome and result in the PKD1 phenotype by haploinsufficiency, or only after loss of the second PKD1 homologue by somatic mutation.

At least one mutation which seems to delete the entire PKD1 gene has been identified (WS-53) but in this case it also disrupts the adjacent TSC2 gene and the resulting phenotype is of TSC with severe cystic kidney disease. Renal cysts are common in TSC so that the phenotypic significance of deletion of the PKD1 gene in this case is difficult to assess. It is clear that not all cases of renal cystic disease in TSC are due to disruption of the PKD1 gene; chromosome 9 linked TSC (TSC1) families also manifest cystic kidneys and we have analysed many TSC2 patients with kidney cysts who do not have deletion of the PKD1 gene.

Preliminary analysis of the PKD1 protein sequence (Seq. I.D. No. 8) has highlighted two regions which provide some clues to the possible function of the PKD1 gene. At the extreme 5' end of the characterised region are two leucine-rich repeats (LRRs) (amino acids 29–74) flanked by characteristic amino flanking (amino acids 6–28) and carboxy flanking sequences (amino acids 76–133) (Rothberg et al., 1990). LRRs are thought to be involved in protein-protein interations (Kobe and Deisenhofer, 1994) and the flanking sequences are only found in extracellular proteins. Other proteins with LRRs flanked on the amino and carboxy sides are receptors or are involved in adhesion or cellular signalling. Further 3' on the protein (amino acids 350–515) is a C-type lectin domain (Curtis et al., 1992). This indicates that this region binds carbohydrates and is also likely to be extracellular. These two regions of homology indicate that the 5' part of the PKD1 protein is extracellular and involved in protein-protein interactions. It is possible that this protein is a constituent of, or plays a role in assembling, the extracellular matrix (ECM) and may act as an adhesive protein in the ECM. It is also possible that the extracellular portion of this protein is important in signalling to other cells. The function of much of the PKD1 protein is still not fully known but the presence of several hydrophobic regions indicates that the protein may be threaded through the cell membrane.

Familial studies indicate that de novo mutations probably account for only a small minority of all ADPKD cases; a recent study detected 5 possible new mutations in 209 families (Davies, et al., 1991). However in our study one of three intragenic muttions detected was a new mutation and the PKD1 associated translocation was also a de novo event. Furthermore, the mutations detected in the two familial cases do not account for a significant proportion of the local PKD1 . The OX875 deletion was only detected in 1 of 282 unrelated cases, and the splicing defect was seen in only 1 of 48 unrelated cases. Nevertheless, studies of linkage disequilibrium have found evidence of common haplotypes associated with PKD1 in a proportion of some populations (Peral, et al., 1994; Snarey, et al., 1994) suggesting that common mutations will be identified.

Once a larger range of mutations have been characterised it will be possible to evaluate whether the type and location of mutation determines disease severity, and if there is a correlation between mutation and extra-renal manifestations. Previous studies have provided some evidence that the risk of cerebral aneurysms 'runs true' in families (Huston, et al., 1993) and that some PKD1 families exhibit a consistently mild phenotype (Ryynanen, et al., 1987). A recent study has concluded that there is evidence of anticipation in ADPKD families, especially if the disease is transmitted through the mother (Fink, et al., 1994). Furthermore, analysis of families with early manifestations of ADPKD show that there is a significant intra-familial recurrence risk and that childhood cases are most often transmitted maternally (Rink, et al., 1993; Zerres, et al., 1993). This pattern of inheritance is reminiscent of that seen in diseases in which an expanded trinucleotide repeat was found to be the mutational mechanism (reviewed in Mandel, 1993). However, no evidence for an expanding repeat correlating with PKD1 has been found in this region although such a sequence cannot be excluded.

There is ample evidence that early presymptomatic diagnosis of PKD1 is helpful because it allows complications such as hypertension and urinary tract infections to be monitored and treated quickly (Ravine, et al., 1991). The identification of mutations within a family allow rapid screening of that and other families with the same mutation. However, genetic linkage analysis is likely to remain important for presymptomatic diagnosis. The accuracy and ease of linkage based diagnosis will be improved by the identification of the PKD1 gene as a microsatellite lies in the 3' untranslated region of this gene (KG-8) and several CA repeats are located 5' of the gene (see FIGS. 1a and 6; Peral, et al., 1994; Snarey, et al., 1994).

Experimental Procedures
Clinical Details of Patients
Family 77

77-2 and 77-3 are 48 and 17 years old, respectively and have typical ADPKD. Both have bilateral polycystic kidneys and 77-2 has impaired renal function. Neither patient manifests any signs of TSC (apart from cystic kidneys) on clinical and ophthalmological examination or by CT scan of the brain.

77-4 is 13 years old, severely mentally retarded and has multiple signs of tSC including adenoma sebaceum, depigmented macules and periventricular calcification on CT scan. Renal ultrasound reveals a small number of bilateral renal cysts.

ADPKD Patients

OX875 developed ESRD from ADPKD, aged 46. Progressive decline in renal function had been observed over 17 years; ultrasound examinations documented enlarging polycystic kidneys with less extensive hepatic cystic disease. Both kidneys were removed after renal transplantation and pathological examination showed typical advanced cystic disease in kidneys weighing 1920 g and 340 g (normal average 120 g).

OX114 developed ESRD from ADPKD aged 54: diagnosis was made by radiological investigation during an episode of abdominal pain aged 25. A progressive decline in renal function and the development of hypertension was subsequently observed. Ultrasonic examination demonstrated enlarged kidneys with typical cystic disease, with less severe hepatic involvement.

OX32 is a member of a large kindred affected by typical ADPKD in which several members have developed ESRD. The patient himself has been observed for 12 years with progressive renal failure and hypertension following ultrasonic demonstration of polycystic kidneys.

No signs of TSC were observed on clinical examination of any of the ADPKD patients.

DNA Electrophoresis and Hybridisation

DNA extraction, restriction digests, electrophoresis, Southern blotting, hybridisation and washing were performed by standard methods or as previously described (Harris, et al., 1990). FIGE was performed with the Biorad FIGE Mapper using programme 5 to separate fragments from 25–50 kb. High molecular weight DNA for PFGE was isolated in agarose blocks and separated on the Biorad CHEF DRII apparatus using appropriate conditions.

Genomic DNA Probes and Somatic Cell Hybrids

Many of the DNA probes used in this study have been described previously: MS205.2 (D16S309; Royle, et al., 1992); GGG1 (D16S259; Germino, et al., 1990); N54 (D16S139; Himmelbauer, et al., 1991); SM6 (D16S665), CW23, CW21, and JH1 (European Chromosome 16 Tuberous Sclerosis Consortium, 1993). Microsatellite probes for haplotype analysis were KG8 and W5.2 (Snarey, et al., 1994)SM6, CW3 and CW2, (Peral, et al., 1994), 16AC2.5 (Thompson, et al., 1992); SM7 (Harris, et al., 1991), VK5AC (Aksentijevich, et al., 1993).

New probes isolated during this study were: JH4, JH5, JH6, 11 kb, 6 kb and 6 kb BamH I fragments, respectively, and JH13 and JH14, 4 kb and 2.8 kb BamH I-EcoR I fragments, respectively, all from the cosmid JH2A; JH8 and JH10 are 4.5 kb and 2 kb Sac I fragments, respectively and JH12 a 0.6 Sac I-BamH I fragment, all from JH4; 8S1 and 8S3 are 2.4 kb and 0.6 kb Sac II fragments, respectively, from JH8; CW10 (Seq. I.D. No. 4) is a 0.5 kb Not I-Mlu I fragment of SM25A; JH17 is a 2 kb EcoR I fragment of NM17.

The somatic cell hybrids N—OH1 (Germino, et al., 1990), P-MWH2A (European Chromosome 16 Tuberous Sclerosis Consortium, 1993) and Hy145.19 (Himmelbauer, et al., 1991) have previously been described. Somatic cell hybrids containing the paternally derived (BP2-10) and maternally derived (BP2-9) chromosomes from OX114 were produced by the method of Deisseroth and Hendrick (1979).

Constructing a Cosmid Contig

Cosmids were isolated from chromosome 16 specific and total genomic libraries, and a contig was constructed using the methods and libraries previously described (European Chromosome 16 Tuberous Sclerosis Consortium, 1993). To ensure that cosmids were derived from the 16p13.3 region (not the duplicate 16p13.1 area) initially, probes from the single copy area were used to screen libraries (e.g. CW21 and N54). Two cosmids mapped entirely within the area duplicated, CW10III and JC10.2B. To establish that these were from the PKD1 area, they were restriction mapped and hybridised with the probe CW10. The fragment sizes detected were compared to results obtained with hybrids containing only the 16p13.3. are (Hy145.19) or only the 16p13.1 region (P-MWH2A).

FISH

FISH was performed essentially as previously described (Buckle and Rack, 1993). The hybridisation mixture contained 100 ng of biotin-II-dUTP labelled cosmid DNA and 2.5 mg human Cot-1 DNA (BRL), which was denatured and annealled at 37° C. for 15 min prior to hybridisation at 42° C. overnight. After stringent washes the site of hybridisation was detected with successive layers of fluorescein-conjugated avidin (5 mg/ml) and biotinylated ani-avidin (5 mg/ML) Vector Laboratories). Slides were mounted in Vectashield (Vector Laboratories) containing 1 mg/ml propidium iodide and 1 mg/ml 4', 6-diamidino-2-phenylindole (DAPI), to allow concurrent G-banded analysis under UV light. Results were analysed and images captured using a Bio-Rad MRC 600 confocal laser scanning microscope.

cDNA Screening and Characterisation

Foetal brain cDNAs libraries in 7 phage (Clonetech and Stratagene) were screened by standard methods with genomic fragments in the single copy area (equivalent to CW23 and CW21) or with a 0.8 kb Pvu II-Eco RI single copy fragment of AH3. Six PBP cDNAs were characterised; AH4 (1.7 kb). and 3A3 (2.0 kb) are described in European Chromosome 16 Tuberous Sclerosis Consortium, 1993, and four novel cDNAs AH3 (2.2 kb), AH6 (2.0 kb), A1C (2.2 kb) and B1E (2.9 kb). A Striatum library (Stratagene) was screened with JH4 and a HG-C cDNA, 11BHS21 (3.8 kb) was isolated, 21p.9 is a 0.9 kb Pvu II-EcoR I subclone of this cDNA. A HG-A or HG-B cDNA, HG-4 (7 kb) was also isolated by screening the foetal brain library (Stratagene) with JH8. HG-4/1.1 is a 1.1 kb Pvu II-EcoR I fragment from the 3' end of HG-4. 1A1H.6 (Seq. I.D. No. 3) is a 0.6 kb Hind III-EcoR I subclone of a TSC2 cDNA, 1A-1 (1.7 kb), which was isolated from the Clonetech library. Each cDNA was subcloned into Bluescript and sequenced utilising a combination of sequential truncation and liigonucleotide primers using DyeDeoxy Terminators (Applied Biosystems) and an ABI 373A DNA Sequencer (Applied Biosystems) or by hand with 'Sequenase' T7 DNA polymerase OUSB).

RNA Procedures

Total RNA was isolated from cell lines and tissues by the method of Chomczynskiand Sacchi (1987) and enrichment for mRNA made is using the PolyAT tract mRNA Isolation System (Promega). For RNA electrophoresis 0.5% agarose denaturing formaldehyde gels were used which were Northern blotted, hybridised and washed by standard procedures. The 0.24–9.5 kb RNA (Gibco BRL) size standard was used and hybridisation of the probe (1-9B3) to the 13 kb Utrophin transcript (Love, et al., 1989) in total fibroblast RNA was used as a size marker for the large transcripts.

RT-PCR was performed with 2.5 mg of total RNA by the method of Brown et al. (1990) with random hexamer primers, except that AMV-reverse transcriptase (Life Sciences) was employed. To characterise the deletion of the PBP transcript in OX114 we used the primers:

AH# F9 5' TTT GAC AAG CAC ATC TGG CTC TC 3' (Seq. I.D. No. 9)

AH3 B7 5' TAC ACC AGG AGG CTC CGC AG 3' (Seq. I.D. No. 10)

in a DMSO containing PCR buffer (Dode, et al., 1990) with 0.5 mM MgCl$_2$ and 36 cycles of: 94° C., 1 min; 61° C., 1 min; 72° C., 2 min plus a final extension of 10 min. The 3A3 C primers used to amplify the OX32 cDNA and DNA were:

3A3 C1 5' CGC CGC TTC ACT AGC TTC GAC 3' (Seq. I.D. No. 11)

3A3 C2 5' ACG CTC CAG AGG GAG TCC AC 3' (Seq. I.D. No. 12)

These were employed in a PCR buffer and cycle previously described (Harris, et al., 1991) with 1 mM MgCl$_2$ and an annealing temperature of 61° C.

PCR products for sequencing were amplified with Pfu-1 (Stratagene) and ligated into the Srf-1 site in PCR-Script (Stratagene) in the presence of Srf-1.

RNAse Protection

Tissues from normal and end-stage polycystic kidneys were immediately homogenised in guanidinium thiocyanate. RNA was purified on a cesium chloride gradient and 30 mg total RNA was assayed by RNAse protection by the method of Melton, et al., (1984) using a genomic template generated with the 3A3, C primers (Seq. I.D. Nos. 11 and 12).

Heteroduplex Analysis

Heteroduplex analysis was performed essentially as described by Keen et al. (1991). Samples were amplified from genomic DNA with the 3A3, C primers (Seq. I.D. Nos. 11 and 12), heated at 95° C. for 5 minutes and incubated at room temperature for at least 30 minutes before loading on a Hydrolink gel (AT Biochem). Hydrolink gels were run for 12–18 hours at 250V and fragments observed after staining with ethidium bromide.

Extraction and Amplification of Paraffin-embedded DNA

DNA from formalin fixed, paraffin wax embedded kidney tissue was prepared by the method of Wright and Manos (1990), except that after proteinase K digestion overnight at 55° C., the DNA was extracted with phenol plus chloroform before ethanol precipitation. Approximately 50 ng of DNA was used for PCR with 1.5 mM MgCl$_2$ and 40 cycles of 94° C. for 1 min, 50° C. for 1 min and 72° C. for 40 s, plus a 10 min extension at 72° C.

The oligonucleotide primers designed to amplify across the genomic deletion of OX875 were:

AHF42: 5'-GGG CAA GGG AGG ATG ACA AG-3' (Seq. I.D. No. 13)

JH14B3: 5'-GGG TTT ATC AGC AGC AAG CGG-3' (Seq. I.D. No. 14)

which produced a product of about 220 bp in individuals with the OX875 deletion.

3' RACE analysis of WS-212

3' RACE was completed essentially as described (European Polycystic Kidney Disease Consortium (1994)). Reverse transcription was performed with 5 µg total RNA with 0.5 µg of the hybrid dT$_{17}$ adapter primer using conditions previously described (Fronman et al., (1988)). A specific 3' RACE product was amplified with the primer F5 and adapter primer in 0.5 mM MgCl$_2$ with the program: 57° C., 60 s; 72° C., 15 minutes and 30 cycles of 95° C., 40 s; 57° C., 60 s; 72° C., 60 s plus 72° C., 10 minutes. The amplified product was cloned using the TA cloning system (Invitrogen) and sequenced by conventional methods.

Genomic and cDNA Probes and Somatic Cell Hybrids

The genomic clones CW21, JH5, JH6, JH8, JH10, JH12, JH13 and JH14 and the cDNAs A1C, AH3, 3A3 and AH4 are described herein. Newly described probes are: SM3 a 2.0 kb BamH 1 subclone of the cosmid SM11, JH9, 2.4 kb Sac l fragment and JH11, 1.2 kb Sac l—BamH1 fragment, both from JH4. See Eur. Polycystic Kidney Disease Consortium, 1994 and Eur. Chromosome 16 Tuberous Sclerosis Consortium 1993 for all above clones. DFS5 is a 4.2 kb Not l-Hind lll fragment of CW23 (Eur. Chromosome 16 Tuberous Sclerosis Consortium, 1993). The cDNAs; BPG4, BPG6, BPG7C and 13-A were isolated from a fetal brain cDNA library in λ phage (Stratagene) and are 7 kb, 2 kb, 4.5 kb and 1.2 kb respectively.

The somatic cell hybrids have previously been described, P-MWH2A (Eur. Chromosome 16 Tuberous Sclerosis Consortium, 1993) and Hy145.19 (Himmelbauer et al., 1991).

Exon Linking

Total cellular RNA from the radiation hybrid Hy145.19 was reverse transcribed using random hexamers (Eur. Polycystic Kidney Disease Consortium, 1994). This material was used as a template for PCR using the proof reading polymerase Pfu-1 with the primer pairs described in Table 2 (Seq. I.D. No. 7). The resultant products were cloned into the Srf-1 site of pPCRscript (SK+) plasmid.

Sequencing

Full length sequence was obtained from the genomic clones, HG cDNAs and exon link clones using the progressive unidirectional deletion technique of Henikoff, (1984). Both strands were then sequenced using DyeDeoxy Terminator Cycle Sequencing and an Applied Biosystems Sequencer 373A. Contig assembly was done using the programmes Assembly line (vs 1.0.7), SeqEd (vs 1.03) and MacVector (4.1.4).

Primer Extension

Primer extension was performed on total cellular fibroblast RNA. 25 µg of RNA was annealed at 60° C. in the presence of 400 mM NaCl to 0.01 pM of HPLC pure oligonucleotide which had been end labelled to a specific activity of 3×10$^7$ cpm/pM with $^{32}$P. Primer extension was then performed in the presence of 50 mM Tris pH8.2, 10 mM DTT, 6 mM MgCl$_2$, 25 mg/ml Actinomycin D, 0.5 mM dNTPs, and 8 units of AMV reverse transcriptase. The extension reaction was continued for 60 min at 42° C. The extension products were compared to a sequencing ladder generated using the same primer on the genomic clone SM3. The primers used were:

N2765:5'-GGCGCGGCGGGCGGCATCGTTAGGGCAGCG-3'
(Seq. I.D. No. 15)

N5496:5'-GGCGGGCGGCATCGTTAGGGCAGCGCGCGC-3'
(Seq. I.D. No. 16)

N5495:5'-ACCTGCTGCTGAGCGACGCCCGCTCGGGGC-3'
(Seq. I.D. No. 17)

Analysis of Sequence Homology

The predicted PKD1 protein was analyzed for homologies with known proteins in the SwissProt and NBRF database using the BLAST (Altschul et al., 1990) and FASTA (Pearson et al., 1988) algorithms. Layouts were prepared by hand and using the programme Pileup.

Transmembrane Regions

Potential transmembrane segments were identified by the method of Sipos and von Heljne (Sipos et al., 1993), using the GES hydrophobicity scale (Engelmen et al., 1986) and a trapezoid sliding window (a full window of 21 residues and a core window of 11 residues) as recommended. Candidate transmembrane domains were selected on the basis of their average hydrophobicity <H>, and were classified as-certain (<H>≧1.0) or putative (0.6, <H><1).

The best topology for the protein was predicted on the basis of three different criteria: a) the net charge difference between the 15 N-terminal and the 15 C-terminal residues flanking the most N-terminal transmembrane segment (Hartmann et al., 1989); b) the difference in positively charged residues between the two sides of the membrane in loops smaller than 60 residues, and c) the analysis of the overall amino acid composition of loops longer than 60 residues by the compositional distance method (Nakashima et al., 1992). Using the above criteria the TopPred II program (Sipos wt al., 1993) calculated all the possible topologies of the proteins including the certain transmembrane segments and either included or excluded each of the putative segments to determine the most likely structure.

PKD1 Protein Purification

The PKD1 protein may be purified according to conventional protein purification procedures well known in the art. Alternatively, the protein may be purified from cells harboring a plasmid containing an expressible PKD1 gene. For example, the protein may be expressed in an *E.coli* expression system and purified as follows.

Cells are grown in a 10 liter volume in a Chemap Fermentor (Chemapec, Woodbury, N.Y.) in 2 medium. Fermentation temperature may be 37° C., pH 6.8, and air as provided at 1 vvm. Plasmid selection may be provided using ampicillin for a plasmid containing an ampicillin resistance gene. Typical yield (wet weight) is 30 g/l.

For cell lysis, 50 g wet cell weight of *E.coli* containing the recombinant PKD1 plasmid may be resuspended in a final volume of 100ml in 50 mM Tris-HCl pH 8.0, 5 mM EDTA, 5 mM DTT, 15 mM mercaptoethanol, 0.5% triton X-100, and 5 mM PMSF. 300 mg lysozyme is added to the suspension, and incubated for 30 min at room temperature. The material is then lyzed using a BEAD BEATER (R) (Biospec Products, Bartlesville, Okla.) containing an equal volume of 0.1–0.15 um glass beads. The liquid is separated from the beads and the supernatant removed, the pellet dissolved in 20 mM Tris-Cl pH 8.0.

The protein may be purified from the supernatant using DEAE chromatography, as is well known in the art.

Preparation of Antibodies

Antibodies specific for PDK1 protein or a fragment thereof are prepared as follows. A peptide corresponding to at least 8 amino acid residues of the PKD1 sequence of FIG. 15 (Seq. I.D. No. 8), are synthesized. Coupling of the peptide to carrier protein and immunizations is performed as described (Dymecki, S. M., J. Biol. Chem 267:4815–4823, 1992). Rabbit antibodies against this peptide are raised and sera are titered against peptide antigen by ELISA. The sera exhibiting the highest titer (1:27,000) are most useful.

Techniques for preparing monoclonal antibodies are well known, and monoclonal antibodies of this invention may be prepared by using the synthetic polypeptides of this invention, preferably bound to a carrier, as the immunogen as was done by Arnheiter et al., Nature, 294, 278–280 (1981).

Monoclonal antibodies are typically obtained from hybridoma tissue cultures or from ascites fluid obtained from animals into which the hybridoma tissue was introduced. Nevertheless, monoclonal antibodies may be described as being "raised to" or "induced by" the synthetic polypeptides of this invention or their conjugates with a carrier.

Antibodies are utilized along with an "indicating group", also sometimes referred to as a "label". The indicating group or label is utilized in conjunction with the antibody as a means for determining whether an immune reaction has taken place, and in some instances for determining the extent of such a reaction.

The indicating group may be a single atom as in the case of radioactive elements such as iodine 125 or 131, hydrogen 3 or sulfur 35, or NMR-active elements such as fluorine 19 or nitrogen 15. The indicating group may also be a molecule such as a fluorescent dye like fluorescein, or an enzyme, such as horseradish peroxidase (HRP), or the like.

The terms "indicating group" or "label" are used herein to include single atoms and molecules that are linked to the antibody or used separately, and whether those atoms or molecules are used alone or in conjunction with additional reagents. Such indicating groups or labels are themselves well-known in immunochemistry and constitute a part of this invention only insofar as they are utilized with otherwise novel antibodies, methods and/or systems.

Detection of PKD1 and Subcellular Localization

Another embodiment of this invention relates to an assay for the presence of PKD1 protein in cells. Here, an above-described antibody is raised and harvested. The antibody or idiotype-containing polyamide portion thereof is then admixed with candidate tissue and an indicating group. The presence of the naturally occurring amino acid sequence is ascertained by the formation of an immune reaction as signaled by the indicating group. Candidate tissues include any tissue or cell line or bodily fluid to be tested for the presence of PKD1.

Metabolic labeling immunoprecipitation, and immunolocalization assays are performed in cells as described previously (Furth, M. E., et al., Oncogene 1:47–58, 1987; Laemmli, U. K., Nature 227:680–685, 1970; Yarden, Y., et al., EMBO J. 6:3341–3351, 1987; Konopka, J. B., et al., Mol. Cell. Biol. 5:3116–3123, 1985). For immunoblot analysis, total lysates are prepared (using Fruth's lysis buffer) (Fruth, M. E., et al., Oncogene, 1:47–58, 1987). Relative protein concentrations are determined with a calorimetric assay kit (Bio-Rad) with bovine serum albumin as the standard. A protein of lysate containing approximately 0.05 mg of protein is mixed with an equal volume of 2×SDS sample buffer containing 2 mercaptoethanol, boiled for 5 min., fractioned on 10% polyacrylamide-SDS gels (Konopka, J. B., et al., J.Virol., 51:223–232, 1984) and transferred to immunobilon polyvinyldine difluoride (Millipore Corp., Bedford, Mass.) filters. Protein blots are treated with specific antipeptide antibodies (see below). Primary binding of the PKD1-specific antibodies is detected using anti-IgG second antibodies conjugated to horseradish peroxidase and subsequent chemiluminescence development ECL Western blotting system (Amersham International).

For metabolic labeling, $10^6$ cells are labeled with 100 $\mu$Ci of $^{35}$S-methionine in 1 ml of Dulbecco's modified Eagles medium minus methionine (Amersham Corp.) for 16 h. Immunoprecipitation of PKD1 protein from labeled cells with antipeptide antiserum is performed as described (Dymecki, S. M., et al., supra). Portions of lysates containing $10^7$ cpm of acid-insoluble $^{35}$S-methionine are incubated with 1 $\mu$g of the antiserum in 0.5 ml of reaction mixture. Immunoprecipitation samples are analyzed by SDS-polylarcylamide gel electrophoresis and autoradiography.

For immunolocalization studies, $10^7$ CMK cells are resuspended in 1 ml of sonication buffer (60 mM Tris-HCl, pH 7.5, 6 mM EDTA, 15 mM EGTA, 0.75M sucrose, 0.03% leupeptin 12 mM phenylmethylsulfonyl fluoride, 30 mM 2-mercaptoethanol). Cells are sonicated 6 times for 10 seconds each and centrifuged at 25,000×g for 10 min at 4° C. The pellet is dissolved in 1 ml of sonication buffer and centrifuged at 25,000×g for 10 min at 4° C.

The pellet (nucleus fraction) is resuspended in 1 ml of sonication buffer and added to an equal volume of 2×SDS sample buffer. The supernatant obtained above (after the first sonication) is again centrifuged at 100,000×g for 40 min at 4° C. The supernatant (cytosolic fraction) is removed and added to an equal volume of 2×concentrated SDS sample buffer. The remaining pellet (membrane fraction) is washed and dissolved in sonication buffer and SDS sample buffer as described above. Protein samples are analyzed by electrophoresis on 10% polyacrylamide gels, according to the Laemmli method (Konopka, J. B., supra). The proteins are transferred from the gels on a 0.45-$\mu$m polyvinylidine difluoride membrane for subsequent immunoblot analysis. Primary binding of the PKD1 specific antibodies is detected using anti-IgG second antibodies conjugated to horseradish peroxidase.

For immunohistochemical localization of PKD1 protein, CMK cells or U3T3 are grown on cover slips to approximately 50% confluence and are washed with PBS (pH 7.4) after removing the medium. The cells are prefixed for 1 min at 37° C. in 1% paraformaldehyde containing 0.075% Triton X-100, rinsed with PBS and then fixed for 10 min with 4% paraformaldehyde. After the fixation step, cells are rinsed in PBS, quenched in PBS with o.1 and finally rinsed again in PBS. For antibody staining, the cells are first blocked with a blocking solution (3% bovine serum albumin in PBS) and incubated for 1 h at 37° C. The cells are then incubated for 1 h at 37° C. with antiserum (1:100 dilution or with preimmune rabbit serum (1:100). After the incubation with the primary antibody, the cells are washed in PBS containing 3% bovine and serum albumin and 0.1% Tween 20 and incubated for 1 h at 37° C. in fluorescein-conjugated donkey anti-rabbit IgGs (Jackson Immunoresearch, Maine) diluted 1:100 in blocking solution.

The coverslips are washed in PBS (pH 8.0), and glycerol is added to each coverslip before mounting on glass slides and sealing with clear nail polish. All glass slides are examined with a Zeiss Axiophot microscope.

An indicating group or label is preferably supplied along with the antibody and may be packaged therewith or packaged separately. Additional reagents such as hydrogen peroxide and diaminobenzideine may also be included in the system when an indicating group such as HRP is utilized. Such materials are readily available in commerce, as are many indicating groups, and need not be supplied along with the diagnostic system. In addition, some reagents such as hydrogen peroxide decompose on standing, or are otherwise short-lived like some radioactive elements, and are better supplied by the end-user.

Pharmaceutical Compositions of the Invention; Dosage and Administration

Pharmaceutical formulations comprising PKD1 nucleic acid or protein, or mutants thereof, can be prepared by procedures well known in the art. For example, as injectables, e.g., liquid solutions or suspensions. Solid forms for solution in, or suspension in, a liquid prior to injection also can be prepared. Optionally, the preparation also can be emulsified. The active ingredient can be mixed with excipients which are pharmaceutically acceptable and compatible with the active ingredient. For example, water, saline, dextrose, glycerol, ethanol, etc. or combinations thereof. Also useful are wetting or emulsifying agents, pH buffering agents or adjuvants. PKD1 protein or DNA can be administered parenterally, by injection, for example, either subcutaneously or intramuscularly. Additional formulations which are suitable for other modes of administration include suppositories and, in some cases, oral formulations. In each case, the active protein or the nucleic acid will be present in the range of about 0.05% to about 10%, preferably in the range of about 1–2%. by weight. Alternatively, the active protein or the nucleic acid will be administered at a dosage of about 10 mgu-2 kg/kg body weight, preferably 50 mg–400 mg/kg/body weight. Administration may be daily, weekly,:or in a single dosage, as determined by the physician.

TABLE 1

Details of the exons and introns of the PKD1 gene

| Exon No. | position (bp) | Size (nt) bp | positions (aa) | Intron No. | Size (bp) |
|---|---|---|---|---|---|
| 1 | 1–426 | 426 | 1–72 | 1 | -17 kb |
| 2 | 427–498 | 72 | 73–96 | 2 | 121 |
| 3 | 499–570 | 72 | 97–120 | 3 | 268 |
| 4 | 571–740 | 170 | 121–177 | 4 | 213 |
| 5 | 741–1412 | 672 | 177–401 | 5 | 117 |
| 6 | 1413–1596 | 184 | 401–462 | 6 | 435 |
| 7 | 1597–1817 | 221 | 463–536 | 7 | 188 |
| 8 | 1818–1933 | 118 | 536–575 | 8 | 410 |
| 9 | 1934–2060 | 127 | 525–617 | 9 | 363 |
| 10 | 2061–2308 | 248 | 617–700 | 10 | 452 |
| 11 | 2309–3064 | 756 | 700–952 | 11 | 877 |
| 12 | 3065–3196 | 132 | 952–996 | 12 | 196 |
| 13 | 3197–3372 | 176 | 996–1054 | 13 | 314 |
| 14 | 3373–3506 | 134 | 1055–1099 | 14 | 468 |
| 15 | 3507–7126 | 3,620 | 1099–2306 | 15 | 219 |
| 16 | 7127–7276 | 150 | 2306–2356 | 16 | ? |
| 17 | 7277–7420 | 144 | 2356–2404 | 17 | 127 |
| 18 | 7421–7700 | 280 | 2404–2497 | 18 | 93 |
| 19 | 7701–7914 | 214 | 2497–2568 | 19 | 66 |
| 20 | 7915–8074 | 160 | 2569–2622 | 20 | -400 bp |
| 21 | 8075–8227 | 153 | 2622–2673 | 21 | 3.1 kb |
| 22 | 8228–8372 | 145 | 2673–2721 | 22 | 650 |
| 23 | 8373–9002 | 630 | 2721–2931 | 23 | 295 |
| 24 | 9003–9159 | 158 | 2931–2983 | 24 | 180 |
| 25 | 9160–9412 | 254 | 2984–3068 | 25 | 123 |
| 26 | 9413–9608 | 196 | 3068–3133 | 26 | -1.7 kb |
| 27 | 9609–9779 | 171 | 3133–3190 | 27 | 86 |
| 28 | 9780–9923 | 144 | 3190–3238 | 28 | 93 |
| 29 | 9924–10134 | 211 | 3238–3308 | 29 | 90 |
| 30 | 10135–10261 | 127 | 3309–3351 | 30 | -1.8 kb |
| 31 | 10262–10378 | 117 | 3351–3390 | 31 | 88 |
| 32 | 10379–10428 | 50 | 3390–3406 | 32 | 224 |
| 33 | 10429–10613 | 185 | 3407–3468 | 33 | 77 |
| 34 | 10614–10707 | 94 | 3468–3499 | 34 | -3 kb |
| 35 | 10708–10826 | 119 | 3500–3539 | 35 | 78 |
| 36 | 10827–11029 | 203 | 3539–3607 | 36 | 72 |
| 37 | 11030–11224 | 195 | 3607–3672 | 37 | 450 |
| 38 | 11225–11364 | 140 | 3672–3718 | 38 | 361 |
| 39 | 11365–11477 | 113 | 3719–3756 | 39 | 290 |
| 40 | 11478–11619 | 142 | 3756–3803 | 40 | 139 |
| 41 | 11620–11745 | 126 | 3804–3845 | 41 | 183 |
| 42 | 11746–11920 | 175 | 3846–3904 | 42 | -320 |
| 43 | 11921–12211 | 291 | 3904–4001 | 43 | 75 |
| 44 | 12212–12346 | 135 | 4001–4046 | 44 | 83 |
| 45 | 12347–12652 | 306 | 4046–4148 | 45 | 88 |
| 46 | 12653–14148 | 1,496 | 4148–4302 | | |

TABLE 2

Details of the exon link cDNAs

| Product Name | Product Size (bp) | Oligonucleotide Sequences | Position in cDNA | Exon Position |
|---|---|---|---|---|
| rev1 | 652 | AGCGCCAGCGTCCGAGCGG CTGCACCACCCGCACCTGC | 8–658 200–658 | 1–4 |
| S13 | 1285 | CCGGGCGCTGGACGTTGGGCT AGTGCTCGGCTGTGGCTGGGT | 448–1733 | 2–7 |
| S3/4 | 1608 | CACCCAGCCACAGCCGAGCACT GTGTGGCATTGGGGACAGCAC | 1712–3320 | 7–13 |
| S1/3 | 732 | TGCTGTCCCCCAATGCCAC ACGGTCACTGTGCAGTTC | 3300–4032 | 13–15 |
| GAP e | 1983 | CCAATGCCACACTGGTACTGACG TGGTAGGTGCCGGCCTCGAG | 3309–5292 | 13–15 |
| GAP d | 2036 | CCGGCACCTACCATGTGCAGC CCAAGGACACAATGGGCACC | 5280–7316 | 15–17 |
| GAP g | 884 | GAGGTGTATCGCACCGCCAG GCCCAGTGGGAAGAGGCGGC | 6773–7657 | 15–18 |
| GAP a | 1211 | TCTTGCCGCCTCTTCCCA GCAGCCCAGTCCGAGTTG | 7634–8862 | 18–23 |

OTHER EMBODIMENTS

Other embodiments will be evident to those of skill in the arm. It should be understood that the foregoing detailed description is provided for clarity only and is merely exemplary. The spirit and scope of the present invention are not limited thereto, being defined by the claims set forth below.

REFERENCES

Aksentijevich et al., Am. J. Hum. Genet. 53:451–461, (1993).
Altschul et al., J. Mol. Biol. 215:403–410, (1990).
Bevilacqua, M. P., et al., Science 243:1160–1165, (1989).
Bork et al., Protein Science 2:1185–1187, (1993).
Breuning et al., Lancet ii, 1359–1361, (1987).
Breuning et al., J. Med. Genet. 27:603–613, (1990).
Brook-Carter et al., Nature Genetics 8:328–332, (1994).
Brown et al., Nucl. Acids Res. 18:4191–4195, (1990).
Brüendorf, T., et al., Protein Profile 1:951–1058, (1994).
Buckle et al., Human Genetic Disease Analysis; IRL Press (K. E. Davies, Ed.) 2:59–82, Oxford, (1993).
Carone, F. A., et al., Laboratory Investigations 70:437–448, (1994).
Carone, F. A., et al., Kidney International 47:861–868, (1995).
Calvet, J. P., Kidney International 43:101–108, (1993).
Chapman et al., N. Eng. J. Med. 327:916–920, (1992).
Chao, M. V., Neuron 9:583–593, (1992).
Chomczynski et al., Anal. Biochem. 162:156–159, (1987).
Curtis et al., Proc. of the Nat'l. Acad. of Sci., USA 89:8356–8360, (1992).
Dalgaard, O. Z., Acta Medica Scandinavica 158:1–251, (1957).
Daoust, M. C., et al., Genomics 25:733–736, (1995).
Davies et al., Q. J. Med. 79:477–485, (1991).
Deisseroth et al., Proc. Natl. Acad. Sci. USA 76:2185–2189, (1979).
Dode et al., Brit. J. Haemat. 76:275–281, (1990).
Drickamer, K., Kidney Int'l. 32:167–180, (1987).
Drickamer, K., J. Biol. Chem. 263:9557–9560, (1988).
Ekblom, P., FASEB Journal 3:2141–2150, (1989).
Engelman et al., Ann. Rev. Bioph. Chem. 15:321–353, (1986).
European Polycystic Kidney Disease Consortium, Cell 77:881–894, (1994).
European Chromosome 16 Tuberous Sclerosis Consortium, Cell 75:1305–1315, (1993).
Fink et al., J. Amer. Soc. Nephrology 3:1863–1870, (1993).
Fink et al., Kidney Int. 45:1153–1162, (1994).
Fronman et al., Biochemistry 85:8998–9002, (1988).
Gabow, P. A., Kidney Int. 40:989–996, (1991).
Gabow, P. A., N. E. J. of Medicine 329:332–342, (1993).
Gabow, P. A., Amer. J. of Kidney Diseases 16:403–413, (1990).

Germino et al., Am. J. Hum. Genet. 46:925–933, (1990).
Germino et al., Genomics 13:144–151, (1992).
Gower, H. J., et al., Cell 55:955–964, (1988).
Green et al., Nature Genet. 6:193–196, (1994).
Harpaz, Y., et al., J. of the Mol. Biol. 238:528–539 (1994).
Harris et al., Genomics 7:195–206, (1990).
Harris et al., Lancet 338:1484–1487, (1991).
Hartmann et al., Proc. Nat'l. Acad. Sci. USA 86:5786–5790, (1989).
Henikoff, S., Gene 28:351–359, (1984).
Himmelbauer et al., Amer. J. Human Genetics 48:325–334, (1991).
Hossack et al., N. Eng. J. Med. 319:907–912, (1988).
Huston et al., J. Amer. Soc. of Nephrology 3:1871–1877, (1993).
Hyland et al., Hum. Genet. 84:286–288, (1990).
Jia, R., et al., J. of Biol. Chem. 269:1839–1844 (1994).
Jones, E. Y., et al., Nature 373:539–544, (1995).
Keen et al., Trend Genet. 7:5, (1991).
Kimberly, W. J., et al., Genomics 18:467–472, (1993).
Kimberling et al., N. Eng. J. Med. 319:913–918, (1988).
Kobe et al., Trends in Bioch. Sci. 19:415–421, (1994).
Kornblihtt, A. R., et al., EMBO Journal 4:1755–1759, (1985).
Kozak, M., Nucleic Acids Res. 15:8125–8148, (1987).
Kuma et al., Mol. Biol. and Evolution 10:539–551, (1993).
Kwon, B. S., et al., Proc. of the Nat'l. Acad. of Sci., USA 88:9228–9232, (1991).
Lamballe et al., Cell 66:967–979, (1991).
Legius et al., Nature Genet. 3:122–126, (1993).
Love et al., Nature 339:55–58, (1989).
Mandel, J–L, Nature Genetics 4:8–9.
Matsushita, O., et al., Journal of Bacteriology 176:149–156, (1994).
McFarland, K. C., et al., Science 245:494–499, (1989).
Melton et al., Nuc. Acid Res. 12:7035–7056.
Milutinovic, J., et al., Amer. J. of Med. 68:741–744, (1980).
Milutinovic, J., et al., Amer. J. of Clin. Path. 73: 740–747, (1979).
Nakashima et al., FEBS Letters 303:141–146, (1992).
Oldberg, et al., EMBO J. 8:2601–2604, (1989).
Oldberg et al., Biochemical J. 243:255–259, (1987).
Parfrey et al., N. Eng. J. Med. 323:1085–1090, (1990).
Pearson et al., Proc. Nat'l Acad. Sci. USA 85:2444–2448, (1988).
Peral et al., Am. J. Hum. Genet. 54:899–908.
Peral et al., Human Molecular Genetics (in press), (1995).
Peters, D. J. M., et al., Nature Genetics 5:359–362, (1993).
Peters, D. J. M., et al., Contributions to Nephrology: Polychystic Kidney Disease (eds. Breuning, M. H., Devoto, M. & Romeo, G), p. 128–139 (1992).
Pound et al., J. Med. Genet. 29:247–248, (1992).
Ravine et al., Lancet 337:127–129, (1991).
Ravine D., et al., Lancet 340:1330–1333, (1992).
Reeders, S. T., Nature Genet. 1:235–237, (1992).
Reeders et al., Lancet i, 6–8, (1986).
Reeders et al., Nature 317:542–544, (1985).
Reeders et al., Genomics 3:150–155, (1988).
Romeo et al., Lancet ii, 8–10, (1988).
Roth, G. J., Blood 77:5–19, (1991).
Rothberg et al., Genes and Development 4:2169–2187, (1990).
Royle et al., Nucl. Acids Res. 20:1164, (1992).
Ryynanen et al., J. Med. Genet. 24:462–465, (1987).
Schäfer, K., et al., Kidney International 46:134–152, (1994).
Scheff et al., Ann. Intern. Med. 92:202–204, (1980).
Sipos et al., European J. Biochemistry 213:1333–1340, (1993).
Snarey et al., Am. J. Hum. Genet. (in press), (1994).
Somlo et al., Genomics 13:152–158, (1992).
Somlo, S., et al., J. of the Amer. Soc. of Nephrology 4: 1371–1378, (1993).
Streuli, M., et al., Journal of Experimental Medicine 168:1523–1530, (1988).
Takagi et al., J. Bioch. Chem. 265:19721–19727, (1990).
Taylor, M. E., et al., J. of Biol. Chem. 265:12156–12162, (1990).
Thompson et al., Genomics 13:402–408, (1992).
Volkmer H., et al., Journal of Cell Biology 118:149–161, (1992).
von Heijne, G., Nuc. Acids Res. 14:4683–4691, (1986).
Wieringa, B., et al., Cell 37:915–925, (1984).
Weis et al., Nature 360:127–134, (1992).
Williams, A. F., et al., Annual Review of Immunology 6:381–405 (1988).
Wilson, P. D., et al., Kidney International 39:450–463, (1991).
Wright et al., PCR Protocols: A Guide to Methods and Applications, 153–166, (1990).
Zerres et al., J. Med. Genet. 30:583–588, (1993).

```

What is claimed is:

1. A method for screening a subject to determine whether said subject is a carrier of or is afflicted with a PKD1-associated disorder, which method comprises detecting the presence or absence of PKD1 nucleic acid in a biological sample from said subject, wherein detection of a mutant PKD1 nucleic acid or the absence of a PKD1 nucleic acid is indicative of a genetic mutation giving rise to a PKD1-associated disorder, and wherein said mutant PKD1 nucleic acid comprises a nucleic acid sequence wherein a sequence selected from the group consisting of the following ((a)–(l)) is deleted:

(a) (OX114) a nucleic acid comprising 446 base pairs between nucleotides 1746–2192 as defined in Seq. I.D. No. 1;

(b) (OX32) a nucleic acid comprising 135 base pairs between nucleotides 3696–3831 as defined in Seq. I.D. No. 1;

(c) (OX875) a nucleic acid comprising about 5.5 Kb flanked by the two XbaI sites shown in FIG. 3a and encompassing the EcoR1 site separating the CW10 (41 kb) and JH1 (18 kb) fragment;

(d) (WS-53) a nucleic acid comprising about 100 kb encompassing the PKD1 gene, wherein the 3' end of said nucleic acid lies between the JH1 and CW21 fragment and the 5' end of said nucleic acid lies between the SM6 and JH17 fragment shown in FIG. 6;

(e) (WS-215) a nucleic acid comprising about 160 kb encompassing the PKD1 gene, wherein said nucleic acid extends 3' of the PKD1 gene to within fragment CW15 and 5' of the PKD1 gene to between fragments SM6 and JH17 as shown in FIG. 12;

(f) (WS-227) a nucleic acid comprising about 50 kb encompassing the PKD1 gene, wherein said nucleic acid extends 3' of the PKD1 gene to within fragment CW20 and 5' of the PKD1 gene to within fragment JH11 as shown in FIG. 12;

(g) (WS-219) a nucleic acid comprising about 27 kb encompassing a portion of the PKD1 gene, wherein said nucleic acid extends 3' of the PKD1 gene within fragment JH1 and into the PKD1 gene to within fragment JH6 as shown in FIG. 12;

(h) (WS-250) a nucleic acid comprising about 160 kb encompassing the PKD1 gene, wherein said nucleic acid extends 3' of the PKD1 gene to within fragment CW20 and 5' of the PKD1 gene to within fragment BLu24 as shown in FIGS. 1*a* and 12:

(i) (WS-194) a nucleic acid comprising about 65 kb encompassing the PKD1 gene, wherein said nucleic acid extends 3' of the PKD1 gene to within fragment CW20 and 5' of the PKD1 gene to within fragment CW10;

(j) (461) a nucleic acid comprising 18 base pairs in the 75 base pair intron amplified by the primer pair 3A3C (Seq. I.D. No.s: 11 and 12) insert at position 3696 of the 3' sequence as shown in FIG. 11;

(k) (OX1054) a nucleic acid comprising 20 base pairs in the 75 base pair intron amplified by the primer pair 3A3C (Seq. I.D. No.s: 11 and 12) insert at position 3696 of the 3' sequence as shown in Figure; and (l) (WS-212) a nucleic acid comprising about 75 kb located downstream of the PKD1 gene and located between fragments SM9 and CW9 distal of the PKD1 gene and the PKD1 3'UTR proximal to the PKD1 gene as shown in FIG. 12.

2. A method according to claim 1, comprising detecting a genomic DNA fragment comprising a PKD1 nucleic acid, a genomic DNA fragment comprising a flanking region of a PKD1 gene, or a PKD1 nucleic acid comprising RNA.

3. A method according to claim 2, wherein said detection comprises hybridizing a nucleic acid probe comprising the PKD1 gene, or a genomic DNA fragment comprising a flanking region of the PKD1 gene, to nucleic acid from said biological sample and comparing the results thereof with results obtained using a biological sample from a subject who is not a carrier of a PKD1-associated disorder.

4. A method according to claim 3 which comprises digesting said nucleic acid of said biological sample to provide BamH1 fragments and hybridizing with a DNA probe which hybridizes to a BamH1 fragment encompassing the 8S3 and 8S1 regions identified in FIG. 3(*a*).

5. A method according to claim 4, wherein said DNA probe comprises the DNA probe 1A1H.6 (Seq. I.D. No. 3) identified herein.

6. A method according to claim 2 wherein said detection step comprises digesting nucleic acid from said biological sample to restriction fragments with one or more restriction enzymes selected from the group consisting of BamH1, EcoR1, SacI, XbaI, MluI, ClaI, PvuI, and NruI and hybridizing with a DNA probe selected from the group consisting of JH1, JH12, JH8, JH10, 8S3, 8S1, CW23, CW21, JH14, JH5, JH6, JH4, JH13, CW10 (Seq. I.D. No. 4), SM3, SM9, CW9, CW15, H2, CW18, CW20, CW21, JH11, CW36, SM6 and JH17, which hybridizes to a restriction fragment identified in FIG. 3(*a*) or 12.

7. A method according to claim 6, wherein nucleic acid from said biological sample is digested with EcoR1 and said DNA probe is selected from the group consisting of the probes CW10 (Seq. I.D. No. 4), JH14, JH5, JH6, JH4, JH13, JH8, JH11 and CW36 identified in FIGS. 3*a* and 12.

8. A method according to claim 1, wherein said detection includes applying a nucleic acid amplification process to said nucleic acid from said biological sample to amplify a fragment of the nucleic acid comprising the PKD1 gene, or a DNA fragment comprising a flanking region of the PKD1 gene, in said sample.

9. A method according to claim 8, wherein said nucleic acid amplification process comprises amplifying a fragment of nucleic acid in said biological sample utilizing a set of primers selected from the group consisting of:

AH3 F9 (Seq. I.D. No. 9): AH3 B7 (Seq. I.D. No. 10); 3A3 C1 (Seq. I.D. No. 11): 3A3 C2 (Seq. I.D. No. 12); and AH4 F2 (Seq. I.D. No. 13): JH14 B3 (Seq. I.D. No. 14).

10. A diagnostic kit for amplifying a mutant PKD1 gene, comprising a pair of nucleic acid primers complementary to the PKD1 nucleic acid sequence according to Seq. I.D. No.: 7, wherein said mutant PKD1 gene comprises a nucleic acid sequence wherein a sequence selected from the group consisting of the following ((a)–(l)) is deleted:

(a) (OX114) a nucleic acid comprising 446 base pairs between nucleotides 1746–2192 as defined in Seq. I.D. No. 1;

(b) (OX32) a nucleic acid comprising 135 base pairs between nucleotides 3696–3831 as defined in Seq. I.D. No. 1;

(c) (OX875) a nucleic acid comprising about 5.5 Kb flanked by the two Xbal sites shown in FIG. 3*a* and encompassing the EcoR1 site separating the CW10 (41 kb) and JH1 (18 kb) fragment;

(d) (WS-53) a nucleic acid comprising about 100 kb encompassing the PKD1 gene, wherein the 3' end of said nucleic acid lies between the JH1 and CW21 fragment and the 5' end of said nucleic acid lies between the SM6 and JH17 fragment shown in FIG. 6;

(e) (WS-215) a nucleic acid comprising about 160 kb encompassing the PKD1 gene, wherein said nucleic acid extends 3' of the PKD1 gene to within fragment CW15 and 5' of the PKD1 gene to between fragments SM6 and JH17 as shown in FIG. 12;

(f) (WS-227) a nucleic acid comprising about 50 kb encompassing the PKD1 gene, wherein said nucleic acid extends 3' of the PKD1 gene to within fragment CW20 and 5' of the PKD1 gene to within fragment JH11 as shown in FIG. 12;

(g) (WS-219) a nucleic acid comprising about 27 kb encompassing a portion of the PKD1 gene, wherein said nucleic acid extends 3' of the PKD1 gene within fragment JH1 and into the PKD1 gene to within fragment JH6 as shown in FIG. 12;

(h) (WS-250) a nucleic acid comprising about 160 kb encompassing the PKD1 gene, wherein said nucleic acid extends 3' of the PKD1 gene to within fragment CW20 and 5' of the PKD1 gene to within fragment BLu24 as shown in FIGS. 1*a* and 12:

(i) (WS-194) a nucleic acid comprising about 65 kb encompassing the PKD1 gene, wherein said nucleic acid extends 3' of the PKD1 gene to within fragment CW20 and 5' of the PKD1 gene to within fragment CW10;

(j) (461) a nucleic acid comprising 18 base pairs in the 75 base pair intron amplified by the primer pair 3A3C (Seq. I.D. No.s: 11 and 12) insert at position 3696 of the 3' sequence as shown in FIG. 11;

(k) (OX1054) a nucleic acid comprising 20 base pairs in the 75 base pair intron amplified by the primer pair 3A3C (Seq. I.D. Nos.: 11 and 12) insert at position 3696 of the 3' sequence as shown in FIG. 11; and (l) (WS-212) a nucleic acid comprising about 75 kb located downstream of the PKD1 gene and located between fragments SM9 and CW9 distal of the PKD1 gene and the PKD1 3'UTR proximal to the PKD1 gene as shown in FIG. 12.

11. A diagnostic kit according to claim 10, wherein the nucleic acid primers comprise one or more of the following sets:

AH3 F9 (Seq. I.D. No. 9): AH3 B7 (Seq. I.D. No. 10); 3A3 C1 (Seq. I.D. No. 11): 3A3 C2 (Seq. I.D. No. 12); and AH4 F2 (Seq. I.D. No. 13): JH14 B3 (Seq. I.D. No. 14).

12. A diagnostic kit for carrying out a method for determining whether said subject is a PKD1-associated disorder carrier or a patient having a PKD1-associated disorder, which method comprises detecting the presence or absence of PKD1 nucleic acid in a biological sample from a subject, wherein detection of a mutant PKD1 nucleic acid or the absence of a PKD1 nucleic acid is indicative of a genetic mutation giving rise to a PKD1-associated disorder, wherein said mutant PKD1 comprises a nucleic acid wherein a sequence selected from the group consisting of the following ((a)–(l)) is deleted:

(a) (OX114) a nucleic acid comprising 446 base pairs between nucleotides 1746–2192 as defined in Seq. I.D. No. 1;

(b) (OX32) a nucleic acid comprising 135 base pairs between nucleotides 3696–3831 as defined in Seq. I.D. No. 1;

(c) (OX875) a nucleic acid comprising about 5.5 Kb flanked by the two XbaI sites shown in FIG. 3a and encompassing the EcoR1 site separating the CW10 (41 kb) and JH1 (18 kb) fragment;

(d) (WS-53) a nucleic acid comprising about 100 kb encompassing the PKD1 gene, wherein the 3' end of said nucleic acid lies between the JH1 and CW21 fragment and the 5' end of said nucleic acid lies between the SM6 and JH17 fragment shown in FIG. 6;

(e) (WS-215) a nucleic acid comprising about 160 kb encompassing the PKD1 gene, wherein said nucleic acid extends 3' of the PKD1 gene to within fragment CW15 and 5' of the PKD1 gene to between fragments SM6 and JH17 as shown in FIG. 12;

(f) (WS-227) a nucleic acid comprising about 50 kb encompassing the PKD1 gene, wherein said nucleic acid extends 3' of the PKD1 gene to within fragment CW20 and 5' of the PKD1 gene to within fragment JH11 as shown in FIG. 12;

(g) (WS-219) a nucleic acid comprising about 27 kb encompassing a portion of the PKD1 gene, wherein said nucleic acid extends 3' of the PKD1 gene within fragment JH1 and into the PKD1 gene to within fragment JH6 as shown in FIG. 12;

(h) (WS-250) a nucleic acid comprising about 160 kb encompassing the PKD1 gene, wherein said nucleic acid extends 3' of the PKD1 gene to within fragment CW20 and 5' of the PKD1 gene to within fragment BLu24 as shown in FIGS. 1a and 12:

(i) (WS-194) a nucleic acid comprising about 65 kb encompassing the PKD1 gene, wherein said nucleic acid extends 3' of the PKD1 gene to within fragment CW20 and 5' of the PKD1 gene to within fragment CW10;

(j) (461) a nucleic acid comprising 18 base pairs in the 75 base pair intron amplified by the primer pair 3A3C (Seq. I.D. No.s: 11 and 12) insert at position 3696 of the 3' sequence as shown in FIG. 11;

(k) (OX1054) a nucleic acid comprising 20 base pairs in the 75 base pair intron amplified by the primer pair 3A3C (Seq. I.D. No.s: 11 and 12) insert at position 3696 of the 3' sequence as shown in FIG. 11; and (l) (WS-212) a nucleic acid comprising about 75 kb located downstream of the PKD1 gene and located between fragments SM9 and CW9 distal of the PKD1 gene and the PKD1 3'UTR proximal to the PKD1 gene as shown in FIG. 12, and which kit includes a nucleic acid probe capable of hybridizing to a sequence according to Seq. I.D. No. 7, wherein said probe is selected from the group consisting of 8S3, 8S1, 1A1H.6, AH3, CW10, JH17, JH5, JH6, JH8, JH4, JH13, HG-4/1.1, CE18, Blu24, H2, gap α 22, gap gamma, S1-S3, SM3, JH12, JH10, DFS5, JH14, SM9, CW9, CW15, CW18, CW20, JH11, CW36, JH14, A1C, 461, OX1054, B1E, 21p.9, 1A-7, AH6, BFS5 and JH9.

13. A diagnostic kit for carrying out a method for determining whether said subject is a PKD1-associated disorder carrier or a patient having a PKD1-associated disorder, which kit includes a nucleic acid probe capable of detecting an isolated mutant PKD1 nucleic acid and;

wherein said nucleic acid probe is an RNA transcript comprising a sequence complementary to the coding region of the nucleic acid sequence as presented in Seq. I.D. No. 7 or the complementary strand and comprising a length of about 14 kB, and wherein said mutant PKD1 nucleic acid comprises a nucleic acid sequence wherein a sequence selected from the group consisting of the following ((a)–(l)) is deleted:

(a) (OX114) a nucleic acid comprising 446 base pairs between nucleotides 1746–2192 as defined in Seq. I.D. No. 1;

(b) (OX32) a nucleic acid comprising 135 base pairs between nucleotides 3696–3831 as defined in Seq. I.D. No. 1;

(c) (OX875) a nucleic acid comprising about 5.5 Kb flanked by the two XbaI sites shown in FIG. 3a and encompassing the EcoR1 site separating the CW10 (41 kb) and JH1 (18 kb) fragment;

(d) (WS-53) a nucleic acid comprising about 100 kb encompassing the PKD1 gene, wherein the 3' end of said nucleic acid lies between the JH11 and CW21 fragment and the 5' end of said nucleic acid lies between the SM6 and JH17 fragment shown in FIG. 6;

(e) (WS-215) a nucleic acid comprising about 160 kb encompassing the PKD1 gene, wherein said nucleic acid extends 3' of the PKD1 gene to within fragment CW15 and 5' of the PKD1 gene to between fragments SM6 and JH17 as shown in FIG. 12;

(f) (WS-227) a nucleic acid comprising about 50 kb encompassing the PKD1 gene, wherein said nucleic acid extends 3' of the PKD1 gene to within fragment CW20 and 5' of the PKD1 gene to within fragment JH11 as shown in FIG. 12;

(g) (WS-219) a nucleic acid comprising about 27 kb encompassing a portion of the PKD1 gene, wherein said nucleic acid extends 3' of the PKD1 gene within fragment JH1 and into the PKD1 gene to within fragment JH6 as shown in FIG. 12;

(h) (WS-250) a nucleic acid comprising about 160 kb encompassing the PKD1 gene, wherein said nucleic acid extends 3' of the PKD1 gene to within fragment CW20 and 5' of the PKD1 gene to within fragment BLu24 as shown in FIGS. 1a and 12:

(i) (WS-194) a nucleic acid comprising about 65 kb encompassing the PKD1 gene, wherein said nucleic acid extends 3' of the PKD1 gene to within fragment CW20 and 5' of the PKD1 gene to within fragment CW10;

(j) (461) a nucleic acid comprising 18 base pairs in the 75 base pair intron amplified by the primer pair 3A3C (Seq. I.D. No.s: 11 and 12) insert at position 3696 of the 3' sequence as shown in FIG. 11;

(k) (OX1054) a nucleic acid comprising 20 base pairs in the 75 base pair intron amplified by the primer pair 3A3C (Seq. I.D. No.s: 11 and 12) insert at position 3696 of the 3' sequence as shown in FIG. 11; and (l) (WS-212) a nucleic acid comprising about 75 kb located downstream of the PKD1 gene and located between fragments SM9 and CW9 distal of the PKD1 gene and the PKD1 3'UTR proximal to the PKD1 gene as shown in FIG. 12.

14. A diagnostic kit for detecting a mutant PKD1 nucleic acid, wherein said mutant PKD1 nucleic acid comprises a nucleic acid sequence wherein a sequence selected from the group consisting of the following ((a)–(l)) is deleted:

(a) (OX114) a nucleic acid comprising 446 base pairs between nucleotides 1746–2192 as defined in Seq. I.D. No. 1;

(b) (OX32) a nucleic acid comprising 135 base pairs between nucleotides 3696–3831 as defined in Seq. I.D. No. 1;

(c) (OX875) a nucleic acid comprising about 5.5 Kb flanked by the two XbaI sites shown in FIG. 3a and encompassing the EcoR1 site separating the CW10 (41 kb) and JH1 (18 kb) fragment;

(d) (WS-53) a nucleic acid comprising about 100 kb encompassing the PKDD1 gene, wherein the 3' end of said nucleic acid lies between the JH1 and CW21 fragment and the 5' end of said nucleic acid lies between the SM6 and JH17 fragment shown in FIG. 6;

(e) (WS-215) a nucleic acid comprising about 160 kb encompassing the PKD1 gene, wherein said nucleic acid extends 3' of the PKD1 gene to within fragment CW15 and 5' of the PKD1 gene to between fragments SM6 and JH17 as shown in FIG. 12;

(f) (WS-227) a nucleic acid comprising about 50 kb encompassing the PKD1 gene, wherein said nucleic acid extends 3' of the PKD1 gene to within fragment CW20 and 5' of the PKD1 gene to within fragment JH11 as shown in FIG. 12;

(g) (WS-219) a nucleic acid comprising about 27 kb encompassing a portion of the PKD1 gene, wherein said nucleic acid extends 3' of the PKD1 gene within fragment JH1 and into the PKD1 gene to within fragment JH6 as shown in FIG. 12;

(h) (WS-250) a nucleic acid comprising about 160 kb encompassing the PKD1 gene, wherein said nucleic acid extends 3' of the PKD1 gene to within fragment CW20 and 5' of the PKD1 gene to within fragment BLu24 as shown in FIGS. 1a and 12:

(i) (WS-194) a nucleic acid comprising about 65 kb encompassing the PKD1 gene, wherein said nucleic acid extends 3' of the PKD1 gene to within fragment CW20 and 5' of the PKD1 gene to within fragment CW10;

(j) (461) a nucleic acid comprising 18 base pairs in the 75 base pair intron amplified by the primer pair 3A3C (Seq. I.D. No.s: 11 and 12) insert at position 3696 of the 3' sequence as shown in FIG. 11;

(k) (OX1054) a nucleic acid comprising 20 base pairs in the 75 base pair intron amplified by the primer pair 3A3C (Seq. I.D. No.s: 11 and 12) insert at position 3696 of the 3' sequence as shown in FIG. 11; and (l) (WS-212) a nucleic acid comprising about 75 kb located downstream of the PKD1 gene and located between fragments SM9 and CW9 distal of the PKD1 gene and the PKD1 3'UTR proximal to the PKD1 gene as shown in FIG. 12, and wherein said kit includes the DNA probe CW10 (Seq. I.D. No. 4).

15. A diagnostic kit for detecting a mutant PKD1 nucleic acid, wherein said mutant PKD1 nucleic acid comprises a nucleic acid sequence wherein a sequence selected from the group consisting of the following ((a)–(l)) is deleted:

(a) (OX114) a nucleic acid comprising 446 base pairs between nucleotides 1746–2192 as defined in Seq. I.D. No. 1;

(b) (OX32) a nucleic acid comprising 135 base pairs between nucleotides 3696–3831 as defined in Seq. I.D. No. 1;

(c) (OX875) a nucleic acid comprising about 5.5 Kb flanked by the two XbaI sites shown in FIG. 3a and encompassing the EcoR1 site separating the CW10 (41 kb) and JH1 (18 kb) fragment;

(d) (WS-53) a nucleic acid comprising about 100 kb encompassing the PKD1 gene, wherein the 3' end of said nucleic acid lies between the JH1 and CW21 fragment and the 5' end of said nucleic acid lies between the SM6 and JH17 fragment shown in FIG. 6;

(e) (WS-215) a nucleic acid comprising about 160 kb encompassing the PKD1 gene, wherein said nucleic acid extends 3' of the PKD1 gene to within fragment CW15 and 5' of the PKD1 gene to between fragments SM6 and JH17 as shown in FIG. 12;

(f) (WS-227) a nucleic acid comprising about 50 kb encompassing the PKD1 gene, wherein said nucleic acid extends 3' of the PKD1 gene to within fragment CW20 and 5' of the PKD1 gene to within fragment JH11 as shown in FIG. 12;

(g) (WS-219) a nucleic acid comprising about 27 kb encompassing a portion of the PKD1 gene, wherein said nucleic acid extends 3' of the PKD1 gene within fragment JH1 and into the PKD1 gene to within fragment JH6 as shown in FIG. 12;

(h) (WS-250) a nucleic acid comprising about 160 kb encompassing the PKD1 gene, wherein said nucleic acid extends 3' of the PKD1 gene to within fragment CW20 and 5' of the PKD1 gene to within fragment BLu24 as shown in FIGS. 1a and 12:

(i) (WS-194) a nucleic acid comprising about 65 kb encompassing the PKD1 gene, wherein said nucleic acid extends 3' of the PKD1 gene to within fragment CW20 and 5' of the PKD1 gene to within fragment CW10;

(j) (461) a nucleic acid comprising 18 base pairs in the 75 base pair intron amplified by the primer pair 3A3C (Seq. I.D. No.s: 11 and 12) insert at position 3696 of the 3' sequence as shown in FIG. 1;

(k) (OX1054) a nucleic acid comprising 20 base pairs in the 75 base pair intron amplified by the primer pair 3A3C (Seq. I.D. No.s: 11 and 12) insert at position 3696 of the 3' sequence as shown in FIG. 11; and (l) (WS-212) a nucleic acid comprising about 75 kb located downstream of the PKD1 gene and located between fragments SM9 and CW9 distal of the PKD1 gene and the PKD1 3'UTR proximal to the PKD1 gene as shown in FIG. 12, and wherein said kit includes the DNA probe 1A1H.6 (Seq. I.D. No. 3).

16. A diagnostic kit for carrying out a method for determining whether said subject is a PKD1 associated disorder carrier or a patient having a PKD1-associated disorder, which kit includes a nucleic acid probe capable of detecting a nucleic acid sequence wherein a sequence selected from the group consisting of the following ((a)–(l)) is deleted:

(a) (OX114) a nucleic acid comprising 446 base pairs between nucleotides 1746–2192 as defined in Seq. I.D. No. 1;

(b) (OX32) a nucleic acid comprising 135 base pairs between nucleotides 3696–3831 as defined in Seq. I.D. No. 1;

(c) (OX875) a nucleic acid comprising about 5.5 Kb flanked by the two XbaI sites shown in FIG. 3a and encompassing the EcoR1 site separating the CW10 (41 kb) and JH1 (18 kb) fragment;

(d) (WS-53) a nucleic acid comprising about 100 kb encompassing the PKD1 gene, wherein the 3' end of said nucleic acid lies between the JH1 and CW21 fragment and the 5' end of said nucleic acid lies between the SM6 and JH17 fragment shown in FIG. 6;

(e) (WS-215) a nucleic acid comprising about 160 kb encompassing the PKD1 gene, wherein said nucleic acid extends 3' of the PKD1 gene to within fragment CW15 and 5' of the PKD1 gene to between fragments SM6 and JH17 as shown in FIG. 12;

(f) (WS-227) a nucleic acid comprising about 50 kb encompassing the PKD1 gene, wherein said nucleic acid extends 3' of the PKD1 gene to within fragment CW20 and 5' of the PKD1 gene to within fragment JH11 as shown in FIG. 12;

(g) (WS-219) a nucleic acid comprising about 27 kb encompassing a portion of the PKD1 gene, wherein said nucleic acid extends 3' of the PKD1 gene within fragment JH1 and into the PKD1 gene to within fragment JH6 as shown in FIG. 12;

(h) (WS-250) a nucleic acid comprising about 160 kb encompassing the PKD1 gene, wherein said nucleic acid extends 3' of the PKD1 gene to within fragment CW20 and 5' of the PKD1 gene to within fragment BLu24 as shown in FIGS. 1a and 12:

(i) (WS-194) a nucleic acid comprising about 65 kb encompassing the PKD1 gene, wherein said nucleic acid extends 3' of the PKD1 gene to within fragment CW20 and 5' of the PKD1 gene to within fragment CW10;

(j) (461) a nucleic acid comprising 18 base pairs in the 75 base pair intron amplified by the primer pair 3A3C (Seq. I.D. No.s: 11 and 12) insert at position 3696 of the 3' sequence as shown in FIG. 11;

(k) (OX1054) a nucleic acid comprising 20 base pairs in the 75 base pair intron amplified by the primer pair 3A3C (Seq. I.D. No.s: 11 and 12) insert at position 3696 of the 3' sequence as shown in FIG. 11; and (l) (WS-212) a nucleic acid comprising about 75 kb located downstream of the PKD1 gene and located between fragments SM9 and CW9 distal of the PKD1 gene and the PKD1 3'UTR proximal to the PKD1 gene as shown in FIG. 12, and wherein said probe is selected from the group consisting of 8S3, 8S1, 1A1H.6, AH3, CW10, JH17, JH5, JH6, JH8, JH4, JH13, HG-4/1.1, CE18, Blu24, H2, gap α 22, gap gamma, S1-S3, SM3, JH12, JH10, DFS5, JH14, SM9, CW9, CW15, CW18, CW20, JH11, CW36, JH14, A1C, 461, OX1054, B1E, 21p.9, 1A-7, AH6, BFS5 and JH9.

* * * * *